(12) United States Patent
Huletsky et al.

(10) Patent No.: US 10,801,074 B2
(45) Date of Patent: *Oct. 13, 2020

(54) **METHOD FOR THE DETECTION AND IDENTIFICATION OF METHICILLIN-RESISTANT *STAPHYLOCOCCUS AUREUS***

(71) Applicant: GENEOHM SCIENCES CANADA, INC., Quebec (CA)

(72) Inventors: Ann Huletsky, Sillery (CA); Valery Rossbach, Gatineau (CA)

(73) Assignee: GeneOhm Sciences Canada, Inc., Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/568,156

(22) Filed: Sep. 11, 2019

(65) Prior Publication Data
US 2020/0109442 A1    Apr. 9, 2020

Related U.S. Application Data

(63) Continuation of application No. 15/707,421, filed on Sep. 18, 2017, which is a continuation of application No. 11/416,500, filed on May 2, 2006, now Pat. No. 9,777,335, which is a continuation of application No. 10/479,674, filed as application No. PCT/CA02/00824 on Jun. 4, 2002, now Pat. No. 7,449,289.

(30) Foreign Application Priority Data

Jun. 4, 2001    (CA) ........................................ 2348042

(51) Int. Cl.
C12Q 1/689    (2018.01)

(52) U.S. Cl.
CPC ....... *C12Q 1/689* (2013.01); *C12Q 2600/156* (2013.01); *C12Q 2600/16* (2013.01)

(58) Field of Classification Search
CPC .................................................... C12Q 1/689
See application file for complete search history.

(56) References Cited

U.S. PATENT DOCUMENTS

| 4,458,066 A | 7/1984 | Caruthers et al. |
| 4,683,195 A | 7/1987 | Mullis et al. |
| 4,683,202 A | 7/1987 | Mullis |
| 5,272,236 A | 12/1993 | Lai et al. |

(Continued)

FOREIGN PATENT DOCUMENTS

| AU | 731850 | 4/2001 |
| AU | 775763 | 8/2004 |

(Continued)

OTHER PUBLICATIONS

Al-Soud, et al. "Capacity of nine thermostable DNA Polymerases to mediate DNA amplification in the presence of PCR-Inhibiting samples." Appl. Environ. Microbiol. 64(10): 3748-3753 (1998).

(Continued)

*Primary Examiner* — Diana B Johannsen
(74) *Attorney, Agent, or Firm* — Knobbe, Martens, Olson & Bear, LLP

(57) ABSTRACT

The present invention describes novel SCCmec right extremity junction sequences for the detection of methicillin-resistant *Staphyloccocus aureus* (MRSA). It relates to the use of these DNA sequences for diagnostic purposes.

18 Claims, 10 Drawing Sheets

Specification includes a Sequence Listing.

(56) References Cited

U.S. PATENT DOCUMENTS

| | | |
|---|---|---|
| 5,437,978 A | 8/1995 | Ubukata et al. |
| 5,475,610 A | 12/1995 | Atwood et al. |
| 5,496,706 A | 3/1996 | Kuusela et al. |
| 5,538,871 A | 7/1996 | Nuovo et al. |
| 5,602,756 A | 2/1997 | Atwood et al. |
| 5,612,473 A | 3/1997 | Wu et al. |
| 5,702,895 A | 12/1997 | Matsunaga et al. |
| 5,776,712 A | 7/1998 | Kuusela et al. |
| 5,780,610 A | 7/1998 | Collins et al. |
| 5,783,638 A | 7/1998 | Lai et al. |
| 5,866,366 A | 2/1999 | Kallender |
| 5,994,066 A | 11/1999 | Bergeron et al. |
| 6,001,564 A | 12/1999 | Bergeron et al. |
| 6,083,587 A | 7/2000 | Smith et al. |
| 6,090,592 A | 7/2000 | Adams et al. |
| 6,117,635 A | 9/2000 | Nazarenko et al. |
| 6,117,986 A | 9/2000 | Nardone et al. |
| 6,156,507 A | 12/2000 | Hiramatsu et al. |
| 6,271,351 B1 | 8/2001 | Gawryl et al. |
| 6,380,370 B1 | 4/2002 | Doucette-Stamm et al. |
| 7,108,974 B2 | 9/2006 | Ecker et al. |
| 7,205,111 B2 | 4/2007 | Christensen et al. |
| 7,226,739 B2 | 6/2007 | Ecker et al. |
| 7,255,992 B2 | 8/2007 | Ecker et al. |
| 7,399,590 B2 | 7/2008 | Piepenburg et al. |
| 7,435,561 B2 | 10/2008 | Piepenburg et al. |
| 7,449,289 B2 | 11/2008 | Huletsky et al. |
| 7,466,908 B1 | 12/2008 | Lem et al. |
| 7,666,588 B2 | 2/2010 | Ecker et al. |
| 7,666,592 B2 | 2/2010 | Ecker et al. |
| 7,718,354 B2 | 5/2010 | Ecker et al. |
| 7,741,036 B2 | 6/2010 | Ecker et al. |
| 7,781,162 B2 | 8/2010 | Ecker et al. |
| 7,838,221 B2 | 11/2010 | Huletsky et al. |
| 7,955,796 B2 | 6/2011 | Schrenzel et al. |
| 7,956,175 B2 | 6/2011 | Sampath et al. |
| 8,013,142 B2 | 9/2011 | Sampath et al. |
| 8,017,322 B2 | 9/2011 | Ecker et al. |
| 8,017,337 B2 | 9/2011 | Paitan |
| 8,017,358 B2 | 9/2011 | Ecker et al. |
| 8,017,743 B2 | 9/2011 | Ecker et al. |
| 8,034,588 B2 | 10/2011 | Bergeron et al. |
| 8,062,850 B2 | 11/2011 | Piepenburg et al. |
| 8,067,207 B2 | 11/2011 | Bergeron et al. |
| 8,071,309 B2 | 12/2011 | Ecker et al. |
| 8,084,207 B2 | 12/2011 | Sampath et al. |
| 8,097,416 B2 | 1/2012 | Hall et al. |
| 8,114,601 B2 | 2/2012 | Bergeron et al. |
| 8,163,895 B2 | 4/2012 | Sampath et al. |
| 8,182,992 B2 | 5/2012 | Sampath |
| 8,182,996 B2 | 5/2012 | Bergeron et al. |
| 8,187,812 B2 | 5/2012 | Zhang et al. |
| 8,187,814 B2 | 5/2012 | Ecker et al. |
| 8,214,154 B2 | 7/2012 | Ecker et al. |
| 8,242,254 B2 | 8/2012 | Sampath et al. |
| 8,265,848 B2 | 9/2012 | Ecker et al. |
| 8,268,565 B2 | 9/2012 | Ecker et al. |
| 8,288,523 B2 | 10/2012 | Sampath et al. |
| 8,323,898 B2 | 12/2012 | Niimi et al. |
| 8,362,228 B2 | 1/2013 | Paitan |
| 8,367,337 B2 | 2/2013 | Jay et al. |
| 8,394,945 B2 | 3/2013 | Sampath et al. |
| 8,426,137 B2 | 4/2013 | Bergeron et al. |
| 8,518,646 B2 | 8/2013 | Jean et al. |
| 9,777,335 B2 | 10/2017 | Huletsky et al. |
| 10,577,664 B2 | 3/2020 | Huletsky et al. |
| 2002/0055101 A1 | 5/2002 | Bergeron et al. |
| 2002/0103338 A1 | 8/2002 | Choi |
| 2002/0106646 A1 | 8/2002 | Remacle et al. |
| 2003/0027135 A1 | 2/2003 | Ecker et al. |
| 2003/0049636 A1 | 3/2003 | Bergeron et al. |
| 2003/0054436 A1 | 3/2003 | Kunsch et al. |
| 2003/0124556 A1 | 7/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0180733 A1 | 9/2003 | Bergeron et al. |
| 2003/0190605 A1 | 10/2003 | Ecker et al. |
| 2003/0198943 A1 | 10/2003 | Remacle et al. |
| 2004/0082002 A1 | 4/2004 | Choi |
| 2004/0110138 A1 | 6/2004 | Lem et al. |
| 2004/0110169 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121313 A1 | 6/2004 | Ecker et al. |
| 2004/0121314 A1 | 6/2004 | Ecker et al. |
| 2004/0121335 A1 | 6/2004 | Ecker et al. |
| 2004/0161770 A1 | 8/2004 | Ecker et al. |
| 2004/0180328 A1 | 9/2004 | Ecker et al. |
| 2004/0185437 A1 | 9/2004 | Hermet et al. |
| 2004/0185438 A1 | 9/2004 | Ecker |
| 2004/0185478 A1 | 9/2004 | Bergeron et al. |
| 2004/0202997 A1 | 10/2004 | Ecker et al. |
| 2004/0219517 A1 | 11/2004 | Ecker et al. |
| 2004/0241824 A1 | 12/2004 | Schrenzel et al. |
| 2004/0253583 A1 | 12/2004 | Ecker et al. |
| 2004/0253619 A1 | 12/2004 | Ecker et al. |
| 2005/0019893 A1 | 1/2005 | Huletsky et al. |
| 2005/0037408 A1 | 2/2005 | Christensen et al. |
| 2005/0059064 A1 | 3/2005 | Obst et al. |
| 2005/0112631 A1 | 5/2005 | Piepenburg et al. |
| 2005/0115903 A1 | 6/2005 | Hallier-Soulier et al. |
| 2006/0057613 A1 | 3/2006 | Ramakrishnan et al. |
| 2006/0105354 A1 | 4/2006 | Remacle et al. |
| 2006/0121520 A1 | 6/2006 | Ecker et al. |
| 2006/0205040 A1 | 9/2006 | Sampath |
| 2006/0240412 A1 | 10/2006 | Hall et al. |
| 2006/0252069 A1 | 11/2006 | Zhang et al. |
| 2006/0252078 A1 | 11/2006 | Huletsky et al. |
| 2006/0263810 A1 | 11/2006 | Bergeron et al. |
| 2006/0275749 A1 | 12/2006 | Sampath et al. |
| 2006/0275788 A1 | 12/2006 | Ecker et al. |
| 2006/0281112 A1 | 12/2006 | Remacle et al. |
| 2007/0009947 A1 | 1/2007 | Bergeron et al. |
| 2007/0037187 A1 | 2/2007 | Alexandre et al. |
| 2007/0048735 A1 | 3/2007 | Ecker et al. |
| 2007/0054296 A1 | 3/2007 | Piepenburg et al. |
| 2007/0082340 A1 | 4/2007 | Huletsky et al. |
| 2007/0099204 A1 | 5/2007 | Alexandre et al. |
| 2007/0105129 A1 | 5/2007 | Bergeron et al. |
| 2007/0218489 A1 | 9/2007 | Sampath et al. |
| 2007/0224614 A1 | 9/2007 | Sampath et al. |
| 2007/0238116 A1 | 10/2007 | Sampath et al. |
| 2007/0243544 A1 | 10/2007 | Sampath et al. |
| 2007/0248969 A1 | 10/2007 | Sampath et al. |
| 2007/0298423 A1 | 12/2007 | Remacle et al. |
| 2008/0038737 A1 | 2/2008 | Smith et al. |
| 2008/0057544 A1 | 3/2008 | Lem et al. |
| 2008/0085515 A1 | 4/2008 | Remacle et al. |
| 2008/0138808 A1 | 6/2008 | Hall et al. |
| 2008/0145847 A1 | 6/2008 | Hall et al. |
| 2008/0146455 A1 | 6/2008 | Hall et al. |
| 2008/0160512 A1 | 7/2008 | Ecker et al. |
| 2008/0220428 A1 | 9/2008 | Aichinger et al. |
| 2008/0227087 A1 | 9/2008 | Huletski et al. |
| 2008/0233570 A1 | 9/2008 | Hall et al. |
| 2008/0311558 A1 | 12/2008 | Ecker et al. |
| 2009/0004643 A1 | 1/2009 | Ecker et al. |
| 2009/0035780 A1 | 2/2009 | McCarthy et al. |
| 2009/0047665 A1 | 2/2009 | Hall et al. |
| 2009/0047669 A1 | 2/2009 | Zhang et al. |
| 2009/0047671 A1 | 2/2009 | Bergeron et al. |
| 2009/0053702 A1 | 2/2009 | Bergeron et al. |
| 2009/0053703 A1 | 2/2009 | Bergeron et al. |
| 2009/0061446 A1 | 3/2009 | Niimi et al. |
| 2009/0068641 A1 | 3/2009 | Bergeron et al. |
| 2009/0111134 A1 | 4/2009 | Zhang et al. |
| 2009/0148829 A1 | 6/2009 | Ecker et al. |
| 2009/0148836 A1 | 6/2009 | Ecker et al. |
| 2009/0148837 A1 | 6/2009 | Ecker et al. |
| 2009/0181395 A1 | 7/2009 | Becker et al. |
| 2009/0182511 A1 | 7/2009 | Ecker et al. |
| 2009/0203013 A1 | 8/2009 | Jay et al. |

(56) References Cited

U.S. PATENT DOCUMENTS

| | | |
|---|---|---|
| 2009/0220937 A1 | 9/2009 | Sampath |
| 2009/0239224 A1 | 9/2009 | Ecker et al. |
| 2009/0280471 A1 | 11/2009 | Ecker et al. |
| 2010/0035232 A1 | 2/2010 | Ecker et al. |
| 2010/0035239 A1 | 2/2010 | Sampath et al. |
| 2010/0099860 A1 | 4/2010 | Remacle et al. |
| 2010/0129811 A1 | 5/2010 | Sampath et al. |
| 2010/0136515 A1 | 6/2010 | Sampath et al. |
| 2010/0145626 A1 | 6/2010 | Ecker et al. |
| 2010/0152432 A1 | 6/2010 | Wu et al. |
| 2010/0204266 A1 | 8/2010 | Ecker et al. |
| 2010/0267012 A1 | 10/2010 | Bergeron et al. |
| 2010/0304366 A1 | 12/2010 | Wu et al. |
| 2011/0091886 A1 | 4/2011 | Hirama et al. |
| 2011/0151452 A1 | 6/2011 | Jean et al. |
| 2012/0015349 A1 | 1/2012 | Sampath et al. |
| 2012/0015367 A1 | 1/2012 | Piepenburg et al. |
| 2012/0035071 A1 | 2/2012 | Bergeron et al. |
| 2012/0058487 A1 | 3/2012 | Bergeron et al. |
| 2012/0077684 A1 | 3/2012 | O'Hara |
| 2012/0107795 A1 | 5/2012 | Ecker et al. |
| 2012/0122086 A1 | 5/2012 | Ecker et al. |
| 2012/0122096 A1 | 5/2012 | Sampath et al. |
| 2012/0122097 A1 | 5/2012 | Sampath et al. |
| 2012/0122098 A1 | 5/2012 | Sampath et al. |
| 2012/0122099 A1 | 5/2012 | Sampath et al. |
| 2012/0122100 A1 | 5/2012 | Sampath et al. |
| 2012/0122101 A1 | 5/2012 | Sampath et al. |
| 2012/0122102 A1 | 5/2012 | Sampath et al. |
| 2012/0122103 A1 | 5/2012 | Sampath et al. |
| 2012/0142085 A1 | 6/2012 | Ecker et al. |
| 2012/0164625 A1 | 6/2012 | Ecker et al. |
| 2012/0171679 A1 | 7/2012 | Ecker et al. |
| 2012/0171692 A1 | 7/2012 | Sampath et al. |
| 2012/0208179 A1 | 8/2012 | Sampath et al. |
| 2013/0065774 A1 | 3/2013 | Zhang et al. |
| 2013/0266942 A1 | 10/2013 | Menard et al. |
| 2013/0338036 A1 | 12/2013 | Jean et al. |
| 2013/0338037 A1 | 12/2013 | Jean et al. |
| 2015/0232919 A1 | 8/2015 | Menard et al. |

FOREIGN PATENT DOCUMENTS

| | | |
|---|---|---|
| AU | 2008255266 | 1/2009 |
| AU | 2010202418 | 7/2010 |
| AU | 2012247038 | 11/2012 |
| CA | 2283458 | 3/2001 |
| CA | 2348042 A1 | 12/2002 |
| CN | 1505685 | 6/2004 |
| DE | 10051174 | 5/2002 |
| EP | 0 497 272 | 8/1992 |
| EP | 0 526 876 A1 | 2/1993 |
| EP | 0 527 628 | 2/1993 |
| EP | 0 543 942 | 6/1993 |
| EP | 0 887 424 | 12/1998 |
| EP | 1 136 566 A | 9/2001 |
| EP | 1 522 595 | 4/2005 |
| EP | 1 529 847 A | 5/2005 |
| EP | 1 541 696 A | 6/2005 |
| EP | 1 659 183 A | 5/2006 |
| EP | 1 788 095 A1 | 5/2007 |
| EP | 1 903 116 A1 | 3/2008 |
| EP | 1 997 886 A1 | 12/2008 |
| EP | 0 943 009 B1 | 6/2009 |
| EP | 1 397 510 B1 | 11/2009 |
| EP | 2 128 268 A1 | 12/2009 |
| EP | 2 150 625 A2 | 2/2010 |
| EP | 2 236 621 A1 | 10/2010 |
| EP | 2 253 712 A1 | 11/2010 |
| EP | 1 934 613 B1 | 1/2011 |
| EP | 2 302 074 | 3/2011 |
| EP | 2 311 992 | 4/2011 |
| EP | 2 322 649 | 5/2011 |
| EP | 2 322 655 A1 | 5/2011 |
| EP | 2 322 661 A1 | 5/2011 |
| EP | 2 322 663 A1 | 5/2011 |
| EP | 2 322 664 A1 | 5/2011 |
| EP | 2 322 666 A2 | 5/2011 |
| EP | 2 322 667 A2 | 5/2011 |
| EP | 2 322 668 A2 | 5/2011 |
| EP | 2 322 930 A2 | 5/2011 |
| EP | 2 325 643 A2 | 5/2011 |
| EP | 2 325 644 A2 | 5/2011 |
| EP | 2 325 645 A2 | 5/2011 |
| EP | 2 325 646 A2 | 5/2011 |
| EP | 2 325 647 A2 | 5/2011 |
| EP | 2 333 118 | 6/2011 |
| EP | 2 336 364 A1 | 6/2011 |
| EP | 2 336 365 A1 | 6/2011 |
| EP | 2 336 366 A2 | 6/2011 |
| EP | 2 339 033 A1 | 6/2011 |
| EP | 2 339 034 A1 | 6/2011 |
| EP | 2 345 746 A1 | 7/2011 |
| EP | 2 385 140 A1 | 11/2011 |
| EP | 2 064 332 B1 | 7/2012 |
| EP | 2 016 186 B1 | 1/2013 |
| EP | 1 929 049 B1 | 4/2013 |
| JP | H11056371 | 3/1999 |
| JP | 2004-534537 | 11/2004 |
| JP | 2006271370 | 10/2006 |
| JP | 2010057495 | 3/2010 |
| KR | 20030003576 | 1/2003 |
| MX | PA03007927 | 10/2004 |
| MY | 141881 A | 7/2010 |
| WO | WO 1992/02638 | 2/1992 |
| WO | WO 1992/05281 | 4/1992 |
| WO | WO 1995/13395 A1 | 5/1995 |
| WO | WO 1996/008582 | 3/1996 |
| WO | WO 1997/31125 | 8/1997 |
| WO | WO 1998/20157 | 5/1998 |
| WO | WO 1999/47706 | 9/1999 |
| WO | WO 2001/016292 | 3/2001 |
| WO | WO 2001/023604 A2 | 4/2001 |
| WO | WO 2001/077372 | 10/2001 |
| WO | WO 2002/070866 | 9/2002 |
| WO | WO 2002/082086 | 10/2002 |
| WO | WO 2002/099034 | 12/2002 |
| WO | WO 2004/052175 | 6/2004 |
| WO | WO 2004/053076 | 6/2004 |
| WO | WO 2004/053141 | 6/2004 |
| WO | WO 2004/053164 | 6/2004 |
| WO | WO 2004/055205 | 7/2004 |
| WO | WO 2004/060278 | 7/2004 |
| WO | WO 2005/014857 | 2/2005 |
| WO | WO 2005/024046 | 3/2005 |
| WO | WO 2005/094421 | 10/2005 |
| WO | WO 2005/098047 | 10/2005 |
| WO | WO 2005/100538 | 10/2005 |
| WO | WO 2006/028601 | 3/2006 |
| WO | WO 2006/053769 | 5/2006 |
| WO | WO 2006/053770 | 5/2006 |
| WO | WO 2006/071241 | 7/2006 |
| WO | WO 2006/094238 | 9/2006 |
| WO | WO 2006/111028 | 10/2006 |
| WO | WO 2006/116127 | 11/2006 |
| WO | WO 2006/135400 | 12/2006 |
| WO | WO 2007/023461 | 3/2007 |
| WO | WO 2007/044873 | 4/2007 |
| WO | WO 2007/086904 | 8/2007 |
| WO | WO 2007/096702 | 8/2007 |
| WO | WO 2007/100397 | 9/2007 |
| WO | WO 2007/130951 A2 | 11/2007 |
| WO | WO 2007/131995 | 11/2007 |
| WO | WO 2007/131999 | 11/2007 |
| WO | WO 2007/132001 | 11/2007 |
| WO | WO 2007/132002 | 11/2007 |
| WO | WO 2007/133732 | 11/2007 |
| WO | WO 2008/061376 | 5/2008 |
| WO | WO 2008/080620 | 7/2008 |
| WO | WO 2008/140612 | 11/2008 |
| WO | WO 2008/143627 | 11/2008 |
| WO | WO 2009/049007 | 4/2009 |

(56) References Cited

FOREIGN PATENT DOCUMENTS

| WO | WO 2009/090310 | 7/2009 |
|---|---|---|
| WO | WO 2009/123667 | 10/2009 |
| WO | WO 2011/038197 | 3/2011 |

OTHER PUBLICATIONS

Al-Soud, et. al. "Effects of amplification facilitators on diagnostic PCR in the presence of blood, feces, and meat." J. Clin. Microbiol. 38(12): 4463-4470 (2002).
Arakere, et al. "A novel type-III *Staphylococcal cassette chromosome mec* (SCCmec) variant among Indian isolates of methicillin-resistant *Staphylococcus aureus*." FEMS Microbiol. Lett. 292(1): 141-148 (Mar. 2009).
Archer, et al. "Origin and evolution of DNA associated with resistance to methicillin in staphylococci." Trends in Microbiology. 2(10):343-347 (1994).
Archer, et al. "Dissemination among staphylococci of DNA sequences associated with methicillin resistance." Antimicrobial Agents and Chemotherapy. 38(3):447-54 (1994).
Arnheim, et al "Polymerase Chain Reaction." C&EN. 36-47 (1990).
Ausubel et al., Current Protocols in Molecular Biology, 3rd Ed. Wiley Interscience Publishers (1995) [Table of Contents Only].
Baba, et al. "Genome and virulence determinants of high virulence community-acquired MRSA." Lancet. 359(9320): 1819-1827 (2002).
Baba et al. "*Staphylococcus aureus* subsp. *aureus* MW2 DNA, complete genome", retrieved from EBI Database accession No. AP004822 (May 27, 2002), replaced by Accession No. BA000033.
Barany et al., "Genetic disease detection and DNA amplification using cloned thermostable ligase," Proc Natl Acad Sci. USA (Jan. 1991) 88: 189-193.
Barberis-Maino. IS431, a staphylococcal insertion sequence-like element related to IS26 from *Proteus vulgaris*. Gene. 59:107-13 (1983).
Barringer, et al. "Blunt-end and single strand ligations by *Escherichia coli* ligase: Influence on an in vitro amplification scheme." Gene. 89:117-122 (1990).
Barski et al., "Rapid assay for detection of methicillin-resistant *Staphylococcus aureus* using multiplex PCR," Mol Cell Probes (1996) 10(6):471-475.
Bartels et al., "An unexpected location of the Arginine Catabolic Mobile Element (ACME) in a USA300-related MRSA." PLoS ONE 6(1): e16193 (Jan. 2011).
Bastos et al., "Molecular characterization and transfer among *Staphylococcus* strains of a plasmid conferring high-level resistance to mupirocin", Eur. J. Clin. Microbiol. Infect. Dis. (1999) 18(6):393-8.
Beaucage et al. "Deoxynucleoside Phosphoramidites—A New Class of Key Intermediates for Deoxypolynucleotide Syntesis," Tetra Lttrs. (1981) 22(20): 1859-1862.
Becker et al., "Thermonuclease gene as a target for specific identification of *Staphylococcus intermedius* isolates: use of a PCR-DNA enzyme immunoassay", Diagn. Microbiol. Infect. Dis. (Apr. 2005) 51(4):237-44.
Becker et al., "Does Nasal Cocolonization by Methicillin-Resistant Coagulase-Negative Staphylococci and Methicillin-Susceptible *Staphylococcus aureus* Strains Occur Frequently Enough to Represent a Risk of False Positive Methicillin-Resistant *S. aureus* Determinations by Molecular Methods?", J Clin Microbiol. (Jan. 2006) 44(1): 229-231.
Benson et al., "Direct detection of mecA and nuc genes for rapid species and resistance determination of staphylococci from blood cultures," Abstracts of the Interscience Conference on Antimicrobial Agents and Chemotherapy, (1999) vol. 39, Abstract #877; pp. 208. cd-rom; 39th Interscience Conference on Antimicrobial Agents and Chemotherapy. San Francisco, California, USA. Sep. 26-29, 1999. American Society for Microbiology.
Berger-Bächi, et al. "Insertional inactivation of staphylococcal methicillin resistance by Tn551." J. Bacter. 154(1):479-87 (1983).
Bishop et al., "Concurrent Analysis of Nose and Groin Swab Specimens by the IDI-MRSA PCR Assay is Comparable to Analysis by Individual-Specimen PCR and Routine Culture Assays for Detection of Colonization by Methicillin-Resistant *Staphylococcus aureus*", J Clin Microbiol. (Aug. 2006) 44(8): 2904-2908.
Boye et al., "A new multiplex PCR for easy screening of methicillin-resistant *Staphylococcus aureus* SCCmec types I-V.", Clin Microbiol Infect. (Jul. 2007) 13(7): 725-727.
Brakstad et al., "Detection of *Staphylococcus aureus* by polymerase chain reaction amplification of the nuc gene", *J. Clin. Microbiol.* (1992) 30(7):1654-60.
Brakstad et al., "Multiplex polymerase chain reaction for detection of genes for *Staphylococcus aureus* thermonuclease and methicillin resistance and correlation with oxacillin resistance," APMIS (1993) 101(:681-688.
Brakstad et al., "Simultaneous detection of the staphylococcal MecA and Nuc genes by a multiplex PCR," Zentralblatt für Bakteriologie (Inter'l J Med Microbiol.), (1994) Supplement 26, 246-248.
Brakstad et al., "Comparison of tests designed to identify *Staphylococcus aureus* thermostable nuclease", *APMIS* (1995) 103(3):219-24.
Brown et al., "Chemical Synthesis and Cloning of a Tyrosine tRNA Gene," Meth Enzymol. (1979) 68:109-151.
Brown et al., "Real-time PCR detection of *S-aureus* and MRSA from wound, fluid and respiratory samples," Abstracts of the General Meeting of the American Society for Microbiology, (2006) vol. 106, Abs. C-074, pp. 110-111; 106th General Meeting of the American Society for Microbiology. Orlando, FL, USA. May 21-25, 2006.
Buck, et al. "Design strategies and performance of custom DNA sequencing primers." BioTechniques, 27(3): 528-536, (Sep. 1999).
Bustin S.A., "Absolute quantification of mRNA using real-time reverse transcription polymerase chain reaction assays", J Mol Endocrinol. (2000) 25: 169-193.
Carroll, K.C. "Rapid diagnostics for methicillin-resistant *Staphylococcus aureus*", Mol Diagn Therapy, (Jan. 2008) 12(1): 15-24.
Chakrabarti, et al. "Novel sulfoxides facilitate GC-rich template amplification." Biotechniques. 32:866-874 (2002).
Chesneau et al., "Thermonuclease gene as a target nucleotide sequence for specific recognition of *Staphylococcus aureus*", Mol. Cell. Probes. (1993) 7(4):301-10.
Cheng et al., "Effective amplification of long targets from cloned inserts and human genomic DNA," Proc Natl Acad Sci. USA, (Jun. 1994) 91: 5695-5699.
Ciardo et al., "GeneXpert Captures Unstable Methicillin-Resistant *Staphylococcus aureus* Prone to Rapidly Losing the mecAGene," J. Clin. Microbio. (Aug. 2010) 48(8):3030-3031.
Cho et al., "Detection of methicillin resistance in *Staphylococcus aureus* isolates using two-step triplex PCR and conventional methods", J Microbiol Biotechnol. (Apr. 2007) 17(4): 673-676.
Chongtrakool et al., "Staphylococcal cassette chromosome mec (SCCmec) typing of methicillin-resistant *Staphylococcus aureus* strains isolated in 11 Asian countries: a proposal for a new nomenclature for SCCmec elements", Antimicrob. Agents Chemother. (2006) 50(3):1001-12.
Costa et al., "Rapid detection of mecA and nuc genes in staphylococci by real-time multiplex polymerase chain reaction", Diagn. Microbiol. Infect. Dis. (Jan. 2005) 51(1):13-17.
Crisóstomo et al., "The evolution of methicillin resistance in *Staphylococcus aureus*: Similarity of genetic backgrounds in historically early methicillin-susceptible and -resistant isolates and contemporary epidemic clones", Proc Natl Acad Sci USA, (Aug. 2001) 98(17): 9865-9870.
Cuny et al., "PCR for the identification of methicillin-resistant *Staphylococcus aureus* (MRSA) strains using a single primer pair specific for SCCmec elements and the neighbouring chromosome-borne orfX."—Research Note, Clin Microbio Infect., 11(10): 834-837 (Oct. 2005).
Cuny et al., "Rare Occurrence of Methicillin-Resistant *Staphylococcus aureus* CC130 with a Novel mecA Homologue in Humans in Germany", PloS One (2011) 6(9):e24360; 5 pages.

(56) References Cited

OTHER PUBLICATIONS

Database Geneseq [Online]. "Polymorphic right extremity junction (MREJ) DNA #1." EBI accession No. GSN:ACD02065; Database accession No. ACD02065 (2003).
Database Geneseq [Online]. Sequence provided in Fig. 4 of JP11056371. Retrieved from EBI accession No. GSN:AAX32450 (Oct. 25, 2010).
Database Geneseq [Online]. "Identification method" JP1999056371, Retrieved from EBI accession No. EM-PRO:E60314 (Oct. 26, 2010).
Database Geneseq [Online]. "Sequence of Primer KC1". Retrieved from EBI accession No. GSN:AAX32446 (Jun. 22, 1999).
Database Geneseq [Online]. "*Staphylococcus aureus* downstream junction sequence Psj10-3J3rc.", Retrieved from EBI accession No. GSN:AAT84818 (Mar. 23, 1998).
Database EMBL [Online]. "*Staphylococcus aureus* DNA, 3' flanking region of MecDNA, strain 64/4176", Retrieved from EBI accession No. AB014434 (Jan. 7, 2000).
Database EMBL [Online]. "*Staphylococcus aureus* M type 1 capsular polysaccharide biosynthesis gene cluster, complete sequence and unknown genes", Retrieved from EBI accession No. SA10927 (Nov. 8, 1994).
Database EMBL [Online]. "*Staphylococcus aureus* DNA, type-IV.1 (Iva) staphylococcal cassette chromosome mec: strain CA05 (JCSC1968)", retrieved from EBI accession No. AB063172 (Nov. 21, 2001).
De Lencastre, et al. Methicillin-resistant *Staphylococcus aureus* disease in a Portuguese Hospital: Characterization of clonal types by a combination of DNA typing methods. Eur. J. Clin. Microbiol. Infect. Dis. 13(1): 64-73 (1994).
Denis et al., "Rapid screening of methicillin resistant *Staphylococcus aureus* carriers by direct PCR on enrichment broth culture of superficial swab samples," Abstracts of the Interscience Conference on Antimicrobial Agents and Chemotherapy, (2002) vol. 42, Abs. K-101, pp. 304; 42nd Interscience Conference on Antimicrobial Agents and Chemotherapy. San Diego, CA, USA. Sep. 27-30, 2002. American Society for Microbiology.
Deplano, et al. "In Vivo deletion of the methicillin resistance mec region from the chromosome of *Staphylococcus aureus* strains." J. Antimicrob. Chemother., 46-617-619 (2000).
Derbise, et al. "Mapping the regions carrying the three contiguous antibiotic resistance genes aadE, sat4, and aphA-3 in the genomes of staphylococci." Antimicro. Agen. Chemother. 41(5): 1024-32 (1997).
De San et al., Controlled Evaluation of the IDI-MRSA Assay for Detection of Colonization by Methicillin-Resistant *Staphylococcus aureus* in Diverse Mucocutaneous Specimens, J Clin Microbiol. (2007) 45(4): 1098-1101.
Desbouchages et al., "Direct screening of MRSA from swab specimens using duplex real-time PCR assay: implication for antibiotic prophylaxis," International Journal of Antimicrobial Agents, (2004) vol. 24 (212/47O, pp. S104-S105; 6th European Congress of Chemotherapy and Infection/24th Interdisciplinary Meeting on Anti-Infectious Chemotherapy. Paris, France. Dec. 1-3, 2004.
Desjardins et al., "Evaluation of the IDI-MRSA Assay for Detection of Methicillin-Resistant *Staphylococcus aureus* from Nasal and Rectal Specimens Pooled in a Selective Broth", J Clin Microbiol. (Apr. 2006) 44(4): 1219-1223.
Diekema et al., "Survey of infections due to *Staphylococcus* species: frequency of occurrence and antimicrobial susceptibility of isolates collected in the United States, Canada, Latin America, Europe, and the Western Pacific region for the Sentry Antimicrobial Surveillance Program, 1997-1999", Clin Infect Dis. (2001) 32(Suppl. 2):S114-132.
Dieffenbach et al. "PCR Primer: A Laboratory Manual", 1995, Cold Spring Harbor Laboratory Press (Cover & Contents pages only).
Dieffenbach et al. "General Concepts for PCR Primer Design." Genome Res. 3: S30-S37 (1993).

Domann et al. "Schneller und zuverlaessiger Nachweis multiresistenter multiplex-PCR." Deutsche Medizinische Wochenschrift. 125(20): 613-618 (2000). w/EN Abstract.
Donnio et al., "Partial Excision of the Chromosomal Cassette Containing the Methicillin Resistance Determinant Results in Methicillin-Susceptible *Staphylococcus aureus*", J Clin Microbiol. (Aug. 2005) 43(8): 4191-4193.
Dubin, et al. "Physical mapping of the mec region of an American methicillin-resistant *Staphylococcus aureus* strain." Antimicrob. Agents Chemother. 35(8):1661-65 (1991).
Edwards et al., "Multiplex PCR: advantages, development, and applications", Genome Res. (1994) 3: S65-75.
Egholm, et al. "PNA hybridizes to complementary oligonucleotides obeying the Watson-Crick hydrogen-bonding rules." Nature. 365: 566-568 (1993).
Elghanian et al. "Selective Colorimetric Detection of Polynucleotides Based on the Distance-Dependent Optical Properties of Gold Nanoparticles." (1997) Science 277:1078-1081.
Elsayed et al., "Development and Validation of a Molecular Beacon Probe-Based Real-Time Polymerase Chain Reaction Assay for Rapid Detection of Methicillin Resistance in *Staphylococcus aureus*", Arch Pathol Lab Med. (Jul. 2003) 127(7): 845-849.
Fan et al., "Rapid detection of methicillin-resistant Staphylococci by DNA probe," Linchuang Jianyan Zazhi 24(5) 351-352 (2006).
Fang et al. "Rapid Screening and Identification of Methicillin-Resistant *Staphylococcus aureus* from Clinical Samples by Selective-Broth and Real-Time PCR Assay." (Jul. 2003) 41(7): 2894-2899 and 1 page Erratum.
Flores, et. al. "A rapid, inexpensive method for eluting DNA from Agarose or Acrylamide gel slices without using toxic or chaotropic materials." Biotechniques. 13(2): 205-206 (1992).
Francois et al., "Evaluation of Three Molecular Assays for Rapid Identification of Methicillin-Resistant *Staphylococcus aureus*", J Clin Microbiol. (2007) 45(6): 2011-2013.
García-Álvarez et al. "Meticillin-resistant *Staphylococcus aureus* with a novel mecA homologue in human and bovine populations in the UK and Denmark: a descriptive study," Lancet Infect Dis. (Aug. 2011) 11(8):595-603.
GenBank accession No. D86934.1, "*Staphylococcus aureus* genes, mec region, partial and complete cds.", Jul. 3, 1999; pp. 25.
GenBank accession No. X53818.1, "*Staphylococcus aureus* IS431 mec gene associated with methilicillin resistance", Oct. 23, 2008.
Gerberding, et al. Comparison of conventional susceptibility tests with direct detection of penicillin-binding protein 2a in borderline oxacillin-resistant strains of *Staphylococcus aureus*. Antimicrob. Agents Chemother. 35(12):2574-79 (1991).
Goldmeyer et al., "Identification of *Staphylococcus aureus* and Determination of Methicillin Resistance Directly from Positive Blood Cultures by Isothermal Amplification and a Disposable Detection Device," J. Clin. Microbiol. (2008) vol. 46 No. 4, 1534-1536.
Grisold et al., "Detection of Methicillin-Resistant *Staphylococcus aureus* and Simultaneous Confirmation by Automated Nucleic Acid Extraction and Real-Time PCR," J Clin. Microbiol. (2002) 40(7):2392-2397.
Grisold et al., "Use of hybridization probes in a real-time PCR assay on the LightCycler® for the detection of methicillin-resistant *Staphylococcus aureus*", Methods Mol. Biol. (2006) 345:79-89.
Gröbner et al., "Development of a real-time *Staphylococcus aureus* and MRSA (SAM-) PCR for routine blood culture," European Journal of Clinical Microbiology & Infectious Diseases (2007) (26)10:751-754.
Guatelli, et al. "Isotherma, in vitro amplification of nucleic acids by a multienzyme reaction modeled after retroviral replication." Proc. Natl. Acad. Sci. USA, 87:1874-1878 (1990).
Guintu et al., "Detection of MRSA Directly from Positive Blood Culture Bottles using MRSA Evigene (Advandx)," Abstracts of the Interscience Conference on Antimicrobial Agents and Chemotherapy, 45th Interscience Conference on Antimicrobial Agents and Chemotherapy. Washington, DC, USA.; Abs. D-1716; (2005) vol. 45, pp. 151.
Hagen, et al. "Development of a real-time PCR assay for rapid identification of methicillin-resistant *Staphylococcus aureus* from

(56) References Cited

OTHER PUBLICATIONS clinical samples." International Journal of Medical Microbiology, Urban and Fischer, DE. 295(2):77-86 (2005).
Hanaki et al., Loop-mediated isothermal amplification assays for identification of antiseptic- and methicillin-resistant *Staphylococcus aureus*, J Microbiol Meth. (2011) 84(2): 251-254; Epub Dec. 16, 2010.
Hanssen et al., "Local Variants of Staphylococcal Cassette Chromosome mec in Sporadic Methicillin-Resistant *Staphylococcus aureus* and Methicillin-Resistant Coagulase-Negative Staphylococci: Evidence of Horizontal Gene Transfer?" Antimicrob Agents Chemothera., 48(1): 285-296 (Jan. 2004).
Hanssen et al., Mini Review "SCCmecin staphylococci: genes on the move." FEMS Immunol Med Microbiol., 46: 8-20 (Sep. 2005).
He et al., "Identification of *Staphylococcus aureus* and detection of its multiple-resistant genes by multiplex PCR," Linchuang Jianyan Zazhi (2004) 22(4): 249-251.
Hiramatsu, et al. "Molecular cloning and nucleotide sequence determination of the regulator region of mecA gene in methicillin-resistant *Staphylococcus aureus*." FEBS. 298(2/3):133-36 (1992).
Hiramatsu et al. "Analysis of borderline-resistant strains of methicillin-resistant *Staphylococcus aureus* using polymerase chain reaction," Microbiol Immunol. (1992) 36(5): 445-453.
Hiramatsu, et al. "Genetic basis for molecular epidemiology of MRSA." J Infect Chemother. 2:117-129 (1996).
Hiramatsu, et al. "The emergence and evolution of methicillin-resistant *Staphylococcus aureus*." Trends in Microbiology. 9(10): 486-493 (2001).
Hiramatsu et al. "*Staphylococcus aureus* DNA, type-IV.1 (IV a) staphylococcal cassette chromosome mec: strain CA05 (JCSC1968)." GenBank accession No. AB063172, version AB063172.2, Jun. 12, 2001.
Holden et al. "*Staphylococcus aureus* subsp. *aureus* strain MRSA252, complete genome." GenBank accession No. BX571856, version BX571856.1, Jun. 23, 2004.
Holden, et al. "Complete genomes of two clinical *Staphylococcus aureus* strains: Evidence for the rapid evolution of virulence and drug resistance." PNAS. 101(26):9786-9791 (2004).
Hope et al., "A PCR method for the identification of methicillin-resistant *Staphylococcus aureus* (MRSA) from screening swabs," Pathology (2004) 36(3):265-268.
Hougardy et al., "Direct and fast detection of methicillin resistant *Staphylococcus aureus* carriage by automated nucleic acid extraction and real time PCR" [English Abstract Only], Pathologie-Biologie, (Oct.-Nov. 2006) vol. 54, No. 8-9, pp. 477-481. Electronic Publication Date: Oct. 5, 2006.
Huletsky, et al. "New real-time PCR assay for rapid detection of methicillin-resistant *Staphylococcus aureus* directly from specimens containing a mixture of staphylococci." J. Clin. Microbio. 42(5): 1875-84 (May 2004) XP003003502.
Huletsky, et al. "Identification of Methicillin-Resistant *Staphylococcus aureus* Carriage in Less than 1 Hour during a Hospital Surveillance Program." Clin. Infect. Dis. (Apr. 2005) 40: 976-981.
Huletsky, A.—Declaration in Reexamination of U.S. Pat. No. 7,449,289 dated Jul. 30, 2011; pp. 3.
Inglis, et al. "Induced deletions within a cluster of resistance genes in the mec region of the chromosome of *Staphylococcus aureus*." Gen. Microbiol. 136(11):2231-2239 (1990).
Inglis, et al. "Methicillin-sensitive and -resistant homologues of *Staphylococcus aureus* occur together among clinical isolates." J. Infect. Dis. 167(2):323-328 (1993).
Innis et al Eds. PCR Protocols, a Guide to Methods and Applications, Academic Press (1990) Table of Contents.
International Working Group on the Classification of SCC Elements [IWG-SCC]. "Classification of staphylococcal cassette chromosome mec (SCCmec): guidelines for reporting novel SCCmec elements", Antimicrob Agents Chemother. (2009) 53(12):4961-4967.

Ito, et al. "Acquisition of methicillin resistance and progression of multiantibiotic resistance in methicillin-resistant *Staphylococcus aureus*." Yonsei Med. J. 39(6):526-33 (1998).
Ito et al. "*Staphylococcus aureus* genes for orf1, orfX, orf2, orf3, partial and complete cds." GenBank accession No. AB014440, version AB014440.1, Jul. 6, 1999; 2 pages.
Ito et al. "Cloning and nucleotide sequence determination of the entire mec DNA of pre-methicillin-resistant *Staphylococcus aureus* N315." Antimicrob. Agents Chemother. 43(6):1449-1458 (1999).
Ito et al. "*Staphylococcus aureus* DNA, 3' flanking region of mecDNA, strain 61/6219." GenBank accession No. AB014433, Jan. 7, 2000—Abstract only.
Ito et al. "*Staphylococcus aureus* DNA, 3' flanking region of mecDNA, strain 64/4176." GenBank accession No. AB014434, Jan. 7, 2000—Abstract only.
Ito et al. "Structural comparison of three types of staphylococcal cassette chromosome mec integrated in the chromsome in methicillin-resistant *Staphylococcus aureus*." Antimicrob. Agents Chemother. 45(5):1323-1336 (2001).
Ito et al. "*Staphylococcus aureus* DNA, type III staphylococcal cassette chromosome mec, strain 85/2082." GenBank accession No. AB037671, version AB037671.1, May 14, 2001.
GenBank accession No. AB037671, "*Staphylococcus aureus* DNA, type-III staphylococcal cassette chromosome mec and SCCmercury: strain 85/2082", May 12, 2000, pp. 30.
BLAST® Sequence-Alignment 1 between AB037671 (strain 85/2082) and SEQ ID No. 42, printed on Apr. 1, 2011, pp. 2.
BLAST® Microbes RID-V9G669R4015, URL: <https://blast.ncbi.nlm.nik.gov/Blast.cgi, downloaded Oct. 3, 2018, pp. 7.
BLAST® Microbes RID-V9C1J132014, SEQ ID No. 45; URL: <https://blast.ncbi.nlm.nik.gov/Blast.cgi, downloaded Oct. 3, 2018 in pp. 9.
Sequence Alignment 3 printed on Mar. 31, 2011 aligning the Nucleotide Sequence of *Staphylococcal aureas* strains 85/2082, HDG2, and N315(D86934) downstream of mecA, pp. 23.
Ito et al. GenBank accession No. AB121219, version AB121219.1, Sep. 26, 2003.
Ito et al. "Novel type V staphylococcal cassette chromosome mec driven by a novel cassette chromosome recombinase, ccrC." Antimicrob. Agents Chemother. 48(7):2637-2651 (2004).
Jayaratne et al., "DNA-based detection of methicillin-resistant *Staphylococcus aureus* (MRSA) from nosocomial screening: Comparison with culture and cost-benefit analysis," Abstracts of the Interscience Conference on Antimicrobial Agents and Chemotherapy, 38th Interscience Conference on Antimicrobial Agents and Chemotherapy. San Diego, California, USA. Sep. 24-27, 1998. American Society for Microbiology (1998) vol. 38, Abs. D-56; pp. 144-145.
Jiang et al., "Review on Progress of *Staphylococcus aureus* by PCR", Shipin Kexue (Beijing, China) (2006), 27(5): 265-269. [English Abstract].
Jonas et al., "Evaluation of the mecA femB duplex polymerase chain reaction for detection of methicillin-resistant *Staphylococcus aureus*," Eur J Clin Microbiol Infect Dis. (1999) 18(9):643-647.
Jonas et al., "Rapid PCR-based identification of methicillin-resistant *Staphylococcus aureus* from screening swabs," J Clin. Microbiol. (2002) 40(5):1821-1823.
Jovanic et al., "Rapid detection of methicillin-resistant *Staphylococcus aureus* by real-time PCR from clinical specimens", International Journal of Antimicrobial Agents, Abs P907; (Mar. 2007) 29(Suppl. 2): S235-S236.
Jones, R.N., "Use of Surveillance Programs as a Platform for Testing New Antimicrobials Against Multidrug Resistant Bacteria, Recent Experiences", Tufts University School of Medicine, Presentation of JMI Laboratories (61 pages).
Kang et al., "The enhancement of PCR amplification of a random sequence DNA library by DMSO and betaine: application to in vitro combinatorial selection of aptamers", J Biochem Biophys Methods. (Aug. 2005) 64(2):147-51.
Katayama, et al. "A new class of genetic element, *Staphylococcus* cassette chromosome mec, encodes methicillin resistance in *Staphylococcus aureus*." Antimicrob. Agents Chemother. 44(6):1549-1555 (2000).

(56) References Cited

OTHER PUBLICATIONS

Kearns et al., "Rapid detection of methicillin-resistant staphylococci by multiplex PCR." Journal of Hospital Infection. 43(1):33-37 (1999).
Kellogg, et al. "TaqStart Antibody™: "Hot Start" PCR facilitated by a neutralizing monoclonal antibody directed against Taq DNA Polymerase." Biotechniques. 16:1134-1137 (1994).
Kimmel, et al. "Preparations of cDNA and the generation of cDNA libraries: Overview." Meth Enzymol. 152:307-316 (1987).
Kimmerly et al. "*Staphylococcus epidermidis* strains SR1 clone step.1043h05 genomic sequence." GenBank accession No. AF270046, version AF270046.1, Aug. 1, 2000.
Kitagawa, et al. "Rapid diagnosis of methicillin-resistant *Staphylococcus aureus* bacteremia by nested polymerase chain reaction." Annals of Surgery. 224(5):665-71 (1996).
Kloos et al., "Updated on clinical significance of coagulase-negative staphylococci", Clin. Microbiol. Rev. (1994) 7(1):117-40.
Klotz et al., "Detection of *Staphylococcus aureus* Enterotoxins A to D by Real-Time Fluorescence PCR Assay," J Clin Microbiol. (2003) 41(10): 4683-4687.
Kluytmans, et al. "Food-initiated outbreak of methicillin-resistant *Staphylococcus aureus* analyzed by Pheno- and Genotyping." J. Clin. Microbio. 33(5):1121-28 (1995).
Kobayashi et al., "Genomic diversity of mec regulator genes in methicillin-resistant *Staphylococcus aureus* and *taphylococcus epidermidis*", Epidemiol Infect. (1996) 117(2): 289-295.
Kobayashi et al., "Analysis on distribution of insertion sequence IS*431* in clinical isolates of staphylococci", Diag. Micro. Infect. Dis. (2001) 39: 61-64.
Kobayashi et al., "Detection of mecA, femA, and femB genes in clinical strains of staphylococci using polymerase chain reaction," Epidemiol Infect. (1994) 113(2):259-266.
Koshkin, et al. "LNA (locked nucleic acids): Synthesis of the adenine, cytosine, guanine, 5-methylcytosine, thymine and uracil bicyclonucleoside monomers, oligomerisation, and unprecedented nucleic acid recognition." Tetrahedron. 54:3607-3630 (1998).
Kovacevic et al., "Secretion of staphylococcal nuclease by Bacillus subtilis", J. Bacteriol. (1985), 162(2):521-8.
Kowalski et al., "Evaluation of the SmartCycler II System for Real-Time Detection of Viruses and *Chlamydia*from Ocular Specimens", Arch Ophthalmol. (Aug. 2006) 124: 1135-1139.
Kuroda, et al. "Whole genome sequencing of meticillin-resistant *Staphylococcus aureus*." The Lancet. 357(9264): 1225-1240 (2001).
Kwoh, et al. "Transcription-based amplification system and detection of amplified human immunodeficiency virus type 1 with a bead-based sandwich hybridization format." Proc. Natl. Acad. Sci. USA 86: 1173-1177 (1989).
Landegren, et al. "A ligase-mediated gene detection technique." Science 241:1077-1080 (1988).
Lawrence et al. "Consecutive isolation of homologous strains of methicillin-resistant and methicillin-susceptible *Staphylococcus aureus* from a hospitalized child." J. Hosp. Infect. 33:49-53 (1996).
Lawrence, et al. "Use of the coagulase gene typing method for detection of carriers of methicillin-resistant *Staphylococcus aureus*." J. Antimicro. Chemo. 37:687-96 (1996).
Leach et al. "Theoretical investigations of novel nucleic acid bases." J. Am. Chem. Soc. 114:3675-3683 (1992).
Lee et al., "Detection of MecA gene in clinical isolates of *Staphylococcus aureus* by multiplex-PCR, and antimicrobial susceptibility of MRSA," Journal of Microbiology and Biotechnology 13(3) 354-359 (2003).
Lee et al., "Nucleic Acid Amplification Technologies: Application to Disease Diagnosis", 1997, Eaton Publishing (Cover pages Only).
Lem et al., "Direct detection of mecA, nuc and 16S rRNA genes in BacT/Alert blood culture bottles," Diagn Microbiol Infect Dis. 41(3):165-168 (2001).
Levenson, Deborah, "The Path to Better MRSA Control", Clin Lab News. (Aug. 2007) 33(8): 6 pages.
Levi et al., "Evaluation of an Isothermal Signal Amplification Method for Rapid Detection of Methicillin-Resistant *Staphylococcus aureus* from Patient-Screening Swabs", J Clin Microbiol. (Jul. 2003) 41(7): 3187-3191.
Levi et al., "Detection of methicillin-resistant *Staphylococcus aureus* (MRSA) in blood with the EVIGENE MRSA detection kit", J. Clin. Microbiol. (2003) 41(8):3890-2.
Lewin, "Genes IV", 1990, John Wiley & Sons, Chapter 3, Genes are Mutable Units, pp. 41-56.
Li et al., "Typing SCCmec Gene of Methicillin-Resistant *Staphylococcus aureus* by Novel Multiplex PCR Method," Journal of Modern Laboratory Medicine (2008) 23(1): 32-35. [English Abstract].
Liao et al., "Blinded comparison of repetitive-sequence PCR and multilocus sequence typing for genotyping methicillin-resistant *Staphylococcus aureus* isolates from a children's hospital in St. Louis, Missouri", J Clin Microbiol. (Jun. 2006) 44(6): 2254-2257.
Lin, et al. "Sequence analysis and molecular characterization of genes required for the biosynthesis of type 1 capsular polysaccharide in *Staphylococcus aureus*." J. Bacter. 176(22):7005-16 (1994).
Lin et al. "*Staphylococcus aureus* M type 1 capsular polysaccharide biosynthesis gene cluster, complete sequence and unknown genes." GenBank accession No. U10927, version U10927.2, Nov. 1, 2001.
Lizardi et al., "Exponential Amplification of Recombinant-RNA Hybridization Probes," BioTech. (Oct. 1988) 6: 1197-1202.
Lomell et al. "Quantitative assays based on the use of replicatable hybridization probes." Clin. Chem. 35(9):1826-1831 (1989).
Louahabi et al., "Screening of methicillin-resistant *Staphylococcus aureus* directly from clinical specimens by real-time PCR," International Journal of Antimicrobial Agents, (Dec. 2004) vol. 24S, Abstract 365/79P, pp. S130. Meeting Info.: 6th European Congress of Chemotherapy and Infection/24th Interdisciplinary Meeting on Anti-Infectious Chemotherapy. Paris, France. Dec. 1-3, 2004.
Louie et al., "Rapid Detection of Methicillin-Resistant Staphylococci from Blood Culture Bottles by Using a Multiplex PCR Assay," J Clin Microbiol. 40(8):2786-2790 (2002).
Lowe et al., "A Computer Program for Selection of Oligonucleotide Primers for Polymerase Chain Reactions", Nucl Acids Res. (1990) 18(7): 1757-1761.
Lu et al., "One tube multiplex PCR for simple screening of SCCmec I-V types of methicillin-resistant *Staphylococcus aureus*", J Chemother. (Dec. 2008) 20(6): 690-696.
Luchansky et al. "Isolation of transposon Tn551 insertions near chromosomal markers of interest in *Staphylococcus aureus*." J. Bacter. 159(3):894-99 (1984).
Luijendijk, et al. "Comparison of five tests for identification of *Staphylococcus aureus* clinical samples." J. Clin. Microbio. 34(9):2267-69 (1996).
Luong, et al. "Type I capsule genes of *Staphylococcus aureus* are carried in a staphyloccal cassette chromosome genetic element." J Bacter. 184(13):3623-3629 (2002).
Ma et al. "Novel type of staphylococcal cassette chromosome mec identified in community-acquired methicillin-resistant *Staphylococcus aureus* strains." Antimicrob. Agents Chemother. 46(4):1147-1152 (2002).
Ma et al. "*Staphylococcus aureus* DNA, type-IV.2 (Ivb) staphylococcal cassette chromosome mec: strain JCSC1978 (8/6-3P)", EBI GenBank accession No. AB063173, Nov. 21, 2001.
Maes et al., "Evaluation of a triplex PCR assay to discriminate *Staphylococcus aureus* from coagulase-negative Staphylococci and determine methicillin resistance from blood cultures", J. Clin. Microbiol. (2002) 40(4):1514-7.
Mantsch et al. "Structural and enzymatic properties of adenine 1-oxide nucleotides." Biochem. 14(26):5593-5601 (1975).
Marin et al., "Molecular Diagnosis of Infective Endocarditis by Real-Time Broad-Range Polymerase Chain Reaction (PCR) and Sequencing Directly From Heart Valve Tissue," Medicine (2007) 86(4) 195-202.
Martineau, et. al. "Correlation between the resistance genotype determined by multiplex PCR assays and the antibiotic susceptibility patterns of *Staphylococcus aureus* and *Staphylococcus epidermidis*." Antimicrob. Chemotherapy. 44(2): 231-238 (2000).

(56) References Cited

OTHER PUBLICATIONS

Martineau et al., "Species-Specific and Ubiquitous-DNA-Based Assays for Rapid Identification of *Staphylococcus aureus*," J Clin Microb. (Mar. 1998) 36(3): 618-623.
Mason et al., "Multiplex PCR Protocol for the Daignosis of Staphylococcal Infection," J Clin Microbiol. 39(9): 3332-3338 (2001).
McBride et al., "Quantitative PCR Technology" in *Gene Quantification*, The Immune Response Corporation, Francois Ferre (Ed.), Birkhaeuser Boston (1998) pp. 97-110.
McDonald et al., "Development of a triplex real-time PCR assay for detection of Panton-Valentine leukocidin toxin genes in clinical isolates of methicillin-resistant *Staphylococcus aureus*", J. Clin. Microbiol. (Dec. 2005) 43(12):6147-9.
Menon et al., "Comparison of rapid method of DNA extraction using microwave irradiation with conventional phenol chloroform technique for use in multiplex PCR for mec A and fem B genes to identify genotypes of MRSA from cultures," Medical Journal Armed Forces India, (2001) 57(3): 194-196.
Merlino et al., "Detection and expression of methicillin/oxacillin resistance in multidrug-resistant and non-multidrug-resistant *Staphylococcus aureus* in Central Sydney, Australia," J Antimicrob Chemother. (2002) 49: 793-801.
Mongkolrattanothai et al. "TPA exp: *Staphylococcus epidermidis* ATCC 12228 composite island SCCpbp4 region." GenBank accession No. BK001539, version BK001539.1, Aug. 15, 2003.
Mongkolrattanothai et al. "Novel Non-mecA-Containing Staphylococcal Chromosomal Cassette Composite Island Containing pbp4 and tagF Genes in a Commensal Staphylococcal Species: a Possible Reservoir for Antibiotic Resistance Islands in *Staphylococcus aureus*." Antimicrob. Agents Chemother. (May 2004) 48(5): 1823-1836.
Mulligan, et al. "Methicillin-resistant *Staphylococcus aureus*: A consensus review of the microbiology, pathogenesis, and epidemiology with implications for prevention and management." Am J Med. 94(3):313-28 (1993). (Abstract Only).
Murakami, et al. "Identification of methicillin-resistant strains of *Staphylococci* by polymerase chain reaction." J. Clin Microbiol. 29(10):2240-2244 (1991).
Muraki, et al. Detection of methicillin-resistant *Staphylococcus aureus* using PCR and non-radioactive DNA probes (II). Rinsho Byori. 41(10): 1159-66 (1993).
Murray et al., Manual of Clinical Microbiology, 8th Ed., ASM Press (2003) [Content pages only].
Narang et al. "Improved Phosphotriester Method for the Synthesis of Gene Fragments," Meth Enzymol. (1979) 68: 90-98.
NCBI BLAST Sequence Alignment 1 between AB037671 (strain 85/2082) and SEQ ID No. 42, printed on Apr. 1, 2011.
NCBI BLAST 2 Sequence—AF411934.1—*Staphylococcus aureus* strain HDG2 genomic sequence downstream of mecA, printed on Mar. 16, 2012, pp. 2.
NCBI BLAST 2 Sequences downloaded Aug. 13, 2013 from http://blast.ncbi.nlm.nih.gov/Blast.cgi, 4 pages.
NCBI BLAST Sequence ID No. 18 downloaded Feb. 13, 2015 from http://blast.ncbi.nlm.nih.gov/Blast.cgi; 14 pages.
NCBI BLAST AX720590: Sequence 167 from Patent WO02099034; [D16—Exhibit in European Opposition Proceeding: EP 2 322 655] downloaded on Aug. 21, 2015; 57 pages.
Newton et al. "Instrumentation, Reagents and Consumables." PCR, 2nd Ed., Springer-Verlag (New York: 1997), Chapter 2, p. 8-28.
Nichols, et al. "A universal nucleoside for use at ambiguous sites in DNA primers." Nature. 369:492-493 (1994).
Niemeyer et al., "Rapid DNA extraction for direct PCR identification of methicillin resistant staphylococci in clinical samples," Abstracts of the General Meeting of the American Society for Microbiology, (1998) vol. 98, Abs. C-419, pp. 201; 98th General Meeting of the American Society for Microbiology. Atlanta, Georgia, USA. May 17-21, 1998. American Society for Microbiology.
Ohno, Akira, Japan Medical Journal (2001) 4051: 19-24.
Okuma et al., "Dissemination of new methicillin-resistant *Staphylococcus aureus* clones in the community." J Clin Microbio., 40(11): 4289-4294 (Nov. 2002).
Oliveira et al. "Genetic organization of the downstream region of the mecA element in methicillin-resistant *Staphylococcus aureus* isolates carrying different polymorphisms of this region." Antimicrob. Agents Chemother. 44(7):1906-1910 (2000).
Oliveira et al. "The evolution of pandemic clones of methicillin-resistant *Staphylococcus aureus*: Identification of two ancestral genetic backgrounds and the associated mec elements." Microb. Drug Resist. 7(4):349-361 (2001).
Oliveira, et al. "Multiplex PCR strategy for rapid identification of structural types and variants of the mec element in methicillin-resistant *Staphylococcus aureus*." Antimicrob. Agents Chemother. 46:2155-2161 (2002).
Oliveira et al. "Secrets of success of a human pathogen: molecular evolution of pandemic clones of meticillin-resistant *Staphylococcus aureus*." Lancet Infect Dis. 2:180-9 (2002).
Oliveira et al. "*Staphylococcus aureus* staphylococcal cassette chromosome mec type III sequence; and putative transposase gene, partial cds." GenBank Accession Version No. AF422691, Apr. 29, 2002, pp. 2. (Abstract Only).
Oliveira et al. "*Staphylococcus aureus* strain HDG2 genomic sequence downstream of mecA." GenBank Accession Version No. AF411934, Mar. 8, 2002, pp. 2. (Abstract Only).
Alignment of SEQ ID Nos. 42-46 and 51 with HDG2 sequence; GenBank Accession Version No. AF411934; Exhibit D9a in European Opposition of Patent No. 1397510, issued Mar. 17, 2004; pp. 10.
Oliveira et al. "*Staphylococcus aureus* strain HDE288 type-VI SCCmec element, complete sequence" GenBank Accession Version No. AF411935, Mar. 5, 2002, pp. 8.
Oliveira et al. "*Staphylococcus aureus* strain PL72 genomic sequence upstream of mecA" GenBank Accession Version No. AF411936, Mar. 5, 2002, pp. 3.
Oliveira et al., "Redefining a structural variant of staphylococcal cassette chromosome mec, SCCmec type VI", Antimicrob. Agents Chemother. (Oct. 2006) 50(10):3457-9.
Oliveira, D.—Email re Sequence Question with Hema Pande, Beckman Coulter, Inc. (Jul. 2010).
Oliveira, D—Declaration in Opposition to EP Patent 1397510 dated Nov. 29, 2012; pp. 2.
Pattee, et al. "Genetic and physical mapping of the chromosome of *Staphylococcus aureus*." Molecular Biology of the Staphylococci. VCH Publishers.pp. 41-58 (1990).
Perez-Roth et al., "Multiplex PCR for Simultaneous Identification of *Staphylococcus aureus* and Detection of Methicillin and Mupirocin Resistance," J Clin Microbiol. 39(11):4037-4041 (2001).
Persing et al., Diagnostic Molecular Microbiology: Principles and Applications, American Society for Microbiology, Washington, D.C. (1993), Contents pages only.
Piccirilli et al. "Enzymatic incorporation of a new base pair into DNA and RNA extends the genetic alphabet." Nature. 343:33-37 (1990).
Podzorski et al., Evaluation of the MVPlex Assay for Direct and Rapid Detection of Methicillin-Resistant *Staphylcoccus aureus* from Nares and Other Swab Speciments, (Abstract C-237), American Society for Microbiology 107th Meeting, Toronto, Canada May 21-25, 2007, p. 186.
Podzorski et al., MVPlex Assay for Direct Detection of Methicillin-Resistant *Staphylococcus aureus* in Naris and Other Swab Specimens, J Clin Microbiol. (Sep. 2008) 46(9): 3107-3109.
Poulsen et al., "Detection of methicillin resistance in coagulase-negative staphylococci and in staphylococci directly from simulated blood cultures using the EVIGENE MRSA Detection Kit", J. Antimicrob. Chemother. (2003) 51(2):419-21.
Ralser et al., "An efficient and economic enhancer mix for PCR", Biochem. Biophys. Res. Communi. (Sep. 2006) 347(3):747-51.
Ramos-Trujillo et al., Multiplex PCR for simultaneous detection of enterococcal genes vanA and vanB and staphylococcal genes mecA, ileS-2 and femB, Int Microbiol. (2003) 6(2):113-115.
Random House Unabridged Dictionary, (1993) Definition of "extremity", p. 686.
Reischl et al., "Rapid identification of methicillin-resistant *Staphylococcus aureus* and simultaneous species confirmation using real-time fluorescence PCR," J Clin. Microbiol. (2000) 38:2429-2433.

(56) References Cited

OTHER PUBLICATIONS

Ruiz-Pérez de Pipaón et al., "Detection of methicillin resistance and identification of *Staphylococcus* spp. from positive blood culture bottles using the mecA and nucA genes with the LightCycler System", [English Abstract Only] Enfermedades infecciosas y microbiologia clinica (2005) vol. 23, No. 4, pp. 208-212.

Rupp et al., "Be Aware of the Possibility of False-Positive Results in Single-Locus PCR Assays for Methicillin-Resistant *Staphylococcus aureus*", (Jun. 2006) 44(6): 2317-8.

Rushdy et al., "Detection of methicillin/oxacillin resistant *Staphylococcus aureus* isolated from some clinical hospitals in Cairo using Meca/Nuc genes and antibiotic susceptibility profile," Internaitonal Journal of Agriculture and Biology (2007) 9(6):800-806.

Sabat et al., "Comparison of PCR-based methods for typing *Stapholococcus aureus* isolates," J Clin Micrbiol. 44(10) 3804-3807 (2006).

Sabet et al., "Simultaneous species identification and detection of methicillin resistance in staphylococci using triplex real-time PCR assay", Diagn Microbiol Infect Dis. Sep. 2006;56(1):13-8. Epub 2006-05-2.

Saiful et al., "Detection of methicillin-resistant *Staphylococcus aureus* using mecA/nuc genes and antibiotic susceptibility profile of Malaysian clnical isolates," World J Microbiol Biotechnol. (2006) 22:1289-1294 [online: Apr. 20, 2006].

Saiki et al., "Enzymatic amplification of beta-globin genomic sequences and restriction site analysis for diagnosis of sickle cell anemia," Science (Dec. 1985) 230(4732): 1350-1354.

Saito, et. al. "Immunological detection of penicillin-binding protein 2' of methicillin-resistant Staphylococci by using monoclonal antibodies prepared from synthetic peptides." J. Clin. Microbiol. 33(9): 2498-2500 (1995).

Sambrook et al., "Molecular Cloning: A Laboratory Manual", 1989 Cold Spring Harbor Laboratory Press (Cover & Contents pages only) & pp. 14.15-14.16.

Sanches et al., "Tracing the Origin of an Outbreak of Methicillin-Resistant *Staphylococcus aureus* Infections in a Portuguese Hospital by Molecular Fingerprinting Methods." Microbial Drug Resist. 2(3): 319-329 (1996).

Schuenck et al., "Improved and rapid detection of methicillin-resistant *Staphylococcus aureus* nasal carriage using selective broth and multiplex PCR", Res. Microbiol. (Sep. 2006) 157(10):971-5.

Seki et al., Amplification of long targets of approximately 50 kb from cloned cosmid inserts of *Arabidopsis thaliana*, DNA Research (Jul. 1996) 3: 107-108.

Sekiguchi et al., "Rapid and simple method for detecting qacA, mecA and femB in antiseptics- and methicillin-resistant *Staphylococcus aureus* by loop-mediated isothermal amplification," Abstracts of the General Meeting of the American Society for Microbiology, (2006) vol. 106, pp. 108; 106th General Meeting of the American Society for Microbiology. Orlando, FL, USA. May 21-25, 2006. Amer Soc Microbiol.

Shittu et al., "Molecular identification and characterization of mannitol-negative methicillin-resistant *Staphylococcus aureus*", Diagn. Microbiol. Infect Dis. (2007) 57(1):93-5.

Shore et al. "Characterization of a Novel Arginine Catabolic Mobile Element (ACME) and Staphylococcal Chromosomal Cassette mec Composite Island with Significant Homology to *Staphylococcus epidermidis* ACME Type II in Methicillin-Resistant *Staphylococcus aureus* Genotype ST22-MRSA-IV." Antimicrob Agents Chemother. (May 2011) 55(5): 1896-1905.

Shore et al. "Detection of Staphylococcal Cassette Chromosome mec Type XI Carrying Highly Divergent mecA, mecI, mecR1, blZ, and ccr Genes in Human Clinical Isolates of Clonal Complex 130 Methicillin-Resistant *Staphylococcus aureus*", Antimicrob Agents Chemother. (Aug. 2011) 55(8): 3765-3773.

Simor, et al. "Characterization and proposed nomenclature of epidemic strains of methicillin-resistant *Staphylococcus aureus* in Canada." CCDR 25(12):105-112 (Jun. 1999).

Simor, et al. "Characterization and proposed nomenclature of epidemic strains of methicillin-resistant *Staphylococcus aureus* in Canada." Can J Infect Dis. Sep.-Oct. 1999; 10(5): 333-336.

Singh et al. "PCR Primer Design." Mol Biol Today 2(2): 27-32 (2001).

Singleton P., DNA Methods in Clinical Microbiology, (2000) Dordrecht, Boston: Kluwer Academic. TOC only.

Sinsimer et al., "Use of a Multiplex Molecular Beacon Platform for Rapid Detection of Methicillin and Vancomycin Resistance in *Staphylococcus aureus*", J Clin Microbiol. (2005) 45(9): 4585-4591.

Sooknanan et al. NASBA. A detection and amplification system uniquely suited for RNA. (1995) Biotechnology 13:563-564.

Spiess et al. "Trehalose Is a Potent PCR Enhancer: Lowering of DNA Melting Temperature and Thermal Stabilization of Taq Polymerase by the Disaccharide Trehalose," Clin Chem., Jul. 2004, 50(7):1256-1259.

Stegger et al. "Rapid detection, differentiation and typing of methicillin-resistant *Staphylococcus aureus* harbouring either mecA or the new mecA homologue mecALGA251", Clin Microbiol Infect (Online: Nov. 7, 2011); (2012) 18:395-400.

Stewart, et al. "IS257 and small plasmid insertions in the mec region of the chromosome of *Staphylococcus aureus*." Plasmid. 31:12-20 (1994).

Stratidis et al., Use of real-time polymerase chain reaction for identification of methicillin-resistant *Staphylococcus aureus* directly from positive blood culture bottles, Diagn Microbiol Infect Dis. (2007) 58(2): 199-202.

Suzuki, et al. "Survey of methicillin-resistant clinical strains of coagulase-negative Staphylococci for mecA gene distribution." Antimicrob. Agents Chemother. 36(2): 429-434 (1992).

Suzuki, et al. "Distribution of mec regulator genes in methicillin-resistant *Staphylococcus* clinical strains." Antimicro. Agents Chemother.. 37(6):1219-26 (1993).

Switzer et al. "Enzymatic Recognition of the Base Pair between Isocytidine and Isoguanosine." Biochemistry 32:10489-10496 (1993).

Tan et al., "Rapid identification of methicillin-resistant *Staphylococcus aureus* from positive blood cultures by real-time fluorescence PCR," Journal of Clinical Microbiology (2001) 39(12):4529-4531.

Tang et al., StaphPlex System for Rapid and Simultaneous Identification of Antibiotic Resistance Determinants and Panton-Valentine Leukocidin Detection of Staphylococci from Positive Blood Cultures, J Clin Microbiol. (Jun. 2007) 45(6): 1867-1873.

Taylor et al. GenBank accession No. AF270046, version AF270046. 1, May 22, 2000.

Thelwell et al. "Mode of action and application of Scorpion primers to mutation detection." Nucl. Acids Res. 28(19):3752-3761 (2000).

Thomas et al., "Development of a real-time *Staphylococcus aureus* and MRSA (SAM-) PCR for routine blood culture," J Microbiol Methods (2007) 38(2):296-302 [Online: Oct. 12, 2006].

Tijssen, Laboratory Techniques in Biochemistry and Molecular Biology—Hybridization with Nucleic Acid Probes, (1993) Part I, Chapter 2, pp. 19-78 (Elsevier, New York).

Tokue, et al. "Comparison of a polymerase chain reaction assay and a conventional microbiologic method for detection of methicillin-resistant *Staphylococcus aureus*." Antimicro. Agents Chemother. 36(1):6-9 (1992).

Tor et al. "Site-specific enzymatic incorporation of an unnatural base, $N^6$-(6-Aminohexyl)isoguanosine, into RNA." J. Am. Chem. Soc. 115:4461-4467 (1993).

Towner et al., "Development and evaluation of a PCR-based immunoassay for the rapid detection of methicillin-resistant *Staphylococcus aureus*," J Med Microbiol (1998) 47(7):607-613.

Turbeville et al., "Amplification of the complete mitochondrial genome of two protostome worms: a useful technique for comparative studies of metazoan mitochondrial DNA", Mol Marine Bio Biotech., 6(2): 141-143 (1997).

Turlej et al., "Staphylococcal Cassette Chromosome mec (SCCmec) Classification and Typing Methods: an Overview", Polish J Microbiol. (2011) 60(2):95-103.

Tyagi et al. "Molecular beacons: Probes that fluoresce upon hybridization." Nat. Biotech. 14:303-308 (1996).

(56) References Cited

OTHER PUBLICATIONS

Tyagi et al., "Molecular Beacons: Hybridization Probes for Detection of Nucleic Acids in Homogeneous Solutions," in *Nonradioactive Analysis of Biomolecules* (Part D); Springer Lab Manuals pp. 606-616 ; [Exh. D29]; 2000; 8 pages.
Ubukata, et al. "Restriction maps of the regions coding for methicillin and tobramycin resistances on chromosomal DNA in methicillin-resistant staphylococci." Antimicrob. Agents Chemother. 33(9):1624-26 (1989).
Ubukata, et. al. "Homology of mecA gene in methicillin-resistant *Staphylococcus haemolyticus* and *Staphylococcus simulans* to that of *Staphylococcus aureus*." Antimicrob. Agents Chemother. 34(1):170-172 (1990).
Ubukata, et. al. "Rapid detection of the mecA gene in methicillin-resistant Staphylococci by enzymatic detection of polymerase chain reaction products." J. Clin. Microbiol. 30(7):1728-1733 (1992).
Ünal, et al. "Detection of methicillin-resistant staphylococci by using the polymerase chain reaction." J Clin. Microbiol. 30(7):1685-91 (1992).
Ünal, et al. "Comparison of tests for detection of methicillin-resistant *Staphylococci aureus* in a clinical microbiology laboratory." Antimicrob. Agents Chemother. 38(2):345-47 (1994).
Van Belkum, et al. "Comparison of phage typing and DNA fingerprinting by polymerase chain reaction of discrimination of methicillin-resistant *Staphylococcus aureus* strains." J. Clin. Microbiol. 31(4):798-803 (1993).
Van Brunt, J. "Amplifying genes: PCR and its alternatives." Biotechnology, 8:291-294 (1990).
Van Hal et al., "Methicillin-Resistant *Staphylococcus aureus* (MRSA) Detection: Comparison of Two Molecular Methods (IDI-MRSA PCR Assay and GenoType MRSA Direct PCR Assay) with Three Selective MRSA Agars (MRSA ID, MRSASelect, and CHROMagar MRSA) for Use with Infection-Control Swabs", J Clin Microbiol. (Aug. 2007) 45(8): 2486-2490.
Van Leeuwen et al., "Genetic diversification of methicillin-resistant *Staphylococcus aureus* as a function of prolonged geographic dissemination and as measured by binary typing and other genotyping methods," Res Microbiol, 149: 497-507 (1998).
Vanguilder et al., "Twenty-five years of quantitative PCR for gene expression analysis", Biotechniques 25th Anniversary (2008) 44(5): 619-626.
Vannuffel, et al. "Specific detection of methicillin-resistant *Staphylococcus* species by multiplex PCR." J. Clin. Microbiol. 33(11):2864-67 (1995).
Wada, et al. "Southern hybridization analysis of the mecA deletion from methicillin-resistant *Staphylococcus aureus*." Biochem. Biophys. Res. Comm., 176(3):1319-1326 (1991).
Walker, et al., "Isothermal in vitro Amplification of DNA by a Restriction Enzyme/DNA Polymerase System," Proc Natl Acad Sci. USA, 89: 392-396 (Jan. 1992).
Walker et al., "Strand displacement amplification—an isothermal, in vitro DNA amplification technique," Nucl Acids Res. (1992) 20(7): 1691-1696.
Wallet, et al. "Choice of a routine method for detecting methicillin-resistance in staphylococci." J. Antimicrob. Chemother. 37:901-909 (1996).
Wang at al., "Rapid detection of methicillin-resistant *Staphylococcus aureus* with duplex real-time PCR assay," Zhongguo Kangshengsu Zazhi (2007) 32(4) 225-228 [w/English Abstract].
Warren et al., "Detection of Methicillin-Resistant *Staphylococcus aureus* Directly from Nasal Swab Specimens by a Real-Time PCR Assay", J Clin Microbiol. (Dec. 2004) 42(12): 5578-5581.
Watson et al., "Molecular Biology of the Gene", 1987, The Benjamin/Cummings Publishing Company (Cover pages only).
Wei et al., "Detection of *Staphylococcus* isolates and their multidrug resistance genes by multiple PCR," Zhongguo Renshou Gonghuanbing Zazhi (Sep. 2004) 20(9), 814.
Westin, et al. "Anchored multiplex amplification on a microelectronic chip array." Nat. Biotechnol. 18:199-204 (2000).
White, "Molecular Cloning to Genetic Engineering", in Methods in Molecular Biology Humana Press (1997) vol. 67, Contents pages only.
Wichelhaus et al., "Rapid molecular typing of methicillin-resistant *Staphylococcus aureus* by PCR-RFLP", Infect Cont Hosp Epidem. (May 2001) 22(5): 294-298.
Wilson et al., "Detection of enterotoxigenic *Staphylococcus aureus* in dried skimmed milk: use of the polymerase chain reaction for amplification and detection of staphylococcal enterotoxin genes entB and entC1 and the thermonuclease gene nuc", Appl. Environ. Microbiol. (1991) 57:1793-8.
Wilson, et al. "Inhibition and facilitation of nucleic acid amplification." Appl. Environ. Microbiol. 63(10): 3741-3751 (1997).
Wisplinghoff et al., "Related clonges containing SCCmec type IV predominate among clinically significant *Staphylococcus epidermidis* Isolates." Antimicrob Agents Chemothera. 47(11): 3574-3579 (2003).
Wittwer et al., "Fluorescence Monitoring of Rapid Cycle PCR for Quantification" in *Gene Quantification*, The Immune Response Corporation, Francois Ferre (Ed.), Birkhaeuser Boston (1998) pp. 97-110.
Woron et al., "Multiplex rt-PCR detection of MRSA from bacterial isolates," Abstracts of the General Meeting of the American Society for Microbiology, (2004) vol. 104, Abs C-116, pp. 143; 104th General Meeting of the American Society for Microbiology. New Orleans, LA, USA.
Wren et al., "Rapid molecular detection of methillin-resistant *Staphylococcus aureus*," Journal of Clinical Microbiology (2006) 44(4):1604-1605.
Wu, et a. "The ligation amplification reaction (LAR)— Amplification of specific DNA sequences using sequential sounds of template-dependent ligation." Genomics 4:560-569 (1989).
Wu, et al. "Genetic organization of the mecA region in methicillin-susceptible and methicillin-resistant strains of *Staphylococcus sciuri*." J. Bacter. 180(2):236-42 (1998).
Wu et al., "Rapid detection of *Staphylococcus aureus* and methicillin resistance from blood cultures using a real-time PCR SmartCycler assay," Abstracts of the General Meeting of the American Society for Microbiology, 105th General Meeting of the American-Society-for-Microbiology. Atlanta, GA, USA; Abs. C-085; (2005) vol. 105, pp. 119.
Wu et al., Caenorhabditis elegans as a host model for community-associated methicillin-resistant *Staphylococcus aureus*. (2010) 16(3):245-254.
Xue, et al. "*Staphylococcus aureus* DNA, type-V staphylococcal cassette chromosome mec: strain JCSC3624." GenBank accession No. AB121219, Jan. 7, 2000—Abstract only.
Zhang, et al. "Genome-based analysis of virulence genes in a non-biofilm-forming *Staphylococcus epidermidis* strain (ATCC 12228)." Molecular Microbiology. 49(6): 1577-1593 (2003).
Zhang et al., "New quadriplex PCR assay for detection of methicillin and mupirocin resistance and simultaneous discrimination of *Staphylococcus aureus* from coagulase-negative staphylococci", J. Clin. Microbiol. (2004) 42(11):4947-55.
Zhang et al., "Novel multiplex PCR assay for characterization and concomitant subtyping of staphylococcal cassette chromosome mec types I to V in methicillin-resistant *Staphylococcus aureus*.", J. Clin. Microbiol. (Oct. 2005) 43(10): 5026-33.
Zhang et al., "Novel multiplex PCR assay for simultaneous identification of community-associated methicillin-resistant *Staphylococcus aureus* strains USA300 and USA400 and detection of mecA and Panton-Valentine leukocidin genes, with discrimination of *Staphylococcus aureus* from coagulase-negative staphylococci", J Clin Microbiol. (Mar. 2008) 46(3): 1118-1122; Epub Dec. 26, 2007.
D3—Exhibit in European Opposition Proceeding: Applicant Response dated Dec. 2, 2009 in EP Application No. 06825875.5, filed Oct. 10, 2006; 5 pages.
D6—Exhibit in European Opposition Proceeding:: BLAST alignment of SEQ ID 46 from EP 1 397 510 and SEQ ID 19 from EP 1 934 613; 1 page.
D7—Exhibit in European Opposition Proceeding:: EP 1 93 4613 Claimed sequences with EP 1 397 510 primer binding sites shown; 3 pages.

(56) References Cited

OTHER PUBLICATIONS

D7—Exhibit in European Opposition Proceeding: EP 2 322 661, EP 2 322 664 and EP 2 322 655; MREJ type viii sequence (SEQ ID No. 167) with orfX and SCCmec portions highlighted—WO2002099034 Sequence 1; 1 page.
D8—Exhibit in European Opposition Proceeding: EP 2 322 661, EP 2 322 664 and EP 2 322 655; MREJ type i, ii and iii sequences with orfX and SCCmec portions highlighted—WO2002099034 Sequence 1; 14 pages.
D9—Exhibit in European Opposition Proceeding: EP 2 322 661, EP 2 322 664 and EP 2 322 655; Alignmeht of type ii (SEQ ID No. 2) and type viii (SEQ ID No. 167) MREJ sequences confirming lack of MREJ specificity of primers in patent; 2 pages.
D10—Exhibit in European Opposition Proceeding: EP 2 322 661, EP 2 322 664 and EP 2 322 655; Alignment of type ii (SEQ ID No. 2) and type ix (SEQ ID No. 168) MREJ sequences confirming lack of MREJ specificity of primers in the Patent; AX720425; 2 pages.
D11—Exhibit in European Opposition Proceeding: EP 2 322 661, EP 2 322 664 & 2 322 655 Alignment of type iii (SEQ ID No. 104) and type vii (SEQ ID No. 165) MREJ sequences confirming lack of MREJ specificity of primers in the patent; 1 page.
D12—Exhibit in European Opposition Proceeding: EP 2 322 664 and EP 2 322 655; Alignment of type vi (SEQ ID No. 171) and *S. haemolyticus* MREJ sequences confirming lack of MRSA specificity of primers in the patent; 2 pages.
D57—Exhibit in Appeal Procedure—2nd Declaration by Prof. Mark C. Enright on Jan. 19, 2018 re 1st declaration of Sep. 29, 2017 in 2 pages.
D12a—Exhibit in European Opposition Proceeding: EP 2 322 661; Example of overlap between type ix (SEQ ID No. 168) and other category of MRSA sequences confirming lack of MREJ specificity of primers claimed in the Patent; AB774374; 3 pages.
D12b—Exhibit in European Opposition Proceeding: EP 2 322 661; Example of overlap between type ix (SEQ ID No. 168) and other category of MRSA sequences confirming lack of MREJ specificity of primers claimed in the Patent; HF569115; 2 pages.
D71—Exhibit in European Opposition Proceeding/Appeal: EP 2 322 661; Declaration of Marie-Hélene Tremblay (with 1 Annex (CV) Jan. 10, 2018 in 7 pages.
D75—Exhibit in European Opposition Proceeding/Appeal: EP 2 322 661; Maloy S.R., (1990) *Experimental Techniques in bacterial genetics*. Jones & Bartlett Learning; Genetic Nomenclature—2 page excerpt.
D77—Exhibit in European Opposition Proceeding/Appeal: EP 2 322 661; Rosenbach *Staphylococcus aureus* subsp. *aureus*—ATTC BAA-40, Strain Designations CPS22; Jan. 31, 2018 in 2 Pages.
D78—Exhibit in European Opposition Proceeding/Appeal: EP 2 322 661; Third Declaration of Prof Mark C. Enright dated Mar. 9, 2018 in 5 pages.
D79—Exhibit in European Opposition Proceeding/Appeal: EP 2 322 661; Declaration of Dr Duarte C. Oliveira dated Mar. 13, 2018 including Appendices in 16 pages.
D16—Exhibit in European Opposition Proceeding: EP 2 322 664; Results of BLAST search using MREJ type vi sequence as query (SEQ ID No. 171)—AB665981; 19 pages.
D22—Exhibit in European Opposition Proceeding: EP 2 322 664 and EP 2 322 655; Alignmennt of MREJ type iii sequence from D1 and MREJ type vi sequence of SEQ ID No. 171—AX720594; 1 page.
D22—Exhibit in European Opposition Proceeding: EP 2 322 661; Alignment of MREJ type ii sequence from D1 and MREJ type ix sequence of SEQ ID No. 168; Mec lower junction around DNA of MRSA; E13725; 1 page.
D25—Exhibit in European Opposition Proceeding: EP 2 322 664 and EP 2 322 655; MREJ type iv sequence of HDG2 strain showing orfX and SCCmec sequence; 1 page.
D13—Exhibit in European Opposition Proceeding: CLUSTALW2 Multiple sequence alignment of rjmec primer from Cuny et al. and various MREJ type sequences; 1 page.

D14—Exhibit in European Opposition Proceeding: Primer binding sites of Cuny et al. in EP 1 934 613; 2 pages.
D17—Exhibit in European Opposition Proceeding: Primer binding site for SEQ ID No. 35 in SEQ ID No. 20 of EP 1 934 613; 1 page.
D18—Exhibit in European Opposition Proceeding: Overlap between ORFX2r primer binding sites of Cuny et al. and primer binding site of SEQ ID No. 45 from EP 1 934 613 in type xi MREJ sequences claimed in the EP patent; 6 pages.
D19—Exhibit in European Opposition Proceeding: Primer binding sites for primers of Cuny et al. in MREJ Types I-XX (sequences taken from EP 1934 613 and EP 1 397 510; 10 pages.
D32—Exhibit in European Opposition Proceeding: Lawrence et al. "Poisonous EPC Divisionals—Implications for Risk Management and Opportunistic Advantage." epi Information Feb. 2011; 54-61 (D32—Exhibit in European Opposition Proceeding).
D36—Exhibit in European Opposition Proceeding: Alignment of SEQ ID No. 18 from U.S. Appl. No. 11/248,438 and WO 2007/044873 With OrfX sequence from Ito et al., AB014440; 3 pages.
D37—Exhibit in European Opposition Proceeding: Alignment of SEQ ID No. 19 from U.S. Appl. No. 11/248,438 and WO 2007/044873 with orfX sequence from Ito et al., AB014440; 1 page.
D38—Exhibit in European Opposition Proceeding: Alignment of MREJ type xi (SEQ ID No. 17) and mrfj Type iii (SEQ ID No. 184 from WO 2002/099034 showing asserted binding sites of primers pair (SEQ ID Nos. 64/98) from WO 2002/099034; 3 pages.
D39—Exhibit in European Opposition Proceeding: Alignment of MREJ type xi (SEQ ID No. 17) and MREJ type iii (SEQ ID No. 184 From wo 2002/099034 showing asserted binding sites of primers (SEQ ID Nos. 1-5) from EP 1 529 847; 1 page.
D49—Exhibit in European Opposition Proceeding: FDA Approval of K033415 (IDI-MRSA Assay) to market; Letter, Mar. 18, 2004 with Summary & Indications for Use; 7 pages.
D51—Exhibit in European Opposition Proceeding: Gentechnische Methoden: Eine Sammlung von Arbeitsanleitungen fur das Molekularbiologische Labor. Publ. Gangolf Schrimpf (2002) Spektrum Akademischer Verlag GmbH; 3rd Edition; pp. 147-168.
D63—Exhibit in European Opposition Proceeding: NCBI—Nucleotide H569115-569102/4. *Staphylococcus aureus* subsp. *aureus* SCCmec . . . ; (Dec. 2012); 3 pages.
D55b—Exhibit in European Opposition Proceeding: NCBI—Nucleotide AY267380.1; AY267381.1; AY267376.1; AY267377.1. *Staphylococcus aureus* strain CCRI-1311 SCCmec . . . ; (2004); 6 pages.
Comparison of the nucleotide sequence of MRSA strain V14 (deposited under Accession No. AB425427) with the nucleotide sequence of SEQ ID No. 165 from the Patent. Primer binding sites for some of the primers claimed in claim 4 of the EP2236621 [D12] cited on May 8, 2013; pp. 1-7.
Nucleotide Sequence of MRSA strain M08/1026 ACME/SCCmecCI of ST22-MRSA-Ivh deposited in Genbank Accession No. FR753166 with orfX and SCCmec portions of SEQ ID No. 165 highlighted thereon. Also shown are primers binding sites for the primers of SEQ ID Nos. 64 and 112 from claim 5 of the EP2236621 [D14] cited on May 8, 2013; pp. 1-16.
CLUSTALW2 Multiple nucleotide sequence alignment (generated using ClustalW2). The sequence of each of MREJ types I to xx (excluding type x) is aligned around the integratioin site. The sequence of the rjmec primer from D7 is also included; [D9] cited on May 8, 2013; p. 1.
Nucleotide Sequence alignment of SEQ ID No. 165 of EP2236621 [D17] with *Staphylococcus epidermidis* strain ATCC 12228 (Accession No. AE015929.1) cited on May 8, 2013; p. 1.
BLAST Sequence-Alignment between the orfX sequence from *Staphyloccocus aureus* and the equivalent *Staphylococcus epidermidis* sequence taken from a number of strains; [D19] cited on May 8, 2013; pp. 1-6.
SEQ ID No. 6—Figure 19 of D1 and D2. Primer biding sites for SEQ ID Nos. 64 and 98 from EP2236621 as underlined; [D22] cited on May 8, 2013; p. 1.
European Decision T 1496/11 of the Technical Boards of Appeal in re EP Patent No. 930979 [D28] of Sep. 12, 2012; pp. 1-28.
Annotated version of figure 4A of EP 2236621 cited on May 8, 2013; p. 1.

(56) References Cited

OTHER PUBLICATIONS

Sequence Alignment of SEQ ID No. 64 and SEQ ID No. 98 on SEQ ID No. 165 and SEQ ID No. 166 of EP2236621 [D31] cited on May 8, 2013; pp. 1-3.
Partial International Search Report dated May 12, 2003 for International Application No. PCT/CA 02/00824, filed Jun. 4, 2002.
International Search Report dated Sep. 24, 2003 for International Patent Application No. PCT/CA02/000824, filed Jun. 4, 2002.
International Search Report and Written Opinion dated Nov. 23, 2007 for International Patent Application No. PCT/US06/39996, filed Oct. 10, 2006.
International Preliminary Report on Patentability (Rule 44bis) dated Apr. 16, 2008 for International Patent Application No. PCT/US06/39996, filed Oct. 10, 2006.
Australian Office Action dated Jun. 6, 2011 for Australian Application No. 2006302044, filed Oct. 10, 2006.
Australian Office Action dated May 1, 2015 for Australian Application No. 2013200217, filed Jan. 16, 2013.
Australian Office Action dated May 1, 2015 for Australian Application No. 2013200218, filed Jan. 16, 2013.
Australian Office Action dated May 1, 2015 for Australian Application No. 2013200220, filed Jan. 16, 2013.
Canadian Office Action dated Jul. 23, 2014 for Canadian Application No. 2,625,072, filed Oct. 10, 2006.
Supplementary European Search Report dated Apr. 7, 2009 for European Application No. 06825875.5, filed Oct. 10, 2006.
Partial European Search Report dated Mar. 31, 2011 for European Patent Application No. 10016072.0, filed Oct. 10, 2006.
Extended European Search Report dated Aug. 10, 2011 for European Patent Application No. 10016072.0, filed Oct. 10, 2006.
Office Action dated Sep. 11, 2012 for European Patent Application No. 10016072.0, filed Oct. 10, 2006.
Partial European Search Report dated Mar. 31, 2011 for European Patent Application No. 10016073.8, filed Oct. 10, 2006.
Extended European Search Report dated Aug. 10, 2011 for European Patent Application No. 10016073.8, filed Oct. 10, 2006.
Office Action dated Sep. 11, 2012 for European Patent Application No. 10016073.8, filed Oct. 10, 2006.
Partial European Search Report dated Mar. 10, 2011 for European Patent Application No. 10016074.6, filed Oct. 10, 2006.
Extended European Search Report dated Jul. 20, 2011 for European Patent Application No. 10016074.6, filed Oct. 10, 2006.
Office Action dated Sep. 11, 2012 for European Patent Application No. 10016074.6, filed Oct. 10, 2006.
Partial European Search Report dated Mar. 31, 2011 for European Patent Application No. 10016031.6, filed Oct. 10, 2006.
Extended European Search Report dated Aug. 10, 2011 for European Patent Application No. 10016031.6, filed Oct. 10, 2006.
Office Action dated Sep. 11, 2012 for European Patent Application No. 10016031.6, filed Oct. 10, 2006.
Partial European Search Report dated Mar. 30, 2011 for European Patent Application No. 10016019.1, filed Oct. 10, 2006.
Extended European Search Report dated Aug. 10, 2011 for European Patent Application No. 10016019.1, filed Oct. 10, 2006.
Office Action dated Sep. 11, 2012 for European Patent Application No. 10016019.1, filed Oct. 10, 2006.
Partial European Search Report dated Mar. 30, 2011 for European Patent Application No. 10016020.9, filed Oct. 10, 2006.
Extended European Search Report dated Aug. 10, 2011 for European Patent Application No. 10016020.9, filed Oct. 10, 2006.
Office Action dated Sep. 12, 2012 for European Patent Application No. 10016020.9, filed Oct. 10, 2006.
Japanese Office Action dated Mar. 13, 2012 for JP Patent Application No. 2008-535692, filed Oct. 10, 2006.
Japanese Office Action dated Aug. 8, 2012 for JP Patent Application No. 2008-535692, filed Oct. 10, 2006.
Partial International Search Report dated Dec. 19, 2008 for International Application No. PCT/US07/088004, filed Dec. 18, 2007.
International Preliminary Report on Patentability and Written Opinion dated Jul. 2, 2009 for International Application No. PCT/US07/088004, filed Dec. 18, 2007.
European Search Report dated Dec. 3, 2009 for European Application No. 07874372.1, filed Dec. 18, 2007.
European Office Action dated Sep. 28, 2011 for European Application No. 07874372.1, filed Dec. 18, 2007.
European Office Action dated Apr. 16, 2012 for European Application No. 07874372.1, filed Dec. 18, 2007.
Australian Office Action dated Sep. 5, 2012 for Australian Application No. 2007353522, filed Dec. 19, 2006.
Canadian Office Action dated Feb. 13, 2014 for Canadian Application No. 2,673,357, filed Dec. 18, 2007.
Canadian Office Action dated May 1, 2015 for Canadian Application No. 2,673,357, filed Dec. 18, 2007.
Japanese Office Action dated Nov. 27, 2012 in Japanese Patent Application No. 2009-543155, filed Dec. 18, 2007.
Japanese Office Action dated Dec. 24, 2013 in Japanese Patent Application No. 2009-543155, filed Dec. 18, 2007.
Canadian Office Action dated Nov. 7, 2016 in Application No. 2,899,816, filed Jun. 4, 2002.
European Extended Search Report dated Apr. 18, 2011 in European Patent Application No. 10181533.0, filed Jun. 4, 2002.
European Extended Search Report dated Apr. 18, 2011 in European Patent Application No. 10181534.8, filed Jun. 4, 2002.
European Extended Search Report dated Apr. 18, 2011 in European Patent Application No. 10181535.5, filed Jun. 4, 2002.
European Extended Search Report dated Apr. 15, 2011 in European Patent Application No. 10181536.3, filed Jun. 4, 2002.
European Extended Search Report dated Aug. 10, 2010 in European Patent Application No. 09174581.0, filed Jun. 4, 2002. [D33].
Response to Extended Search Report filed Mar. 3, 2011 in European Patent Application No. 09174581.0, filed Jun. 4, 2002. [D34].
Supplementary Response to Extended Search Report filed Nov. 16, 2011 in European Patent Application No. 09174581.0, filed Jun. 4, 2002. [D35].
European Office Action dated Apr. 26, 2011 in European Patent Application No. 09174581.0, filed Jun. 4, 2002.
European Extended Search Report dated Aug. 25, 2014 in European Patent Application No. 14168417.5, filed May 15, 2014.
European Office Action dated Dec. 9, 2014 in European Patent Application No. 14168417.5, filed May 15, 2014.
Notice of Observations by 3rd Party dated Nov. 18, 2015 in European Patent Application No. 14168417.5, filed May 15, 2014.
European Extended Search Report dated Aug. 25, 2014 in European Patent Application No. 14168420.9, filed May 15, 2014.
European Office Action dated Dec. 17, 2014 in European Patent Application No. 14168420.9, filed May 15, 2014.
European Extended Search Report dated Aug. 10, 2016 in European Patent Application No. 15195621.6, filed Nov. 20, 2015.
European Office Action dated Aug. 2, 2018 in EP Application No. 15195621.6, filed Nov. 20, 2015.
International Search Report and Written Opinion dated Aug. 13, 2013 for International Patent Application No. PCT/IB2013/000900, filed Mar. 14, 2013.
European Extended Search Report dated Oct. 9, 2015 in European Patent Application No. 13772940.6, filed Oct. 24, 2014.
Third Party Observations dated Jan. 17, 2008 in European Patent Application No. 02740158.7, filed Jun. 4, 2002.
Notice of Opposition dated Aug. 3, 2010 in in European Opposition to Patent No. No 1397510.
EPO Communication dated Sep. 10, 2010 in in European Opposition to Patent No. No 1397510.
Patentee Response to Opposition dated Mar. 17, 2011 in European Opposition to Patent No. No 1397510.
EPO Communication dated May 10, 2012 re Oral Proceeding Schedule in European Opposition to Patent No. No 1397510.
Patentee Response dated Nov. 19, 2012 to EP Summons to Oral Proceeding in European Opposition to Patent No. 1397510.
Opposer Hain Lifescience GmbH Response dated Nov. 26, 2012 to EP Summons to Oral Proceeding in European Opposition to Patent No. 1397510. (English Translation Only).

(56) References Cited

OTHER PUBLICATIONS

Opposer Beckman Coulter, Inc. further Response dated Nov. 30, 2012 to EP Summons to Oral Proceeding in European Opposition to Patent No. 1397510.
Minutes of the Oral Proceedings on Jan. 30, 2013 in European Opposition to Patent No. 1397510 [D37] mailed Apr. 5, 2013.
EPO Decision of the Opposition Division of Mar. 26, 2013 in European Opposition to Patent No. No 1397510 [D36].
Patentee Appeal dated Jun. 3, 2013 and Grounds for Appeal dated Aug. 12, 2013 against EPO Decision of Mar. 26, 2013 to Revoke Patent No. 1397510 [T 1294/13-3.3.08].
Opponent Beckman Coulter's Response dated Dec. 16, 2013 to Patentee's EPO Appeal and Grounds for Appeal in T 1294/13-3.3.08 against EPO Decision in Re EP Patent No. 1397510.
Opponent Hain Lifescience's Response dated Dec. 20, 2013 to Patentee's EPO Appeal and Grounds for Appeal in T 1294/13-3.3.08 against EPO Decision in Re EP Patent No. 1397510.
EPO Notice of Opposition and supporting documents filed by Beckman Coulter on Dec. 17, 2015 against European Patent No. 2322663, granted Mar. 18, 2015 (50 pages).
EPO Notice of Opposition and supporting documents filed by R-Biopharm AG on Dec. 18, 2015 against European Patent No. 2322663, granted Mar. 18, 2015 (84 pages).
Patent Proprietor's Reply to both Oppositions and supporting documents filed Aug. 3, 2016 in EP 2322663, granted Mar. 18, 2015 (231 pages).
EPO Notice re Beckman Coulter's Response to Summons to Oral Proceedings dated Nov. 30, 2017 in Opposition of European Patent No. 2322663, granted Nov. 26, 2014 (306 pages).
EPO Interlocutory Decision in Opposition Proceedings and supporting documents dated Apr. 11, 2018 against EP 2322663; (52 pages).
Patentee/Appellant Submission re Appeal filed Jun. 18, 2018 and Grounds for Appeal dated Aug. 21, 2018 against EPO Decision in European Patent No. 2322663 [T 1522/18-3.3.08]; (111 Pages).
Reply by Beckman Coulter to Opposition Appeal on Jan. 7, 2019 in EP 2322663, granted Mar. 18, 2015 (157 pages).
EPO Notice of Opposition and supporting documents filed by Beckman Coulter on Aug. 25, 2015 against European Patent No. 2322664, granted Oct. 30, 2014.
EPO Notice of Opposition and supporting documents filed by R-Biopharm AG on Aug. 26, 2015 against European Patent No. 2322664, granted Oct. 30, 2014.
Patent Proprietor's Reply to both Oppositions and supporting documents filed Apr. 11, 2016 in EP 2322664, granted Oct. 30, 2014 (201 pages).
EPO Interlocutory Decision in Opposition Proceedings and supporting documents dated Apr. 19, 2018 against EP 2322664; (263 pages).
Patentee/Appellant Submission re Appeal dated Aug. 18, 2018 and Grounds for Appeal dated Aug. 16, 2018 against EPO Decision of Apr. 19, 2018 to Revoke Patent No. 2322664 [T 1582/18-3.3.08]; 236 pages.
Reply by Opposer Beckman Coulter to Opposition Appeal on Jan. 10, 2019 in EP 2322664 [T 1582/18-3.3.08];(158 pages).
EPO Notice of Opposition and supporting documents filed by Beckman Coulter on Aug. 26, 2015 against European Patent No. 2322655, granted Nov. 26, 2014.
EPO Notice of Opposition and supporting documents filed by R-Biopharm AG on Aug. 26, 2015 against European Patent No. 2322655, granted Nov. 26, 2014.
Patent Proprietor's Reply to both Oppositions and supporting documents filed Apr. 10, 2016 in EP 2322655, granted Nov. 26, 2014 (251 pages).
EPO Notice re Beckman Coulter Response to Summons to Oral Proceedings dated Dec. 6, 2017 against European Patent No. 2322655, granted Nov. 26, 2014 (154 pages).
EPO Interlocutory Decision in Opposition Proceedings dated Mar. 27, 2018 against EP 2322655; (29 pages).
Patentee/Appellee's Submission re Appeal dated Aug. 6, 2018 and Grounds for Appeal against EPO Decision of Mar. 27, 2018 in re Patent No. 2322655 [T1421/18-3.3.08] (82 pages).
Opponent/Respondent Beckman Coulter Reply to Opposition Appeal on Dec. 19, 2018 in EP 2322655; [T1421/18-3.3.08] (258 pages).
EPO Notice of Opposition and supporting documents filed by Beckman Coulter on Aug. 26, 2015 against European Patent No. 2322661, granted Nov. 26, 2014.
EPO Notice of Opposition and supporting documents filed by R-Biopharm AG on Aug. 26, 2015 against European Patent No. 2322661, granted Nov. 26, 2014.
Patent Proprietor's Reply to both Oppositions and supporting documents filed Apr. 11, 2016 in EP 2322661 granted Nov. 26, 2014 (446 pages).
EPO Notice re Beckman Coulter Response to Summons to Oral Proceedings dated Dec. 6, 2017 against European Patent No. 2322661, granted Nov. 26, 2014 (153 pages).
EPO Interlocutory Decision of Apr. 19, 2018 in EP Opposition proceedings against Patent No. 2322661, granted Nov. 26, 2014 (38 pages).
Opponent/Respondent Beckman Coulter's Statement re Grounds of Appeal [T1521/18-3.3.08] filed Aug. 29, 2018 in Patent No. 2322661 (70 pages).
Patentee/Appellee's Submission re Opposition Appeal dated Jan. 14, 2019 in re Patent No. 2322661 [T1521/18-3.3.08] (118 pages).
EPO Opposition Notice filed May 8, 2013 against European Patent No. 2236621, granted Aug. 8, 2012.
EPO Opposition Notice dated May 17, 2013 by Beckman Coulter, Inc. against European Patent No. 2236621, granted Aug. 8, 2012.
Patentee Reply filed Dec. 23, 2013 in EP Opposition proceedings against Patent No. 2236621.
EPO Interlocutory Decision of Apr. 10, 2015 in EP Opposition proceedings against Patent No. 2236621.
Appeal by Patentee/Appellant against EPO Interlocutory Decision filed May 28, 2015 including Grounds for Appeal filed Aug. 5, 2015 in EP Opposition proceedings against Patent No. 2236621; 119 pages.
Opponent Beckman Coulter's Reply to Patentee's Grounds for Appeal filed Dec. 29, 2015 & Opponent's Reply to same filed Jan. 4, 2016 in EP Opposition proceedings against Patent No. 2236621; 19 pages.
Opponent Beckman Coulter's Submission in Opposition Appeal No. T1146/15-3.3.08 (EP 2236621) dated Nov. 30, 2017 in 221 pages.
Patentees/Appellee's Written Submission on Grounds of Appeal filed Sep. 26, 2018 and additional Appendices/Exhibits in Opposition Appeal No. T1146/15-3.3.08 (EP 2236621); in 227 pages.
EPO Opposition Notice dated Dec. 2, 2016 with supporting documentation by Beckman Coulter Inc. against European Patent No. 2781603, granted Mar. 2, 2016; 234 pages.
Reply of the Patent Proprietor to Notice of Opposition dated May 19, 2017 in European Patent No. EP 2781603; 49 pages.
EPO Decision to Revoke EP 2781603 & Minutes of Oral Proceedings in Opposition Proceedings dated Jun. 25, 2018 ; 37 pages.
Patentee/Appellee's Submission re Appeal dated Sep. 5, 2018 against EPO Interlocutory Decision including Grounds for Appeal filed Nov. 5, 2018 in EP Opposition proceedings against Revocation of Patent No. 2781603; [T2261/18-3.3.08]; (27 pages).
EPO Opposition Notice dated Dec. 2, 2016 with supporting documentation by Beckman Coulter Inc. against European Patent No. 2781604, granted Mar. 2, 2016; 186 pages.
Reply of the Patent Proprietor to Notice of Opposition dated May 19, 2017 in European Patent No. EP 2781604; 35 pages.
EPO Interlocutory Decision of Jul. 5, 2018 and Minutes of Oral Proceeding in EP Opposition against Patent No. 2781604; 40 pages.
Patentees/Appellee's Written Submission on Grounds of Appeal filed Nov. 15, 2018 and additional Appendices/Exhibits in Opposition Appeal No. T2255/18-3.3.08 (EP 2781604); in 188 pages.
Notice of Opposition & Discussion filed Oct. 19, 2011 against European Patent No. 1934613 (Koenig et al.).
Notice of Opposition and Statement filed Oct. 18, 2011 against European Patent No. 1934613 (BC).

(56) References Cited

OTHER PUBLICATIONS

EPO Communication dated Nov. 25, 2011 in European Opposition to Patent No. 1934613.
Patentees Reply filed May 30, 2012 in European Opposition to Patent No. 1934613.
EPO Summons to Oral Proceedings dated Nov. 23, 2012 in European Opposition to Patent No. 1934613.
EPO Board Decision and Minutes of Oral Proceedings dated Aug. 2, 2013 in European Opposition to Patent No. 1934613.
Patentee Appeal dated Sep. 12, 2013 and Grounds for Appeal dated Dec. 11, 2013 against EPO Decision of Aug. 2, 2013 to Revoke Patent No. 1934613 [T 2002/13-3.3.08].
Opponents' Replies dated Apr. 30, 2014 to Patentee's EPO Appeal and Grounds for Appeal in T 2002/13-3.3.08 against EPO Decision in Re EP Patent No. 1934613; 100 pages.
EPO Minutes of Oral Proceedings dated May 24, 2017 in Appeal No. T2002/13-3.3.08 against revocation of EP Patent No. 1934613; 6 pages.
EPO Board Decision dated Nov. 9, 2017 in Appeal No. T2002/13-3.3.08 against revocation of EP Patent No. 1934613; 32 pages.
Shulzhenko et al., Specificity of alternative splice form detection using RT-PCR with a primer spanning the exon junction. Biotechniques (2003) 34(6):1244-1249.
Tarantul, V.Z., Explanatory dictionary of biotechnology. Russian-English, M. Yaziki slavyanskih kultur, 2009, p. 553.
Yadav S. et al., Detection of methicillin-resistant *Staphylococcus aureus* (MRSA) from nasal samples by multiplex real-time PCR based on dual priming AT-rich primers. Folia microbiologica (Jan. 2012) 57(1):37-45.
Further Reply by Opposer Beckman Coulter to Opposition Appeal re Reinstatement on Mar. 1, 2019 in EP 2322664, [T 1582/18-3.3.08]; (14 pages).
Opponent/Respondent Beckman Coulter's Reply dated Mar. 18, 2019 to Patentee's Grounds for Appeal filed Nov. 5, 2018 in EP Opposition proceedings against Revocation of Patent No. 2781603; [T2261/18-3.3.08]; (102 pages).
Patentee's/Appellee's Reply to Appeal dated Apr. 9, 2019 to Opponent/Respondent Beckman Coulter's Grounds of Appeal filed Apr. 1, 2019 in EP Opposition proceedings against Revocation of Patent No. 2781604; [T2255/18-3.3.08]; (66 pages).

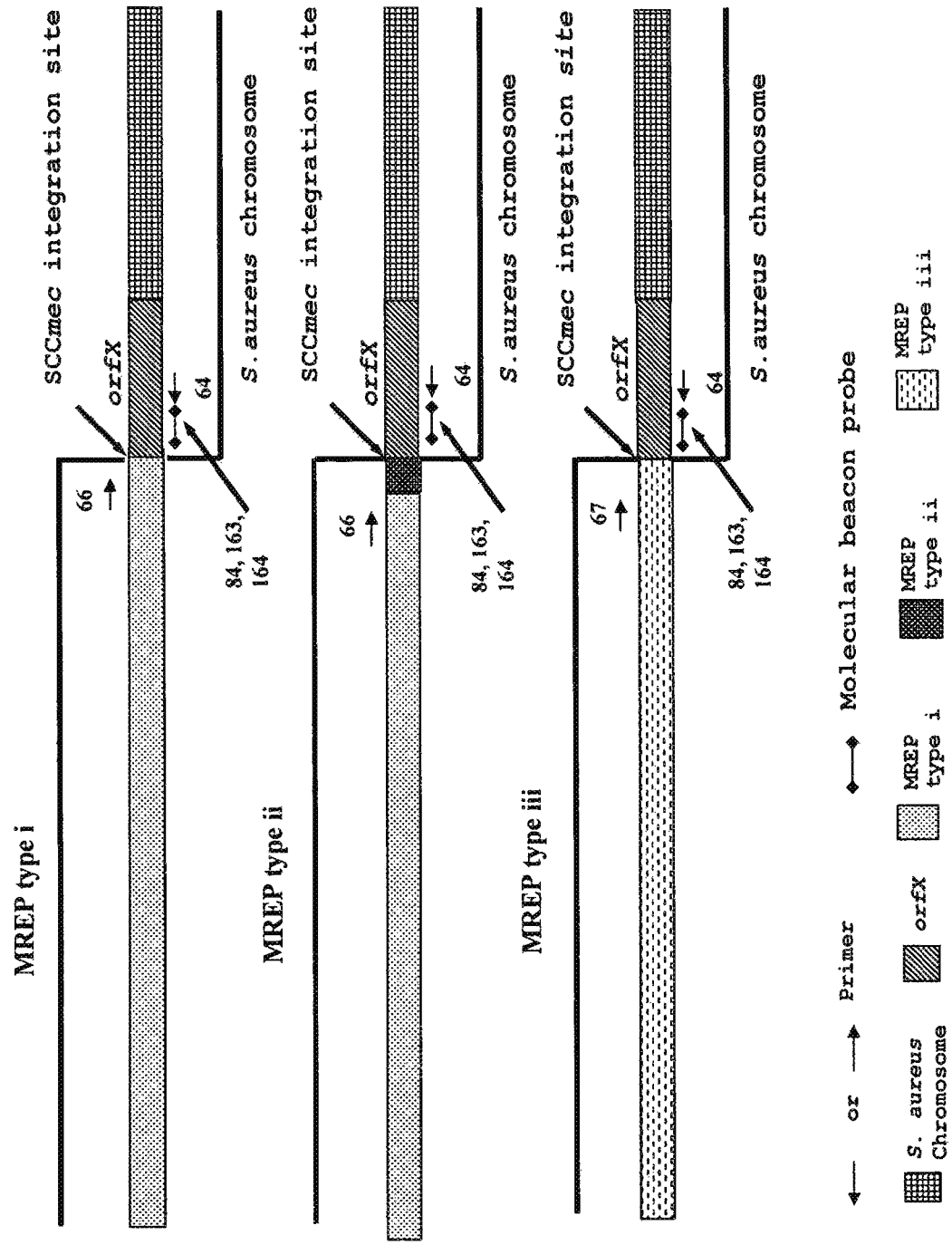

FIG. 4A

| FIG. 4A | FIG. 4B |
|---------|---------|
| FIG. 4C | FIG. 4D |

SEQUENCE LISTING

<160> NUMBER OF SEQ IDS NOS: 269

<210> SEQ ID NO 1
<211> LENGTH: 3050
<212> TYPE: DNA
<213> ORGANISM: Staphylococcus aureus

<400> SEQUENCE: 1
tcgtgccatt gatgcagagg gacatacatt agatatttgg ttgcgtaagc aacgagataa    60
tcattcagca tatgcgtttta tcaaacgtct cattaaacaa tttggtaaac ctcaaaaggt   120
aattacagat caggcacctt caacgaaggt agcaatggct aaagtaatta agcttttaa    180 acttaaacct gactgtcatt gtacatcgaa atatctgaat aacctcattg agcaagatca   240

```
ccgtcatatt aaagtaagaa agacaaggta tcaaagtatc aatacagcaa agaatacttt      300
aaaaggtatt gaatgtattt acgctctata taaaaagaac cgcaggtctc ttcagatcta      360
cggattttcg ccatgccacg aaattagcat catgctagca agttaagcga acactgacat      420
gataaattag tggttagcta tattttttta ctttgcaaca gaaccgaaaa taatctcttc      480
aatttatttt tatatgaatc ctgtgactca atgattgtaa tatctaaaga tttcagttca      540
tcatagacaa tgttcttttc aacatttttt atagcaaatt gattaaataa attctctaat      600
ttctcccgtt tgatttcact accatagatt atattatcat tgatatagtc aatgaataat      660
gacaaattat cactcataac agtcccaacc cctttatttt gatagactaa ttatcttcat      720
cattgtaaaa caaattacac cctttaaatt taactcaact taaatatcga caaattaaaa      780
aacaataaaa ttacttgaat attattcata atatattaac aactttatta tactgctctt      840
tatatataaa atcattaata attaaacaag ccttaaaata tttaactttt ttgtgattat      900
tacacattat cttatctgct ctttatcacc ataaaaatag aaaaaacaag attcctaaag      960
aatataggaa tcttgtttca gactgtggac aaactgattt tttatcagtt agcttattta     1020
gaaagtttta tttaaattac agttctatt tttattagat cacaatttta ttttagctct      1080
tgttcaagta atcatttttc gccaaaaact ttatactgaa tagcttctac attaaatact     1140
ttgtcaatga gatcatctac atctttaaat tcagaataat ttgcatatgg atctataaaa     1200
taaaattgtg gttctttacc ggaaacatta aatattctta atattaaata tttctgctta     1260
tattctttca tagcaaacat ttcatttagc gacataaaaa atggttcctc aatactagaa     1320
gatgtagatg ttttaatttc aataaatttt tctacagctt tatctgtatt tgttggatca     1380
aaagctacta aatcatagcc atgaccgtgt tgagagcctg gattatcatt taaaatattc     1440
ctaaactgtt ctttcttatc ttcgtctatt ttattatcaa ttagctcatt aaagtaattt     1500
agcgctaatt tttctccaac tttaccggtt aatttattct ctttatttga ttttttcaatt    1560 tctgaatcat tttagtagt ctttgataca ccttttttat attttggaat tattcctttta    1620 ggtgcttcca cttccttgag tgtcttatct ttttgtgctg ttctaatttc ttcaatttcg     1680
ctgtcttcct gtatttcgtc tatgctattg accaagctat cataggatgt ttttgtaact     1740
tttgaagcta attcattaaa tagttctaaa aatttcttta aatcctctag catatcttct     1800
tctgtgaatc cttcattcaa atcataatat ttgaatctta ttgatccatg agaatatcct     1860
gatggataat cattttttaa atcataagat gaatctttat tttctgcgta ataaaatctt     1920
ccagtattaa attcatttga tgtaatatat ttattgagtt cggaagataa agttaatgct     1980
ctttgttttg cagcattttt atcccgcgga aacatatcac ttatctttga ccatccttga     2040
ttcaaagata agtatatgcc ttctccttcc ggatgaaaaa gatataccaa ataatatcca     2100
tcctttgttt cttttgttat attctcatca tatattgaaa tccaaggaac tttactatag     2160
ttcccagtag caaccttccc tacaactgaa tatttatctt cttttatatg cacttttaac     2220
tgcttgggta acttatcatg gactaaagtt ttatatagat caccttttatc ccaatcagat    2280 tttttaacta cattattggt acgtttctct ttaattaatt taaggacctg cataaagttg     2340
tctatcattt gaaattccct cctattataa aatatattat gtctcatttt cttcaatatg     2400 tacttatttta tattttaccg taatttacta tatttagttg cagaaagaat tttctcaaag    2460
ctagaacttt gcttcactat aagtattcag tataaagaat atttcgctat tatttacttg     2520
aaatgaaaga ctgcggaggc taactatgtc aaaaatcatg aacctcatta cttatgataa     2580
gcttctcctc gcataatctt aaatgctctg tacacttgtt caattaacac aacccgcatc     2640
```

```
atttgatgtg ggaatgtcat tttgctgaat gatagtgcgt agttactgcg ttgtaagacg     2700
tccttgtgca ggccgtttga tccgccaatg acgaaaacaa agtcgctttg cccttgggtc     2760
atgcgttggt tcaattcttg ggccaatcct tcggaagata gcatctttcc ttgtatttct     2820
aatgtaatga ctgtggattg tggtttgatt ttggctagta ttcgttggcc ttcttttttct    2880 tttacttgct caatttcttt gtcactcata ttttctggtg cttttttcgtc tggaacttct    2940 atgatgtcta tcttggtgta tgggcctaaa cgttttttcat attctgctat ggcttgcttc    3000
caatatttct ctttttagttt ccctacagct aaaatggtga ttttcatgtc               3050
```

<210> SEQ ID NO 2
<211> LENGTH: 3050
<212> TYPE: DNA
<213> ORGANISM: Staphylococcus aureus

<400> SEQUENCE: 2

```
acctcattga gcaagatcac cgtcatatta aagtaagaaa gacaaggtat caaagtatca      60
atacagcaaa gaatacttta aaaggtattg aatgtattta cgctctatat aaaaagaacc     120
gcaggtctct tcagatctac ggattttcgc catgccacga aattagcatc atgctagcaa     180
gttaagcgaa cactgacatg ataaattagt ggttagctat attttttttac tttgcaacag    240 aaccgaaaat aatctcttca atttattttt atatgaatcc tgtgactcaa tgattgtaat     300
atctaaagat ttcagttcat catagacaat gttcttttca cattttttta tagcaaattg     360
attaaataaa ttctctaatt tctcccgttt gatttcacta ccatagatta tattatcatt     420
gatatagtca atgaataatg acaaattatc actcataaca gtcccaaccc ctttcttttg     480
atagactaat tatcttcatc attgtaaaac aaattacacc ctttaaattt aactcaactt     540
aaatatcgac aaattaaaaa acaataaaat tacttgaata ttattcataa tatattaaca     600
actttattat actgctcttt atatataaaa tcattaataa ttaaacaagc cttaaaatat     660 ttaactttt tgtgattatt acacattatc ttatctgctc tttatcacca taaaaataga     720
aaaaacaaga ttcctaaaga atataggaat cttgtttcag actgtggaca aactgatttt     780
ttatcagtta gcttatttag aaagttttat ttaaattaca gtttctattt ttattagatc     840 acaatttat tttagctctt gttcaagtaa tcattttcg ccaaaaactt tatactgaat       900
agcttctaca ttaaatactt tgtcaatgag atcatctaca tctttaaatt cagaataatt     960
tgcatatgga tctataaaat aaaattgtgg ttctttaccg gaaacattaa atattcttaa    1020
tattaaatat ttctgcttat attctttcat agcaaacatt tcatttagcg acataaaaaa    1080
tggttcctca atactagaag atgtagatgt tttaatttca ataaattttt ctacagcttt    1140
atctgtattt gttggatcaa aagctactaa atcatagcca tgaccgtgtt gagagcctgg    1200
attatcattt aaaatattcc taaactgttc tttcttatct tcgtctattt tattatcaat    1260
tagctcatta aagtaattta gcgctaattt ttctccaact ttaccggtta atttattctc    1320
tttatttgat ttttcaattt ctgaatcatt tttagtagtc tttgatacac cttttttata    1380
ttttggaatt attcctttag gtgcttccac ttccttgagt gtcttatctt tttgtgctgt    1440
tctaatttct tcaattcgc tgtcttcctg tatttcgtct atgctattga ccaagctatc     1500
ataggatgtt tttgtaactt ttgaagctaa ttcattaaat agttctaaaa atttctttaa    1560
atcctctagc atatcttctt ctgtgaatcc ttcattcaaa tcataatatt tgaatcttat    1620
tgatccatga gaatatcctg atggataatc attttttaaa tcataagatg aatctttatt    1680
```

| | |
|---|---|
| ttctgcgtaa taaaatcttc cagtattaaa ttcatttgat gtaatatatt tattgagttc | 1740 |
| ggaagataaa gttaatgctc tttgttttgc agcattttta tcccgcggaa acatatcact | 1800 |
| tatctttgac catccttgat tcaaagataa gtatatgcct tctccttccg gatgaaaaag | 1860 |
| ataccaaa taatatccat cctttgtttc ttttgttata ttctcatcat atattgaaat | 1920 |
| ccaaggaact ttactatagt tcccagtagc aaccttccct acaactgaat atttatcttc | 1980 |
| ttttatatgc acttttaact gcttgggtaa cttatcatgg actaaagttt tatatagatc | 2040 |
| acctttatcc caatcagatt ttttaactac attattggta cgtttctctt taattaattt | 2100 |
| aaggacctgc ataaagttgt ctatcatttg aaattccctc ctattataaa atatattatg | 2160 |
| tctcattttc ttcaatatgt acttatttat attttaccgt aatttactat atttagttgc | 2220 |
| agaaagaatt ttctcaaagc tagaactttg cttcactata agtattcagt ataaagaata | 2280 |
| tttcgctatt atttacttga aatgaaagac tgcggaggct aactatgtca aaaatcatga | 2340 |
| acctcattac ttatgataag cttcttaaaa acataacagc aattcacata aacctcatat | 2400 |
| gttctgatac attcaaaatc cctttatgaa gcggctgaaa aaaccgcatc atttatgata | 2460 |
| tgcttctcca cgcataatct aaatgctct atacacttgc tcaattaaca caacccgcat | 2520 |
| catttgatgt gggaatgtca ttttgctgaa tgatagtgcg tagttactgc gttgtaagac | 2580 |
| gtccttgtgc aggccgtttg atccgccaat gacgaataca aagtcgcttt gcccttgggt | 2640 |
| catgcgttgg ttcaattctt gggccaatcc ttcggaagat agcatctttc cttgtatttc | 2700 |
| taatgtaatg actgtggatt gtggtttaat tttggctagt attcgttggc cttctttttc | 2760 |
| ttttacttgc tcaatttctt tgtcgctcat atttttctggt gcttttcgt ctggaacttc | 2820 |
| tatgatgtct atcttggtgt atgggcctaa acgttttca tattctgcta tggcttgctt | 2880 |
| ccaatatttc tcttttagtt tccctacagc taaaatggtg attttcatgt cgtttggtcc | 2940 |
| tccaaattgt tatcaacttt ccagttatcc acaagttatt aacttgttca cactgttccc | 3000 |
| tcttattata ccaatatttt ttgcagtttt tgatatttc ctgacattta | 3050 |

<210> SEQ ID NO 3
<211> LENGTH: 3183
<212> TYPE: DNA
<213> ORGANISM: Staphylococcus aureus

<400> SEQUENCE: 3

| | |
|---|---|
| ctgcagaggt aattattcca acaatacca ttgatttcaa aggagaaaga gatgacgtta | 60 |
| gaacgcgtga aacaaattta ggaaacgcga ttgcagatgc tatggaagcg tatggcgtta | 120 |
| agaatttctc taaaaagact gactttgccg tgacaaatgg tggaggtatt cgtgcctcta | 180 |
| tcgcaaaagg taaggtgaca cgctatgatt taatctcagt attaccattt ggaaatacga | 240 |
| ttgcgcaaat tgatgtaaaa ggttcagacg tctggacggc tttcgaacat agtttaggcg | 300 |
| caccaacaac acaaaaggac ggtaagacag tgttaacagc gaatggcggt ttactacata | 360 |
| tctctgattc aatccgtgtt tactatgata taaataaacc gtctggcaaa cgaattaatg | 420 |
| ctattcaaat tttaaataaa gagacaggta agtttgaaaa tattgattta aaacgtgtat | 480 |
| atcacgtaac gatgaatgac ttcacagcat caggtggcga cggatatagt atgttcggtg | 540 |
| gtcctagaga agaaggtatt tcattagatc aagtactagc aagttattta aaaacagcta | 600 |
| acttagctaa gtatgatacg acagaaccac aacgtatgtt attaggtaaa ccagcagtaa | 660 |
| gtgaacaacc agctaaagga caacaaggta gcaaaggtag taagtctggt aaagatacac | 720 |
| aaccaattgg tgacgacaaa gtgatggatc cagcgaaaaa accagctcca ggtaaagttg | 780 |

```
ttttgttgct agcgcataga ggaactgtta gtagcggtac agaaggttct ggtcgcacaa      840
tagaaggagc tactgtatca agcaagagtg ggaaacaatt ggctagaatg tcagtgccta      900
aaggtagcgc gcatgagaaa cagttaccaa aaactggaac taatcaaagt tcaagcccag      960
aagcgatgtt tgtattatta gcaggtatag gtttaatcgc gactgtacga cgtagaaaag     1020
ctagctaaaa tatattgaaa ataatactac tgtatttctt aaataagagg tacggtagtg     1080 ttttttatg aaaaaaagcg ataaccgttg ataaatatgg gatataaaaa cgaggataag      1140
taataagaca tcaaggtgtt tatccacaga atggggata gttatccaga attgtgtaca      1200
atttaaagag aaatacccac aatgcccaca gagttatcca caaatacaca ggttatacac     1260
taaaaatcgg gcataaatgt caggaaaata tcaaaaactg caaaaaatat tggtataata     1320
agagggaaca gtgtgaacaa gttaataact tgtggataac tggaaagttg ataacaattt     1380
ggaggaccaa acgacatgaa aatcaccatt ttagctgtag ggaaactaaa agagaaatat     1440
tggaagcaag ccatagcaga atatgaaaaa cgtttaggcc catacaccaa gatagacatc     1500
atagaagttc cagacgaaaa agcaccagaa atatgagtg acaaagaaat tgagcaagta      1560
aaagaaaaag aaggccaacg aatactagcc aaaatcaaac cacaatccac agtcattaca     1620
ttagaaatac aaggaaagat gctatcttcc gaaggattgg cccaagaatt gaaccaacgc     1680
atgacccaag ggcaaagcga cttttgttttc gtcattggcg gatcaaacgg cctgcacaag     1740
gacgtcttac aacgcagtaa ctacgcacta tcattcagca aaatgacatt cccacatcaa     1800
atgatgcggg ttgtgttaat tgaacaagtg tacagagcat ttaagattat gcgaggagag     1860
gcgtatcata agtaaaacta aaaaattctg tatgaggaga taataatttg gagggtgtta     1920
aatggtggac attaaatcca cgttcattca atatataaga tatatcacga taattgcgca     1980
tataacttaa gtagtagcta acagttgaaa ttaggcccta tcaaattggt ttatatctaa     2040
aatgattaat atagaatgct tctttttgtc cttattaaat tataaaagta actttgcaat     2100
agaaacagtt atttcataat caacagtcat tgacgtagct aagtaatgat aaataatcat     2160
aaataaaatt acagatattg acaaaaaata gtaaatattc caatgaagtt tcaaaagaac     2220
aattccaaga aattgagaat gtaaataata aggtcaaaga attttattaa gatttgaaag     2280
agtatcaatc aagaaagatg tagtttttta ataaactatt tggaaaataa ttatcataat     2340
ttaaaaactg acaatttgcg agactcataa aatgtaataa tggaaataga gtaaaatat      2400 aattaagggg tgtaatatga agattaatat ttataaatct atttataatt tcaggaaaac     2460
aaatacaaat tttttagaga atctagaatc tttaaatgat gacaattatg aactgcttaa     2520
tgataaagaa cttgttagtg attcaaatga attaaaatta attagtaaag tttatatacg     2580
taaaaaagac aaaaaactat tagattggca attattaata aagaatgtat acctagatac     2640
tgaagaagat gacaatttat tttcagaatc cggtcatcat tttgatgcaa tattatttct     2700
caaagaagat actacattac aaaataatgt atatattata cctttggac aagcatatca      2760 tgatataaat aatttgattg attatgactt cggaattgat tttgcagaaa gagcaatcaa     2820
aaatgaagac atagttaata aaaatgttaa tttttttcaa caaaacaggc ttaaagagat     2880
tgttaattat agaaggaata gtgtagatta cgttagacct tcagaatctt atatatcagt     2940
ccaaggacat ccacagaatc ctcaaatttt tggaaaaaca atgacttgtg gtacaagtat     3000
ttcattgcgt gtaccgaata gaaagcagca attcatagat aaaattagtg tgataatcaa     3060
agaaataaac gctattatta atcttcctca aaaaattagt gaatttccta gaatagtaac     3120
```

| | |
|---|---|
| tttaaaagac ttgaataaaa tagaagtatt agatacttta ttgctaaaaa aactatcgaa | 3180 |
| ttc | 3183 |

<210> SEQ ID NO 4
<211> LENGTH: 479
<212> TYPE: DNA
<213> ORGANISM: Staphylococcus aureus

<400> SEQUENCE: 4

| | |
|---|---|
| ttcgtcattg gcggatcaaa cggcctgcac aaggacgtct tacaacgcag taactacgca | 60 |
| ctatcattca gcaaaatgac attcccacat caaatgatgc gggttgtgtt aattgaacaa | 120 |
| gtgtacagag catttaagat tatgcgtgga gaagcgtatc ataaataaaa ctaaaaatta | 180 |
| ggttgtgtat aatttaaaaa tttaatgaga tgtggaggaa ttacatatat gaaatattgg | 240 |
| attataccct gcaatatcat acgatgttta tagagtgttt aataaaccat ttttcaacta | 300 |
| ttgatgatct agaatatata ataactgtac aaattatatt gattatggaa ctacaattaa | 360 |
| attaagaaat tgatgatgaa attttaaatt taaactaatg gaatcaagaa agaatgaaag | 420 |
| gaaatataca atgcctacga ttaataaaag gaagtttatt agattttgtg ttagaaaca | 479 |

<210> SEQ ID NO 5
<211> LENGTH: 480
<212> TYPE: DNA
<213> ORGANISM: Staphylococcus aureus

<400> SEQUENCE: 5

| | |
|---|---|
| ttcgtcattg gcggatcaaa cggcctgcac aaggacgtct tacaacgcag taactacgca | 60 |
| ctatcattca gcaaaatgac attcccacat caaatgatgc gggttgtgtt aattgaacaa | 120 |
| gtgtacagag catttaagat tatgcgtgga gaagcgtatc ataaataaaa ctaaaaatta | 180 |
| ggttgtgtat aatttaaaaa tttaatgaga tgtggaggaa ttacatatat gaaatattgg | 240 |
| attataccct gcaatatcat acgatgttta tagagtgttt aataaaccat ttttcaacta | 300 |
| ttgatgatct agaatatata ataactgtac aaattatatt gattatggaa ctacaattaa | 360 |
| attaagaaat tgatgatgaa attttaaatt taaactaatg gaatcaagaa agaatgaaag | 420 |
| gaaatataac atgcctacga ttaataaaag gaagtttatt agattttgtg ttagaaacag | 480 |

<210> SEQ ID NO 6
<211> LENGTH: 480
<212> TYPE: DNA
<213> ORGANISM: Staphylococcus aureus

<400> SEQUENCE: 6

| | |
|---|---|
| ttcgtcattg gcggatcaaa cggcctgcac aaggacgtct tacaacgcag taactacgca | 60 |
| ctatcattca gcaaaatgac atccccacat caaatgatgc gggttgtgtt aattgaacaa | 120 |
| gtgtacagag catttaagat tatgcgtgga gaagcgtatc ataaataaaa ctaaaaatta | 180 |
| ggttgtgtat aatttaaaaa tttaatgaga tgtggaggaa ttacatatat gaaatattgg | 240 |
| attataccct gcaatatcat acgatgttta tagagtgttt aataaaccat ttttcaacta | 300 |
| ttgatgatct agaatatata ataactgtac aaattatatt gattatggaa ctacaattaa | 360 |
| attaagaaat tgatgatgaa attttaaatt taaactaatg gaatcaagaa agaatgaaag | 420 |
| gaaatataca atgcctacga ttaataaaag gaagtttatt agatttgtgt tagaaacagt | 480 |

<210> SEQ ID NO 7
<211> LENGTH: 480

```
<212> TYPE: DNA
<213> ORGANISM: Staphylococcus aureus

<400> SEQUENCE: 7
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaagcgtatc ataaataaaa ctaaaaatta     180
ggttgtgtat aatttaaaaa tttaatgaga tgtggaggaa ttacatatat gaaatattgg     240
attatacctt gcaatatcat acgatgttta tagagtgttt aataaaccat ttttcaacta     300 tgatgatct agaatatata ataactgtac aaattatatt gattatggaa ctacaattaa     360
attaagaaat tgatgatgaa attttaaatt taaactaatg aatcaagaa agaatgaaag     420 gaaatataca atgcctacga ttaataaaag gaagtttatt agattttgtg ttagaaacag     480

<210> SEQ ID NO 8
<211> LENGTH: 309
<212> TYPE: DNA
<213> ORGANISM: Staphylococcus aureus
<220> FEATURE:
<221> NAME/KEY: misc_feature
<222> LOCATION: 237
<223> OTHER INFORMATION: n = A,T,C or G

<400> SEQUENCE: 8
ggcggatcaa acggcctgca caaggacgtc ttacaacgca gtaactacgc actatcattc      60
agcaaaatga cattcccaca tcaaatgatg cgggttgtgt taattgaaca agtgtacaga     120
gcatttaaga ttatgcgtgg agaagcgtat cataaataaa actaaaaatt aggttgtgta     180
taatttaaaa atctaatgag atgtggagga attacatata tgaaatattg gattatncct     240
tgcaatatca tacgatgttt atagagtgtt taataaacca tttttcaact attgatgatc     300
tacaatata                                                             309

<210> SEQ ID NO 9
<211> LENGTH: 471
<212> TYPE: DNA
<213> ORGANISM: Staphylococcus aureus

<400> SEQUENCE: 9
ttggcggatc aaacggcctg cacaaggacg tcttacaacg cagtaactac gcactatcat      60
tcagcaaaat gacattccca catcaaatga tgcgggttgt gttaattgaa caagtgtaca     120
gagcatttaa gattatgcgt ggagaagcgt atcataaata aaactaaaaa ttaggttgtg     180
tataatttaa aaatttaatg agatgtggag gaattacata tatgaaatat tggattatac     240
cttgcaatat catacgatgt ttatagagtg tttaataaac catttttcaa ctattgatga     300
tctagaatat ataataactg tacaaattat attgattatg gaactacaat taaattaaga     360
aattgatgat gaaattttaa atttaaacta tggaatcaa gaaagaatga aggaaatat     420 acaatgccta cgattaataa aaggaagttt attagatttt gtgttagaaa c              471

<210> SEQ ID NO 10
<211> LENGTH: 480
<212> TYPE: DNA
<213> ORGANISM: Staphylococcus aureus

<400> SEQUENCE: 10
ttcgtcattg gcggatcaaa cggcctgcac aaggacgtct tacaacgcag taactacgca      60
```

```
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240 attataccett gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaacag    480
```

```
<210> SEQ ID NO 11
<211> LENGTH: 480
<212> TYPE: DNA
<213> ORGANISM: Staphylococcus aureus

<400> SEQUENCE: 11
```

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240 attataccett gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaacag    480
```

```
<210> SEQ ID NO 12
<211> LENGTH: 480
<212> TYPE: DNA
<213> ORGANISM: Staphylococcus aureus

<400> SEQUENCE: 12
```

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240 attataccett gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaacag    480
```

```
<210> SEQ ID NO 13
<211> LENGTH: 478
<212> TYPE: DNA
<213> ORGANISM: Staphylococcus aureus

<400> SEQUENCE: 13
```

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240 attataccett gcaatatcat acgatgttta tagagtgttt aataaaccat ttttcaacta    300
```

```
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaac     478
```

<210> SEQ ID NO 14
<211> LENGTH: 479
<212> TYPE: DNA
<213> ORGANISM: Staphylococcus aureus

<400> SEQUENCE: 14

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcaagaa agaatgaaag    420
gaaatataca atgcctacga ttaataaaag gaagtttatt agattttgtg ttagaaaca    479
```

<210> SEQ ID NO 15
<211> LENGTH: 480
<212> TYPE: DNA
<213> ORGANISM: Staphylococcus aureus
<220> FEATURE:
<221> NAME/KEY: misc_feature
<222> LOCATION: 406
<223> OTHER INFORMATION: n = A,T,C or G

<400> SEQUENCE: 15

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
attaagaaat tgatgatgaa attttaaatt taaactaatg gaatcncgaa agaatgaaag    420
gaaatataca atgcctacga ttaataaaag gaagtttatt agattttgtg ttagaaacag    480
```

<210> SEQ ID NO 16
<211> LENGTH: 480
<212> TYPE: DNA
<213> ORGANISM: Staphylococcus aureus

<400> SEQUENCE: 16

```
ttcgtcattg gcggatcaaa cggcctgcac aaggacgtct tacaacgcag taactacgca     60
ctatcattca gcaaaatgac attcccacat caaatgatgc gggttgtgtt aattgaacaa    120
gtgtacagag catttaagat tatgcgtgga gaagcgtatc ataaataaaa ctaaaaatta    180
ggttgtgtat aatttaaaaa tttaatgaga tgtggaggaa ttacatatat gaaatattgg    240
attatacctt gcaatatcat acgatgttta tagagtgttt aataaaccat ttttcaacta    300
ttgatgatct agaatatata ataactgtac aaattatatt gattatggaa ctacaattaa    360
```
attaagaaat tgatgatgaa attttaaatt taaactaatg gaatcaagaa agaatgaaag      420
gaaatataca atgcctacga ttaataaaag gaagtttatt agattttgtg ttagaaacag      480

<210> SEQ ID NO 17
<211> LENGTH: 480
<212> TYPE: DNA
<213> ORGANISM: Staphylococcus aureus

<400> SEQUENCE: 17
ttcgtcattg gcggatcaaa cggcctgcac aaggacgtct tacaacgcag taactacgca       60
ctatcattca gcaaaatgac attcccacat caaatgatgc gggttgtgtt aattgaacaa      120
gtgtacagag catttaagat tatgcgtgga gaagcatatc ataaatgatg cggttttttc      180
agccgcttca taagggatt ttgaatgtat cagaacatat gaggtttatg tgaattgctg      240
ttatgttttt aagaagctta tcataagtaa tgaggttcat gatttttgac atagttagcc      300
tccgcagtct ttcatttcaa gtaaataata gcgaaatatt ctttatactg aatacttata      360
gtgaagcaaa gttctagctt tgagaaaatt ctttctgcaa ctaaatatag taaattacgg      420
taaaatataa ataagtacat attgaagaaa atgagacata atatatttta taataggagg      480

<210> SEQ ID NO 18
<211> LENGTH: 480
<212> TYPE: DNA
<213> ORGANISM: Staphylococcus aureus

<400> SEQUENCE: 18
ttcgtcattg gcggatcaaa cggcctgcac aaggacgtct tacaacgcag taactacgca       60
ctatcattca gcaaaatgac attcccacat caaatgatgc gggttgtgtt aattgagcaa      120
gtgtatagag catttaagat tatgcgtgga gaagcatatc ataaatgatg cggttttttc      180
agccgcttca taagggatt ttgaatgtat cagaacatat gaggtttatg tgaattgctg      240
ttatgttttt aagaagctta tcataagtaa tgaggttcat gatttttgac atagttagcc      300
tccgcagtct ttcatttcaa gtaaataata gcgaaatatt ctttatactg aatacttata      360
gtgaagcaaa gttctagctt tgagaaaatt ctttctgcaa ctaaatatag taaattacgg      420
taaaatataa ataagtacat attgaagaaa atgagacata atatatttta taataggagg      480

<210> SEQ ID NO 19
<211> LENGTH: 458
<212> TYPE: DNA
<213> ORGANISM: Staphylococcus aureus

<400> SEQUENCE: 19
ttcgtcattg gcggatcaaa cggcctgcac aaggacgtct tacaacgcag taactacgca       60
ctatcattca gcaaaatgac attcccacat caaatgatgc gggttgtgtt aattgaacaa      120
gtgtacagag catttaagat tatgcgtgga gaagcatatc ataaatgatg cggttttttc      180
agccgcttca taagggatt ttgaatgtat cagaacatat gaggtttatg tgaattgctg      240
ttatgttttt aagaagctta tcataagtaa tgaggttcat gatttttgac atagttagcc      300
tccgcagtct ttcatttcaa gtaaataata gcgaaatatt ctttatactg aatacttata      360
gtgaagcaaa gttctagctt tgagaaaatt ctttctgcaa ctaaatatag taaattacgg      420
taaaatataa ataagtacat attgaagaaa atgagaca                              458

<210> SEQ ID NO 20
<211> LENGTH: 385

<212> TYPE: DNA
<213> ORGANISM: Staphylococcus aureus

<400> SEQUENCE: 20

```
ttcgtcattg gcggatcaaa cggcctgcac aaggacgtct tacaacgcag taactacgca      60
ctatcattca gcaaaatgac attcccacat caaatgatgc gggttgtgtt aattgagcaa     120
gtgtatagag catttaagat tatgcgtgga gaagcttatc ataagtaatg aggttcatga     180
tttttgacat agttagcctc cgcagtcttt catttcaagt aaataatagc gaaatattct     240
ttatactgaa tacttatagt gaagcaaagt tctagctttg agaaaattct ttctgcaact     300
aaatatagta aattacggta aaatataaat aagtacatat tgaagaaaat gagacataat     360
atattttata ataggaggga atttc                                           385
```

<210> SEQ ID NO 21
<211> LENGTH: 385
<212> TYPE: DNA
<213> ORGANISM: Staphylococcus aureus

<400> SEQUENCE: 21

```
ttcgtcattg gcggatcaaa cggcctgcac aaggacgtct tacaacgcag taactacgca      60
ctatcattca gcaaaatgac attcccacat caaatgatgc gggttgtgtt aattgagcaa     120
gtgtatagag catttaagat tatgcgtgga gaagcttatc ataagtaatg aggttcatga     180
tttttgacat agttagcctc cgcagtcttt catttcaagt aaataatagc gaaatattct     240
ttatactgaa tacttatagt gaagcaaagt tctagctttg agaaaattct ttctgcaact     300
aaatatagta aattacggta aaatataaat aagtacatat tgaagaaaat gagacataat     360
atattttata ataggaggga atttc                                           385
```

<210> SEQ ID NO 22
<211> LENGTH: 385
<212> TYPE: DNA
<213> ORGANISM: Staphylococcus aureus

<400> SEQUENCE: 22

```
ttcgtcattg gcggatcaaa cggcctgcac aaggacgtct tacaacgcag taactacgca      60
ctatcattca gcaaaatgac attcccacat caaatgatgc gggttgtgtt aattgagcaa     120
gtgtatagag catttaagat tatgcgtgga gaagcttatc ataagtaatg aggttcatga     180
tttttgacat agttagcctc cgcagtcttt catttcaagt aaataatagc gaaatattct     240
ttatactgaa tacttatagt gaagcaaagt tctagctttg agaaaattct ttctgcaact     300
aaatatagta aattacggta aaatataaat aagtacatat tgaagaaaat gagacataat     360
atattttata ataggaggga atttc                                           385
```

<210> SEQ ID NO 23
<211> LENGTH: 385
<212> TYPE: DNA
<213> ORGANISM: Staphylococcus aureus

<400> SEQUENCE: 23

```
ttcgtcattg gcggatcaaa cggcctgcac aaggacgtct tacaacgcag taactacgcg      60
ctatcattca gcaaaatgac attcccacat caaatgatgc gggttgtgtt aattgaacaa     120
gtgtacaaag catttaagat tatgcgagga gaagcttatc ataagtaatg aggttcatga     180
tttttgacat agttagcctc cgcagtcttt catttcaagt aaataatagc gaaatattct     240
```

```
ttatactgaa tacttatagt gaagcaaagt tctagctttg agaaaattct ttctgcaact    300
aaatatagta aattacggta aaatataaat aagtacatat tgaagaaaat gagacataat    360
atattttata ataggaggga atttc                                          385
```

<210> SEQ ID NO 24
<211> LENGTH: 340
<212> TYPE: DNA
<213> ORGANISM: Staphylococcus aureus

<400> SEQUENCE: 24

```
cgcagtaact acgcgctatc attcagcaaa atgacattcc cacatcaaat gatgcgggtt     60
gtgttagttg agcaagtgta catagcattt aagattatgc gaggagaagc ttatcataag    120
taatgaggtt catgattttt gacatagtta gcctccgcag tctttcattt caagtaaata    180
atagcgaaat attctttata ctgaatactt atagtgaagc aaagttctag ctttgagaaa    240 attcttctg caactaaata tagtaaatta cggtaaaata taaataagta catattgaag    300
aaaatgagac ataatatatt ttataatagg agggaatttc                          340
```

<210> SEQ ID NO 25
<211> LENGTH: 369
<212> TYPE: DNA
<213> ORGANISM: Staphylococcus aureus

<400> SEQUENCE: 25

```
caaacggcct gcacaaggac gtcttacaac gcagtaacta cgcactatca ttcagcaaaa     60
tgacattccc acatcaaatg atgcggggttg tgttaattga acaagtgtac agagcattta   120
agattatgcg aggagaagct tatcataagt aatgaggttc atgattttg acatagttag    180 cctccgcagt ctttcatttc aagtaaataa tagcgaaata ttctttatac tgaatactta    240
tagtgaagca aagttctagc tttgagaaaa ttctttctgc aactaaatat agtaaattac    300
ggtaaaatat aaataagtac atattgaaga aaatgagaca taatatattt tataatagga    360
gggaatttc                                                            369
```

<210> SEQ ID NO 26
<211> LENGTH: 3050
<212> TYPE: DNA
<213> ORGANISM: Staphylococcus aureus

<400> SEQUENCE: 26

```
aatttggtaa acctcaaaag gtaattacag atcaggcacc ttcaacgaag gtagcaatgg     60
ctaaagtaat taaagctttt aaacttaaac ctgactgtca ttgtacatcg aaatatctga    120
ataacctcat tgagcaagat caccgtcata ttaaagtaag aaagacaagg tatcaaagta    180
tcaatacagc aaagaatact ttaaaaggta ttgaatgtat tcacgctcta tataaaaaga    240
accgcaggtc tcttcagatc tacggatttt cgccatgcca cgaaattagc atcatgctag    300
caagttaagc gaacactgac atgataaatt agtggttagc tatattttt tactttgcaa    360 cagaaccgaa ataatctct tcaatttatt tttatatgaa tcctgtgact caatgattgt    420
aatatctaaa gatttcagtt catccatgac aatgttcttt tcaacatttt ttatagcaaa    480
ttgattaaat aaattctcta atttctcccg tttgatttca ctaccataga ttatattatc    540
attgatatag tcaatgaata atgacaaatt atcactcata acagtcccaa ccccttttatt    600 ttgatagact aattatcttc atcattgtaa acaaattac acccttttaa tttaactcaa    660
cttaaatatc gacaaattaa aaaacaataa aattacttga atattattca taatatatta    720
```

```
acaactttat tatactgctc tttatatata aaatcattaa taattaaaca agccttaaaa    780
tatttaactt ttttgtgatt attacacatt atcttatctg ctctttatca ccataaaaat    840
agaaaaaaca agattcctaa agaatatagg aatcttgttt cagactgtgg acaaactgat    900
tttttatcag ttagcttatt tagaaagttt tatttaaatt acagtttcta ttttattag     960 atcacaattt tattttagct cttgttcaag taatcatttt tcgccaaaaa ctttatactg   1020
aatagcttct acattaaata cttgtcaatg agatcatcta catctttaaa ttcagaataa   1080
ttcgcatatg gatctataaa ataaaattgt ggttctttac cggaaacatt aaatattctt   1140
aatattaaat atttctgctt atattctttc atagcaaaca tttcatttag cgacataaaa   1200
aatggttcct caatactaga agatgtagat gttttaattt caataaattt ttctacagct   1260
ttatctgtat ttgttggatc aaaagctact aaatcatagc catgaccgtg ttgagagcct   1320
ggattatcat ttaaaatatt cctaaactgt tctttcttat cttcgtctat tttattatca   1380
attagctcat taaagtaatt tagcgctaat ttttctccaa ctttaccggt taatttattc   1440
tctttatttg attttttcaat ttctgaatca tttttagtag tctttgatac acctttttta   1500
tattttggaa ttattccttt aggtgcttcc acttccttga gtgtcttatc tttttgtgct   1560
gttctaattt cttcaatttc gctgtcttcc tgtatttcgt ctatgctatt gaccaagcta   1620
tcataggatg ttttttgtaac ttttgaagct aattcattaa atagttctaa aaatttcttt   1680
aaatcctcta gcatatcttc ttctgtgaat ccttcattca aatcataata tttgaatctt   1740
attgatccat gagaatatcc tgatggataa tcatttttta aatcataaga tgaatcttta   1800
ttttctgcgt aataaaatct tccagtatta aattcatttg atgtaatata tttattgagt   1860
tcggaagata aagttaatgc tcttgttttt gcagcatttt tatcccgcgg aaacatatca   1920
cttatctttg accatccttg attcaaagat aagtatatgc cttctccttc cggatgaaaa   1980
agatatacca ataatgtcc atcctttgtt tcttttgtta tattctcatc atatattgaa   2040
atccaaggaa ctttactata gttcccagta gcaaccttcc ctacaactga atatttatct   2100
tcttttatat gcactttttaa ctgcttgggt aacttatcat ggactaaagt tttatataga   2160
tcacctttat cccaatcaga ttttttaact acattattgg tacgtttctc tttaattaat   2220
ttaaggacct gcataaagtt gtctatcatt tgaaattccc tcctattata aaatatatta   2280
tgtctcattt tcttcaatat gtacttattt atattttacc gtaatttact atatttagtt   2340
gcagaaagaa ttttctcaaa gctagaactt tgcttcacta taagtattca gtataaagaa   2400
tatttcgcta ttatttactt gaaatgaaag actgcggagg ctaactatgt caaaaatcat   2460
gaacctcatt acttatgata agcttcttaa aaacataaca gcaattcaca taaacctcat   2520
atgttctgat acattcaaaa tcccttatg aagcggctga aaaaaccgca tcattatga    2580 tatgcttctc ctcgcataat cttaaatgct ctgtacactt gttcaattaa cacaacccgc   2640
atcatttgat gtgggaatgt catttttgctg aatgatagtg cgtagttact gcgttgtaag   2700
acgtccttgt gcaggccgtt tgatccgcca atgacgaaaa caaagtcgct ttgcccttgg   2760
gtcatgcgtt ggttcaattc ttgggccaat ccttcggaag atagcatctt tccttgtatt   2820
tctaatgtaa tgactgtgga ttgtggtttg attttggcta gtattcgttg gccttctttt   2880
tcttttactt gctcaatttc tttgtcactc atattttctg gtgcttttc gtctggaact    2940 tctatgatgt ctatcttggt gtatgggcct aaacgttttt catattctgc tatggcttgc   3000
ttccaatatt tctctttag tttccctaca gctaaaatgg tgattttcat              3050
```

<210> SEQ ID NO 27
<211> LENGTH: 657
<212> TYPE: DNA
<213> ORGANISM: Staphylococcus aureus

<400> SEQUENCE: 27

| | | | | | |
|---|---|---|---|---|---|
| ccaccttcat | atgacgtcta | tccatttatg | tatggcatga | gtaacgaaga | atataataaa | 60 |
| ttaaccgaag | ataaaaaaga | acctctgctc | aacaagttcc | agattacaac | ttcaccaggt | 120 |
| tcaactcaaa | aaatattaac | agcaatgatt | gggttaaata | caaaacatt | agacgataaa | 180 |
| acaagttata | aaatcgatgg | taaaggttgg | caaaaagata | atcttggggt | tggttacaac | 240 |
| gttacaagat | atgaagtggt | aaatggtaat | atcgacttaa | aacaagcaat | agaatcatca | 300 |
| gataacattt | tctttgctag | agtagcactc | gaattaggca | gtaagaaatt | tgaaaaaggc | 360 |
| atgaaaaaac | taggtgttgg | tgaagatata | ccaagtgatt | atccattta | taatgctcaa | 420 |
| atttcaaaca | aaatttaga | taatgaaata | ttattagctg | attcaggtta | cggacaaggt | 480 |
| gaaatactga | ttaacccagt | acagatcctt | tcaatctata | gcgcattaga | aaataatggc | 540 |
| aatattaacg | cacctcactt | attaaaagac | acgaaaaaca | agtttggaa | gaaaatatt | 600 |
| atttccaaag | aaaatatcaa | tctattaact | gatggtatgc | aacaagtcgt | aaataaa | 657 |

<210> SEQ ID NO 28
<211> LENGTH: 782
<212> TYPE: DNA
<213> ORGANISM: Staphylococcus aureus

<400> SEQUENCE: 28

| | | | | | |
|---|---|---|---|---|---|
| caccttcata | tgacgtctat | ccatttatgt | atggcatgag | taacgaagaa | tataataaat | 60 |
| taaccgaaga | taaaaagaa | cctctgctca | acaagttcca | gattacaact | tcaccaggtt | 120 |
| caactcaaaa | aatattaaca | gcaatgattg | ggttaaataa | caaaacatta | gacgataaaa | 180 |
| caagttataa | aatcgatggt | aaaggttggc | aaaaagataa | atcttggggt | ggttacaacg | 240 |
| ttacaagata | tgaagtggta | aatggtaata | tcgacttaaa | acaagcaata | gaatcatcag | 300 |
| ataacatttt | ctttgctaga | gtagcactcg | aattaggcag | taagaaattt | gaaaaaggca | 360 |
| tgaaaaaact | aggtgttggt | gaagatatac | caagtgatta | tccattttat | aatgctcaaa | 420 |
| tttcaaacaa | aaatttagat | aatgaaatat | tattagctga | ttcaggttac | ggacaaggtg | 480 |
| aaatactgat | taacccagta | cagatccttt | caatctatag | cgcattagaa | aataatggca | 540 |
| atattaacgc | acctcactta | ttaaaagaca | cgaaaaacaa | agtttggaag | aaaatatta | 600 |
| tttccaaaga | aaatatcaat | ctattaactg | atggtatgca | acaagtcgta | aataaaacac | 660 |
| ataaagaaga | tatttataga | tcttatgcaa | acttaattgg | caaatccggt | actgcagaac | 720 |
| tcaaaatgaa | acaaggagaa | actggcagac | aaattgggtg | gtttatatca | tatgataaag | 780 |
| at | | | | | | 782 |

<210> SEQ ID NO 29
<211> LENGTH: 744
<212> TYPE: DNA
<213> ORGANISM: Staphylococcus aureus

<400> SEQUENCE: 29

| | | | | | |
|---|---|---|---|---|---|
| tatgacgtct | atccatttat | gtatggcatg | agtaacgaag | aatataataa | attaaccgaa | 60 |
| gataaaaaag | aacctctgct | caacaagttc | cagattacaa | cttcaccagg | ttcaactcaa | 120 |
| aaatattaa | cagcaatgat | tgggttaaat | aacaaaacat | tagacgataa | aacaagttat | 180 |

```
aaaatcgatg gtaaaggttg gcaaaaagat aaatcttggg gtggttacaa cgttacaaga    240
tatgaagtgg taaatggtaa tatcgactta aaacaagcaa tagaatcatc agataacatt    300
ttctttgcta gagtagcact cgaattaggc agtaagaaat tgaaaaagg catgaaaaaa     360 ctaggtgttg gtgaagatat accaagtgat tatccatttt ataatgctca aatttcaaac    420
aaaaatttag ataatgaaat attattagct gattcaggtt acggacaagg tgaaatactg    480
attaacccag tacagatcct ttcaatctat agcgcattag aaaataatgg caatattaac    540
gcacctcact tattaaaaga cacgaaaaac aaagtttgga agaaaaatat tatttccaaa    600
gaaaatatca atctattaac tgatggtatg caacaagtcg taaataaaac acataaagaa    660
gatatttata gatcttatgc aaacttaatt ggcaaatccg gtactgcaga actcaaaatg    720
aaacaaggag aaactggcag acaa                                          744

<210> SEQ ID NO 30
<211> LENGTH: 652
<212> TYPE: DNA
<213> ORGANISM: Staphylococcus aureus

<400> SEQUENCE: 30
ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aatattaac agcaatgatt gggttaaata caaaacatt agacgataaa      180 acaagttata aatcgatgg taaggttgg caaaaagata aatcttgggg tggttacaac      240
gttacaagat atgaagtggt aaatggtaat atcgacttaa acaagcaat agaatcatca    300 gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aa            652

<210> SEQ ID NO 31
<211> LENGTH: 2436
<212> TYPE: DNA
<213> ORGANISM: Staphylococcus aureus

<400> SEQUENCE: 31
ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aatattaac agcaatgatt gggttaaata caaaacatt agacgataaa      180 acaagttata aatcgatgg taaggttgg caaaaagata aatcttgggg tggttacaac      240
gttacaagat atgaagtggt aaatggtaat atcgacttaa acaagcaat agaatcatca    300 gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
```

```
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga acaaggaga aactggcaga caaattgggt ggtttatatc atatgataaa    780
gataatccaa acatgatgat ggctattaat gttaaagatg tacaagataa aggaatggct    840
agctacaatg ccaaaatctc aggtaaagtg tatgatgagc tatatgagaa cggtaataaa    900
aaatacgata tagatgaata acaaaacagt gaagcaatcc gtaacgatgg ttgcttcact    960
gttttattat gaattattaa taagtgctgt tacttctccc ttaaatacaa tttcttcatt   1020
ttcattgtat gttgaaagtg acactgtaac gagtccattt tcttttttta tggatttctt   1080
atttgtaatt tcagcgataa cgtacaatgt attacctggg tatacaggtt taataaattt   1140
aacgttattc atttgtgttc ctgctacaac ttcttctccg tatttacctt cttctaccca   1200
taatttaaat gatattgaaa gtgtatgcat gccagatgca atgatacctt taaatctact   1260
ttgttctgct ttttctttat ctatatgcat atattgagga tcaaaagttg ttgcaaattg   1320
gataatttct tcttctgtaa tatgaaggct ttttgttttg aatgtttctc ctactataaa   1380
atcatcgtat ttcatatatg tctctctttc ttattcaaat taattttta gtatgtaaca   1440 tgttaaaggt aagtctaccg tcactgaaac gtaagactca cctctaactt tctattgaga   1500
caaatgcacc attttatctg cattgtctgt aaagatacca tcaactcccc aattagcaag   1560
ttggtttgca cgtgctggtt tgtttacagt ccatacgttc aattcataac ccgcttcttt   1620
taccattttt actttgctt tagtaagttt ggcatcttca gtgtttacta ttttagcatt   1680
acagtaatct aaaagtgttc tccagtcttc acgaaacgaa gttgtatgga atataactgc   1740
tctgttatat tgtggcatga tttcttctgc aagtttaaca agcacaacat taaagcttga   1800
aatgagcact tcttgattct gatttaagtt tgttaattgt tcttccactt gcttaaccat   1860
acttttagaa agtgctagtc cattcggtcc agtaatacct tttaattcta catttaaatt   1920
catattatat tcatttgcta tttttactac atcatcgaaa gttggcaaat gttcatcttt   1980 gaattttttca ccaaaccaag atcctgcaga agcatcttta atttcatcat aattcaattc   2040
agttatttcc ccggacatat ttgtagtccg ttctaaataa tcatcatgaa tgataatcag   2100
ttgttcatct tttgtaattg caacatctaa ctccaaccag tttataccttt ctacttctga   2160 agcagcttta aatgatgcaa ttgtatttttc cggagcttta ctaggtaatc ctctatgtcc   2220
atatacagtt agcatattac ctctccttgc attttttattt ttttaattaa cgtaactgta   2280
ttatcacatt aatcgcactt ttatttccat taaaaagaga tgaatatcat aaataaagaa   2340
gtcgatagat tcgtattgat tatggagtta atctacgtct catctcattt ttaaaaaatc   2400
atttatgtcc caagctccat tttgtaatca agtcta                              2436
```

<210> SEQ ID NO 32
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 32

```
cgcttgccac atcaaatgat gcgggttgtg caagcg                               36
```

<210> SEQ ID NO 33
<211> LENGTH: 336
<212> TYPE: DNA
<213> ORGANISM: Staphylococcus epidermis

```
<400> SEQUENCE: 33
ctcattactt atgataagct tcttaaaaac ataacagcaa ttcacataaa cctcatatgt      60
tctgatacat tcaaaatccc tttatgaagc ggctgaaaaa accgcatcat ttatgatatg     120
cttcgcctct catgatctta aatgcgcgat aaatttgttc gatcaatatg acgcgcatat     180
ttggtgtggg aaggtcatat tgctaaaaga taaagcatag ttgctgcgtt gtaagacgtc     240
ttggtgtaaa ccattggagc cacctatgac aaatgtaaag tcgctttgac cttgtgtcat     300
gcgtgtttgt agttctttag cgagtccttc tgaaga                              336

<210> SEQ ID NO 34
<211> LENGTH: 260
<212> TYPE: DNA
<213> ORGANISM: Staphylococcus haemolyticus

<400> SEQUENCE: 34
ctcattactt atgataagct tcttaaaaac ataacagcaa tccacataaa cctcatatgt      60
tctgatacat tcaaaatccc tttatgaagc ggctgaaaaa accgcatcat ttatgatatg     120
cttccctcgc atgattttaa atgctctgta tacttgctcg attaagacaa cgcgcatcat     180 tgatgtggg aatgtcattt tactgaatga aagtgcgtag ttgctgcgtt gtaagacgtc      240
ctcatgcaat ccatttgatc                                                260

<210> SEQ ID NO 35
<211> LENGTH: 225
<212> TYPE: DNA
<213> ORGANISM: Staphylococcus aureus

<400> SEQUENCE: 35
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaggcgtatc acaaataaaa ctaaaaatgg     180
agtaactatt aatatagtat aaattcaata tggtgataaa aacag                    225

<210> SEQ ID NO 36
<211> LENGTH: 225
<212> TYPE: DNA
<213> ORGANISM: Staphylococcus aureus

<400> SEQUENCE: 36
ttcgtcattg gcggatcaaa cggcctgcac aaggacgtct tacaacgcag taactacgca      60
ctatcattca gcaaaatgac attcccacat caaatgatgc gggttgtgtt aattgaacaa     120
gtgtacagag catttaagat tatgcgtgga gaggcgtatc acaaataaaa ctaaaaatgg     180
agtaactatt aatatagtat aaattcaata tggtgataaa aacag                    225

<210> SEQ ID NO 37
<211> LENGTH: 225
<212> TYPE: DNA
<213> ORGANISM: Staphylococcus aureus

<400> SEQUENCE: 37
ttcgtcattg gcggatcaaa cggcctgcac aaggacgtct tacaacgtag taactacgca      60
ctatcattca gcaaaatgac atttccacat caaatgatgc gggttgtgtt aattgaacaa     120
gtgtacagag catttaagat tatgcgtgga gaggcgtatc ataagtaatg aggttcatga     180
```
tttttgacat agttagcctc cgcagtctttt caagtaaata atatc         225

<210> SEQ ID NO 38
<211> LENGTH: 225
<212> TYPE: DNA
<213> ORGANISM: Staphylococcus aureus

<400> SEQUENCE: 38
ttcgtcattg gcggatcaaa cggcctgcac aaggacgtct tacaacgcag taactacgca    60
ctatcattta gcaaaatgac attcccacat caaatgatgc gggttgtgtt aattgaacaa   120
gtgtatagag catttaagat tatgcgtgga gaggcgtatc ataagtgatg cttgttagaa   180
tgattttttaa caatatgaaa tagctgtgga agctcaaaca tttgt                  225

<210> SEQ ID NO 39
<211> LENGTH: 1500
<212> TYPE: DNA
<213> ORGANISM: Staphylococcus aureus

<400> SEQUENCE: 39
tgagtctggt aaagatacac aaccaattgg taaagagaaa gtgatgaatc cagcgaaaca    60
accagcgaca ggtaaagttg tgttgttacc agcgcataga ggaactgtta gtagcggtac   120
agaaggttct gatcgcgcat tagaaggaac tgctgtatca agtaagagtg ggaaacaatt   180
ggctaacatg tcagcgccta aaggtagcgc acatgagaaa cagttaccaa aaactggaac   240
tgatcaaagt tcaagcccag cagcgatgtt tgtattagta acaggtatag gtttaatcgc   300
gactgtacga cgtagaaaag ctagctaaaa tatattgaaa acaatactac tgtatttctt   360
aaataagagg tacggtagtg ttttttttatg gaaaaaagct ataaccgttg ataaatatgg   420
gatataaaaa cggggataag taataagaca tcaaggtatt tatccacaga aatggggata   480
gttatccaga attgtgtaca atttaaagag aaatacccac aatgcccaca gagttatcca   540
caaatacaca agttatacac tgaaaattgg gcatgaatgt cagaaaaata tcaaaaactg   600
caaaaaaact tggtataata agagggaaaa gtgtgaacaa gttaataact tgtggataac   660
tggaaagttg ataacaattt ggaggaccaa acgacatgaa atcaccatt ttagctgtag   720
ggaaactaaa agagaaatat tggaagcaag ccatagcaga atatgaaaaa cgtttaggcc   780
catacaccaa gatagacatc atagaagtta cagacgaaaa agcaccagaa atatgagcg   840
acaaagaaat cgagcaagta aagaaaaag aaggccaacg aatactagcc aaaatcaaac   900
cacaatccac agtcattaca ttagaaatac aaggaaagat gctatcttcc gaaggattgg   960
cccaagaatt gaaccaacgc atgacccaag gcaaagcga ctttgtattc gtcattggcg  1020
gatcaaacgg cctgcacaag gacgtcttac aacgtagtaa ctacgcacta tcattcagca  1080
aaatgacatt tccacatcaa atgatgcggg ttgtgttaat tgaacaagtg tacagagcat  1140
ttaagattat gcgtggagaa gcttatcata atgatgcgg ttttttcttg aaaaatttaa  1200
ttagatatta gaatccttta atttatttga aaatcagaag tgagtaacaa tggtaagtga  1260
aatagttagt gcaataattg gaattatagg gatttattga gatgtatgga gatgcgggc  1320
atttatcgag tagattacaa ttagagcatg taggtgatt gcttttttcat gcaagtaaag  1380
ataaactttt aaaaatccta taagaattta gaaactttag aataactaaa tattaaaaaa  1440
atatcgtatg aaagtgaaat taggatgaga gaccatagct aaattaaaaa ttttagcaaa  1500

<210> SEQ ID NO 40
<211> LENGTH: 1501

```
<212> TYPE: DNA
<213> ORGANISM: Staphylococcus aureus

<400> SEQUENCE: 40
ttgcacaacc aattggtaaa gacaaagtga tggatccagc gaaacaacca gcgccaagta    60
aagttgtatt gttgccagcg catagaggaa ctgttagtag tggtagagaa ggttctgatc   120
gcgcattgga aggaactgct gtatcaagta agagcgggaa acaattggct agcatgtcag   180
cgcctaaagg tagcacacat gagaagcagt taccaaaaac tggaactgat caaagttcaa   240
gcccagcagc gatgtttgta ttagtagcag gtataggttt aattgcgact gtacgacgta   300
gaaaagctag ctaaaatata ttgaaaacaa tactactgta tttcttaaac aagaggtacg   360
gtagtgtttt tttatgaaaa aaagctataa ccgttgataa atatgggata taaaaacggg   420
gataagtaat aagacatcaa ggtatttatc cacagaaatg gggatagtta tccagaattg   480
tgtacaattt aaagagaaat acccacaatg cccacagagt tatccacaaa tacacaggtt   540
atacactaaa aattgggcat gaatgtcaga aaaatatcaa aaactgcaaa gaatattggt   600
ataataagag ggaacagtgt gaacaagtta ataacttgtg gataactgga agttgataa    660 caatttggag gaccaaacga catgaaaatc accattttag ctgtagggaa actaaaagag   720
aaatattgga agcaagccat agcagaatat gaaaaacgtt taggcccata ccaagata    780 gacatcatag aagttccaga cgaaaaagca ccagaaaata tgagcgacaa agaaattgag   840
caagtaaaag aaaagaagg ccaacgaata ctagccaaaa tcaaaccaca atcaacagtc    900
attacattag aaatacaagg aaagatgcta tcttccgaag gattgggccca agaattgaac   960 caacgcatga cccaagggca aagcgacttt gtattcgtca ttggcggatc aaacggcctg  1020
cacaaggacg tcttacaacg cagtaactac gcactatcat tcagcaaaat gacattccca  1080
catcaaatga tgcgggttgt gttaattgaa caagtgtaca gagcatttaa gattatgcgt  1140
ggagaagcat atcataaatg atgcggtttt ttcagccgct tcataaaggg attttgaatg  1200
tatcagaaca tatgaggttt atgtgaattg ctgttatgtt tttaagaagc ttatcataag  1260
taatgaggtt catgattttt gacatagtta gcctccgcag tctttcattt caagtaaata  1320
atagcgaaat attctttata ctgaatactt atagtgaagc aaagttctag ctttgagaaa  1380
attctttctg caactaaata tagtaaatta cggtaaaata taaataagta catattgaag  1440
aaaatgagac ataatatatt ttataatagg agggaatttc aaatgataga caactttatg  1500
c                                                                  1501

<210> SEQ ID NO 41
<211> LENGTH: 2480
<212> TYPE: DNA
<213> ORGANISM: Staphylococcus aureus

<400> SEQUENCE: 41
aaaccgtctg gcaaacgaat taatgctatt caaattttaa ataaagagac aggtaagttt    60
gaaaatattg atttaaaacg tgtatatcac gtaacgatga atgacttcac agcatcaggt   120
ggcgacggat atagtatgtt cggtggtcct agagaagaag gtatttcatt agatcaagta   180
ctagcaagtt atttaaaaac agctaactta gctaagtatg tacgacagga accacaacgt   240
atgttattag gtaaaccagc agtaagtgaa caaccagcta aggacaacaa ggtagcaaaa   300
ggtagtaagt ctggtaaaga tacacaacca attggtgacg acaaagtgat ggatccagcg   360
aaaaaaccag ctccaggtaa agttgtattg ttgctagcgc atagaggaac tgttagtagc   420
```

```
ggtacagaag gttctggtcg cacaatagaa ggagctactg tatcaagcaa gagtgggaaa      480
caattggcta aatgtcagt gcctaaaggt agcgcgcatg agaaacagtt accaaaaact       540
ggaactaatc aaagttcaag cccagaagcg atgtttgtat tattagcagg tataggttta     600
atcgcgactg tacgacgtag aaaagctagc taaaatatat tgaaataat actactgtat      660 ttcttaaata agaggtacgg tagtgttttt ttatgaaaaa aagcgataac cgttgataaa     720
tatgggatat aaaaacgagg ataagtaata agacatcaag gtgtttatcc acagaaatgg    780
ggatagttat ccagaattgt gtacaattta agagaaata cccacaatgc ccacagagtt     840
acccacaaat acacaggtta tacactaaaa atcgggcata atgtcagga aaatatcaaa      900 aactgcaaaa atattggta taataagagg gaacagtgtg aacaagttaa taacttgtgg     960
ataactggaa agttgataac aatttggagg accaaacgac atgaaaatca ccattttagc    1020
tgtagggaaa ctaaaagaga aatattggaa gcaagccata gcagaatatg aaaaacgttt    1080
aggcccatac accaagatag acatcataga agttccagac gaaaaagcac cagaaaatat    1140
gagtgacaaa gaaattgagc aagtaaaaga aaaagaaggc caacgaatac tagccaaaat    1200
caaaccacaa tccacagtca ttacattaga aatacaagga aagatgctat cttccgaagg    1260
attggcccaa gaattgaacc aacgcatgac ccaagggcaa agcgactttg ttttcgtcat    1320
tggcggatca aacggcctgc acaaggacgt cttacaacgc agtaactacg cactatcatt    1380
cagcaaaatg acattcccac atcaaatgat gcgggttgtg ttaattgaac aagtgtacag    1440
agcatttaag attatgcgag gagaagctta tcataagtaa tgaggttcat gattttttgac    1500 atagttagcc tccgcagtct ttcatttcaa gtaaataata gcgaaatatt ctttatactg    1560
aatacttata gtgaagcaaa gttctagctt tgagaaaatt ctttctgcaa ctaaatatag    1620
taaattacgg taaaatataa ataagtacat attgaagaaa atgagacata atatatttta    1680
taataggagg gaatttcaaa tgatagacaa ctttatgcag gtccttaaat taattaaaga    1740
gaaacgtacc aataatgtag ttaaaaaatc tgattgggat aaaggtgatc tatataaaac    1800
tttagtccat gataagttac ccaagcagtt aaaagtgcat ataaaagaag ataaatattc    1860
agttgtaggg aaggttgcta ctgggaacta tagtaaagtt ccttggattt caatatatga    1920
tgagaatata acaaaagaaa caaaggatgg atattatttg gtatatcttt ttcatccgga    1980
aggagaaggc atatacttat ctttgaatca aggatggtca aagataagtg atatgtttcc    2040
gcgggataaa aatgctgcaa acaaagagc attaacttta tcttccgaac tcaataaata    2100
tattacatca aatgaattta atactggaag atttttattac gcagaaaata agattcatc    2160 ttatgattta aaaaatgatt atccatcagg atattctcat ggatcaataa gattcaaata    2220
ttatgatttg aatgaaggat tcacagaaga agatatgcta gaggatttaa agaaattttt    2280
agaactattt aatgaattag cttcaaaagt tacaaaaaca tcctatgata gcttggtcaa    2340
tagcatagac gaaatacagg aagacagcga aattgaagaa attagaacag cacaaaaaga    2400
taagacactc aaggaagtgg aagcacctaa aggaataatt ccaaaatata aaaaaggtgt    2460
atcaaagact actaaaaatg                                                 2480
```

<210> SEQ ID NO 42
<211> LENGTH: 1045
<212> TYPE: DNA
<213> ORGANISM: Staphylococcus aureus

<400> SEQUENCE: 42

```
ccagtttttt gtttaatgaa caaggtaaat tacgagataa tatttgaaga aaacaataaa        60
```

```
gtagagatgg atttccatat cctctttagt agcggttttt atctgtaagg tttattaata      120
attaaataaa taggcgggat agttatatat agcttattaa tgaaagaata tgattattaa      180
tttagtatta tattttaata ttaaaaagaa gatatgaaat aattattcat accttccacc      240
ttacaataat tagttttcaa tcgaatatta agattattag tagtcttaaa agttaagact      300
tccttatatt aatgacctaa tttattattt gcctcatgaa ttatcttttt atttctttga      360
tatgtcccaa accacatcgt gatatacact acaataaata ttatgatgaa actaataata      420
ttctcaaagt tcagatggaa ccaacctgct agaatagcga gtgggaagaa taggattatc      480
atcaatataa agtgaactac agtctgtttt gttatactcc aatcggtatc tgtaaatatc      540
aaattaccat aagtaaacaa aattccaatc aatgcccata gtgctacaca tattagcata      600 ataccgctt cattaaagtt ttcataataa attttaccca taaaagaatc tggatatagt       660
ggtacatatt tatcccttga aaaaaataag tgaagtaatg acagaaatca taagaccagt      720
gaacgcacct ttttgaacag cgtggaataa ttttttcata gtgagatgga ccattccatt      780
tgtttctaac ttcaagtgat caatgtaatt tagattgata atttctgatt ttgaaatacg      840
cacgaatatt gaaccgacaa gctcttcaat ttggtaaagt cgctgataaa gttttaaagc      900
tttattattc attgttatcg catacctgtt tatcttctac tatgaactgt gcaatttgtt      960
ctagatcaat tgggtaaaca tgatggttct gttgcaaagt aaaaaaatat agctaaccac     1020
taatttatca tgtcagtgtt cgctt                                           1045

<210> SEQ ID NO 43
<211> LENGTH: 1118
<212> TYPE: DNA
<213> ORGANISM: Staphylococcus aureus

<400> SEQUENCE: 43
cagagcattt aagattatgc gtggagaagc gtaccacaaa tgatgcggtt ttttatccag       60
ttttttgttt aatgaacaag gtaaattacg agataatatt tgaagaaaac aataaagtag      120
agatggattc ccatatcctc tttagtagcg gttttatct gtaaggttta ttaataatta      180
aataaatagg cgggatagtt atatatagct tattaatgaa agaatatgat tattaattta      240
gtattatatt ttaatattaa aaagaagata tgaaataatt attcatacct tccaccttac      300
aataattagt tttcaatcga atattaagat tattagtagt cttaaaagtt aagcttcct      360 tatattaatg acctaattta ttatttgcct catgaattat ctttttattt ctttgatatg      420
tcccaaacca catcgtgata tacactacaa taaatattat gatgaaacta ataatattct      480
caaagttcag atggaaccaa cctgctagaa tagcgagtgg gaagaatagg attatcatca      540
atataaagtg aactacagtc tgttttgtta tactccaatc ggtatctgta aatatcaaat      600
taccataagt aaacaaaatt ccaatcaatg cccatagtgc tacacatatt agcataataa      660
ccgcttcatt aaagttttca taataaattt tacccataaa agaatctgga tatagtagta      720
catatttatc ccttgaaaaa aataagtgaa gtaatgacag aaatcataag accagtgaac      780
gcaccttttt gaacagcgtg gaataatttt tcatagtga gatggaccat tccatttgtt      840
tctaacttca agtgatcaat gtaatttaga ttgataattt ctgattttga aatacgcacg      900
aatattgaac cgacaagctc ttcaatttgg taaagtcgct gataaagttt taaagcttta      960
ttattcattg ttatcgcata cctgtttatc ttctactatg aactgtgcaa tttgttctag     1020
atcaattggg taaacatgat ggttctgttg caaagtaaaa aatatagct aaccactaat     1080
```

```
ttatcatgtc agtgttcgct taacttgcta gcatgatg              1118
```

<210> SEQ ID NO 44
<211> LENGTH: 1118
<212> TYPE: DNA
<213> ORGANISM: Staphylococcus aureus

<400> SEQUENCE: 44

```
cagagcattt aagattatgc gtggagaagc gtaccacaaa tgatgcggtt ttttatccag    60
tttttttgttt aatgaacaag gtaaattacg agataatatt tgaagaaaac aataaagtag   120
agatggattc ccatatcctc tttagtagcg gtttttatct gtaaggttta ttaataatta   180
aataaatagg cgggatagtt atatatagct tattaatgaa agaatatgat tattaattta   240
gtattatatt ttaatattaa aaagaagata tgaaataatt attcatacct tccaccttac   300
aataattagt tttcaatcga atattaagat tattagtagt cttaaaagtt aagacttcct   360
tatattaatg acctaattta ttatttgcct catgaattat cttttttattt ctttgatatg   420
tcccaaacca catcgtgata tacactacaa taaatattat gatgaaacta ataatattct   480
caaagttcag atggaaccaa cctgctagaa tagcgagtgg aagaatagg attatcatca   540
atataaagtg aactacagtc tgttttgtta tactccaatc ggtatctgta aatatcaaat   600
taccataagt aaacaaaatt ccaatcaatg cccatagtgc tacacatatt agcataataa   660
ccgcttcatt aaagttttca taataaattt tacccataaa agaatctgga tatagtagta   720
catatttatc ccttgaaaaa aataagtgaa gtaatgacag aaatcataag accagtgaac   780
gcaccttttt gaacagcgtg gaataatttt ttcatagtga gatggaccat tccatttgtt   840
tctaacttca gtgatcaat gtaatttaga ttgataattt ctgattttga aatacgcacg   900
aatattgaac cgacaagctc ttcaatttgg taaagtcgct gataaagttt taagcttta   960
ttattcattg ttatcgcata cctgtttatc ttctactatg aactgtgcaa tttgttctag  1020
atcaattggg taaacatgat ggttctgttg caaagtaaaa aaatatagct aaccactaat  1080
ttatcatgtc agtgttcgct taacttgcta gcatgatg                          1118
```

<210> SEQ ID NO 45
<211> LENGTH: 1113
<212> TYPE: DNA
<213> ORGANISM: Staphylococcus aureus

<400> SEQUENCE: 45

```
agcatttaag attatgcgtg gagaagcgta ccacaaatga tgcggttttt tatccagttt    60
tttgtttaat gaacaaggta aattacgaga taatatttga agaaaacaat aaagtagaga   120
tggatttcca tatcctcttt agtagcggtt tttatctgta aggtttatta ataattaaat   180
aaataggcgg gatagttata tatagcttat taatgaaaga atatgattat taatttagta   240
ttatatttta atattaaaaa gaagatatga ataattatt catccttcc accttacaat   300
aattagtttt caatcgaata ttaagattat tagtagtctt aaaagttaag acttccttat   360
attaatgacc taatttatta tttgcctcat gaattatctt tttatttctt tgatatgtcc   420
caaaccacat cgtgatatac actacaataa atattatgat gaaactaata atattctcaa   480
agttcagatg gaaccaacct gctagaatag cgagtgggaa gataggatt atcatcaata   540
taaagtgaac tacagtctgt tttgttatac tccaatcggt atctgtaaat atcaaattac   600
cataagtaaa caaaattcca atcaatgccc atagtgctac acatattagc ataataaccg   660
cttcattaaa gttttcataa taaattttac ccataaaaga atctggatat agtggtacat   720
```

```
atttatccct tgaaaaaaat aagtgaagta atgacagaaa tcataagacc agtgaacgca      780
cctttttgaa cagcgtggaa taatttttc  atagtgagat ggaccattcc atttgtttct      840
aacttcaagt gatcaatgta atttagattg ataatttctg attttgaaat acgcacgaat      900
attgaaccga caagctcttc aatttggtaa agtcgctgat aaagttttaa agctttatta      960
ttcattgtta tcgcatacct gtttatcttc tactatgaac tgtgcaattt gttctagatc     1020
aattgggtaa acatgatggt tctgttgcaa agtaaaaaaa tatagctaac cactaattta     1080
tcatgtcagt gttcgcttaa cttgctagca tga                                  1113
```

<210> SEQ ID NO 46
<211> LENGTH: 2153
<212> TYPE: DNA
<213> ORGANISM: Staphylococcus aureus

<400> SEQUENCE: 46

```
ctgtagggaa actaaaagag aaatactgga agcaagccat agcagaatat gaaaaacgtt       60
taggcccata caccaagata gacatcatag aagttccaga cgaaaaagca ccagaaaata      120
tgagcgacaa agaaatcgag caagtaaaag aaaaagaagg ccaacgaata ctagccaaaa      180
tcaaaccaca atccacagtc attacattag aaatacaagg aaagatgcta tcttccgaag      240
gattggccca agaattgaac caacgcatga cccaagggca aagcgacttt gtattcgtca      300
ttggcggatc aaacggcctg cacaaggacg tcttacaacg cagtaactac gcactatcat      360
tcagcaaaat gacattccca catcaaatga tgcgggttgt gttaattgaa caagtgtaca      420
gagcatttaa gattatgcgt ggagaagcgt accacaaatg atgcggtttt ttatccagtt      480
ttttgtttaa tgaacaaggt aaattacgag ataatatttg aagaaaacaa taaagtagag      540
atggatttcc atatcctctt tagtagcggt ttttatctgt aaggtttatt ataattaaa      600 taaataggcg ggatagttat atatagctta ttaatgaaag aatatgatta ttaatttagt      660
attatatttt aatattaaaa agaagatatg aaataattat tcataccttc caccttacaa      720
taattagttt tcaatcgaat attaagatta ttagtagtct taaaagttaa gacttcctta      780
tattaatgac ctaatttatt atttgcctca tgaattatct tttatttct  ttgatatgtc      840 ccaaaccaca tcgtgatata cactacaata aatattatga tgaaactaat aatattctca      900
aagttcagat ggaaccaacc tgctagaata gcgagtggga agaataggat tatcatcaat      960
ataaagtgaa ctacagtctg ttttgttata ctccaatcgg tatctgtaaa tatcaaatta     1020
ccataagtaa acaaaattcc aatcaatgcc catagtgcta cacatattag cataataacc     1080
gcttcattaa agttttcata ataaatttta cccataaaag aatctggata tagtggtaca     1140
tatttatccc ttgaaaaaaa taagtgaagt aatgacagaa atcataagac cagtgaacgc     1200 accttttttga acagcgtgga ataatttttt catagtgaga tggaccattc catttgtttc     1260
taacttcaag tgatcaatgt aatttagatt gataatttct gattttgaaa tacgcacgaa     1320
tattgaaccg acaagctctt caatttggta aagtcgctga taaagtttta aagctttatt     1380
attcattgtt atcgcatacc tgtttatctt ctactatgaa ctgtgcaatt tgttctagat     1440
caattgggta aacatgatgg ttctgttgca agtaaaaaaa tatagctaac cactaatttt     1500
atcatgtcag tgttcgctta acttgctagc atgatgctaa tttcgtggca tggcgaaaat     1560
ccgtagatct gatgagacct gcggttcttt ttatatagag cgtaaataca ttcaatacct     1620
tttaaagtat tctttgctgt attgatactt tgataccttg tctttcttac tttaatatga     1680
```

| | |
|---|---:|
| cggtgatctt gctcaatgag gttattcaaa tatttcgatg tacaatgaca gtcaggttta | 1740 |
| agtttaaaag ctttaattac tttagccatt gctaccttcg ttgaaggtgc ctgatctgta | 1800 |
| attacctttt gaggtttacc aaattgttta atgagacgtt taataaacgc atatgctgaa | 1860 |
| tgattatctc gttgcttacg caaccaaata tctaatgtat gtccctctgc atcaatggca | 1920 |
| cgatataaat agctccattt tccttttatt ttgatgtacg tctcatcaat acgccatttg | 1980 |
| taataagctt tttatgctt tttcttccaa atttgatata aaattggggc atattcttga | 2040 |
| acccaacggt agaccgttga atgatgaacg tttacaccac gtccccttaa tatttcagat | 2100 |
| atatcacgat aactcaatgc atatcttaga tagtagccaa cggctacagt gat | 2153 |

<210> SEQ ID NO 47
<211> LENGTH: 737
<212> TYPE: DNA
<213> ORGANISM: Staphylococcus aureus

<400> SEQUENCE: 47

| | |
|---|---:|
| tttaagatta tgcgtggaga agcatatcat aaatgatgcg gttatttcag ccgtaatttt | 60 |
| ataatataaa gcagagttta ttaaatttta atgattactt tttattaaga attaattcta | 120 |
| gttgatatat tataatgtga aacacaaaat aataatttgt aattgttagt ttataggcat | 180 |
| ctgtatttgg aattttttgt agactattta aaaaatagtg tatataagta ttgagttcat | 240 |
| gtattaactg tcttttttca tcgttcatca agtataagga tgtagagatt tgttggataa | 300 |
| ttcttcgga tgttttaaa attatcatta aattagatgg tatctgatct tgagttttgt | 360 |
| ttttagtgta tgtatatttt aaaaaatttt tgattgttgt tatttgactc tcttttaatt | 420 |
| tgacaccctc atcaataaat gtgttaaata tatcttcatt tgtacttaaa tcatcaaaat | 480 |
| ttgccaacaa atatttgaac gtctctaaat cattatgttt gagttccgtt ttgctattcc | 540 |
| ataattccaa accatttggt agaaagccca agctgtgatt ttgatctccc catatagctg | 600 |
| aatttaaatc agtgagttga ttaattttt caacacagaa atgtaatttt ggaatgagga | 660 |
| atcgaagttg ttcttctact tgctgtactt ttcttttgtt ttcaataaaa tttctacacc | 720 |
| atactgttat caaaccg | 737 |

<210> SEQ ID NO 48
<211> LENGTH: 1592
<212> TYPE: DNA
<213> ORGANISM: Staphylococcus aureus

<400> SEQUENCE: 48

| | |
|---|---:|
| aactaaaaga gaaatattgg aagcaagcca tagcagaata tgaaaaacgt ttaggcccat | 60 |
| acaccaagat agacatcata gaagttccag acgaaaaagc accagaaaat atgagtgaca | 120 |
| aagaaattga gcaagtaaaa gaaaaagaag gccaacgaat actagccaaa atcaaaccac | 180 |
| aatccacagt cattacatta gaaatacaag gaaagatgct atcttccgaa ggattggccc | 240 |
| aagaattgaa ccaacgcatg acccaagggc aaagcgactt tgttttcgtc attggcggat | 300 |
| caaacggcct gcacaaggac gtcttacaac gcagtaacta cgcactatca ttcagcaaaa | 360 |
| tgacattccc acatcaaatg atgcgggttg tgttaattga acaagtgtac agagcattta | 420 |
| agattatgcg aggagaagca tatcataaat gatgcggtta tttcagccgt aattttataa | 480 |
| tataaagcag agtttattaa atttaatga ttacttttta ttaagaatta attctagttg | 540 |
| atatattata atgtgaaaca caaataata atttgtaatt gttagtttat aggcatctgt | 600 |
| atttggaatt tttgtagac tatttaaaaa atagtgtata taagtattga gttcatgtat | 660 |

```
taactgtctt ttttcatcgt tcatcaagta taaggatgta gagatttgtt ggataatttc        720
ttcggatgtt tttaaaatta tcattaaatt agatggtatc tgatcttgag ttttgttttt        780
agtgtatgta tattttaaaa aattttgat tgttgttatt tgactctctt ttaatttgac         840
accctcatca ataaatgtgt taaatatatc ttcatttgta cttaaatcat caaaatttgc        900
caacaaatat ttgaacgtct ctaaatcatt atgtttgagt tccgttttgc tattccataa        960
ttccaaacca tttggtagaa agcccaagct gtgattttga tctccccata tagctgaatt       1020
taaatcagtg agttgattaa ttttttcaac acagaaatgt aattttggaa tgaggaatcg       1080
aagttgttct tctacttgct gtacttttct tttgttttca ataaaatttc tacaccatac       1140
tgttatcaaa ccgccaatta ttgtgcacaa tcctccaatg attgtagata aaattgacaa       1200
tatattacac acctttctta gaggtttatt aacatctatt tttgaattta aaattattac       1260
tttggtagcg ttataaccta tttaacagat tagagaaaaa ttgaatgatc gattgaagaa       1320
tttccaaaat accgtcccat atgcgttgaa ggagatttct attttcttct gtattcaaat       1380
ctttggcttt atcctttgct ttattcaata aatcatctga gttttttca atattttta        1440 atacatcttt ggcattttgt ttaaatactt taggatcgga agttagggca ttagagtttg       1500
ccacattaat catattatta ttaatcattt gaatttgatt atctgataat atctctgata       1560
acctacgctc atcgaggact ttattaacag tg                                     1592

<210> SEQ ID NO 49
<211> LENGTH: 730
<212> TYPE: DNA
<213> ORGANISM: Staphylococcus aureus

<400> SEQUENCE: 49
agcatttaag attatgcgtg agaagcata tcataaatga tgcggttatt tcagccgtaa         60
ttttataata taaagcagag tttattaaat tttaatgatt acttttttatt aagaattaat      120 tctagttgat atattataat gtgaaacaca aaataataat ttgtaattgt tagttttatag      180 gcatctgtat ttggaatttt ttgtagacta tttaaaaaat agtgtatata agtattgagt      240
tcatgtatta actgtcttt ttcatcgttc atcaagtata aggatgtaga gatttgttgg       300 ataattttctt cggatgtttt taaaattatc attaaattag atggtatctg atcttgagtt     360 ttgttttttag tgtatgtata tttttaaaaaa ttttgattgt tgttattg actctcttt        420 aatttgacac cctcatcaat aaatgtgtta aatatatctt catttgtact taaatcatca      480
aaatttgcca acaaatattt gaacgtctct aaatcattat gtttgagttc cgttttgcta      540
ttccataatt ccaaaccatt tggtagaaag cccaagctgt gattttgatc tccccatata      600
gctgaattta aatcagtgag ttgattaatt ttttcaacac agaaatgtaa ttttggaatg      660
aggaatcgaa gttgttcttc tacttgctgt acttttcttt tgttttcaat aaaatttcta      720
caccatactg                                                              730

<210> SEQ ID NO 50
<211> LENGTH: 1696
<212> TYPE: DNA
<213> ORGANISM: Staphylococcus aureus

<400> SEQUENCE: 50
aaagagaaat attggaagca agccatagca gaatatgaaa aacgtttagg cccatacacc        60
aagatagaca tcatagaagt tccagacgaa aaagcaccag aaaatatgag tgacaaagaa       120
```

| | |
|---|---|
| attgagcaag taaagaaaaa agaaggccaa cgaatactag ccaaaatcaa accacaatcc | 180 |
| acagtcatta cattagaaat acaaggaaag atgctatctt ccgaaggatt ggcccaagaa | 240 |
| ttgaaccaac gcatgaccca agggcaaagc gactttgttt cgtcattgg cggatcaaac | 300 |
| ggcctgcaca aggacgtctt acaacgcagt aactacgcac tatcattcag caaaatgaca | 360 |
| ttcccacatc aaatgatgcg ggttgtgtta attgaacaag tgtacagagc atttaagatt | 420 |
| atgcgaggag aagcatatca taaatgatgc ggttatttca gccgtaattt tataatataa | 480 |
| agcagagttt attaaatttt aatgattact ttttattaag aattaattct agttgatata | 540 |
| ttataatgtg aaacacaaaa taataatttg taattgttag tttataggca tctgtatttg | 600 |
| gaattttttg tagactattt aaaaaatagt gtatataagt attgagttca tgtattaact | 660 |
| gtcttttttc atcgttcatc aagtataagg atgtagagat tgttggata atttcttcgg | 720 |
| atgttttttaa aattatcatt aaattagatg gtatctgatc ttgagttttg ttttagtgt | 780 |
| atgtatattt taaaaaattt ttgattgttg ttatttgact ctcttttaat ttgacaccct | 840 |
| catcaataaa tgtgttaaat atatcttcat ttgtacttaa atcatcaaaa tttgccaaca | 900 |
| aatatttgaa cgtctctaaa tcattatgtt tgagttccgt tttgctattc cataattcca | 960 |
| aaccatttgg tagaaagccc aagctgtgat tttgatctcc ccatatagct gaatttaaat | 1020 |
| cagtgagttg attaattttt tcaacacaga aatgtaattt tggaatgagg aatcgaagtt | 1080 |
| gttcttctac ttgctgtact tttcttttgt tttcaataaa atttctacac catactgtta | 1140 |
| tcaaaccgcc aattattgtg cacaatcctc caatgattgt agataaaatt gacaatatat | 1200 |
| tacacacctt tcttagaggt ttattaacat ctattttga atttaaaatt attactttgg | 1260 |
| tagcgttata acctatttaa cagattagag aaaaattgaa tgatcgattg aagaatttcc | 1320 |
| aaaataccgt cccatatgcg ttgaaggaga tttctattt cttctgtatt caaatctttg | 1380 |
| gctttatcct ttgctttatt caataaatca tctgagtttt tttcaatatt ttttaataca | 1440 |
| tctttggcat tttgtttaaa tactttagga tcggaagtta gggcattaga gtttgccaca | 1500 |
| ttaatcatat tattattaat catttgaatt tgattatctg ataatatctc tgataaccta | 1560 |
| cgctcatcga ggactttatt aacagtgtct tcaacttgtt gttgtgtgat tgtttatct | 1620 |
| tgattttgtt taatatctgc aagttgttct ttaatatctg ctatagaagc atttaaagct | 1680 |
| tcatctgaat acccat | 1696 |

<210> SEQ ID NO 51
<211> LENGTH: 2122
<212> TYPE: DNA
<213> ORGANISM: Staphylococcus aureus

<400> SEQUENCE: 51

| | |
|---|---|
| ggaaactaaa agagaaatat tggaagcaag ccatagcaga atatgaaaaa cgtttaggcc | 60 |
| catacaccaa gatagacatc atagaagttc cagacgaaaa agcaccagaa atatgagcg | 120 |
| acaaagaaat tgagcaagta aagaaaaag aaggccaacg aatactagcc aaaatcaaac | 180 |
| cacaatcaac agtcattaca ttagaaatac aaggaaagat gctatcttcc gaaggattgg | 240 |
| cccaagaatt gaaccaacgc atgacccaag ggcaaagcga ctttgtattc gtcattggcg | 300 |
| gatcaaacgg cctgcacaag gacgtcttac aacgcagtaa ctacgcacta tcattcagca | 360 |
| aaatgacatt cccacatcaa atgatgcggg ttgtgttaat tgaacaagtg tacagagcat | 420 |
| ttaagattat gcgtggagaa gcgtaccaca atgatgcgg ttttttatcc agttttttgt | 480 |
| ttaatgaaca aggtaaatta cgagataata tttgaagaaa acaataaagt agagatggat | 540 |

```
ttccatatcc tctttagtag cggttttat ctgtaaggtt tattaataat taaataaata    600
ggcgggatag ttatatatag cttattaatg aaagaatatg attattaatt tagtattata    660
ttttaatatt aaaagaaga tatgaaataa ttattcatac cttccacctt acaataatta     720
gttttcaatc gaatattaag attattagta gtcttaaaag ttaagacttc cttatattaa    780
tgacctaatt tattatttgc ctcatgaatt atctttttat ttctttgata tgtcccaaac    840
cacatcgtga tatacactac aataaatatt atgatgaaac taataatatt ctcaaagttc    900
agatggaacc aacctgctag aatagcgagt gggaagaata ggattatcat caatataaag    960
tgaactacag tctgttttgt tatactccaa tcggtatctg taaatatcaa attaccataa   1020
gtaaacaaaa ttccaatcaa tgcccatagt gctacacata ttagcataat aaccgcttca   1080
ttaaagttttt cataataaat tttacccata aaagaatctg gatatagtgg tacatattta  1140
tcccttgaaa aaataagtg aagtaatgac agaaatcata agaccagtga acgcaccttt    1200
ttgaacagcg tggaataatt tttttcatagt gagatggacc attccatttg tttctaactt  1260
caagtgatca atgtaattta gattgataat ttctgatttt gaaatacgca cgaatattga   1320
accgacaagc tcttcaattt ggtaaagtcg ctgataaagt tttaaagctt tattattcat    1380
tgttatcgca tacctgttta tcttctacta tgaactgtgc aatttgttct agatcaattg    1440
ggtaaacatg atggttctgt tgcaaagtaa aaaatatag ctaaccacta atttatcatg    1500
tcagtgttcg cttaacttgc tagcatgatg ctaatttcgt ggcatggcga aaatccgtag    1560
atctgatgag acctgcggtt cttttatat agagcgtaaa tacattcaat acctttaaa     1620
gtattctttg ctgtattgat actttgatac cttgtctttc ttactttaat atgacggtga    1680
tcttgctcaa tgaggttatt cagatatttc gatgtacaat gacagtcagg tttaagttta    1740
aaagctttaa ttactttagc cattgctacc ttcgttgaag gtgcctgatc tgtaattacc    1800
ttttgaggtt taccaaattg tttaatgaga cgtttgataa acgcatatgc tgaatgatta    1860
tctcgttgct tacgcaacca aatatctaat gtatgtccct ctgcatcaat ggcacgatat    1920
aaatagctcc attttccttt tattttgatg tacgtctcat caatacgcca tttgtaataa    1980
gcttttttat gcttttctt ccaaatttga tacaaaattg gggcatattc ttgaacccaa     2040
cggtagaccg ttgaatgatg aacgtttaca ccacgttccc ttaatatttc agatatatca    2100
cgataactca atgtatatct ta                                             2122
```

<210> SEQ ID NO 52
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 52
gatagactaa ttatcttcat c                                               21

<210> SEQ ID NO 53
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 53
cagactgtgg acaaactgat t                                               21

<210> SEQ ID NO 54
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 54
tgagatcatc tacatcttta                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 55
ggatcaaaag ctactaaatc                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 56
atgctctttg ttttgcagca                                               20

<210> SEQ ID NO 57
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 57
atgaaagact gcggaggcta act                                           23

<210> SEQ ID NO 58
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 58
atattctaga tcatcaatag ttg                                           23

<210> SEQ ID NO 59
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 59
aagaattgaa ccaacgcatg a                                             21

<210> SEQ ID NO 60
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 60
gttcaagccc agaagcgatg t                                                 21

<210> SEQ ID NO 61
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 61
tcgggcataa atgtcaggaa aat                                               23

<210> SEQ ID NO 62
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 62
aaacgacatg aaaatcacca t                                                 21

<210> SEQ ID NO 63
<211> LENGTH: 33
<212> TYPE: DNA
<213> ORGANISM: Artificial Sequence
<220> FEATURE:
<223> OTHER INFORMATION: Synthetic nucleic acid sequence

<400> SEQUENCE: 63
ttattaggta aaccagcagt aagtgaacaa cca                                    33

<210> SEQ ID NO 64
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 64
ggatcaaacg gcctgcaca                                                    19

<210> SEQ ID NO 65
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 65
cacagaaatg taattttgga atgagg                                            26

<210> SEQ ID NO 66
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 66
gtcaaaaatc atgaacctca ttacttatg                                         29

<210> SEQ ID NO 67

```
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 67
atttcatata tgtaattcct ccacatctc                                    29

<210> SEQ ID NO 68
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 68
tctacggatt ttcgccatgc                                              20

<210> SEQ ID NO 69
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 69
aacaggtgaa ttattagcac ttgtaag                                      27

<210> SEQ ID NO 70
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 70
atcaaatgat gcgggttgtg t                                            21

<210> SEQ ID NO 71
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 71
tcattggcgg atcaaacgg                                               19

<210> SEQ ID NO 72
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 72
acaacgcagt aactacgcac ta                                           22

<210> SEQ ID NO 73
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 73
```

| | |
|---|---|
| taactacgca ctatcattca gc | 22 |

```
<210> SEQ ID NO 74
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 74
```

| | |
|---|---|
| acatcaaatg atgcgggttg tg | 22 |

```
<210> SEQ ID NO 75
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 75
```

| | |
|---|---|
| tcaaatgatg cgggttgtgt ta | 22 |

```
<210> SEQ ID NO 76
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 76
```

| | |
|---|---|
| caaatgatgc gggttgtgtt aatt | 24 |

```
<210> SEQ ID NO 77
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 77
```

| | |
|---|---|
| ctactatgaa ctgtgcaatt tgttct | 26 |

```
<210> SEQ ID NO 78
<211> LENGTH: 2007
<212> TYPE: DNA
<213> ORGANISM: Staphylococcus aureus

<400> SEQUENCE: 78
```

| | |
|---|---|
| atgaaaaaga taaaaattgt tccacttatt ttaatagttg tagttgtcgg gtttggtata | 60 |
| tatttttatg cttcaaaaga taagaaatt aataatacta ttgatgcaat tgaagataaa | 120 |
| aatttcaaac aagtttataa agatagcagt tatatttcta aaagcgataa tggtgaagta | 180 |
| gaaatgactg aacgtccgat aaaaatatat aatagtttag gcgttaaaga tataaacatt | 240 |
| caggatcgta aaataaaaaa agtatctaaa aataaaaaac gagtagatgc tcaatataaa | 300 |
| attaaaacaa actacggtaa cattgatcgc aacgttcaat ttaattttgt taaagaagat | 360 |
| ggtatgtgga gttagattg ggatcatagc gtcattattc caggaatgca gaaagaccaa | 420 |
| agcatacata ttgaaaattt aaaatcagaa cgtggtaaaa ttttagaccg aaacaatgtg | 480 |
| gaattggcca atacaggaac acatatgaga ttaggcatcg ttccaaagaa tgtatctaaa | 540 |
| aaagattata agcaatcgc taagaactta agtatttctg aagactatat caacaacaaa | 600 |

```
tggatcaaaa ttgggtacaa gatgatacct tcgttccact ttaaaaccgt taaaaaaatg    660
gatgaatatt taagtgattt cgcaaaaaaa tttcatctta caactaatga aacagaaagt    720
cgtaactatc ctctagaaaa agcgacttca catctattag gttatgttgg tcccattaac    780
tctgaagaat taaaacaaaa agaatataaa ggctataaag atgatgcagt tattggtaaa    840
aagggactcg aaaaacttta cgataaaaag ctccaacatg aagatggcta tcgtgtcaca    900
atcgttgacg ataatagcaa tacaatcgca catacattaa tagagaaaaa gaaaaaagat    960
ggcaaagata ttcaactaac tattgatgct aaagttcaaa agagtattta taacaacatg   1020
aaaaatgatt atggctcagg tactgctatc caccctcaaa caggtgaatt attagcactt   1080
gtaagcacac cttcatatga cgtctatcca tttatgtatg gcatgagtaa cgaagaatat   1140
aataaattaa ccgaagataa aaagaaacct ctgctcaaca agttccagat tacaacttca   1200
ccaggttcaa ctcaaaaaat attaacagca atgattgggt taaataacaa acattagac   1260 gataaaacaa gttataaaat cgatggtaaa ggttggcaaa aagataaatc ttggggtggt   1320
tacaacgtta caagatatga agtggtaaat ggtaatatcg acttaaaaca agcaatagaa   1380
tcatcagata acattttctt tgctagagta gcactcgaat taggcagtaa gaaatttgaa   1440
aaaggcatga aaaaactagg tgttggtgaa gatataccaa gtgattatcc attttataat   1500
gctcaaattt caaacaaaaa tttagataat gaaatattat tagctgattc aggttacgga   1560
caaggtgaaa tactgattaa cccagtacag atcctttcaa tctatagcgc attagaaaat   1620
aatggcaata ttaacgcacc tcacttatta aaagacacga aaaacaaagt ttggaagaaa   1680
aatattattt ccaaagaaaa tatcaatcta ttaaatgatg gtatgcaaca agtcgtaaat   1740
aaaacacata agaagatat ttatagatct tatgcaaact taattggcaa atccggtact   1800
gcagaactca aaatgaaaca aggagaaagt ggcagacaaa ttgggtggtt tatatcatat   1860
gataaagata atccaaacat gatgatggct attaatgtta aagatgtaca agataaagga   1920
atggctagct acaatgccaa aatctcaggt aaagtgtatg atgagctata tgagaacggt   1980
aataaaaaat acgatataga tgaataa                                       2007

<210> SEQ ID NO 79
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 79
caaatattat ctcgtaattt accttgttc                                       29

<210> SEQ ID NO 80
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 80
ctctgcttta tattataaaa ttacggctg                                       29

<210> SEQ ID NO 81
<211> LENGTH: 27
<212> TYPE: DNA
<213> ORGANISM: Artificial Sequence
<220> FEATURE:
<223> OTHER INFORMATION: Synthetic nucleic acid sequence
```

<400> SEQUENCE: 81
attgctgtta atattttttg agttgaa                                27

<210> SEQ ID NO 82
<211> LENGTH: 2007
<212> TYPE: DNA
<213> ORGANISM: Staphylococcus aureus

<400> SEQUENCE: 82
atgaaaaaga taaaaattgt tccacttatt ttaatagttg tagttgtcgg gtttggtata      60
tatttttatg cttcaaaaga taagaaatt aataatacta ttgatgcaat tgaagataaa     120
aatttcaaac aagtttataa agatagcagt tatatttcta aaagcgataa tggtgaagta    180
gaaatgactg aacgtccgat aaaaatatat aatagtttag gcgttaaaga tataaacatt    240
caggatcgta aaataaaaaa agtatctaaa aataaaaaac gagtagatgc tcaatataaa    300
attaaaacaa actacggtaa cattgatcgc aacgttcaat ttaattttgt taagaagat     360 ggtatgtgga agttagattg ggatcatagc gtcattattc caggaatgca gaaagaccaa    420
agcatacata ttgaaaattt aaaatcagaa cgtggtaaaa ttttagaccg aaacaatgtg    480
gaattggcca atacaggaac agcatatgag ataggcatcg ttccaaagaa tgtatctaaa    540
aaagattata aagcaatcgc taagaactta agtatttctg aagactatat caaacaacaa    600
atggatcaaa attgggtaca agatgatacc ttcgttccac ttaaaaccgt taaaaaaatg    660
gatgaatatt taagtgattt cgcaaaaaaa tttcatctta caactaatga aacagaaagt    720
cgtaactatc ctctagaaaa agcgacttca catctattag gttatgttgg tcccattaac    780
tctgaagaat taaaacaaaa agaatataaa ggctataaag atgatgcagt tattggtaaa    840
aagggactcg aaaaacttta cgataaaaag ctccaacatg aagatggcta tcgtgtcaca    900
atcgttgacg ataatagcaa tacaatcgca catacattaa tagagaaaaa gaaaaaagat    960
ggcaaagata ttcaactaac tattgatgct aaagttcaaa agagtatta taacaacatg   1020 aaaaatgatt atggctcagg tactgctatc caccctcaaa caggtgaatt attagcactt   1080
gtaagcacac cttcatatga cgtctatcca tttatgtatg gcatgagtaa cgaagaatat   1140
aataaattaa ccgaagataa aaaagaacct ctgctcaaca agttccagat tacaacttca   1200
ccaggttcaa ctcaaaaaat attaacagca atgattgggt aaataacaa aacattagac   1260 gataaaacaa gttataaaat cgatggtaaa ggttggcaaa agatataatc ttggggtggt   1320
tacaacgtta caagatatga agtggtaaat ggtaatatcg acttaaaaca agcaatagaa   1380
tcatcagata acattttctt tgctagagta gcactcgaat taggcagtaa gaaatttgaa   1440
aaaggcatga aaaaactagg tgttggtgaa gatataccaa gtgattatcc attttataat   1500
gctcaaattt caaacaaaaa tttagataat gaaatattat tagctgattc aggttacgga   1560
caaggtgaaa tactgattaa cccagtacag atcctttcaa tctatagcgc attagaaaat   1620
aatggcaata ttaacgcacc tcacttatta aaagacacga aaaacaaagt ttggaagaaa   1680
aatattattt ccaaagaaaa tatcaatcta ttaactgatg gtatgcaaca agtcgtaaat   1740
aaaacacata agaagatat ttatagatct tatgcaaact taattggcaa atccggtact   1800
gcagaactca aaatgaaaca aggagaaact ggcagacaaa ttgggtggtt tatatcatat   1860
gataaagata atccaaacat gatgatggct attaatgtta aagatgtaca agataaagga   1920
atggctagct acaatgccaa aatctcaggt aaagtgtatg atgagctata tgagaacggt   1980
aataaaaaat acgatataga tgaataa         2007

<210> SEQ ID NO 83
<211> LENGTH: 36
<212> TYPE: DNA
<213> ORGANISM: Artificial Sequence
<220> FEATURE:
<223> OTHER INFORMATION: Synthetic nucleic acid sequence

<400> SEQUENCE: 83
cccaccccac atcaaatgat gcgggttgtg ggtggg         36

<210> SEQ ID NO 84
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 84
cccgcgcgta gttactgcgt tgtaagacgt ccgcggg         37

<210> SEQ ID NO 85
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 85
gtttttatca ccatattgaa tttatac         27

<210> SEQ ID NO 86
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 86
atttacttga aagactgcgg aggag         25

<210> SEQ ID NO 87
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 87
tgtttgagct tccacagcta tttc         24

<210> SEQ ID NO 88
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 88
ccctataatt ccaattattg cactaac         27

<210> SEQ ID NO 89
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 89
atgaggagat aataatttgg agggt                                         25

<210> SEQ ID NO 90
<211> LENGTH: 2007
<212> TYPE: DNA
<213> ORGANISM: Staphylococcus aureus

<400> SEQUENCE: 90

| | | | | | |
|---|---|---|---|---|---|
| atgaaaaaga | taaaaattgt | tccacttatt | ttaatagttg | tagttgtcgg | gtttggtata | 60 |
| tatttttatg | cttccaaaga | taaagaaatt | aataatacta | ttgatgcaat | tgaagataaa | 120 |
| aatttcaaac | aagtttataa | agatagcagt | tatatttcta | aaagcgataa | tggtgaagta | 180 |
| gaaatgactg | aacgtccgat | aaaaatatat | aatagtttag | gcgttaaaga | tataaacatt | 240 |
| caggatcgta | aataaaaaaa | agtatctaaa | aataaaaaac | gagtagatgc | tcaatataaa | 300 |
| attaaaacaa | actacggtaa | cattgatcgc | aacgttcaat | taattttgt | taaagaagat | 360 |
| ggtatgtgga | agttagattg | ggatcatagc | gtcattattc | caggaatgca | gaaagaccaa | 420 |
| agcatacata | ttgaaaattt | aaaatcagaa | cgtggtaaaa | ttttagaccg | aaacaatgtg | 480 |
| gaattggcca | atacaggaac | agcatatgag | ataggcatcg | ttccaaagaa | tgtatctaaa | 540 |
| aaagattata | agcaatcgc | taaagaacta | agtatttctg | aagactatat | caaacaacaa | 600 |
| atggatcaaa | attgggtaca | agatgatacc | ttcgttccac | ttaaaaccgt | taaaaaaatg | 660 |
| gatgaatatt | taagtgattt | cgcaaaaaaa | tttcatctta | caactaatga | aacagaaagt | 720 |
| cgtaactatc | ctctaggaaa | agcgacttca | catctattag | gttatgttgg | tcccattaac | 780 |
| tctgaagaat | taaacaaaa | agaatataaa | ggctataaag | atgatgcagt | tattggtaaa | 840 |
| aagggactcg | aaaaacttta | cgataaaaag | ctccaacatg | aagatggcta | tcgtgtcaca | 900 |
| atcgttgacg | ataatagcaa | tacaatcgca | catacattaa | tagagaaaaa | gaaaaaagat | 960 |
| ggcaaagata | ttcaactaac | tattgatgct | aaagttcaaa | agagtattta | taacaacatg | 1020 |
| aaaaatgatt | atggctcagg | tactgctatc | caccctcaaa | caggtgaatt | attagcactt | 1080 |
| gtaagcacac | cttcatatga | cgtctatcca | tttatgtatg | gcatgagtaa | cgaagaatat | 1140 |
| aataaattaa | ccgaagataa | aaaagaacct | ctgctcaaca | agttccagat | tacaacttca | 1200 |
| ccaggttcaa | ctcaaaaaat | attaacagca | atgattgggt | taaataacaa | aacattagac | 1260 |
| gataaaacaa | gttataaaat | cgatggtaaa | ggttggcaaa | aagataaatc | ttggggtggt | 1320 |
| tacaacgtta | caagatatga | agtggtaaat | ggtaatatcg | acttaaaaca | agcaatagaa | 1380 |
| tcatcagata | acatttttctt | tgctagagta | gcactcgaat | taggcagtaa | gaaatttgaa | 1440 |
| aaaggcatga | aaaaactagg | tgttggtgaa | gatataccaa | gtgattatcc | attttataat | 1500 |
| gctcaaattt | caaacaaaaa | tttagataat | gaaatattat | tagctgattc | aggttacgga | 1560 |
| caaggtgaaa | tactgattaa | cccagtacag | atcctttcaa | tctatagcgc | attagaaaat | 1620 |
| aatggcaata | ttaacgcacc | tcacttatta | aaagacacga | aaacaaagt | ttggaagaaa | 1680 |
| aatattattt | ccaagaaaaa | tatcaatcta | ttaactgatg | gtatgcaaca | agtcgtaaat | 1740 |
| aaaacacata | agaagatat | ttatagatct | tatgcaaact | taattggcaa | atccggtact | 1800 |
| gcagaactca | aaatgaaaca | aggagaaact | ggcagacaaa | ttgggtggtt | tatatcatat | 1860 |
| gataaagata | atccaaacat | gatgatggct | attaatgtta | aagatgtaca | agataaagga | 1920 |

| | |
|---|---|
| atggctagct acaatgccaa atctcaggt aaagtgtatg atgagctata tgagaacggt | 1980 |
| aataaaaaat acgatataga tgaataa | 2007 |

<210> SEQ ID NO 91
<211> LENGTH: 2007
<212> TYPE: DNA
<213> ORGANISM: Staphylococcus aureus

<400> SEQUENCE: 91

| | |
|---|---|
| atgaaaaaga taaaaattgt tccacttatt ttaatagttg tagttgtcgg gtttggtata | 60 |
| tatttttatg cttcaaaaga taagaaaatt aataatacta ttgatgcaat tgaagataaa | 120 |
| aatttcaaac aagtttataa agatagcagt tatattcta aaagcgataa tggtgaagta | 180 |
| gaaatgactg aacgtccgat aaaaatatat aatagtttag gcgttaaaga tataaacatt | 240 |
| caggatcgta aaataaaaaa agtatctaaa aataaaaaac gagtagatgc tcaatataaa | 300 |
| attaaaacaa actacggtaa cattgatcgc aacgttcaat ttaattttgt taaagaagat | 360 |
| ggtatgtgga gttagattg gatcatagc gtcattattc caggaatgca gaaagaccaa | 420 |
| agcatacata ttgaaaattt aaatcagaa cgtggtaaaa ttttagaccg aaacaatgtg | 480 |
| gaattggcca atacaggaac agcatatgag ataggcatcg ttccaaagaa tgtatctaaa | 540 |
| aaagattata agcaatcgc taaagaacta gtatttctg aagactatat caaacaacaa | 600 |
| atggatcaaa gtgggtaca agatgatacc ttcgttccac ttaaaaccgt taaaaaaatg | 660 |
| gatgaatatt taagtgattt cgcaaaaaaa tttcatctta caactaatga aacagaaagt | 720 |
| cgtaactatc ctctagaaaa agcgacttca catctattag gttatgttgg tcccattaac | 780 |
| tctgaagaat taaaacaaaa agaatataaa ggctataaag atgatgcagt tattggtaaa | 840 |
| aagggactcg aaaaacttta cgataaaaag ctccaacatg aagatggcta tcgtgtcaca | 900 |
| atcgttgacg ataatagcaa tacaatcgca catacattaa tagagaaaaa gaaaaaagat | 960 |
| ggcaaagata ttcaactaac tattgatgct aaagttcaaa agagtattta taacaacatg | 1020 |
| aaaaatgatt atggctcagg tactgctatc caccctcaaa caggtgaatt attagcactt | 1080 |
| gtaagcacac cttcatatga cgtctatcca tttatgtatg gcatgagtaa cgaagaatat | 1140 |
| aataaattaa ccgaagataa aaaagaacct ctgctcaaca agttccagat tacaacttca | 1200 |
| ccaggttcaa ctcaaaaaat attaacagca atgattgggt taataacaa aacattagac | 1260 |
| gataaaacaa gttataaaat cgatggtaaa ggttggcaaa aagataaatc ttggggtggt | 1320 |
| tacaacgtta caagatatga agtggtaaat ggtaatatcg acttaaaaca agcaatagaa | 1380 |
| tcatcagata acatttttctt tgctagagta gcactcgaat taggcagtaa gaaatttgaa | 1440 |
| aaaggcatga aaaactagg tgttggtgaa gataTaccaa gtgattatcc attttataat | 1500 |
| gctcaaattt caaacaaaaa tttagataat gaaatattat tagctgattc aggttacgga | 1560 |
| caaggtgaaa tactgattaa cccagtacag atcctttcaa tctatagcgc attagaaaat | 1620 |
| aatggcaata ttaacgcacc tcacttatta aaagacacga aaacaaagt ttggaagaaa | 1680 |
| aatattattt ccaaagaaaa tatcaatcta ttaactgatg gtatgcaaca agtcgtaaat | 1740 |
| aaaacacata agaagatat ttatagatct tatgcaaact taattggcaa atccggtact | 1800 |
| gcagaactca aaatgaaaca aggagaaact ggcagacaaa ttgggtggtt tatatcatat | 1860 |
| gataaagata atccaaacat gatgatggct attaatgtta agatgtaca agataaagga | 1920 |
| atggctagct acaatgccaa aatctcaggt aaagtgtatg atgagctata tgagaacggt | 1980 |
| aataaaaaat acgatataga tgaataa | 2007 |

<210> SEQ ID NO 92
<211> LENGTH: 675
<212> TYPE: DNA
<213> ORGANISM: Staphylococcus aureus

<400> SEQUENCE: 92

```
atgaactatt tcagatataa acaatttaac aaggatgtta tcactgtagc cgttggctac      60
tatctaagat atacattgag ttatcgtgat atatctgaaa tattaaggga acgtggtgta     120
aacgttcatc attcaacggt ctaccgttgg gttcaagaat atgccccaat tttgtatcaa     180
atttggaaga aaaagcataa aaaagcttat tacaaatggc gtattgatga gacgtacatc     240
aaaataaaag gaaaatggag ctatttatat cgtgccattg atgcagaggg acatacatta     300
gatatttggt tgcgtaagca acgagataat cattcagcat atgcgtttat caaacgtctc     360
attaaacaat ttggtaaacc tcaaaaggta attacagatc aggcaccttc aacgaaggta     420
gcaatggcta agtaattaa agcttttaaa cttaaacctg actgtcattg tacatcgaaa      480
tatctgaata acctcattga gcaagatcac cgtcatatta agtaagaaa gacaaggtat      540 caaagtatca atacagcaaa gaatacttta aaaggtattg aatgtattta cgctctatat     600
aaaaagaacc gcaggtctct tcagatctac ggattttcgc catgccacga aattagcatc     660
atgctagcaa gttaa                                                     675
```

<210> SEQ ID NO 93
<211> LENGTH: 675
<212> TYPE: DNA
<213> ORGANISM: Staphylococcus aureus

<400> SEQUENCE: 93

```
atgaactatt tcagatataa acaatttaac aaggatgtta tcactgtagc cgttggctac      60
tatctaagat atacattgag ttatcgtgat atatctgaaa tattaaggga acgtggtgta     120
aacgttcatc attcaacggt ctaccgttgg gttcaagaat atgccccaat tttgtatcaa     180
atttggaaga aaaagcataa aaaagcttat tacaaatggc gtattgatga gacgtacatc     240
aaaataaaag gaaaatggag ctatttatat cgtgccattg atgcagaggg acatacatta     300
gatatttggt tgcgtaagca acgagataat cattcagcat atgcgtttat caaacgtctc     360
attaaacaat ttggtaaacc tcaaaaggta attacagatc aggcaccttc aacgaaggta     420
gcaatggcta agtaattaa agcttttaaa cttaaacctg actgtcattg tacatcgaaa      480
tatctgaata acctcattga gcaagatcac cgtcatatta agtaagaaa gacaaggtat      540 caaagtatca atacagcaaa gaatacttta aaaggtattg aatgtattta cgctctatat     600
aaaaagaacc gcaggtctct tcagatctac ggattttcgc catgccacga aattagcatc     660
atgctagcaa gttaa                                                     675
```

<210> SEQ ID NO 94
<211> LENGTH: 675
<212> TYPE: DNA
<213> ORGANISM: Staphylococcus aureus

<400> SEQUENCE: 94

```
atgaactatt tcagatataa acaatttaac aaggatgtta tcactgtagc cgttggctac      60
tatctaagat atacattgag ttatcgtgat atatctgaaa tattaaggga acgtggtgta     120
aacgttcatc attcaacggt ctaccgttgg gttcaagaat atgccccaat tttgtatcaa     180
```

```
atttggaaga aaaagcataa aaaagcttat tacaaatggc gtattgatga gacgtacatc    240
aaaataaaag gaaaatggag ctatttatat cgtgccattg atgcagaggg acatacatta    300
gatatttggt tgcgtaagca acgagttaat cattcagcat atgcgtttat caaacgtctc    360
attaaacaat ttggtaaacc tcaaaaggta attacagatc aggcaccttc aacgaaggta    420
gcaatggcta agtaattaa agcttttaaa cttaaacctg actgtcattg tacatcgaaa     480
tatctgaata acctcattga gcaagatcac cgtcatatta agtaagaaa gacaaggtat     540 caaagtatca atacagcaaa gaatacttta aaaggtattg aatgtattca cgctctatat    600
aaaaagaacc gcaggtctct tcagatctac ggattttcgc catgccacga aattagcatc    660
atgctagcaa gttaa                                                     675

<210> SEQ ID NO 95
<211> LENGTH: 675
<212> TYPE: DNA
<213> ORGANISM: Staphylococcus aureus

<400> SEQUENCE: 95
atgaactatt tcagatataa acaatttaac aaggatgtta tcactgtagc cgttggctac    60
tatctaagat atacattgag ttatcgtgat atatctgaaa tattaaggga acgtggtgta   120
aacgttcatc attcaacggt ctaccgttgg gttcaagaat atgccccaat tttgtatcaa   180
atttggaaga aaaagcataa aaaagcttat tacaaatggc gtattgatga gacgtacatc   240
aaaataaaag gaaaatggag ctatttatat cgtgccattg atgcagaggg acatacatta   300
gatatttggt tgcgtaagca acgagataat cattcagcat atgcgtttat caaacgtctc   360
attaaacaat ttggtaaacc tcaaaaggta attacagatc aggcaccttc aacgaaggta   420
gcaatggcta agtaattaa agcttttaaa cttaaacctg actgtcattg tacatcgaaa   480
tatctgaata acctcattga gcaagatcac cgtcatatta agtaagaaa gacaaggtat   540 caaagtatca atacagcaaa gaatacttta aaaggtattg aatgtattta cgctctatat   600
aaaaagaacc gcaggtctct tcagatctac ggattttcgc catgccacga aattagcatc   660
atgctagcaa gttaa                                                    675

<210> SEQ ID NO 96
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 96
gtaaagtgta tgatgagcta tatgagaa                                       28

<210> SEQ ID NO 97
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 97
gctgaaaaaa ccgcatcatt trtgrta                                        27

<210> SEQ ID NO 98
<211> LENGTH: 29
<212> TYPE: DNA
<213> ORGANISM: Artificial Sequence
```

```
<220> FEATURE:
<223> OTHER INFORMATION: Synthetic nucleic acid sequence

<400> SEQUENCE: 98 tttagttttta tttatgatac gcttctcca                                      29

<210> SEQ ID NO 99
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 99
gctgaaaaaa ccgcatcatt tatgata                                         27

<210> SEQ ID NO 100
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 100
ctatgtcaaa aatcatgaac ctcattac                                        28

<210> SEQ ID NO 101
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 101
ggaggctaac tatgtcaaaa atc                                             23

<210> SEQ ID NO 102
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 102
ctctataaac atcgtatgat attgc                                           25

<210> SEQ ID NO 103
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 103
accaaacgac atgaaaatca                                                 20

<210> SEQ ID NO 104
<211> LENGTH: 1256
<212> TYPE: DNA
<213> ORGANISM: Staphylococcus aureus

<400> SEQUENCE: 104
ttcagaaaaa tgattaatgt gtttcaataa aatctctcct tctttgtgaa catattcatt     60
tttatactaa ttaatataat ttccaaaaaa gtttctgttt aaaagtgaaa aatatatttt    120
```

```
accgtttgac ttaaatcttc aatatatagg tgtttatatg tatcattttg cgccaatttg    180
aataaacggg aatcaagtct gtttctgagt ttatttcaac tttcttatag taaacattgt    240
cttaatatga tgaacttcaa taaaactttc cctatgcccc ataaaatttt ctcaaaatca    300
aaaataacat accttacaac ttttaccgtc gatatcaatt gctcttttct taatttagga    360
ttgctttcaa attttgtact ataacgtgaa actactttc cttctttata attaaaattt     420
actaattcac aatcattttt acttccattt acaaaaacat ccactgtttc taacacaaaa    480
tctaataaac ttcctttat taatcgtagg cattgtatat ttcctttcat tctttcttga     540
ttccattagt ttaaatttaa aatttcatcc atcaatttct taatttaatt gtagttccat    600
aatcaatata atttgtacag ttattatata ttctagatca tcaatagttg aaaaatggtt    660
tattaaacac tctataaaca tcgtatgata ttgcaaggta taatccaata tttcatatat    720
gtaattcctc cacatctcat taaattttta aattatacac aacctaattt ttagttttat    780
ttatgatacg cttctccacg cataatctta aatgctctgt acacttgttc aattaacaca    840
acccgcatca tttgatgtgg gaatgtcatt ttgctgaatg atagtgcgta gttactgcgt    900
tgtaagacgt ccttgtgcag gccgtttgat ccgccaatga cgaatacaaa gtcgctttgc    960
ccttgggtca tgcgttggtt caattcttgg gccaatcctt cggaagatag catctttcct   1020
tgtatttcta atgtaatgac tgttgattgt ggtttgattt tggctagtat tcgttggcct   1080 tcttttctt ttacttgctc aatttcttg tcgctcatat tttctggtgc tttttcgtct    1140
ggaacttcta tgatgtctat cttggtgtat gggcctaaac gttttcata ttctgctatg    1200 gcttgcttcc aatatttctc ttttagtttc cctacagcta aaatggtgat tttcat       1256

<210> SEQ ID NO 105
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 105
tcatgaacct cattacttat gataagnt                                        28

<210> SEQ ID NO 106
<211> LENGTH: 28
<212> TYPE: DNA
<213> ORGANISM: Artificial Sequence
<220> FEATURE:
<221> NAME/KEY: misc_feature
<222> LOCATION: 27
<223> OTHER INFORMATION: n = inosine
<220> FEATURE:
<223> OTHER INFORMATION: Synthetic nucleic acid sequence

<400> SEQUENCE: 106
gaaaaaaccg catcatttat gatatgnt                                        28

<210> SEQ ID NO 107
<211> LENGTH: 30
<212> TYPE: DNA
<213> ORGANISM: Artificial Sequence
<220> FEATURE:
<221> NAME/KEY: misc_feature
<222> LOCATION: 29
<223> OTHER INFORMATION: n =  inosine
```

```
<220> FEATURE:
<223> OTHER INFORMATION: Synthetic nucleic acid sequence

<400> SEQUENCE: 107
cctaattttt agttttattt atgatacgnt                                    30

<210> SEQ ID NO 108
<211> LENGTH: 35
<212> TYPE: DNA
<213> ORGANISM: Artificial Sequence
<220> FEATURE:
<221> NAME/KEY: misc_feature
<222> LOCATION: 34
<223> OTHER INFORMATION: n = inosine
<220> FEATURE:
<223> OTHER INFORMATION: Synthetic nucleic acid sequence

<400> SEQUENCE: 108
cacaacctaa ttttagttt tatttatgat acgnt                                35

<210> SEQ ID NO 109
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 109
tgataagcca ttcattcacc ctaa                                           24

<210> SEQ ID NO 110
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 110
aaggactcct aatttatgtc taattcc                                        27

<210> SEQ ID NO 111
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 111
atgggagtcc ttcgctattc tgtg                                           24

<210> SEQ ID NO 112
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 112
cactttttat tcttcaaaga tttgagc                                        27

<210> SEQ ID NO 113
<211> LENGTH: 28
<212> TYPE: DNA
<213> ORGANISM: Artificial Sequence
<220> FEATURE:
<223> OTHER INFORMATION: Synthetic nucleic acid sequence
```

<400> SEQUENCE: 113
atggaaattc ttaatcttta cttgtacc                                28

<210> SEQ ID NO 114
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 114
agcatcttct ttacatcgct tact                                    24

<210> SEQ ID NO 115
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 115
cagcaattcw cataaacctc ata                                     23

<210> SEQ ID NO 116
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 116
acaaactttg agggattttt tagtaaa                                 27

<210> SEQ ID NO 117
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 117
tatattgtgg catgatttct tc                                      22

<210> SEQ ID NO 118
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 118
cgaatggact agcactttct aaa                                     23

<210> SEQ ID NO 119
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 119
ttgaggatca aaagttgttg c                                       21

<210> SEQ ID NO 120
<211> LENGTH: 21

```
<212> TYPE: DNA
<213> ORGANISM: Artificial Sequence
<220> FEATURE:
<223> OTHER INFORMATION: Synthetic nucleic acid sequence

<400> SEQUENCE: 120
cgatgatttt atagtaggag a                                              21

<210> SEQ ID NO 121
<211> LENGTH: 28
<212> TYPE: DNA
<213> ORGANISM: Artificial Sequence
<220> FEATURE:
<223> OTHER INFORMATION: Synthetic nucleic acid sequence

<400> SEQUENCE: 121
ttcaatctct aaatctaaat cagttttg                                       28

<210> SEQ ID NO 122
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 122
aggcgagaaa atggaacata tcaa                                           24

<210> SEQ ID NO 123
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 123
ggtacaagta aagattaaga atttcc                                         26

<210> SEQ ID NO 124
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 124
agacaacttt atgcaggtcc tt                                             22

<210> SEQ ID NO 125
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 125
taactgcttg ggtaacctta tc                                             22

<210> SEQ ID NO 126
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 126
```
tattgcaggt ttcgatgttg a              21

<210> SEQ ID NO 127
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 127
tgacccatat cgcctaaaat ac             22

<210> SEQ ID NO 128
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 128
aaaggacaac aaggtagcaa ag             22

<210> SEQ ID NO 129
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 129
tctgtggata aacaccttga tg             22

<210> SEQ ID NO 130
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 130
gtttgatccg ccaatgac                  18

<210> SEQ ID NO 131
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 131
ggcataaatg tcaggaaaat atc            23

<210> SEQ ID NO 132
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 132
gaggaccaaa cgacatgaaa atc            23

<210> SEQ ID NO 133
<211> LENGTH: 20
<212> TYPE: DNA
<213> ORGANISM: Artificial Sequence

```
<220> FEATURE:
<223> OTHER INFORMATION: Synthetic nucleic acid sequence

<400> SEQUENCE: 133
ttcgaggttg atgggaagca                                                    20

<210> SEQ ID NO 134
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 134
cgctcgactc agggtgtt                                                      18

<210> SEQ ID NO 135
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 135
cgttgaagat gcctttga                                                      18

<210> SEQ ID NO 136
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 136
ttttgcaaca gccattcg                                                      18

<210> SEQ ID NO 137
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 137
gcacacatgt tgtaagtttg c                                                  21

<210> SEQ ID NO 138
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 138
acgcaaactt acaacatgtg tg                                                 22

<210> SEQ ID NO 139
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 139
cgtttgtctg atttggagga ag                                                 22
```

<210> SEQ ID NO 140
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 140
tttcttcatc atcggtcata aaat                                          24

<210> SEQ ID NO 141
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 141
ctacgtgaat caaaaacaat gga                                           23

<210> SEQ ID NO 142
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 142
tactgcaaag tctcgttcat cc                                            22

<210> SEQ ID NO 143
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 143
cataccattt tgaacgatga cctc                                          24

<210> SEQ ID NO 144
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 144
atgtctggtc aactttccga ctc                                           23

<210> SEQ ID NO 145
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 145
caatcggtat ctgtaaatat caaat                                         25

<210> SEQ ID NO 146
<211> LENGTH: 24
<212> TYPE: DNA
<213> ORGANISM: Artificial Sequence
<220> FEATURE:
<223> OTHER INFORMATION: Synthetic nucleic acid sequence

```
<400> SEQUENCE: 146
tcgcatacct gtttatcttc tact                                          24

<210> SEQ ID NO 147
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 147
ttggttccat ctgaactttg ag                                            22

<210> SEQ ID NO 148
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 148
aatggcttat caaagtgaat atgc                                          24

<210> SEQ ID NO 149
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 149
taatttcctt ttttccatt cctc                                           24

<210> SEQ ID NO 150
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 150
actagaatct ccaaatgaat ccagt                                         25

<210> SEQ ID NO 151
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 151
tggagttaat ctacgtctca tctc                                          24

<210> SEQ ID NO 152
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 152
gttcatacag aagactcctt tttg                                          24

<210> SEQ ID NO 153
```

```
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 153
agttttgatt atccgaataa atgct                                          25

<210> SEQ ID NO 154
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 154
tttaaattca gctatatggg gaga                                           24

<210> SEQ ID NO 155
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 155
ttccgttttg ctattccata at                                             22

<210> SEQ ID NO 156
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 156
cctctgataa aaacttgtg aaat                                            24

<210> SEQ ID NO 157
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 157
actactcctg gaattacaaa ctgg                                           24

<210> SEQ ID NO 158
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 158
gccaaaatta aaccacaatc cac                                            23

<210> SEQ ID NO 159
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 159
``` catttttgctg aatgatagtg cgta 24

<210> SEQ ID NO 160
<211> LENGTH: 48
<212> TYPE: DNA
<213> ORGANISM: Artificial Sequence
<220> FEATURE:
<223> OTHER INFORMATION: Synthetic nucleic acid sequence

<400> SEQUENCE: 160
cgaccggatt cccacatcaa atgatgcggg ttgtgttaat tccggtcg 48

<210> SEQ ID NO 161
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 161
cccgcgcrta gttactrcgt tgtaagacgt ccgcggg 37

<210> SEQ ID NO 162
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 162
ccccgtagtt actgcgttgt aagacgggg 29

<210> SEQ ID NO 163
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 163
cccgcgcata gttactgcgt tgtaagacgt ccgcggg 37

<210> SEQ ID NO 164
<211> LENGTH: 37
<212> TYPE: DNA
<213> ORGANISM: Artificial Sequence
<220> FEATURE:
<223> OTHER INFORMATION: Synthetic nucleic acid sequence

<400> SEQUENCE: 164
cccgcgcgta gttactacgt tgtaagacgt ccgcggg 37

<210> SEQ ID NO 165
<211> LENGTH: 1282
<212> TYPE: DNA
<213> ORGANISM: Staphylococcus aureus

<400> SEQUENCE: 165
accattttag ctgtagggaa actaaaagag aaatattgga agcaagccat agcagaatat 60
gaaaaacgtt taggcccata caccaagata gacatcatag aagttccaga cgaaaaagca 120
ccagaaaata tgagcgacaa agaaattgag caagtaaaag aaaagaagg ccaacgaata 180 ctagccaaaa tcaaaccaca atccacagtc attacattag aaatacaagg aaagatgcta 240

```
tcttccgaag gattggccca agaattgaac caacgcatga cccaagggca aagcgacttt        300
gtattcgtca ttggcggatc aaacggcctg cacaaggacg tcttacaacg cagtaactat        360
gcactatcat ttagcaaaat gacattccca catcaaatga tgcgggttgt gttaattgaa        420
caagtgtata gagcatttaa gattatgcgt ggagaagcgt accacaaata aaactaaaaa        480
atatgagaaa attattaaat tagctcaaat ctttgaagaa taaaaagtga atattaagtt        540
tgataattta ggtacaagta aagattaaga atttccatta tttaatacat ggtgtgtaaa        600
tcgacttctt tttgtattag atgtttgcag taagcgatgt aaagaagatg ctaataaata        660
tgtgaggaat gattacgata ctagataagc ggctaatgaa attttttaaa gtacatatat        720
agacatattt ttcatttagt aaaatttttga atttcacttt gctaagacta gtgtctagaa        780
atttataatg atttattaac acctatttga aacttaagta taataaatga ttcggatttt        840 attttttaata aagacaaact tgaacgtagc aaagtagttt ttatgataaa taataagttt        900
taataatgtg acgcttttat ataagcacat tattatgaac aatgtgaatt gagcatctac        960
aattacatta ataaatatat aaatgatgat ttaaattcac atatatttat aatacacata       1020
ctatatgaaa gttttgatta tccgaataaa tgctaaaatt aataaaataa ttaaaggaat       1080
catacttatt atacgtatac gtttagctac tgaactactg gattcatttg gagattctag       1140
tagttctttt tcaatctcta aatctaaatc agttttgtaa taaccattaa ttcctaatct       1200
ttcatctagc tctgtacttt tttcatcatt tttatctttg ttgatatgtt ccattttctc       1260
gcctcttttt aatcaagtag aa                                                 1282

<210> SEQ ID NO 166
<211> LENGTH: 1108
<212> TYPE: DNA
<213> ORGANISM: Staphylococcus aureus

<400> SEQUENCE: 166
accattttag ctgtagggaa actaaaagag aaatattgga agcaagccat agcagaatat         60
gaaaaacgtt taggcccata caccaagata gacatcatag aagttccaga cgaaaaagca        120
ccagaaaata tgagcgacaa agaaattgag caagtaaaag aaaagaaagg ccaacgaata        180
ctagccaaaa tcaaaccaca atccacagtc attacattag aaatacaagg aaagatgcta        240
tcttccgaag gattggccca agaattgaac caacgcatga cccaagggca aagcgacttt        300
gtattcgtca ttggcggatc aaacggcctg cacaaggacg tcttacaacg cagtaactat        360
gcactatcat ttagcaaaat gacattccca catcaaatga tgcgggttgt gttaattgaa        420
caagtgtata gagcatttaa gattatgcgt ggagaagcgt accacaaata aaactaaaaa        480
atatgagaaa attattaaat tagctcaaat ctttgaagaa taaaaagtga atattaagtt        540
tgataattta ggtacaagta aagattaaga atttccatta tttaatacat ggtgtgtaaa        600
tcgacttctt tttgtattag atgtttgcag taagcgatgt aaagaagatg ctaataaata        660
tgtgaggaat gattacgata ctagataagc ggctaatgaa attttttaaa gtacatatat        720
agacatattt ttcatttagt aaaatttttga atttcacttt gctaagacta gtgtctagaa        780
atttataatg atttattaac acctatttga aacttaagta taataaatga ttcggatttt        840 attttttaata aagacaaact tgaacgtagc aaagtagttt ttatgataaa taataagttt        900
taataatgtg acgcttttat ataagcacat tattatgaac aatgtgaatt gagcatctac        960
aattacatta ataaatatat aaatgatgat ttaaattcac atatatttat aatacacata       1020
ctatatgaaa gttttgatta tccgaataaa tgctaaaatt aataaaataa ttaaaggaat       1080
```

```
catacttatt atacgtatac gtttagct                                      1108
```

<210> SEQ ID NO 167
<211> LENGTH: 1530
<212> TYPE: DNA
<213> ORGANISM: Staphylococcus aureus

<400> SEQUENCE: 167

```
ttagctgtag ggaaactaaa agagaaatat tggaagcaag ccatagcaga atatgaaaaa     60
cgtttaggcc catacaccaa gatagacatc atagaagttc agacgaaaaa agcaccagaa    120
aatatgagcg acaaagaaat tgagcaagta aaagaaaaag aaggccaacg aatactagcc    180
aaaatcaaac cacaatccac agtcattaca ttagaaatac aaggaaagat gctatcttcc    240
gaaggattgg cccaagaatt gaaccaacgc atgacccaag gcaaagcga ctttgtattc     300
gtcattggcg gatcaaacgg cctgcacaag gacgtcttac aacgcagtaa ctatgcacta    360
tcatttagca aaatgacatt cccacatcaa atgatgcggg ttgtgttaat tgaacaagtg    420
tatagagcat ttaagattat gcgtggagaa gcatatcata aatgatgcgg ttttttcagc    480
cgcttcataa aggggggtga tcatatcgga acgtatgagg tttatgagaa ttgctgctat    540
gttttatga agcgtatcat aaatgatgca gttttgata atttttcctt tatcagagat      600
tttactaaaa atcccctcaa agtttgtttt tttcaacttc aacttgaag ggaataaata     660
aggaacttat ttatatttat cctttatctc attaatatct attttttat taataatatt    720
ataaatatta aattctttag aaaagtcact atcactctta ttcttcatac taaacgttat    780
taatctaata atatcagcta ctatttcttt aaattctatt gcatcttctt ttttataagt    840
agcgcctgta tgaacaattt tatttctcat accatagtaa tctttcatat atttttttac    900
acaattttta atttcattag aattatccaa atctagatta tcaattgtct ttaataaatg    960
atcattaaca acattagcat acccacatcc aagcttcttt tttatctctt catcacttaa   1020
attttcatct aatttataat atcttttctaa aaaatttgtg ataaaaactt ctaatgcagt   1080
ctgaatttgt acaattgcta aattatagtc agatttataa aaagaacgtt caccttttct   1140
catagccaaa acataaatat tgctaggatg attattgaaa atattataat tttttttaat   1200
atttaataaa tcacttttttt tgatagatga atactgatct tcttctatct ttccaggcat   1260
gtcaatcatg aaaatactca tctcttttat atttccatct atagtatata ttatataata   1320
tggaatactt aatatatccc ctaatgatag ctggtatata ttatgatact gatatttaac   1380
gctaataatt ttaataagat tatttagaca attaaattgc ttattaaaaa ttttcgttag   1440
actattactt ttctttgatt ccctagaagt agaatttgat ttcaattttt taaactgatt   1500
gtgcttgatt attgaagtta tttcaacata                                    1530
```

<210> SEQ ID NO 168
<211> LENGTH: 1256
<212> TYPE: DNA
<213> ORGANISM: Staphylococcus aureus

<400> SEQUENCE: 168

```
gctgtaggga actaaaaga gaaatattgg aagcaagcca tagcagaata tgaaaaacgt     60
ttaggcccat acaccaagat agacatcata gaagttccag acgaaaaagc accagaaaat   120
atgagcgaca agaaattga gcaagtaaaa gaaaagaag gccaacgaat actagccaaa    180
attaaaccac aatccacagt cattacatta gaaatacaag gaaagatgct atcttccgaa   240
```

```
ggattggccc aagaattgaa ccaacgcatg acccaagggc aaagcgactt tgtattcgtc      300
attggcggat caaacggcct gcacaaggac gtcttacaac gcagtaacta cgcactatca      360
ttcagcaaaa tgacattccc acatcaaatg atgcggttg tgttaattga gcaagtgtat       420
agagcattta agattatgcg tggagaagca tatcataaat gatgcggttt tttcagccgc      480
ttcataaagg gattttgaat gtatcagaac atatgaggtt tatgtgaatt gctgttatgt     540
ttttaagaag catatcataa gtgatgcggt tttattaat tagttgctaa aaaatgaagt       600
atgcaatatt aattattatt aaattttgat atatttaaag aaagattaag tttagggtga     660
atgaatggct tatcaaagtg aatatgcatt agaaaatgaa gtacttcaac aacttgagga    720
attgaactat gaaagagtaa atatacataa tattaaatta gaaattaatg aatatctcaa      780
agaactagga gtgttgaaaa atgaataagc agacaaatac tccagaacta agatttccag      840
agtttgatga ggaatggaaa aaaggaaat taggtgaagt agtaaattat aaaaatggtg       900
gttcatttga agtttagtg aaaaaccatg gtgtatataa actcataact cttaaatctg      960
ttaatacaga aggaaagttg tgtaattctg gaaaatatat cgatgataaa tgtgttgaaa   1020
cattgtgtaa tgatacttta gtaatgatac tgagcgagca agcaccagga ctagttggaa   1080
tgactgcaat tataccaat aataatgagt atgtactaaa tcaacgagta gcagcactag     1140
tgcctaaaca atttatagat agtcaatttc tatctaagtt aattaataga aaccagaaat   1200
atttcagtgt gagatctgct ggaacaaaag tgaaaaatat ttctaaagga catgta        1256
```

<210> SEQ ID NO 169
<211> LENGTH: 846
<212> TYPE: DNA
<213> ORGANISM: Staphylococcus aureus

<400> SEQUENCE: 169

```
ttacattaga aatacaagga aagatgctat cttccgaagg attggcccaa gaattgaacc      60
aacgcatgac ccaagggcaa agcgactttg ttttcgtcat tggcggatca aacggcctgc     120
acaaggacgt cttacaacgc agtaactacg cactatcatt cagcaaaatg acattcccac    180
atcaaatgat gcgggttgtg ttaattgaac aagtgtacag agcatttaag attatgcgag    240
gagaagctta tcataagtaa tgaggttcat gattttgac atagttagcc tccgcagtct     300
ttcatttcaa gtaaataata gcgaaatatt ctttatactg aatacttata gtgaagcaaa    360
gttctagctt tgagaaaatt cttctgcaa ctaaatatag taaattacgg taaaatataa     420
ataagtacat attgaagaaa atgagacata atatatttta taataggagg gaatttcaaa    480
tgatagacaa ctttatgcag gtccttaaat taattaaaga gaaacgtacc aataatgtag    540
ttaaaaaatc tgattgggat aaaggtgatc tatataaaac tttagtccat gataagttac    600
ccaagcagtt aaaagtgcat ataaaagaag ataaatattc agttgtaggg aaggttgcta    660
ctggaaacta tagtaaagtt ccttggattt caatatatga tgagaatata acaaagaaa     720 caaaggatgg atattatttg gtatatcttt ttcatccgga aggagaaggc atatacttat    780
ctttgaatca aggatggtca agataagtg atatgtttcc gcgggataaa aatgctgcaa     840
aacaaa                                                               846
```

<210> SEQ ID NO 170
<211> LENGTH: 1270
<212> TYPE: DNA
<213> ORGANISM: Staphylococcus aureus

<400> SEQUENCE: 170

```
cattagaaat acaaggaaag atgctatctt ccgaaggatt ggcccaagaa ttgaaccaac      60
gcatgaccca agggcaaagc gactttgtat tcgtcattgg cggatcaaac ggcctgcaca     120
aggacgtctt acaacgcagt aactatgcac tatcatttag caaaatgaca ttcccacatc     180
aaatgatgcg ggttgtgtta attgaacaag tgtatagagc atttaagatt atgcgtggag     240
aagcatatca taaatgatgc ggtttttttca gccgcttcat aaagggattt tgaatgtatc     300
agaacatatg aggtttatgt gaattgctgt tatgttttta agaagcttat cataagtaat     360
gaggttcatg atttttgaca tagttagcct ccgcagtctt tcatttcaag taaataatag     420
cgaaatattc tttatactga atacttatag tgaagcaaag ttctagcttt gagaaaattc     480
tttctgcaac taaatatagt aaattacggt aaaatataaa taagtacata ttgaagaaaa     540
tgagacataa tatattttat aataggaggg aatttcaaat gatagacaac tttatgcagg     600
tccttaaatt aattaaagag aaacgtacca ataatgtagt taaaaaatct gattgggata     660
aaggtgatct atataaaact ttagtccatg ataagttacc caagcagtta aaagtgcata     720
taaaagaaga taaatattca gttgtaggga aggttgctac tgggaactat agtaaagttc     780
cttggatttc aatatatgat gagaatataa caaaagaaac aaaggatgga tattatttgg     840
tatatctttt tcatccggaa ggagaaggca tatacttatc tttgaatcaa ggatggtcaa     900
agataagtga tatgtttccg cgggataaaa atgctgcaaa acaaagagca ttaactttat     960
cttccgaact caataaatat attacatcaa atgaatttaa tactggaaga ttttattacg    1020
cagaaaataa agattcatct tatgatttaa aaaatgatta tccatcagga tattctcatg    1080
gatcaataag attcaaatat tatgatttga atgaaggatt cacagaagaa gatatgctag    1140
aggatttaaa gaaattttta gaactatttta atgaattagc ttcaaaagtt acaaaaacat    1200
cctatgatag cttggtcaat agcatagacg aaatacagga agacagcgaa attgaagaaa    1260
ttagaacagc                                                            1270

<210> SEQ ID NO 171
<211> LENGTH: 991
<212> TYPE: DNA
<213> ORGANISM: Staphylococcus aureus

<400> SEQUENCE: 171
accattttag ctgtagggaa actaaaagag aaatactgga agcaagccat agcagaatat      60
gaaaaacgtt taggcccata caccaagata gacatcatag aagttccaga cgaaaaagca     120
ccagaaaata tgaactacaa agaaattgag caagtaaaag aaaagaagg ccaacgaata     180 ctagccaaaa tcaaaccaca atcaacagtc attacattag aaatacaagg aaagatgcta     240
tcttccgaag gattggccca agaattgaac caacgcatga cccaagggca agcgactttt     300
gtattcgtca ttggcggatc aaacggcctg cacaaggacg tcttacaacg cagtaactac     360
gcactatcat tcagcaaaat gacattccca catcaaatga tgcgggttgt gttaattgaa     420
caagtgtaca gagcatttaa gattatgcga ggagaagcgt atcataagtg atggtaaaaa     480
atatgagtaa gtagatgaag agtgaaaatc agattaatta ataataatgt atcaaattta     540 aataagggg ttttaagta tgaatttaag aggtcatgaa aatagactta aatttcatgc     600
gaaatatgat gtgacaccta tatcacattt aaaattatta gaaggtcaaa agaaagacgg     660
tgaaggcggc atactgacag atagctatta ctgttttttca tacagcttaa aaggtaattc     720
taaaaaagtt ttaggtacgt ttaattgtgg ttatcatatt gctgaagatt tactaaaatt     780
```

```
atcaaatcaa gataaattac ctttatttaa cccgtttaaa gtaattaatg aaggtaatca    840
attgcagggc gtaacgaata aaggtaattt aaatattaat aggcaaagaa aacagtataa    900
tgaagtggct ttacagcttt caaatgctat taatttaatc ataatttgtt atgaggataa    960
tattaaagaa ccactttcaa cgataaaata c                                   991

<210> SEQ ID NO 172
<211> LENGTH: 748
<212> TYPE: DNA
<213> ORGANISM: Staphylococcus aureus

<400> SEQUENCE: 172
atcgtttaac gtgtcacatg atgcgataga tccgcaattt tatattttcc ataataacta     60
taagaagttt acgattttaa cagatacggg ttacgtgtct gatcgtatga aaggtatgat    120
acgtggcagc gatgcattta tttttgagag taatcatgac gtcgatatgt tgagaatgtg    180
tcgttatcca tggaagacga aacaacgcat tttaggcgat atgggtcatg tatctaatga    240
ggatgcgggt catgcgatga cagacgtgat tacaggtaac acgaaacgta tttacttatc    300
gcatttatca caagataata atatgaaaga tttggcgcgt atgagtgttg gccaagtatt    360
gaacgaacac gatattgata cggaaaaaga agtattgcta tgtgatacgg ataaagctat    420
tccaacacca atatatacaa tataaatgag agtcatccga taaagttccg cactgctgtg    480
aaacgacttt atcgggtgct tttttatgtt gttggtggga aatggctgtt gttgagttga    540
atcggattga ttgaaatgtg taaaataatt cgatattaaa tgtaatttat aaataattta    600
cataaaatca aacattttaa tataaggatt atgataatat attggtgtat gacagttaat    660
ggagggaacg aaatgaaagc tttattactt aaaacaagtg tatggctcgt tttgcttttt    720
agtgtgatgg gattatggca tgtctcga                                       748

<210> SEQ ID NO 173
<211> LENGTH: 917
<212> TYPE: DNA
<213> ORGANISM: Staphylococcus aureus

<400> SEQUENCE: 173
aaatacaagg aaagatgcta tcttccgaag gattggccca agaattgaac caacgcatga     60
cccaagggca aagcgacttt gtattcgtca ttggcggatc aaacggcctg cacaaggacg    120
tcttacaacg tagtaactac gcactatcat tcagcaaaat gacattccca catcaaatga    180
tgcgggttgt gttaattgag caagtgtata gagcatttaa gattatgcgt ggagaagcat    240
atcataaatg atgcggtttt ttcagccgct tcataaaggg attttgaatg tatcagaaca    300
tatgaggttt atgtgaattg ctgttatgtt tttaagaagc ttatcataag taatgaggtt    360
catgattttt gacatagtta gcctccgcag tctttcattt caagtaaata atagcgaaat    420
attctttata ctgaatactt atagtgaagc aaagttctag ctttgagaaa attctttctg    480
caactaaata tagtaaatta cggtaaaata taaataagta catattgaag aaaatgagac    540
ataatatatt ttataatagg agggaatttc aaatgataga caactttatg caggtcctta    600
aattaattaa agagaaacgt accaataatg tagttaaaaa atctgattgg gataaaggtg    660
atctatataa aactttagtc catgataagt tacccaagca gttaaaagtg catataaaag    720
aagataaata ttcagttgta gggaaggttg ctactgggaa ctatagtaaa gttccttgga    780
tttcaatata tgatgagaat ataacaaaag aaacaaagga tggatattat ttggtatatc    840
tttttcatcc ggaaggagaa ggcatatact tatctttgaa tcaaggatgg tcaaagataa    900
```

```
gtgatatgtt tccgcgg                                                  917
```

<210> SEQ ID NO 174
<211> LENGTH: 1132
<212> TYPE: DNA
<213> ORGANISM: Staphylococcus aureus

<400> SEQUENCE: 174

```
gctgtaggga aactaaaaga gaaatattgg aagcaagcca tagcagaata tgaaaaacgt    60
ttaggcccat acaccaagat agacatcata gaagttccag acgaaaaagc accagaaaat   120
atgagcgaca aagaaattga gcaagtaaaa gaaaagaag gccaacgaat actagccaaa    180
atcaaaccac aatcaacagt cattacatta gaaatacaag gaaagatgct atcttccgaa   240
ggattggccc aagaattgaa ccaacgcatg acccaagggc aaagcgactt tgtattcgtc   300
attggcggat caaacggcct gcacaaggac gtcttacaac gtagtaacta cgcactatca   360
ttcagcaaaa tgacattccc acatcaaatg atgcgggttg tgttaattga gcaagtgtat   420
agagcattta agattatgcg tggagaagca tatcataaat gatgcggttt tttcagccgc   480
ttcataaagg gattttgaat gtatcagaac atatgaggtt tatgtgaatt gctgttatgt   540
ttttaagaag cttatcataa gtaatgaggt tcatgatttt tgacatagtt agcctccgca   600
gtctttcatt tcaagtaaat aatagcgaaa tattctttat actgaatact tatagtgaag   660
caaagttcta gctttgagaa aattctttct gcaactaaat atagtaaatt acggtaaaat   720
ataaataagt acatattgaa gaaaatgaga cataatatat tttataatag gagggaattt   780
caaatgatag acaactttat gcaggtcctt aaattaatta agagaaacg taccaataat    840 gtagttaaaa aatctgattg ggataaaggt gatctatata aaactttagt ccatgataag   900
ttacccaagc agttaaaagt gcatataaaa gaagataaat attcagttgt agggaaggtt   960
gctactggga actatagtaa agttccttgg atttcaatat atgatgagaa tataacaaaa   1020
gaaacaaagg atggatatta tttggtatat ctttttcatc cggaaggaga aggcatatac   1080
ttatctttga atcaaggatg gtcaaagata agtgatatgt tccgcgggga ta           1132
```

<210> SEQ ID NO 175
<211> LENGTH: 1133
<212> TYPE: DNA
<213> ORGANISM: Staphylococcus aureus

<400> SEQUENCE: 175

```
agctgtaggg aaactaaaag agaaatattg gaagcaagcc atagcagaat atgaaaaacg    60
tttaggccca tacaccaaga tagacatcat agaagttcca gacgaaaaag caccagaaaa   120
tatgagcgac aaagaaattg agcaagtaaa agaaaaagaa ggccaacgaa tactagccaa   180
aatcaaacca caatcaacag tcattacatt agaaatacaa ggaaagatgc tatcttccga   240
aggattggcc caagaattga ccaacgcatg acccaaggg caaagcgact tgtattcgt     300 cattggcgga tcaaacggcc tgcacaagga cgtcttacaa cgtagtaact acgcactatc   360
attcagcaaa atgacattcc cacatcaaat gatgcgggtt gtgttaattg agcaagtgta   420
tagagcattt aagattatgc gtggagaagc atatcataaa tgatgcggtt ttttcagccg   480
cttcataaag ggattttgaa tgtatcagaa catatgaggt ttatgtgaat tgctgttatg   540
tttttaagaa gcttatcata gtaatgagg ttcatgattt tgacatagt agcctccgc      600 agtctttcat ttcaagtaaa taatagcgaa atattcttta tactgaatac ttatagtgaa   660
```

```
gcaaagttct agctttgaga aaattctttc tgcaactaaa tatagtaaat tacggtaaaa    720
tataaataag tacatattga agaaaatgag acataatata ttttataata ggagggaatt    780
tcaaatgata gacaacttta tgcaggtcct taaattaatt aaagagaaac gtaccaataa    840
tgtagttaaa aaatctgatt gggataaagg tgatctatat aaaactttag tccatgataa    900
gttacccaag cagttaaaag tgcatataaa agaagataaa tattcagttg tagggaaggt    960
tgctactggg aactatagta aagttccttg gatttcaata tatgatgaga atataacaaa   1020
agaaacaaag gatggatatt atttggtata tcttttcat ccggaaggag aaggcatata    1080
cttatctttg aatcaaggat ggtcaaagat aagtgatatg tttccgcggg ata          1133
```

<210> SEQ ID NO 176
<211> LENGTH: 1087
<212> TYPE: DNA
<213> ORGANISM: Staphylococcus aureus

<400> SEQUENCE: 176

```
actaaaagag aaatattgga agcaagccat agcagaatat gaaaaacgtt taggcccata     60
caccaagata gacatcatag aagttccaga cgaaaaagca ccagaaaata tgagcgacaa    120
agaaattgag caagtaaaag aaaaagaagg ccaacgaata ctagccaaaa tcaaaccaca    180
atcaacagtc attacattag aaatacaagg aaagatgcta tcttccgaag gattggcaca    240
agaattgaac caacgcatga cccaagggca aagcgacttt gtattcgtca ttggcggatc    300
aaacggcctg cacaaggacg tcttacaacg tagtaactac gcactatcat tcagcaaaat    360
gacattccca catcaaatga tgcgggttgt gttaattgag caagtgtata gagcgtttaa    420
gattatgcgt ggagaagcat atcataaatg atgcggtttt ttcagccgct tcataaaggg    480
attttgaatg tatcagaaca tatgaggttt atgtgaattg ctgttatgtt ttaagaagc    540 ttatcataag taatgaggtt catgattttt dacatagtta gcctccgcag tctttcattt    600
caagtaaata atagcgaaat attctttata ctgaatactt atagtgaagc aaagttctag    660 cttttgagaaa attctttctg caactaaata tagtaaatta cggtaaaata taaataagta    720
catattgaag aaaatgagac ataatatatt ttataatagg agggaatttc aaatgataga    780
caactttatg caggtcctta aattaattaa agagaaacgt accaataatg tagttaaaaa    840
atctgattgg gataaaggtg atctatataa aactttagtc catgataagt acccaagca    900 gttaaaagtg catataaaag aagataaata ttcagttgta gggaaggttg ctactgggaa    960
ctatagtaaa gttccttgga tttcaatata tgatgagaat ataacaaaag aaacaaagga   1020
tggatattat ttggtatatc ttttcatcc ggaaggagaa ggcatatact tatctttgaa    1080
tcaagga                                                              1087
```

<210> SEQ ID NO 177
<211> LENGTH: 903
<212> TYPE: DNA
<213> ORGANISM: Staphylococcus aureus

<400> SEQUENCE: 177

```
caaggaaaga tgctatcttc cgaaggattg gcccaagaat tgaaccaacg catgacccaa     60
gggcaaagcg actttgtatt cgtcattggc ggatcaaacg gcctgcacaa ggacgtctta    120
caacgtagta actacgcact atcattcagc aaaatgacat tcccacatca aatgatgcgg    180
gttgtgttaa ttgagcaagt gtatagagca tttaagatta tgcgtggaga agcatatcat    240
aaatgatgcg gttttttcag ccgcttcata agggatttt gaatgtatca gaacatatga    300
```

```
ggtttatgtg aattgctgtt atgtttttaa gaagcttatc ataagtaatg aggttcatga    360
tttttgacat agttagcctc cgcagtcttt catttcaagt aaataatagc gaaatattct    420
ttatactgaa tacttatagt gaagcaaagt tctagctttg agaaaattct ttctgcaact    480
aaatatagta aattacggta aaatataaat aagtacatat tgaagaaaat gagacataat    540
atattttata ataggaggga atttcaaatg atagacaact ttatgcaggt ccttaaatta    600
attaaagaga aacgtaccaa taatgtagtt aaaaaatctg attgggataa aggtgatcta    660
tataaaactt tagtccatga taagttaccc aagcagttaa aagtgcatat aaaagaagat    720
aaatattcag ttgtagggaa ggttgctact gggaactata gtaaagttcc ttggatttca    780
atatatgatg agaatataac aaaagaaaca aaggatggat attatttggt atatcttttt    840
catccggaag gagaaggcat atacttatct ttgaatcaag gatggtcaaa gataagtgat    900
atg                                                                  903

<210> SEQ ID NO 178
<211> LENGTH: 1114
<212> TYPE: DNA
<213> ORGANISM: Staphylococcus aureus

<400> SEQUENCE: 178
ggaaactaaa agagaaatat tggaagcaag ccatagcaga atatgaaaaa cgtttaggcc     60
catacaccaa gatagacatc atagaagttc cagacgaaaa agcaccagaa aatatgagcg    120
acaaagaaat tgagcaagta aaagaaaaag aaggccaacg aatactagcc aaaatcaaac    180
cacaatcaac agtcattaca ttagaaatac aaggaaagat gctatcttcc gaaggattgg    240
cccaagaatt gaaccaacgc atgacccaag ggcaaagcga ctttgtattc gtcattggcg    300
gatcaaacgg cctgcacaag gacgtcttac aacgtagtaa ctacgcacta tcattcagca    360
aaatgacatt cccacatcaa atgatgcggg ttgtgttaat tgagcaagtg tatagagcat    420
ttaagattat gcgtggagaa gcatatcata aatgatgcgg ttttttcagc cgcttcataa    480
agggattttg aatgtatcag aacatatgag gtttatgtga attgctgtta tgttttaag    540 aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aaagaagata atattcagt tgtagggaag gttgctactg    960
ggaactatag taaagttcct tggatttcaa tatatgatga gaatataaca aaagaaacaa   1020
aggatggata ttatttggta tatcttttc atccggaagg agaaggcata tacttatctt   1080
tgaatcaagg atggtcaaag ataagtgata tgtt                               1114

<210> SEQ ID NO 179
<211> LENGTH: 1121
<212> TYPE: DNA
<213> ORGANISM: Staphylococcus aureus

<400> SEQUENCE: 179
ggaaactaaa agagaaatat tggaagcaag ccatagcaga atatgaaaaa cgtttaggcc     60
```

| | |
|---|---|
| catacaccaa gatagacatc atagaagttc cagacgaaaa agcaccagaa aatatgagcg | 120 |
| acaaagaaat tgagcaagta aaagaaaaag aaggccaacg aatactagcc aaaatcaaac | 180 |
| cacaatccac agtcattaca ttagaaatac aaggaaagat gctatcttcc gaaggattgg | 240 |
| cccaagaatt gaaccaacgc atgacccaag ggcaaagcga ctttgtattc gtcattggcg | 300 |
| gatcaaacgg cctgcacaag gacgtcttac aacgcagtaa ctatgcacta tcatttagca | 360 |
| aaatgacatt cccacatcaa atgatgcggg ttgtgttaat tgaacaagtg tatagagcat | 420 |
| ttaagattat gcgtggagaa gcatatcata aatgatgcgg ttttttcagc cgcttcataa | 480 |
| agggattttg aatgtatcag aacatatgag gtttatgtga attgctgtta tgttttttaag | 540 |
| aagcttatca taagtaatga ggttcatgat ttttgacata gttagcctcc gcagtctttc | 600 |
| atttcaagta aataatagcg aaatattctt tatactgaat acttatagtg aagcaaagtt | 660 |
| ctagctttga gaaaattctt tctgcaacta aatatagtaa attacggtaa aatataaata | 720 |
| agtacatatt gaagaaaatg agacataata tattttataa taggagggaa tttcaaatga | 780 |
| tagacaactt tatgcaggtc cttaaattaa ttaaagagaa acgtaccaat aatgtagtta | 840 |
| aaaaatctga ttgggataaa ggtgatctat ataaaacttt agtccatgat aagttaccca | 900 |
| agcagttaaa agtgcatata aaagaagata atattcagt tgtagggaag gttgctactg | 960 |
| ggaactatag taaagttcct tggatttcaa tatatgatga gaatataaca aaagaaacaa | 1020 |
| aggatggata ttatttggta tatcttttc atccggaagg agaaggcata tacttatctt | 1080 |
| tgaatcaagg atggtcaaag ataagtgata tgtttccgcg g | 1121 |

<210> SEQ ID NO 180
<211> LENGTH: 1121
<212> TYPE: DNA
<213> ORGANISM: Staphylococcus aureus

<400> SEQUENCE: 180

| | |
|---|---|
| tagctgtagg gaaactaaaa gagaaatatt ggaagcaagc catagcagaa tatgaaaaac | 60 |
| gtttaggccc atacaccaag atagacatca tagaagttcc agacgaaaaa gcaccagaaa | 120 |
| atatgagcga caaagaaatt gagcaagtaa aagaaaaaga aggccaacga atactagcca | 180 |
| aaatcaaacc acaatccaca gtcattacat tagaaataca aggaaagatg ctatcttccg | 240 |
| aaggattggc ccaagaattg aaccaacgca tgacccaagg gcaaagcgac tttgtattcg | 300 |
| tcattggcgg atcaaacggc ctgcacaagg acgtcttaca acgcagtaac tatgcactat | 360 |
| catttagcaa aatgacattc ccacatcaaa tgatgcgggt tgtgttaatt gaacaagtgt | 420 |
| atagagcatt taagattatg cgtggagaag catatcataa atgatgcggt tttttcagcc | 480 |
| gcttcataaa gggattttga atgtatcaga acatatgagg tttatgtgaa ttgctgttat | 540 |
| gttttttaaga agcttatcat aagtaatgag gttcatgatt tttgacatag ttagcctccg | 600 |
| cagtctttca tttcaagtaa aataatagcga aatattcttt atactgaata cttatagtga | 660 |
| agcaaagttc tagctttgag aaaattcttt ctgcaactaa atatagtaaa ttacggtaaa | 720 |
| atataaataa gtacatattg aagaaaatga gacataatat attttataat aggagggaat | 780 |
| ttcaaatgat agacaacttt atgcaggtcc ttaaattaat taaagagaaa cgtaccaata | 840 |
| atgtagttaa aaaatctgat tgggataaag gtgatctata taaaactta gtccatgata | 900 |
| agttacccaa gcagttaaaa gtgcatataa aagaagataa atattcagtt gtagggaagg | 960 |
| ttgctactgg gaactatagt aaagttcctt ggatttcaat atatgatgag aatataacaa | 1020 |
| aagaaacaaa ggatggatat tatttggtat atcttttca tccggaagga gaaggcatat | 1080 |

```
acttatctttt gaatcaagga tggtcaaaga taagtgatat g                    1121
```

<210> SEQ ID NO 181
<211> LENGTH: 1131
<212> TYPE: DNA
<213> ORGANISM: Staphylococcus aureus

<400> SEQUENCE: 181

```
ctgtagggaa actaaaagag aaatattgga agcaagccat agcagaatat gaaaaacgtt    60
taggcccata caccaagata gacatcatag aagttccaga cgaaaaagca ccagaaaata   120
tgagcgacaa agaaattgag caagtaaaag aaaagaagg ccaacgaata ctagccaaaa   180
tcaaaccaca atccacagtc attacattag aaatacaagg aaagatgcta tcttccgaag   240
gattggccca agaattgaac caacgcatga cccaagggca aagcgacttt gtattcgtca   300
ttggcggatc aaacggcctg cacaaggacg tcttacaacg cagtaactat gcactatcat   360
ttagcaaaat gacattccca catcaaatga tgcgggttgt gttaattgaa caagtgtata   420
gagcatttaa gattatgcgt ggagaagcat atcataaatg atgcggtttt ttcagccgct   480
tcataaaggg atttttgaatg tatcagaaca tatgaggttt atgtgaattg ctgttatgtt   540
tttaagaagc ttatcataag taatgaggtt catgattttt gacatagtta gcctccgcag   600
tctttcattt caagtaaata tagcgaaat attctttata ctgaatactt atagtgaagc   660
aaagttctag ctttgagaaa attctttctg caactaaata tagtaaatta cggtaaaata   720
taaataagta catattgaag aaaatgagac ataatatatt ttataatagg agggaatttc   780
aaatgataga caactttatg caggtcctta aattaattaa agagaaacgt accaataatg   840
tagttaaaaa atctgattgg gataaaggtg atctatataa aactttagtc catgataagt   900
tacccaagca gttaaaagtg catataaaag aagataaata ttcagttgta gggaaggttg   960
ctactgggaa ctatagtaaa gttccttgga tttcaatata tgatgagaat ataacaaaag  1020
aaacaaagga tggatattat ttggtatatc tttttcatcc ggaaggagaa ggcatatact  1080
tatctttgaa tcaaggatgg tcaaagataa gtgatatgtt ccgcgggat a            1131
```

<210> SEQ ID NO 182
<211> LENGTH: 896
<212> TYPE: DNA
<213> ORGANISM: Staphylococcus aureus

<400> SEQUENCE: 182

```
cattagaaat acaaggaaag atgctatctt ccgaaggatt ggcccaagaa ttgaaccaac    60
gcatgaccca agggcaaagc gactttgtat tcgtcattgg cggatcaaac ggcctgcaca   120
aggacgtctt acaacgcagt aactatgcac tatcatttag caaaatgaca ttcccacatc   180
aaatgatgcg ggttgtgtta attgaacaag tgtatagagc atttaagatt atgcgtggag   240
aagcatatca taaatgatgc ggttttttca gccgcttcat aaagggattt tgaatgtatc   300
agaacatatg aggtttatgt gaattgctgt tatgttttta agaagcttat cataagtaat   360
gaggttcatg attttgaca tagttagcct ccgcagtctt tcatttcaag taaataatag   420
cgaaatattc tttatactga atacttatag tgaagcaaag ttctagcttt gagaaaattc   480
tttctgcaac taaatatagt aaattacggt aaaatataaa taagtacata ttgaagaaaa   540
tgagacataa tatattttat aataggaggg aatttcaaat gatagacaac tttatgcagg   600
tccttaaatt aattaaagag aaacgtacca ataatgtagt taaaaatct gattgggata   660
```

```
aaggtgatct atataaaact ttagtccatg ataagttacc caagcagtta aaagtgcata    720
taaaagaaga taaatattca gttgtaggga aggttgctac tgggaactat agtaaagttc    780
cttggatttc aatatatgat gagaatataa caaaagaaac aaaggatgga tattatttgg    840
tatatctttt tcatccggaa ggagaaggca tacttatc tttgaatcaa ggatgg          896
```

<210> SEQ ID NO 183
<211> LENGTH: 1125
<212> TYPE: DNA
<213> ORGANISM: Staphylococcus aureus

<400> SEQUENCE: 183

```
ggaaactaaa agagaaatat tggaagcaag ccatatcaga atatgaaaaa cgtttaggcc     60
catacaccaa gatagacatc atagaagttc cagacgaaaa agcaccagaa atatgagcg    120 acaaagaaat cgagcaagta aagaaaaag aaggccaacg aatactagcc aaaatcaaac    180
cacaatcaac agtcattaca ttagaaatac aaggaaagat gctatcttcc gaaggattgg    240
ctcaagaatt gaaccaacgc atgacccaag gcaaagcga ctttgtattc gttattggcg    300
gatcaaacgg cctgcacaag gacgtcttac aacgcagtaa ctatgcacta tcattcagca    360
aaatgacatt tccacatcag atgatgcggg ttgtgttaat tgagcaagtg tatagagcat    420
ttaagattat gcgtggggaa gcatatcata atgatgcgg tttttcagc cgcttcataa     480 agggattttg aatgtatcag aacatatgag gtttatgtga attgctgtta tgtttttaag    540
aagcttatca taagtaatga ggttcatgat ttttgacata gttagcctcc gcagtctttc    600
atttcaagta aataatagcg aaatattctt tatactgaat acttatagtg aagcaaagtt    660
ctagctttga gaaaattctt tctgcaacta aatatagtaa attacggtaa aatataaata    720
agtacatatt gaagaaaatg agacataata tattttataa taggagggaa tttcaaatga    780
tagacaactt tatgcaggtc cttaaattaa ttaaagagaa acgtaccaat aatgtagtta    840
aaaaatctga ttgggataaa ggtgatctat ataaaacttt agtccatgat aagttaccca    900
agcagttaaa agtgcatata aaagaagata atattcagt tgtagggaag gttgctactg    960
ggaactatag taaagttcct tggatttcaa tatatgatga gaatataaca aaagaaacaa   1020
aggatggata ttatttggta tatcttttc atccggaagg agaaggcata acttatctt    1080 tgaatcaagg atggtcaaag ataagtgata tgtttccgcg ggata                  1125
```

<210> SEQ ID NO 184
<211> LENGTH: 679
<212> TYPE: DNA
<213> ORGANISM: Staphylococcus aureus

<400> SEQUENCE: 184

```
ataagaggga acagtgtgaa caagttaata acttgtggat aactggaaag ttgataacaa     60
tttggaggac caaacgacat gaaaatcacc atttttagctg tagggaaact aaaagagaaa   120
tattggaagc aagccatagc agaatatgaa aaacgtttag gcccatacac caagatagac   180
atcatagaag ttccagacga aaaagcacca gaaaatatga gcgacaaaga aattgagcaa   240
gtaaaagaaa aagaaggcca acgaatacta gccaaaatca aaccacaatc cacagtcatt   300
acattagaaa tacaaggaaa gatgctatct tccgaaggat tggcccaaga attgaaccaa   360
cgcatgaccc aagggcaaag cgactttgta ttcgtcattg gcggatcaaa cggcctgcac   420
aaggacgtct tacaacgcag taactatgca ctatcattta gcaaaatgac attcccacat   480
caaatgatgc gggttgtgtt aattgaacaa gtgtatagag catttaagat tatgcgtgga   540
```

| gaggcttatc ataaataaaa ctaaaaatta gattgtgtat aatttaaaaa tttaatgaga | 600 |
| tgtggaggaa ttacatatat gaaatattgg agtatacctt gcaatatcat acgatgttta | 660 |
| tagagtgttt aataaacca | 679 |

<210> SEQ ID NO 185
<211> LENGTH: 1125
<212> TYPE: DNA
<213> ORGANISM: Staphylococcus aureus

<400> SEQUENCE: 185

| ggaaactaaa agagaaatat tggaagcaag ccatagcaga atatgaaaaa cgtttaggcc | 60 |
| catacaccaa gatagacatc atagaagttc cagacgaaaa agcaccagaa aatatgagcg | 120 |
| acaaagaaat tgagcaagta aaagaaaaag aaggccaacg aatactagcc aaaatcaaac | 180 |
| cacaatcaac agtcattaca ttagaaatac aaggaaagat gctatcttcc gaaggattgg | 240 |
| cacaagaatt gaaccaacgc atgacccaag ggcaaagcga cttttgtattc gtcattggcg | 300 |
| gatcaaacgg cctgcacaag gacgtcttac aacgtagtaa ctacgcacta tcattcagca | 360 |
| aaatgacatt cccacatcaa atgatgcggg ttgtgttaat tgagcaagtg tatagagcgt | 420 |
| ttaagattat gcgtggagaa gcatatcata aatgatgcgg ttttttcagc cgcttcataa | 480 |
| agggattttg aatgtatcag aacatatgag gtttatgtga attgctgtta tgttttaag | 540 |
| aagcttatca taagtaatga ggttcatgat ttttgacata gttagcctcc gcagtctttc | 600 |
| atttcaagta aataatagcg aaatattctt tatactgaat acttatagtg aagcaaagtt | 660 |
| ctagctttga gaaaattctt tctgcaacta aatatagtaa attacggtaa aatataaata | 720 |
| agtacatatt gaagaaaatg agacataata tattttataa taggagggaa tttcaaatga | 780 |
| tagacaactt tatgcaggtc cttaaattaa ttaaagagaa acgtaccaat aatgtagtta | 840 |
| aaaaatctga ttgggataaa ggtgatctat ataaaacttt agtccatgat aagttaccca | 900 |
| agcagttaaa agtgcatata aagaagata aatattcagt tgtagggaag gttgctactg | 960 |
| ggaactatag taaagttcct tggatttcaa tatatgatga gaatataaca aaagaaacaa | 1020 |
| aggatggata ttatttggta tatctttttc atccggaagg agaaggcata tacttatctt | 1080 |
| tgaatcaagg atggtcaaag ataagtgata tgtttccgcg ggata | 1125 |

<210> SEQ ID NO 186
<211> LENGTH: 926
<212> TYPE: DNA
<213> ORGANISM: Staphylococcus aureus

<400> SEQUENCE: 186

| tacattagaa atacaaggaa agatgctatc ttccgaagga ttggcccaag aattgaacca | 60 |
| acgcatgacc caagggcaaa gcgactttgt attcgtcatt ggcggatcaa acggcctgca | 120 |
| caaggacgtc ttacaacgca gtaactatgc actatcattt agcaaaatga cattcccaca | 180 |
| tcaaatgatg cgggttgtgt taattgaaca agtgtataga gcatttaaga ttatgcgtgg | 240 |
| agaagcatat cataaatgat gcggtttttt cagccgcttc ataaagggat tttgaatgta | 300 |
| tcagaacata tgaggtttat gtgaattgct gttatgtttt aagaagcttt atcataagta | 360 |
| atgaggttca tgattttga catagttagc ctccgcagtc tttcatttca agtaaataat | 420 |
| agcgaaatat tctttatact gaatacttat agtgaagcaa agttctagct ttgagaaaat | 480 |
| tctttctgca actaaatata gtaaattacg gtaaaatata aataagtaca tattgaagaa | 540 |

```
aatgagacat aatatatttt ataataggag ggaatttcaa atgatagaca actttatgca      600
ggtccttaaa ttaattaaag agaaacgtac caataatgta gttaaaaaat ctgattggga      660
taaaggtgat ctatataaaa ctttagtcca tgataagtta cccaagcagt taaaagtgca      720
tataaaagaa gataaatatt cagttgtagg gaaggttgct actgggaact atagtaaagt      780
tccttggatt tcaatatatg atgagaatat aacaaaagaa acaaaggatg gatattattt      840
ggtatatctt tttcatccgg aaggagaagg catatactta tctttgaatc aaggatggtc      900
aaagataagt gatatgtttc cgcggg                                          926

<210> SEQ ID NO 187
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 187
ggatgtgggt atgctaatgt tgtt                                             24

<210> SEQ ID NO 188
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 188
tgaacaattt tatttctcat accatag                                          27

<210> SEQ ID NO 189
<211> LENGTH: 2154
<212> TYPE: DNA
<213> ORGANISM: Staphylococcus aureus

<400> SEQUENCE: 189
cggtaataaa aaatacgata tagatgaata acaaaacagt gaagcaatcc gtaacgatgg       60
ttgcttcact gttttattat gaattattaa taagtgctgt tacttctccc ttaaatacaa      120
tttcttcatt tcattgtat gttgaaagtg acactgtaac gagtccattt tctttttta       180 tggatttctt atttgtaatt tcagcgataa cgtacaatgt attacctggg tatacaggtt      240
taataaattt aacgttattc atttgtgttc ctgctacaac ttcttctccg tatttacctt      300
cttctaccca taatttaaat gatattgaaa gtgtatgcat gccagatgca atgatacctt      360
taaatctact ttgttctgct ttttctttat ctatatgcat atattgagga tcaaaagttg      420
ttgcaaattg gataatttct tcttctgtaa tatgaaggct ttttgtttg aatgtttctc      480 ctactataaa atcatcgtat ttcatatatg tctctctttc ttattcaaat taattttta      540 gtatgtaaca tgttaaaggt aagtctaccg tcactgaaac gtaagactca cctctaactt      600
tctattgaga caaatgcacc atttatctg cattgtctgt aaagatacca tcaactcccc      660
aattagcaag ttggtttgca cgtgctggtt tgtttacagt ccatacgttc aattcataac      720
ccgcttcttt taccattttt actttgtgctt tagtaagttt ggcatcttca gtgttactta      780
ttttagcatt acagtaatct aaaagtgttc tccagtcttc acgaaacgaa gttgtatgga      840
atataactgc tctgttatat tgtggcatga tttcttctgc aagtttaaca agcacaacat      900
taaagcttga aatgagcact tcttgattct gatttaagtt tgttaattgt tcttccactt      960
gcttaaccat acttttagaa agtgctagtc cattcggtcc agtaatacct tttaattcta     1020
```

```
catttaaatt catattatat tcatttgcta tttttactac atcatcgaaa gttggcaaat    1080
gttcatcttt gaattttca ccaaaccaag atcctgcaga agcatcttta atttcatcat     1140
aattcaattc agttatttcc ccggacatat ttgtagtccg ttctaaataa tcatcatgaa    1200
tgataatcag ttgttcatct tttgtaattg caacatctaa ctccaaccag tttatacctt    1260
ctacttctga agcagcttta aatgatgcaa ttgtattttc cggagcttta ctaggtaatc    1320
ctctatgtcc atatacagtt agcatattac ctctccttgc atttttattt ttttaattaa    1380
cgtaactgta ttatcacatt aatcgcactt ttatttccat taaaaagaga tgaatatcat    1440
aaataaagaa gtcgatagat tcgtattgat tatggagtta atctacgtct catctcattt    1500
ttaaaaaatc atttatgtcc caagctccat tttgtaatca agtctagttt tcggttctg     1560 ttgcaaagtt gaatttatag tataatttta acaaaaagga gtcttctgta tgaactattt    1620
cagatataaa caatttaaca aggatgttat cactgtagcc gttggctact atctaagata    1680
tacattgagt tatcgtgata tatctgaaat attaagggaa cgtggtgtaa acgttcatca    1740
ttcaacggtc taccgttggg ttcaagaata tgccccaatt ttgtatcaaa tttggaagaa    1800
aaagcataaa aaagcttatt acaaatggcg tattgatgag acgtacatca aaataaaagg    1860
aaaatggagc tatttatatc gtgccattga tgcagaggga catacattag atatttggtt    1920
gcgtaagcaa cgagataatc attcagcata tgcgtttatc aaacgtctca ttaaacaatt    1980
tggtaaacct caaaaggtaa ttacagatca ggcaccttca acgaaggtag caatggctaa    2040
agtaattaaa gcttttaaac ttaaacctga ctgtcattgt acatcgaaat atctgaataa    2100
cctcattgag caagatcacc gtcatattaa agtaagaaag acaaggtatc aaag          2154

<210> SEQ ID NO 190
<211> LENGTH: 2410
<212> TYPE: DNA
<213> ORGANISM: Staphylococcus aureus

<400> SEQUENCE: 190
ccaccttcat atgacgtcta tccatttatg tatggcatga gtaacgaaga atataataaa      60
ttaaccgaag ataaaaaaga acctctgctc aacaagttcc agattacaac ttcaccaggt     120
tcaactcaaa aaatattaac agcaatgatt gggttaaata acaaaacatt agacgataaa     180
acaagttata aaatcgatgg taaaggttgg caaaaagata aatcttgggg tggttacaac     240
gttacaagat atgaagtggt aaatggtaat atcgacttaa acaagcaat agaatcatca      300 gataacattt tctttgctag agtagcactc gaattaggca gtaagaaatt tgaaaaaggc     360
atgaaaaaac taggtgttgg tgaagatata ccaagtgatt atccatttta taatgctcaa     420
atttcaaaca aaaatttaga taatgaaata ttattagctg attcaggtta cggacaaggt     480
gaaatactga ttaacccagt acagatcctt tcaatctata gcgcattaga aaataatggc     540
aatattaacg cacctcactt attaaaagac acgaaaaaca aagtttggaa gaaaaatatt     600
atttccaaag aaaatatcaa tctattaact gatggtatgc aacaagtcgt aaataaaaca     660 cataagaag atatttatag atcttatgca aacttaattg gcaaatccgg tactgcagaa     720
ctcaaaatga acaaggaga aactggcaga caaattgggt ggtttatatc atatgataaa     780
gataatccaa acatgatgat ggctattaat gttaaagatg tacaagataa aggaatggct     840
agctacaatg ccaaaatctc aggtaaagtg tatgatgagc tatatgagaa cggtaataaa     900
aaatacgata tagatgaata acaaaacagt gaagcaatcc gtaacgatgg ttgcttcact     960
```

```
gttttattat gaattattaa taagtgctgt tacttctccc ttaaatacaa tttcttcatt      1020
ttcattgtat gttgaaagtg acactgtaac gagtccattt tcttttttta tggatttctt      1080
atttgtaatt tcagcgataa cgtacaatgt attacctggg tatacaggtt taataaattt      1140
aacgttattc atttgtgttc ctgctacaac ttcttctccg tatttacctt cttctaccca      1200
taatttaaat gatattgaaa gtgtatgcat gccagatgca atgatacctt taaatctact      1260
ttgttctgct ttttctttat ctatatgcat atattgagga tcaaaagttg ttgcaaattg      1320
gataatttct tcttctgtaa tatgaaggct ttttgttttg aatgtttctc ctactataaa      1380
atcatcgtat ttcatatatg tctctctttc ttattcaaat taattttta gtatgtaaca      1440 tgttaaaggt aagtctaccg tcactgaaac gtaagactca cctctaactt tctattgaga      1500
caaatgcacc attttatctg cattgtctgt aaagatacca tcaactcccc aattagcaag      1560
ttggtttgca cgtgctggtt tgtttacagt ccatacgttc aattcataac ccgcttcttt      1620 taccatttt acttttgctt tagtaagttt ggcatcttca gtgttactaa ttttagcatt      1680
acagtaatct aaaagtgttc tccagtcttc acgaaacgaa gttgtatgga atataactgc      1740
tctgttatat tgtggcatga tttcttctgc aagtttaaca agcacaacat taaagcttga      1800
aatgagcact tcttgattct gatttaagtt tgttaattgt tcttccactt gcttaaccat      1860
acttttagaa agtgctagtc cattcggtcc agtaatacct tttaattcta catttaaatt      1920
catattatat tcatttgcta ttttactac atcatcgaaa gttggcaaat gttcatcttt      1980 gaattttca ccaaaccaag atcctgcaga agcatcttta atttcatcat aattcaattc      2040
agttatttcc ccggacatat ttgtagtccg ttctaaataa tcatcatgaa tgataatcag      2100
ttgttcatct tttgtaattg caacatctaa ctccaaccag tttataccctt ctacttctga      2160 agcagcttta aatgatgcaa ttgtattttc cggagcttta ctaggtaatc ctctatgtcc      2220
atatacagtt agcatattac ctctccttgc atttttattt ttttaattaa cgtaactgta      2280
ttatcacatt aatcgcactt ttatttccat taaaaagaga tgaatatcat aaataaagaa      2340
gtcgatagat tcgtattgat tatggagtta atctacgtct catctcattt ttaaaaaatc      2400
atttatgtcc                                                             2410
```

<210> SEQ ID NO 191
<211> LENGTH: 1858
<212> TYPE: DNA
<213> ORGANISM: Staphylococcus aureus

<400> SEQUENCE: 191

```
caccttcata tgacgtctat ccatttatgt atggcatgag taacgaagaa tataataaat       60
taaccgaaga taaaaagaa cctctgctca acaagttcca gattcaaact tcaccaggtt      120
caactcaaaa aatattaaca gcaatgattg ggttaaataa caaaacatta gacgataaaa      180
caagttataa aatcgatggt aaaggttggc aaaaagataa atcttggggt ggttacaacg      240
ttacaagata tgaagtggta aatggtaata tcgacttaaa acaagcaata gaatcatcag      300
ataacatttt ctttgctaga gtagcactcg aattaggcag taagaaattt gaaaaaggca      360
tgaaaaaact aggtgttggt gaagatatac caagtgatta tccatttat aatgctcaaa      420 tttcaaacaa aaatttagat aatgaaatat tattagctga ttcaggttac ggacaaggtg      480
aaatactgat taacccagta cagatccttt caatctatag cgcattagaa ataatggca      540 atattaacgc acctcactta ttaaaagaca cgaaaaacaa agtttggaag aaaaatatta      600
tttccaaaga aaatatcaat ctattaactg atggtatgca acaagtcgta aataaaacac      660
```

```
ataaagaaga tatttataga tcttatgcaa acttaattgg caaatccggt actgcagaac    720
tcaaaatgaa acaaggagaa actggcagac aaattgggtg gtttatatca tatgataaag    780
ataatccaaa catgatgatg gctattaatg ttaaagatgt acaagataaa ggaatggcta    840
gctacaatgc caaaatctca ggtaaagtgt atgatgagct atatgagaac ggtaataaaa    900
aatacgatat agatgaataa caaaacagtg aagcaatccg taacgatggt tgcttcactg    960
ttttattatg aattattaat aagtgctgtt acttctccct aaatacaat tcttcatttt    1020 tcattgtatg ttgaaagtga cactgtaacg agtccatttt cttttttat ggatttctta    1080 tttgtaattt cagcgataac gtacaatgta ttacctgggt atacaggttt aataaattta    1140
acgttattca tttgtgttcc tgctacaact tcttctccgt atttaccttc ttctacccat    1200
aatttaaatg atattgaaag tgtatgcatg ccagatgcaa tgataccttt aaatctactt    1260
tgttctgctt tttctttatc tatatgcata tattgaggat caaaagttgt tgcaaattgg    1320
ataatttctt cttctgtaat atgaaggctt tttgttttga atgtttctcc tactataaaa    1380
tcatcgtatt tcatatatgt ctctctttct tattcaaatt aatttttag tatgtaacat    1440 gttaaaggta agtctaccgt cactgaaacg taagactcac ctctaacttt ctattgagac    1500
aaatgcacca ttttatctgc attgtctgta aagataccat caactcccca attagcaagt    1560
tggtttgcac gtgctggttt gtttacagtc catacgttca attcataacc cgcttctttt    1620 accatttta ctttttgcttt agtaagtttg gcatcttcag tgtttactat tttagcatta    1680
cagtaatcta aaagtgttct ccagtcttca cgaaacgaag ttgtatggaa tataactgct    1740
ctgttatatt gtggcatgat ttcttctgca agtttaacaa gcacaacatt aaagcttgaa    1800
atgagcactt cttgattctg atttaagttt gttaattgtt cttccacttg cttaacca     1858
```

<210> SEQ ID NO 192
<211> LENGTH: 1861
<212> TYPE: DNA
<213> ORGANISM: Staphylococcus aureus

<400> SEQUENCE: 192

```
ccaccttcat atgacgtcta tccatttatg tatggcatga gtaacgaaga atataataaa     60
ttaaccgaag ataaaaaaga acctctgctc aacaagttcc agattacaac ttcaccaggt    120
tcaactcaaa aaatattaac agcaatgatt gggttaaata caaaacatt agacgataaa    180 acaagttata aaatcgatgg taaaggttgg caaaaagata atcttgggg tggttacaac    240 gttacaagat atgaagtggt aaatggtaat atcgacttaa acaagcaat agaatcatca    300 gataacattt tctttgctag agtagcactc gaattaggca gtaagaaatt tgaaaaaggc    360
atgaaaaaac taggtgttgg tgaagatata ccaagtgatt atccatttta taatgctcaa    420
atttcaaaca aaaatttaga taatgaaata ttattagctg attcaggtta cggacaaggt    480
gaaatactga ttaacccagt acagatcctt tcaatctata gcgcattaga aaataatggc    540
aatattaacg cacctcactt attaaaagac acgaaaaaca aagtttggaa gaaaaatatt    600
atttccaaag aaaatatcaa tctattaact gatggtatgc aacaagtcgt aaataaaaca    660
cataaagaag atatttatag atcttatgca aacttaattg gcaaatccgg tactgcagaa    720
ctcaaaatga acaaggagaa actggcagac aaattgggtg gtttatatc atatgataaa    780 gataatccaa acatgatgat ggctattaat gttaaagatg tacaagataa aggaatggct    840
agctacaatg ccaaaatctc aggtaaagtg tatgatgagc tatatgagaa cggtaataaa    900
```

```
aaatacgata tagatgaata acaaaacagt gaagcaatcc gtaacgatgg ttgcttcact      960
gttttattat gaattattaa taagtgctgt tacttctccc ttaaatacaa tttcttcatt     1020
ttcattgtat gttgaaagtg acactgtaac gagtccattt tcttttttta tggatttctt     1080
atttgtaatt tcagcgataa cgtacaatgt attacctggg tatacaggtt taataaattt     1140
aacgttattc atttgtgttc ctgctacaac ttcttctccg tatttacctt cttctaccca     1200
taatttaaat gatattgaaa gtgtatgcat gccagatgca atgatacctt taaatctact     1260
ttgttctgct ttttctttat ctatatgcat atattgagga tcaaaagttg ttgcaaattg     1320
gataatttct tcttctgtaa tatgaaggct ttttgttttg aatgtttctc ctactataaa     1380
atcatcgtat ttcatatatg tctctctttc ttattcaaat taattttta gtatgtaaca      1440
tgttaaaggt aagtctaccg tcactgaaac gtaagactca cctctaactt tctattgaga     1500
caaatgcacc attttatctg cattgtctgt aaagatacca tcaactcccc aattagcaag     1560
ttggtttgca cgtgctggtt tgtttacagt ccatacgttc aattcataac ccgcttcttt     1620
taccattttt acttttgctt tagtaagttt ggcatcttca gtgtttacta ttttagcatt     1680
acagtaatct aaaagtgttc tccagtcttc acgaaacgaa gttgtatgga atataactgc     1740
tctgttatat tgtggcatga tttcttctgc aagtttaaca agcacaacat taaagcttga     1800
aatgagcact tcttgattct gatttaagtt tgttaattgt tcttccactt gcttaaccat     1860
a                                                                    1861

<210> SEQ ID NO 193
<211> LENGTH: 1861
<212> TYPE: DNA
<213> ORGANISM: Staphylococcus aureus

<400> SEQUENCE: 193
ccaccttcat atgacgtcta tccatttatg tatggcatga gtaacgaaga atataataaa       60
ttaaccgaag ataaaaaaga acctctgctc aacaagttcc agattacaac ttcaccaggt      120
tcaactcaaa aaatattaac agcaatgatt gggttaaata caaaacatt agacgataaa       180
acaagttata aaatcgatgg taaaggttgg caaaaagata atcttgggg tggttacaac       240
gttacaagat atgaagtggt aaatggtaat atcgacttaa acaagcaat agaatcatca       300
gataacattt tctttgctag agtagcactc gaattaggca gtaagaaatt tgaaaaaggc      360
atgaaaaaac taggtgttgg tgaagatata ccaagtgatt atccattta taatgctcaa       420
atttcaaaca aaaatttaga taatgaaata ttattagctg attcaggtta cggacaaggt      480
gaaatactga ttaacccagt acagatcctt tcaatctata gcgcattaga aaataatggc      540
aatattaacg cacctcactt attaaaagac acgaaaaaca aagtttggaa gaaaaatatt      600
atttccaaag aaaatatcaa tctattaact gatggtatgc aacaagtcgt aaataaaaca      660
cataagaag atatttatag atcttatgca aacttaattg gcaaatccgg tactgcagaa       720
ctcaaaatga acaaggaga aactggcaga caaattgggt ggtttatatc atatgataaa       780
gataatccaa acatgatgat ggctattaat gttaaagatg tacaagataa aggaatggct      840
agctacaatg ccaaaatctc aggtaaagtg tatgatgagc tatatgagaa cggtaataaa      900
aaatacgata tagatgaata acaaaacagt gaagcaatcc gtaacgatgg ttgcttcact      960
gttttattat gaattattaa taagtgctgt tacttctccc ttaaatacaa tttcttcatt     1020
ttcattgtat gttgaaagtg acactgtaac gagtccattt tcttttttta tggatttctt     1080
atttgtaatt tcagcgataa cgtacaatgt attacctggg tatacaggtt taataaattt     1140
```

-continued

```
aacgttattc atttgtgttc ctgctacaac ttcttctccg tatttacctt cttctaccca    1200
taatttaaat gatattgaaa gtgtatgcat gccagatgca atgataccttt aaatctact    1260 ttgttctgct ttttctttat ctatatgcat atattgagga tcaaagttg ttgcaaattg     1320 gataatttct tcttctgtaa tatgaaggct ttttgttttg aatgtttctc ctactataaa    1380
atcatcgtat ttcatatatg tctctctttc ttattcaaat taattttta gtatgtaaca    1440 tgttaaaggt aagtctaccg tcactgaaac gtaagactca cctctaactt tctattgaga    1500
caaatgcacc attttatctg cattgtctgt aaagatacca tcaactcccc aattagcaag    1560
ttggtttgca cgtgctggtt tgtttacagt ccatacgttc aattcataac ccgcttcttt    1620
taccattttt acttttgctt tagtaagttt ggcatcttca gtgtttacta ttttagcatt    1680
acagtaatct aaaagtgttc tccagtcttc acgaaacgaa gttgtatgga atataactgc    1740
tctgttatat tgtggcatga tttcttctgc aagtttaaca agcacaacat taaagcttga    1800
aatgagcact tcttgattct gatttaagtt tgttaattgt tcttccactt gcttaaccat    1860
a                                                                   1861

<210> SEQ ID NO 194
<211> LENGTH: 1052
<212> TYPE: DNA
<213> ORGANISM: Staphylococcus aureus

<400> SEQUENCE: 194
cggtaataaa aaatacgata tagatgaata acaaaacagt gaagcaatcc gtaacgatgg     60
ttgcttcact gttttattat gaattattaa taagtgctgt tacttctccc ttaaatacaa    120
tttcttcatt ttcattgtat gttgaaagtg acactgtaac gagtccattt tctttttta    180 tggatttctt atttgtaatt tcagcgataa cgtacaatgt attacctggg tatacaggtt    240
taataaattt aacgttattc atttgtgttc ctgctacaac ttcttctccg tatttacctt    300
cttctaccca taatttaaat gatattgaaa gtgtatgcat gccagatgca atgataccttt   360 taaatctact ttgttctgct ttttctttat ctatatgcat atattgagga tcaaagttg     420 ttgcaaattg gataatttct tcttctgtaa tatgaaggct ttttgttttg aatgtttctc    480
ctactataaa atcatcgtat ttcatatatg tctctctttc ttattcaaat taattttta    540 gtatgtaaca tgttaaaggt aagtctaccg tcactgaaac gtaagactca cctctaactt    600
tctattgaga caaatgcacc attttatctg cattgtctgt aaagatacca tcaactcccc    660
aattagcaag ttggtttgca cgtgctggtt tgtttacagt ccatacgttc aattcataac    720
ccgcttcttt taccattttt acttttgctt tagtaagttt ggcatcttca gtgtttacta    780
ttttagcatt acagtaatct aaaagtgttc tccagtcttc acgaaacgaa gttgtatgga    840
atataactgc tctgttatat tgtggcatga tttcttctgc aagtttaaca agcacaacat    900
taaagcttga aatgagcact tcttgattct gatttaagtt tgttaattgt tcttccactt    960
gcttaaccat acttttagaa agtgctagtc cattcggtcc agtaatacct tttaattcta   1020
catttaaatt catattatat tcatttgcta tt                                 1052

<210> SEQ ID NO 195
<211> LENGTH: 3101
<212> TYPE: DNA
<213> ORGANISM: Staphylococcus aureus

<400> SEQUENCE: 195
```

```
cttcatatga cgtctatcca tttatgtatg gcatgagtaa cgaagaatat aataaattaa    60
ccgaagataa aaaagaacct ctgctcaaca agttccagat tacaacttca ccaggttcaa   120
ctcaaaaaat attaacagca atgattgggt taaataacaa acattagac gataaaacaa    180 gttataaaat cgatggtaaa ggttggcaaa aagataaatc ttggggtggt tacaacgtta   240
caagatatga agtggtaaat ggtaatatcg acttaaaaca agcaatagaa tcatcagata   300
acattttctt tgctagagta gcactcgaat taggcagtaa gaaatttgaa aaaggcatga   360
aaaaactagg tgttggtgaa gatataccaa gtgattatcc attttataat gctcaaattt   420
caaacaaaaa tttagataat gaaatattat tagctgattc aggttacgga caaggtgaaa   480
tactgattaa cccagtacag atcctttcaa tctatagcgc attagaaaat aatggcaata   540
ttaacgcacc tcacttatta aaagacacga aaaacaaagt ttggaagaaa atattattt    600 ccaaagaaaa tatcaatcta ttaactgatg gtatgcaaca agtcgtaaat aaaacacata   660
aagaagatat ttatagatct tatgcaaact taattggcaa atccggtact gcagaactca   720
aaatgaaaca aggagaaact ggcagacaaa ttgggtggtt tatatcatat gataaagata   780
atccaaacat gatgatggct attaatgtta aagatgtaca agataaagga atggctagct   840
acaatgccaa atctcaggt aaagtgtatg atgagctata tgagaacggt aataaaaaat   900
acgatataga tgaataacaa acagtgaag caatccgtaa cgatggttgc ttcactgttt   960
tattatgaat tattaataag tgctgttact tctcccttaa atacaatttc ttcattttca  1020
ttgtatgttg aaagtgacac tgtaacgagt ccattttctt tttttatgga tttcttattt  1080
gtaatttcag cgataacgta caatgtatta cctgggtata caggtttaat aaatttaacg  1140
ttattcattt gtgttcctgc tacaacttct tctccgtatt taccttcttc tacccataat  1200
ttaaatgata ttgaaagtgt atgcatgcca gatgcaatga taccttttaaa tctactttgt  1260 tctgcttttt ctttatctat atgcatatat tgaggatcaa aagttgttgc aaattggata  1320
atttcttctt ctgtaaatg aaggcttttt gttttgaatg tttctcctac tataaaatca  1380
tcgtatttca tatatgtctc tctttcttat tcaaattaat ttttttagtat gtaacatgtt  1440 aaaggtaagt ctaccgtcac tgaaacgtaa gactcacctc taactttcta ttgagacaaa  1500
tgcaccattt tatctgcatt gtctgtaaag ataccatcaa ctccccaatt agcaagttgg  1560
tttgcacgtg ctggtttgtt tacagtccat acgttcaatt cataacccgc ttcttttacc  1620
atttttactt ttgctttagt aagtttggca tcttcagtgt ttactatttt agcattacag  1680
taatctaaaa gtgttctcca gtcttcacga aacgaagttg tatggaatat aactgctctg  1740
ttatattgtg gcatgatttc ttctgcaagt ttaacaagca caacattaaa gcttgaaatg  1800
agcacttctt gattctgatt taagtttgtt aattgttctt ccacttgctt aaccatactt  1860
ttagaaagtg ctagtccatt cggtccagta ataccttta attctacatt taaattcata  1920
ttatattcat ttgctatttt tactacatca tcgaaagttg gcaaatgttc atctttgaat  1980
ttttcaccaa accaagatcc tgcagaagca tctttaattt catcataatt caattcagtt  2040
atttccccgg acatatttgt agtccgttct aaataatcat catgaatgat aatcagttgt  2100 tcatctttg taattgcaac atctaactcc aaccagttta taccttctac ttctgaagca  2160
gctttaaatg atgcaattgt attttccgga gctttactag gtaatcctct atgtccatat  2220
acagttagca tattacctct ccttgcattt ttatttttt aattaacgta actgtattat  2280
cacattaatc gcacttttat ttccattaaa aagagatgaa tatcataaat aaagaagtcg  2340
atagattcgt attgattatg gagttaatct acgtctcatc tcattttaa aaaatcattt   2400
```

```
atgtcccaag ctccattttg taatcaagtc tagttttcg gttctgttgc aaagttgaat    2460
ttatagtata attttaacaa aaaggagtct tctgtatgaa ctatttcaga tataaacaat    2520
ttaacaagga tgttatcact gtagccgttg gctactatct aagatataca ttgagttatc    2580
gtgatatatc tgaaatatta agggaacgtg tgtaaacgt tcatcattca acggtctacc    2640
gttgggttca agaatatgcc ccaattttgt atcaaatttg gaagaaaaag cataaaaaag    2700
cttattacaa atggcgtatt gatgagacgt acatcaaaat aaaaggaaaa tggagctatt    2760
tatatcgtgc cattgatgca gagggacata cattagatat ttggttgcgt aagcaacgag    2820
ataatcattc agcatatgcg tttatcaaac gtctcattaa acaatttggt aaacctcaaa    2880
aggtaattac agatcaggca ccttcaacga aggtagcaat ggctaaagta attaaagctt    2940
ttaaacttaa acctgactgt cattgtacat cgaaatatct gaataacctc attgagcaag    3000
atcaccgtca tattaaagta agaaagacaa ggtatcaaag tatcaataca gcaaagaata    3060 cttttaaaagg tattgaatgt atttacgctc tatataaaaa g                      3101
```

<210> SEQ ID NO 196
<211> LENGTH: 3506
<212> TYPE: DNA
<213> ORGANISM: Staphylococcus aureus

<400> SEQUENCE: 196

```
ccaccttcat atgacgtcta tccatttatg tatggcatga gtaacgaaga atataataaa      60
ttaaccgaag ataaaaaaga acctctgctc aacaagttcc agattacaac ttcaccaggt     120
tcaactcaaa aaatattaac agcaatgatt gggttaaata caaaacatt agacgataaa      180 acaagttata aaatcgatgg taaaggttgg caaaaagata atcttggggg tggttacaac     240
gttacaagat atgaagtggt aaatggtaat atcgacttaa acaagcaat agaatcatca      300 gataacattt tctttgctag agtagcactc gaattaggca gtaagaaatt tgaaaaaggc     360
atgaaaaaac taggtgttgg tgaagatata ccaagtgatt atccatttta taatgctcaa     420
atttcaaaca aaaatttaga taatgaaata ttattagctg attcaggtta cggacaaggt     480
gaaatactga ttaacccagt acagatcctt tcaatctata gcgcattaga aaataatggc     540
aatattaacg cacctcactt attaaaagac acgaaaaaca agtttggaa gaaaaatatt      600 atttccaaag aaaatatcaa tctattaact gatggtatgc aacaagtcgt aaataaaaca     660 cataagaag atatttatag atcttatgca aacttaattg gcaaatccgg tactgcagaa      720
ctcaaaatga aacaaggaga aactggcaga caaattgggt ggtttatatc atatgataaa     780
gataatccaa acatgatgat ggctattaat gttaaagatg tacaagataa aggaatggct     840
agctacaatg ccaaaatctc aggtaaagtg tatgatgagc tatatgagaa cggtaataaa     900
aaatacgata tagatgaata acaaaacagt gaagcaatcc gtaacgatgg ttgcttcact     960
gttttattat gaattattaa taagtgctgt tacttctccc ttaaatacaa tttcttcatt    1020
ttcattgtat gttgaaagtg acactgtaac gagtccattt tcttttttta tggatttctt    1080
atttgtaatt tcagcgataa cgtacaatgt attacctggg tatacaggtt taataaattt    1140
aacgttattc atttgtgttc ctgctacaac ttcttctccg tatttacctt cttctaccca    1200
taatttaaat gatattgaaa gtgtatgcat gccagatgca atgatacctt taaatctact    1260
ttgttctgct ttttctttat ctatatgcat atattgagga tcaaaagttg ttgcaaattg    1320
gataatttct tcttctgtaa tatgaaggct ttttgttttg aatgtttctc ctactataaa    1380
```

```
atcatcgtat ttcatatatg tctctctttc ttattcaaat taattttta gtatgtaaca    1440
tgttaaaggt aagtctaccg tcactgaaac gtaagactca cctctaactt tctattgaga    1500
caaatgcacc attttatctg cattgtctgt aaagatacca tcaactcccc aattagcaag    1560
ttggtttgca cgtgctggtt tgtttacagt ccatacgttc aattcataac ccgcttcttt    1620
taccattttt acttttgctt tagtaagttt ggcatcttca gtgtttacta ttttagcatt    1680
acagtaatct aaaagtgttc tccagtcttc acgaaacgaa gttgtatgga atataactgc    1740
tctgttatat tgtggcatga tttcttctgc aagtttaaca agcacaacat taaagcttga    1800
aatgagcact tcttgattct gatttaagtt tgttaattgt tcttccactt gcttaaccat    1860
acttttagaa agtgctagtc cattcggtcc agtaatacct tttaattcta catttaaatt    1920
catattatat tcatttgcta tttttactac atcatcgaaa gttggcaaat gttcatcttt    1980
gaattttca ccaaaccaag atcctgcaga agcatcttta atttcatcat aattcaattc    2040
agttatttcc ccggacatat ttgtagtccg ttctaaataa tcatcatgaa tgataatcag    2100
ttgttcatct tttgtaattg caacatctaa ctccaaccag tttatacctt ctacttctga    2160
agcagcttta aatgatgcaa ttgtattttc cggagcttta ctaggtaatc ctctatgtcc    2220
atatacagtt agcatattac ctctccttgc attttattt ttttaattaa cgtaactgta    2280
ttatcacatt aatcgcactt ttatttccat taaaagaga tgaatatcat aaataaagaa    2340
gtcgatagat tcgtattgat tatggagtta atctacgtct catctcattt ttaaaaaatc    2400
atttatgtcc caagctccat tttgtaatca agtctagttt ttctgtaccc cttatctgca    2460
attttactta ggattgcttt taacttaccc cttatcagca attttactga gaactgcttt    2520
taacgcacct cttatctgca attttgccta gaactgcttt taacgtacct cttatctgca    2580
attttactga gaactgcttt taacttaccc cttatcagca attttgcatg gaattgcttt    2640
taacgtacct cttatctgca attttactta gaactgcttt taacaaacct cttatctgca    2700
attttactta gaactgcttt taacgtacct cttatctgta attttactga gaactgcttt    2760
taacaaacct cttatctgca attttactta gaactgcttt taacaaacct cttatctgca    2820
attttactta gaattgcttt tactattcct cttattagta taatctcagt aagaatgcgt    2880
ataaaaatga aaattacaac cgattttgta agtgctgacg cctgagggaa tagtatgtgc    2940
gagagactaa tggctcgagc catacccta ggcaagcatg cacgtacaaa atcgtaagat    3000
aaaaaaataa gcatatcact gtaaacttta aaaaatcagt ttagtgatat gcttatttat    3060
ttcgagttag gatttatgtc ccaagctcat caagcacaat cggccactag tttatttctc    3120
tatcttatat gttctgatat ggtcttctat actgtataag tatactttg aatatggatc    3180
ttgtgtcaat tcacgttcga aatcaaattc ttgattatca aatctgttaa agaatgtttc    3240
gtattcttcg actgataatt gctctctaga ttctagcata tttaagtgtt tctctttatc    3300
taatgctttg tcatatcctt taacgattga accactaaag attttctccta ctgctcctga    3360
accataacta aatagacata ctttctcttc tggttggaat gtgtggttct gtaataacga    3420
aattaaactt aagtataatg atcctgtata aatgttacca acatctctat tccataatac    3480
ggttctgttg caaagttgaa tttata                                         3506
```

<210> SEQ ID NO 197
<211> LENGTH: 928
<212> TYPE: DNA
<213> ORGANISM: Staphylococcus aureus

<400> SEQUENCE: 197

```
tacattagaa atacaaggaa agatgctatc ttccgaagga ttggcccaag aattgaacca      60
acgcatgacc caagggcaaa gcgactttgt attcgtcatt ggcggatcaa acggcctgca     120
caaggacgtc ttacaacgca gtaactacgc actatcattc agcaaaatga cattcccaca     180
tcaaatgatg cgggttgtgt taattgaaca agtgtacaga gcatttaaga ttatgcgtgg     240
agaagcatat cataaatgat gcggtttttt cagccgcttc ataaagggat tttgaatgta     300
tcagaacata tgaggtttat gtgaattgct gttatgtttt aagaagctt atcataagta      360 atgaggttca tgattttga catagttagc ctccgcagtc tttcatttca agtaaataat      420
agcgaaatat tctttatact gaatacttat agtgaagcaa agttctagct ttgagaaaat     480
tctttctgca actaaatata gtaaattacg gtaaaatata ataagtaca tattgaagaa      540 aatgagacat aatatatttt ataataggag ggaatttcaa atgatagaca actttatgca     600
ggtccttaaa ttaattaaag agaaacgtac caataatgta gttaaaaaat ctgattggga     660
taaaggtgat ctatataaaa ctttagtcca tgataagtta cccaagcagt aaaagtgca      720 tataaagaa gataaatatt cagttgtagg gaaggttgct actgggaact atagtaaagt      780
tccttggatt tcaatatatg atgagaatat aacaaaagaa acaaggatg gatattattt      840 ggtatatctt tttcatccgg aaggagaagg catatactta tctttgaatc aaggatggtc     900
aaagataagt gatatgtttc cgcgggat                                        928
```

<210> SEQ ID NO 198
<211> LENGTH: 782
<212> TYPE: DNA
<213> ORGANISM: Staphylococcus aureus

<400> SEQUENCE: 198

```
caatgcccac agagttatcc acaaatacac aggttataca ctaaaaattg gcatgaatg      60 tcagaaaaat atcaaaaact gcaaagaata ttggtataat aagagggaac agtgtgaaca    120
agttaataac ttgtggataa ctggaaagtt gataacaatt tggaggacca aacgacatga    180
aaatcaccat tttagctgta gggaaactaa aagagaaata ttggaagcaa gccatagcag    240
aatatgaaaa acgtttaggc ccatacacca agatagacat catagaagtt ccagacgaaa    300
aagcaccaga aaatatgagc gacaaagaaa ttgagcaagt aaaagaaaaa gaaggccaac    360
gaatactagc caaaatcaaa ccacaatcaa cagtcattac attagaaata caaggaaaga    420
tgctatcttc cgaaggattg gcccaagaat tgaaccaacg catgacccaa gggcaaagcg    480
actttgtatt cgtcattggc ggatcaaacg gcctgcacaa ggacgtctta caacgcagta    540
actacgcact atcattcagc aaaatgacat cccacatca aatgatgcgg ttgtgttaa      600 ttgaacaagt gtacagagca tttaagatta tgcgtggaga agcgtatcat aaataaaact    660
aaaaattagg ttgtgtataa tttaaaaatt taatgagatg tggaggaatt acatatatga    720
aatattggat tataccttgc aatatcatac gatgtttata gagtgtttaa taaccatttt    780
tt                                                                    782
```

<210> SEQ ID NO 199
<211> LENGTH: 709
<212> TYPE: DNA
<213> ORGANISM: Staphylococcus aureus

<400> SEQUENCE: 199

```
tacattagaa atacaaggaa agatgctatc ttccgaagga ttggcccaag aattgaacca      60
```

-continued

```
acgcatgacc caagggcaaa gcgactttgt tttcgtcatt ggcggatcaa acggcctgca      120
caaggacgtc ttacaacgca gtaactacgc actatcattc agcaaaatga cattcccaca      180
tcaaatgatg cgggttgtgt taattgaaca agtgtacaga gcatttaaga ttatgcgagg      240
agaagcttat cataagtaat gaggttcatg attttttgaca tagttagcct ccgcagtctt      300
tcatttcaag taaataatag cgaaatattc tttatactga atacttatag tgaagcaaag      360
ttctagcttt gagaaaattc tttctgcaac taaatatagt aaattacggt aaaatataaa      420
taagtacata ttgaagaaaa tgagacataa tatattttat aataggaggg aatttcaaat      480
gatagacaac tttatgcagg tccttaaatt aattaaagag aaacgtacca ataatgtagt      540 taaaaatct gattgggata aggtgatct atataaaact ttagtccatg ataagttacc       600
caagcagtta aaagtgcata taaaagaaga taaatattca gttgtaggga aggttgctac      660
tgggaactat agtaaagttc cttggatttc aatatatgat gagaatata                 709
```

<210> SEQ ID NO 200
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 200

```
gtgggaaatg gctgttgttg ag                                              22
```

<210> SEQ ID NO 201
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 201

```
ttcgttccct ccattaactg tc                                              22
```

<210> SEQ ID NO 202
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 202

```
aaaagaaaga cggtgaaggc                                                 20
```

<210> SEQ ID NO 203
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 203

```
cacttcatta tactgttttc tttgc                                           25
```

<210> SEQ ID NO 204
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 204
tcaccgtctt tcttttgacc tt                           22

<210> SEQ ID NO 205
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 205
tgagatctgc tggaacaaaa gtgaa                        25

<210> SEQ ID NO 206
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 206
cggtcgagtt tgctgaagaa                              20

<210> SEQ ID NO 207
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 207
tcccctaatg atagctggta tatatt                       26

<210> SEQ ID NO 208
<211> LENGTH: 27
<212> TYPE: DNA
<213> ORGANISM: Artificial Sequence
<220> FEATURE:
<223> OTHER INFORMATION: Synthetic nucleic acid sequence

<400> SEQUENCE: 208
tctagggaat caaagaaaag taatagt                      27

<210> SEQ ID NO 209
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 209
caacaargrc aatgtgayrt attatgytgt ta                32

<210> SEQ ID NO 210
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 210
gataayatwg gmgaacaagt caraaatgg                    29

<210> SEQ ID NO 211
<211> LENGTH: 35
<212> TYPE: DNA

```
<213> ORGANISM: Artificial Sequence
<220> FEATURE:
<223> OTHER INFORMATION: Synthetic nucleic acid sequence

<400> SEQUENCE: 211
ccrtattgat tgwtracacg rccacartaa ttwgg                    35

<210> SEQ ID NO 212
<211> LENGTH: 32
<212> TYPE: DNA
<213> ORGANISM: Artificial Sequence
<220> FEATURE:
<221> NAME/KEY: misc_feature
<222> LOCATION: 30
<223> OTHER INFORMATION: n = inosine
<220> FEATURE:
<223> OTHER INFORMATION: Synthetic nucleic acid sequence

<400> SEQUENCE: 212
atrttsartg gttcattttt gaaatagatn cc                       32

<210> SEQ ID NO 213
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 213
acgtgtcggt atctatgtwc gtgtatcaac rg                       32

<210> SEQ ID NO 214
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 214
tgttatgrtc tacaaaacaa accgaytagc                          30

<210> SEQ ID NO 215
<211> LENGTH: 34
<212> TYPE: DNA
<213> ORGANISM: Artificial Sequence
<220> FEATURE:
<223> OTHER INFORMATION: Synthetic nucleic acid sequence

<400> SEQUENCE: 215
gawtaataat rggggaatgc ttaccttcag ctat                     34

<210> SEQ ID NO 216
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 216
ggtttttgac tgacttgttt tttacg                              26

<210> SEQ ID NO 217
<211> LENGTH: 29
<212> TYPE: DNA
<213> ORGANISM: Artificial Sequence
<220> FEATURE:
<223> OTHER INFORMATION: Synthetic nucleic acid sequence
```

<400> SEQUENCE: 217
tagaaytgtt ttttatgatt accrtcttt                                          29

<210> SEQ ID NO 218
<211> LENGTH: 26
<212> TYPE: DNA
<213> ORGANISM: Artificial Sequence
<220> FEATURE:
<223> OTHER INFORMATION: Synthetic nucleic acid sequence

<400> SEQUENCE: 218
ggcaaaaaya aagacgaagt gctgag                                             26

<210> SEQ ID NO 219
<211> LENGTH: 721
<212> TYPE: DNA
<213> ORGANISM: Staphylococcus aureus

<400> SEQUENCE: 219
tgtagcttta ggtgaagggt taggtccttc aatagggga ataatagcac attatattca          60
ttggtcttac ctacttatac ttcctatgat tacaatagta actataccct ttcttattaa        120
agtaatggta cctggtaaat caacaaaaaa tacattagat atcgtaggta ttgtttttaat       180 gtctataagt attatatgtt ttatgttatt tacgacaaat tataattgga ctttttttaat      240 actcttcaca atcttttttg tgatttttat taaacatatt tcaagagttt ctaaccctt       300 tattaatcct aaactaggga aaaacattcc gtttatgctt ggtttgtttt ctggtgggct       360 aatatttttct atagtagctg ttttatatc aatggtgcct tatatgatga aaactattta       420
tcatgtaaat gtagcgacaa taggtaatag tgttattttt cctggaacca tgagtgttat      480
tgtttttggt tattttggtg ttttttagt ggatagaaaa ggatcattat tgttttttat      540
tttaggatca ttgtctatct ctataagttt tttaactatt gcatttttg ttgagtttag        600 tatgtggttg actacttta tgtttatatt tgttatgggc ggattatctt ttactaaaac       660
agttatatca aaaatagtat caagtagtct ttctgaagaa gaagttgctt ctggaagagt      720
t                                                                        721

<210> SEQ ID NO 220
<211> LENGTH: 1791
<212> TYPE: DNA
<213> ORGANISM: Staphylococcus aureus

<400> SEQUENCE: 220
atccggtact gcagaactca aaatgaaaca aggagaaact ggcagacaaa ttgggtggtt         60
tatatcatat gataaagata atccaaacat gatgatggct attaatgtta aagatgtaca       120
agataaagga atggctagct acaatgccaa atctcaggt aaagtgtatg atgagctata       180
tgagaacggt aataaaaat acgatataga tgaataacaa acagtgaag caatccgtaa       240 cgatggttgc ttcactgttt tattatgaat tattaataag tgctgttact tctccctta       300 atacaatttc ttcatttca ttgtatgttg aaagtgacac tgtaacgagt ccattttctt        360 ttttatgga tttcttattt gtaatttcag cgataacgta caatgtatta cctgggtata      420
caggtttaat aaatttaacg ttattcattt gtgttcctgc tacaacttct tctccgtatt       480
taccttcttc tacccataat ttaaatgata ttgaaagtgt atgcatgcca gatgcaatga      540
tacctttaaa tctactttgt tctgcttttt ctttatctat atgcatatat tgaggatcaa      600

```
aagttgttgc aaattggata atttcttctt ctgtaatatg aaggcttttt gttttgaatg      660
tttctcctac tataaaatca tcgtatttca tatatgtctc tctttcttat tcaaattaat      720
tttttagtat gtaacatgtt aaaggtaagt ctaccgtcac tgaaacgtaa gactcacctc      780
taactttcta ttgagacaaa tgcaccattt tatctgcatt gtctgtaaag ataccatcaa      840
ctccccaatt agcaagttgg tttgcacgtg ctggtttgtt tacagtccat acgttcaatt      900
cataacccgc ttcttttacc attttttactt ttgcttagt aagtttggca tcttcagtgt      960
ttactatttt agcattacag taatctaaaa gtgttctcca gtcttcacga aacgaagttg     1020
tatggaatat aactgctctg ttatattgtg gcatgatttc ttctgcaagt ttaacaagca     1080
caacattaaa gcttgaaatg agcacttctt gattctgatt taagtttgtt aattgttctt     1140
ccacttgctt aaccatactt ttagaaagtg ctagtccatt cggtccagta atacctttta     1200
attctacatt taaattcata ttatattcat ttgctatttt tactacatca tcgaaagttg     1260
gcaaatgttc atctttgaat ttttcaccaa accaagatcc tgcagaagca tctttaattt     1320
catcataatt caattcagtt atttccccgg acatatttgt agtccgttct aaataatcat     1380
catgaatgat aatcagttgt tcatctttg taattgcaac atctaactcc aaccagttta     1440
taccttctac ttctgaagca gctttaaatg atgcaattg attttccgga gctttactag     1500
gtaatcctct atgtccatat acagttagca tattacctct ccttgcattt ttatttttt     1560 aattaacgta actgtattat cacattaatc gcactttat ttccattaaa aagagatgaa     1620
tatcataaat aaagaagtcg atagattcgt attgattatg gagttaatct acgtctcatc     1680
tcatttttaa aaaatcattt atgtcccaag ctccatttg taatcaagtc tagtttttct     1740 gtaccccta tctgcaattt tacttaggat tgcttttaac ttaccccta t                1791

<210> SEQ ID NO 221
<211> LENGTH: 600
<212> TYPE: DNA
<213> ORGANISM: Staphylococcus aureus

<400> SEQUENCE: 221
aagtgctgac gcctgaggga atagtatgtg cgagagacta atggctcgag ccataccct       60 aggcaagcat gcacgtacaa aatcgtaaga taaaaaaata agcatatcac tgtaaacttt      120
aaaaaatcag tttagtgata tgcttattta tttcgagtta ggatttatgt cccaagctca      180
tcaagcacaa tcggccacta gtttatttct ctatcttata tgttctgata tggtcttcta      240
tactgtataa gtacttttt gaatatggat cttgtgtcaa ttcacgttcg aaatcaaatt      300
cttgattatc aaatctgtta aagaatgttt cgtattcttc gactgataat tgctctctag      360
attctagcat atttaagtgt ttctctttat ctaatgcttt gtcatatcct ttaacgattg      420
aaccactaaa gatttctcct actgctcctg aaccataact aaatagacat actttctctt      480
ctggttggaa tgtgtggttc tgtaataacg aaattaaact taagtataat gatcctgtat      540
aaatgttacc aacatctcta ttccataata cggttctgtt gcaaagttga atttatagta      600

<210> SEQ ID NO 222
<211> LENGTH: 1640
<212> TYPE: DNA
<213> ORGANISM: Staphylococcus aureus

<400> SEQUENCE: 222
gggtggttta tcatatatga taaagataat ccaaacatga tgatggctat taatgttaaa       60
gatgtacaag ataaaggaat ggctagctac aatgccaaaa tctcaggtaa agtgtatgat      120
```

-continued

```
gagctatatg agaacggtaa taaaaaatac gatatagatg aataacaaaa cagtgaagca      180
atccgtaacg atggttgctt cactgtttta ttatgaatta ttaataagtg ctgttacttc      240
tcccttaaat acaatttctt cattttcatt gtatgttgaa agtgacactg taacgagtcc      300
attttctttt tttatggatt tcttattgt aatttcagcg ataacgtaca atgtattacc       360
tgggtataca ggtttaataa atttaacgtt attcatttgt gttcctgcta caacttcttc      420
tccgtattta ccttcttcta cccataattt aaatgatatt gaaagtgtat gcatgccaga     480
tgcaatgata cctttaaatc tactttgttc tgcttttttct ttatctatat gcatatattg    540
aggatcaaaa gttgttgcaa attggataat ttcttcttct gtaatatgaa ggcttttgt      600 tttgaatgtt tctcctacta taaaatcatc gtatttcata tatgtctctc tttcttattc     660
aaattaattt tttagtatgt aacatgttaa aggtaagtct accgtcactg aaacgtaaga     720
ctcacctcta actttctatt gagacaaatg caccatttta tctgcattgt ctgtaaagat     780
accatcaact ccccaattag caagttggtt tgcacgtgct ggtttgttta cagtccatac     840
gttcaattca taacccgctt cttttaccat ttttactttt gctttagtaa gtttggcatc     900
ttcagtgttt actattttag cattacagta atctaaaagt gttctccagt cttcacgaaa     960
cgaagttgta tggaatataa ctgctctgtt atattgtggc atgatttctt ctgcaagttt    1020
aacaagcaca acattaaagc ttgaaatgag cacttcttga ttctgattta agtttgttaa    1080
ttgttcttcc acttgcttaa ccatactttt agaaagtgct agtccattcg gtccagtaat    1140 acctttaat tctacatta aattcatat atattcattt gctattttta ctacatcatc     1200
gaaagttggc aaatgttcat ctttgaattt ttccaccaaac caagatcctg cagaagcatc    1260
tttaatttca tcataattca attcagttat tccccggac atatttgtag tccgttctaa     1320
ataatcatca tgaatgataa tcagttgttc atctttgta attgcaacat ctaactccaa     1380
ccagtttata ccttctactt ctgaagcagc tttaaatgat gcaattgtat tttccggagc    1440
tttactaggt aatcctctat gtccatatac agttagcata ttacctctcc ttgcattttt    1500 attttttaa ttaacgtaac tgtattatca cattaatcgc actttatttt ccattaaaaa    1560
gagatgaata tcataaataa agaagtcgat agattcgtat tgattatgga gttaatctac    1620
gtctcatctc atttttaaaa                                                1640
```

<210> SEQ ID NO 223
<211> LENGTH: 592
<212> TYPE: DNA
<213> ORGANISM: Staphylococcus aureus

<400> SEQUENCE: 223

```
aattcaactt tgcaacagaa ccgtattatg gaatagagat gttggtaaca tttatacagg       60
atcattatac ttaagtttaa tttcgttatt acagaaccac acattccaac cagaagagaa     120
agtatgtcta tttagttatg gttcaggagc agtaggagaa atctttagtg gttcaatcgt     180
taaaggatat gacaaagcat tagataaaga gaaacactta aatatgctag aatctagaga    240
gcaattatca gtcgaagaat acgaaacatt ctttaacaga tttgataatc aagaatttga    300
tttcgaacgt gaattgacac aagatccata ttcaaaagta tacttataca gtatagaaga    360
ccatatcaga acatataaga tagagaaata aactagtggc cgattgtgct tgatgagctt    420
gggacataaa tcctaactcg aaataaataa gcatatcact aaactgattt tttaaagttt    480
acagtgatat gcttatttt ttatcttacg attttgtacg tgcatgcttg cctaggggta     540
```
tggctcgagc cattagtctc tcgcacatac tattccctca ggcgtcagca ct        592

<210> SEQ ID NO 224
<211> LENGTH: 2386
<212> TYPE: DNA
<213> ORGANISM: Staphylococcus aureus

<400> SEQUENCE: 224
caccttcata tgacgtctat ccatttatgt atggcatgag taacgaagaa tataataaat    60
taaccgaaga taaaaagaa cctctgctca acaagttcca gattacaact tcaccaggtt   120
caactcaaaa atattaaca gcaatgattg ggttaaataa caaaacatta gacgataaaa   180
caagttataa aatcgatggt aaaggttggc aaaaagataa atcttggggt ggttacaacg   240
ttacaagata tgaagtggta aatggtaata tcgacttaaa acaagcaata gaatcatcag   300
ataacatttt ctttgctaga gtagcactcg aattaggcag taagaaattt gaaaaaggca   360
tgaaaaaact aggtgttggt gaagatatac caagtgatta tccatttttat aatgctcaaa   420 tttcaaacaa aaatttagat aatgaaatat tattagctga ttcaggttac ggacaaggtg   480
aaatactgat taacccagta cagatccttt caatctatag cgcattagaa aataatggca   540
atattaacgc acctcactta ttaaaagaca cgaaaaacaa agtttggaag aaaaatatta   600
tttccaaaga aatatcaat ctattaactg atggtatgca acaagtcgta aataaaacac   660
ataaagaaga tatttataga tcttatgcaa acttaattgg caaatccggt actgcagaac   720
tcaaaatgaa acaaggagaa actggcagac aaattgggtg gtttatatca tatgataaag   780
ataatccaaa catgatgatg gctattaatg ttaaagatgt acaagataaa ggaatggcta   840
gctacaatgc caaaatctca ggtaaagtgt atgatgagct atatgagaac ggtaataaaa   900
aatacgatat agatgaataa caaaacagtg aagcaatccg taacgatggt tgcttcactg   960
ttttattatg aattattaat aagtgctgtt acttctccct aaatacaat ttcttcattt   1020 tcattgtatg ttgaaagtga cactgtaacg agtccatttt cttttttat ggatttctta   1080 tttgtaattt cagcgataac gtacaatgta ttacctgggt atacaggttt aataaattta   1140
acgttattca tttgtgttcc tgctacaact tcttctccgt atttaccttc ttctacccat   1200
aatttaaatg atattgaaag tgtatgcatg ccagatgcaa tgatacctttt aaatctactt   1260 tgttctgctt tttctttatc tatatgcata tattgaggat caaagttgt tgcaaattgg   1320 ataatttctt cttctgtaat atgaaggctt tttgttttga atgtttctcc tactataaaa   1380
tcatcgtatt tcatatatgt ctctcttttct tattcaaatt aattttttag tatgtaacat   1440
gttaaaggta agtctaccgt cactgaaacg taagactcac ctctaacttt ctattgagac   1500
aaatgcacca ttttatctgc attgtctgta aagataccat caactcccca attagcaagt   1560
tggtttgcac gtgctggttt gtttacagtc catacgttca attcataacc cgcttctttt   1620 accatttttta cttttgcttt agtaagtttg gcatcttcag tgtttactat tttagcatta   1680
cagtaatcta aaagtgttct ccagtcttca cgaaacgaag ttgtatggaa tataactgct   1740
ctgttatatt gtggcatgat ttcttctgca agtttaacaa gcacaacatt aaagcttgaa   1800
atgagcactt cttgattctg atttaagttt gttaattgtt cttccacttg cttaaccata   1860
cttttagaaa gtgctagtcc attcggtcca gtaataccctt ttaattctac atttaaattc   1920
atattatatt catttgctat ttttactaca tcatcgaaag ttggcaaatg ttcatctttg   1980 aattttttcac caaaccaaga tcctgcagaa gcatctttaa tttcatcata attcaattca   2040
gttatttccc cggacatatt tgtagtccgt tctaaataat catcatgaat gataatcagt   2100

```
tgttcatctt ttgtaattgc aacatctaac tccaaccagt ttataccttc tacttctgaa    2160
gcagctttaa atgatgcaat tgtattttcc ggagctttac taggtaatcc tctatgtcca    2220
tatacagtta gcatattacc tctccttgca ttttattttt tttaattaac gtaactgtat    2280
tatcacatta atcgcacttt tatttccatt aaaaagagat gaatatcata aataaagaag    2340
tcgatagatt cgtattgatt atggagttaa tctacgtctc atctca                  2386

<210> SEQ ID NO 225
<211> LENGTH: 623
<212> TYPE: DNA
<213> ORGANISM: Staphylococcus aureus

<400> SEQUENCE: 225
tgaaaattac aaccgatttt gtaagtgctg acgcctgagg aatagtatg tgcgagagac      60 taatggctcg agccataccc ctaggcaagc atgcacgtac aaaatcgtaa gataaaaaaa    120
taagcatatc actgtaaact ttaaaaaatc agtttagtga tatgcttatt tatttcgagt    180
taggatttat gtcccaagct catcaagcac aatcggccac tagtttattt ctctatctta    240
tatgttctga tatggtcttc tatactgtat aagtatactt ttgaatatgg atcttgtgtc    300
aattcacgtt cgaaatcaaa ttcttgatta tcaaatctgt taaagaatgt ttcgtattct    360
tcgactgata attgctctct agattctagc atatttaagt gtttctcttt atctaatgct    420
ttgtcatatc ctttaacgat tgaaccacta agatttctc ctactgctcc tgaaccataa     480
ctaaatagac atactttctc ttctggttgg aatgtgtggt tctgtaataa cgaaattaaa    540
cttaagtata atgatcctgt ataaatgtta ccaacatctc tattccataa tacgggttctg   600 ttgcaaagtt gaatttatag tat                                           623

<210> SEQ ID NO 226
<211> LENGTH: 651
<212> TYPE: DNA
<213> ORGANISM: Staphylococcus aureus

<400> SEQUENCE: 226
atgaaaaata tttcagaatt ctcagcccaa cttgatcaaa cttttgatca aggggaagcc     60
gtctctatgg agtggttatt ccgtccgttg ctaaaaatgc tggcggaggg cgatccagtc    120
cccgttgagg acatcgcggc ggagaccggg aagcccgtcg aggaagttaa gcaagtccta    180
cagactctac ctagtgtgga acttgatgag cagggccgtg tcgtcggtta tggcctcaca    240
ctgttcccta ccccccatcg cttcgaggtt gatgggaagc aactatatgc atggtgcgcc    300
cttgacacac ttatgttccc agcactcatc ggccggacgg tccacatcgc ttcgccttgt    360
cacggcaccg gtaagtccgt ccggttgacg gtggaaccgg accgcgttgt aagcgtcgag    420
ccttcaacag ccgttgtctc gattgttaca ccagatgaaa tggcctcggt tcggtcggcc    480
ttctgtaacg acgttcactt tttcagttca ccgagtgcag cccaagactg gcttaaccaa    540
caccctgagt cgagcgtttt gcccgttgaa gatgcctttg aactgggtcg ccatttggga    600
gcgcgttatg aggagtcagg acctactaat gggtcctgtt gtaacattta a             651

<210> SEQ ID NO 227
<211> LENGTH: 563
<212> TYPE: DNA
<213> ORGANISM: Staphylococcus aureus

<400> SEQUENCE: 227
```

```
atgaatcttg aaaaagggaa tatagaaagg aaaaaacatg gtgtccatgt taatgagtat      60
ttgcaaagtg taagtaaccc gaatgtctat gcagctggag atgctgcagc aacggatggc     120
ttgcccctca cacctgtagc cagtgcagat tctcatgtcg tagcatctaa tttattgaaa     180
gggaacagca aaaaaattga atatcccgtg attccatctg ctgtatttac cgtacctaaa     240
atggcatcgg taggtatgag cgaggaggaa gccaaaaact ctggccggaa tattaaagta     300
aagcagaaaa acatctccga ctggtttacg tataaacgga caaatgagga ctttgctgcg     360
tttaaagtgc tgattgacga agatcatgat caaattgttg gtgctcattt gattagtaat     420
gaagccgatg aactgattaa tcattttgca acagccattc gttttgggat ttcaaccaaa     480
gaattgaaac aaatgatatt tgcctatcca acggcagctt cggacattgc acacatgttg     540
taagtttgcg ttttgtgaga tgt                                             563
```

<210> SEQ ID NO 228
<211> LENGTH: 1380
<212> TYPE: DNA
<213> ORGANISM: Staphylococcus aureus

<400> SEQUENCE: 228

```
ttgtttagtt tatataaaaa atttaaaggt ttgttttata gcgttttatt ttggctttgt      60
attctttcat tttttagtgt attaaatgaa atggttttaa atgtttcttt acctgatatt     120
gcaaatcatt ttaatactac tcctggaatt acaaactggg taaacactgc atatatgtta     180
acttttcga taggaacagc agtatatgga aaattatctg attatataaa tataaaaaaa     240
ttgttaatta ttggtattag tttgagctgt cttggttcat tgattgcttt tattggtcac     300
aatcactttt ttattttgat ttttggtagg ttagtacaag gagtaggatc tgctgcattc     360
ccttcactga ttatggtggt tgtagctaga aatattacaa gaaaaaaaca aggcaaagcc     420
tttggttttta taggatcaat tgtagcttta ggtgaagggt taggtccttc aataggggga     480
ataatagcac attatattca ttggtcttac ctacttatac ttcctatgat tacaatagta     540
actataccttt tcttattaa agtaatggta cctggtaaat caacaaaaaa tacattagat     600
atcgtaggta ttgttttaat gtctataagt attatatgtt ttatgttatt tacgacaaat     660
tataattgga cttttttaat actcttcaca atctttttg tgattttttat taaacatatt     720
tcaagagttt ctaacccttt tattaatcct aaactaggga aaaacattcc gtttatgctt     780
ggtttgtttt ctggtgggct aatatttttct atagtagctg gttttatatc aatggtgcct     840
tatatgatga aaactattta tcatgtaaat gtagcgacaa taggtaatag tgttattttt     900
cctggaacca tgagtgttat tgttttttggt tattttggtg gttttttagt ggatagaaaa     960
ggatcattat ttgttttat tttaggatca ttgtctatct ctataagttt tttaactatt    1020
gcattttttg ttgagtttag tatgtggttg actacttta tgtttatatt tgttatgggc    1080
ggattatctt ttactaaaac agttatatca aaaatagtat caagtagtct ttctgaagaa    1140
gaagttgctt ctggaatgag tttgctaaat ttcacaagtt ttttatcaga gggaacaggt    1200
atagcaattg taggaggttt attgtcacta caattgatta atcgtaaact agttctggaa    1260
tttataaaatt attcttctgg agtgtatagt aatattcttg tagccatggc tatccttatt    1320
attttatgtt gtcttttgac gattattgta tttaaacgtt ctgaaaagca gtttgaatag    1380
```

<210> SEQ ID NO 229
<211> LENGTH: 1365
<212> TYPE: DNA
<213> ORGANISM: Staphylococcus aureus

<400> SEQUENCE: 229

```
atgagaatag tgaatggacc aataataatg actagagaag aaagaatgaa gattgttcat      60
gaaattaagg aacgaatatt ggataaatat ggggatgatg ttaaggctat tggtgtttat     120
ggctctcttg gtcgtcagac tgatgggccc tattcggata ttgagatgat gtgtgtcatg     180
tcaacagaag aagcagagtt cagccatgaa tggacaaccg gtgagtggaa ggtggaagtg     240
aattttgata gcgaagagat tctactagat tatgcatctc aggtggaatc agattggcct     300
cttacacatg gtcaatttt ctctatttg ccgatttatg attcaggtgg atacttagag      360
aaagtgtatc aaactgctaa atcggtgaaa gcccaaacgt tccacgatgc gatttgtgcc     420
cttatcgtag aagagctgtt tgaatatgca ggcaaatggc gtaatattcg tgtgcaagga     480
ccgacaacat ttctaccatc cttgactgta caggtagcaa tggcaggtgc catgttgatt     540
ggtctgcatc atcgcatctg ttatacgacg agcgcttcgg tcttaactga agcagttaag     600
caatcagatc ttccttcagg ttatgaccat ctgtgccagt tcgtaatgtc tggtcaactt     660
tccgactctg agaaacttct ggaatcgcta gagaatttct ggaatgggat tcaggagtgg     720
acagaacgac acggatatat agtggatgtg tcaaaacgca taccattttg aacgatgacc     780
tctaataatt gttaatcatg ttggttacgt atttattaac ttctcctagt attagtaatt     840
atcatggctg tcatggcgca ttaacggaat aaagggtgtg cttaaatcgg gccattttgc     900
gtaataagaa aaaggattaa ttatgagcga attgaattaa taataaggta atagatttac     960
attagaaaat gaaaggggat tttatgcgtg agaatgttac agtctatccc ggcattgcca    1020
gtcgggata ttaaaagag tataggtttt tattgcgata aactaggttt cactttggtt     1080
caccatgaag atggattcgc agttctaatg tgtaatgagg ttcggattca tctatgggag    1140
gcaagtgatg aaggctggcg ctctcgtagt aatgattcac cggtttgtac aggtgcggag    1200
tcgtttattg ctggtactgc tagttgccgc attgaagtag agggaattga tgaattatat    1260
caacatatta agcctttggg cattttgcac cccaatacat cattaaaaga tcagtggtgg    1320
gatgaacgag actttgcagt aattgatccc gacaacaatt tgatt                    1365
```

<210> SEQ ID NO 230
<211> LENGTH: 831
<212> TYPE: DNA
<213> ORGANISM: Staphylococcus aureus

<400> SEQUENCE: 230

```
atgggggttt cttttaatat tatgtgtcct aatagtagca tttattcaga tgaaaaatca      60
agggttttag tggacaagac aaagagtgga aaagtgagac catggagaga aagaaaatc     120
gctaatgttg attactttga acttctgcat attcttgaat ttaaaaggc tgaaagagta     180
aaagattgtg ctgaaatatt agagtataaa caaaatcgtg aaacaggcga agaaagttg     240
tatcgagtgt ggttttgtaa atccaggctt tgtccaatgt gcaactggag gagagcaatg     300
aaacatggca ttcagtcaca aaaggttgtt gctgaagtta ttaaacaaaa gccaacagtt     360
cgttggttgt ttctcacatt aacagttaaa aatgttatg atggcgaaga attaaataag     420
agtttgtcag atatggctca aggatttcgc cgaatgacgc aatataaaaa aattaataaa     480
atcttgttg gttttatgcg tgcaacggaa gtgacaataa ataataaaga taattcttat     540
aatcagcaca tgcatgtatt ggtatgtgtg gaaccaactt atttaagaa tacagaaaac     600
tacgtgaatc aaaaacaatg gattcaattt tggaaaaagg caatgaaatt agactatgat     660
```

```
ccaaatgtaa aagttcaaat gattcgaccg aaaaataaat ataaatcgga tatacaatcg    720
gcaattgacg aaactgcaaa atatcctgta aaggatacgg attttatgac cgatgatgaa    780
gaaaagaatt tgtaacgttt gtctgatttg gaggaaggtt tacaccgtaa a            831

<210> SEQ ID NO 231
<211> LENGTH: 4193
<212> TYPE: DNA
<213> ORGANISM: Staphylococcus aureus

<400> SEQUENCE: 231
atgagccgct tgatacgcat gagtgtatta gcaagtggta gtacaggtaa cgccacttt     60 gtagaaaatg aaaaaggtag tctattagtt gatgttggtt tgactggcaa gaaaatggaa   120
gaattgttta gtcaaattga ccgtaatatt caagatttaa atggtatttt agtaacccat   180
gaacatattg atcatattaa aggattaggt gttttggcgc gtaaatatca attgccaatt   240
tatgcgaatg aaaagacttg gcaggcaatt gaaaagaaag atagtcgcat ccctatggat   300
cagaaattca ttttttaatcc ttatgaaaca aaatctattg caggtttcga tgttgaatcg   360
tttaacgtgt cacatgatgc aatagatccg caattttata ttttccataa taactataag   420
aagtttacga ttttaacgga tacgggtac gtgtctgatc gtatgaaagg tatgatacgt    480
ggcagcgatg cgtttatttt tgagagtaat catgacgtcg atatgttgag aatgtgtcgt    540
tatccatgga agacgaaaca acgtatttta ggcgatatgg gtcatgtatc taatgaggat    600
gcgggtcatg cgatgacaga tgtgattaca ggtaacacga aacgtattta cctatcgcat    660
ttatcacaag acaataacat gaaagatttg gcgcgtatga gtgttggcca agtattgaac    720
gaacacgata ttgatacgga aaagaagta ttgctatgtg atacggataa agctattcca     780
acgccaatat atacaatata atgagagtc accctataaa gttcggcact gctgtgagac    840
gactttatcg ggtgcttttt tatgttattg gtgggaaatg gctgttgttg gaattaaggt    900
tctatttgaa atgtaaaaaa taattcgata ttaaatgtaa tttataaata atttacataa    960
aatcaatcat tttaatataa ggattatgat aatatattgg tgtatgacag ttaatggagg   1020
gaacgaaatg aaagctttat tacttaaaac aagtgtatgg ctcgttttgc ttttttagtgt   1080 gatgggatta tggcaagtct cgaacgcggc tgagcagtat acaccaatca aagcacatgt   1140
agtaacaacg atagacaaag caacaacaga taagcaacaa gtaacgccaa caaggaagc   1200 ggctcatcaa tttggtgaag aagcggcaac caacgtatca gcatcagcac agggaacagc   1260
tgatgaaata aacaataaag taacatccaa cgcatttct aacaaaccat ctacagcagt   1320
ttcaacaaaa gtaacgaaa cgcacgatgt agatacacaa caagcctcaa cacaaaaacc   1380
aactcaatca gcaacattca cattatcaaa tgctaaaaca gcatcacttt caccacgaat   1440
gtttgctgcc aatgtaccac aaacaacaac acataaaata ttacatacaa atgatatcca   1500
tggccgacta gccgaagaaa aagggcgtgt catccggtatg gctaaattaa aaacaataaa   1560
agaacaagaa aagcctgatt taatgttaga cgcaggagac gccttccaag gtttaccact   1620
ttcaaaccag tctaaaggtg aagaaatggc taaagcaatg aatgcagtag gttatgatgc   1680
tatggcagtg ggtaaccatg aatttgactt tggatacgat cagttgaaaa agttagaggg   1740
tatgttagac ttcccgatgc taagtactaa cgtttacaaa gatgggaaac gcgcgtttaa   1800
gccttcaaca attgtaacga aaaatgtat tcgttatgga attattggcg taacgacacc   1860
agaaacaaag acgaaaacaa gacctgaggg cattaaggt gttgaattta gagatccatt   1920
acaaagtgtg acagcagaaa tgatgcgtat ttataaagac gtagatacat tgttgttat    1980
```

```
atcacattta gggattgatc cttcaacaca agaaacatgg cgtggtgatt acttagtgaa    2040
acaattaagt caaatccac aattgaagaa acgtattaca gtcattgatg gtcattcaca    2100
taccgtactt caaatggtc aaatttataa caatgatgca ttagcacaaa caggtacagc    2160
acttgcgaat atcggtaagg ttacatttaa ttaccgcaat ggagaggtat caaatattaa    2220
accgtcattg attaatgtta aagacgttga aaatgtaaca ccgaacaaag cattagctga    2280
acaaattaat caagctgatc aaacatttag agcacaaaca gcagaggtta ttattccaaa    2340
taataccatt gatttcaaag gagaaagaga tgacgttaga acgcgtgaaa caaatttagg    2400
aaacgcgatt gcagatgcta tggaagcgta tggcgttaag aatttctcta aaagactga    2460 ctttgccgtg acaaatggtg gaggtattcg tgcctctatc gcaaaggta aggtgacacg    2520 ctatgattta atctcagtat taccatttgg aaatacgatt gcgcaaattg atgtaaaagg    2580
ttcagacgtc tggacagctt tcgaacatag tttaggtgca ccaacaacac aaaaagacgg    2640
taagacagta ttaacagcga atggcggttt actacatatc tctgattcaa ttcgtgttta    2700
ctatgatatg aataaaccgt ctggcaaacg aattaacgct attcaaattt taaataaaga    2760
gacaggtaag tttgaaaata ttgatttaaa acgtgtatat catgtaacga tgaatgactt    2820
cacagcatca ggtggcgacg gatatagtat gttcggtggc cctagagaag aaggtatttc    2880
attagatcaa gtactagcaa gttatttaaa aacagctaac atagctaagt atgatacgac    2940
agaaccacaa cgtatgttat taggtaaacc agcagtaagt gaacaaccag ctaaaggaca    3000
acaaggtagc aaaggtagtg agtctggtaa agatgtacaa ccaattggtg acgacaaagc    3060
gatgaatcca gcgaaacaac cagcgacagg taaagttgta ttgttaccaa cgcatagagg    3120
aactgttagt agcggtacag aaggttctgg tcgcacatta gaaggagcta ctgtatcaag    3180
caagagtggg aaccaattgg ttagaatgtc agtgcctaaa ggtagcgcgc atgagaaaca    3240
gttaccaaaa actggaacta atcaaagctc aagcccagca gcgatgtttg tattagtagc    3300
aggtataggt ttaatcgcga ctgtacgacg tagaaaagct agttaaaata tattgaaaac    3360
aatactactg tatttcttaa ataagaggta cggtagtgtt tttttatgga aaaaagctat    3420
aaacgttgat aaacatggga tataaaaacg gggataagta ataagacatc aaggtgttta    3480
tccacagaaa tggggatagt tatccagaat tgtgtacaat ttaaagagaa atacccacaa    3540
tgcccacaga gttatccaca aatacacaag ttatacacta aaaattgggc ataaatgtca    3600
ggaaaatatc aaaaactgca aaaaatattg gtataataag agggaacagt gtgaacaagt    3660
taataacttg tggataactg gaaagttgat aacaatttgg aggaccaaac gacatgaaaa    3720
tcaccatttt agctgtaggg aaactaaaag agaaatattg gaagcaagcc atagcagaat    3780
atgaaaaacg tttaggccca tacaccaaga tagacatcat agaagttcca gacgaaaaag    3840
caccagaaaa tatgagcgac aaagaaattg agcaagtaaa agaaaagaa ggccaacgaa    3900 tactagccaa aattaaacca caatccacag tcattacatt agaaatacaa ggaaagatgc    3960
tatcttccga aggattggcc caagaattga accaacgcat gacccaaggg caaagcgact    4020
ttgtattcgt cattggcgga tcaaacggcc tgcacaagga cgtcttacaa cgcagtaact    4080
acgcactatc attcagcaaa atgacattcc cacatcaaat gatgcgggtt gtgttaattg    4140
agcaagtgta tagagcattt aagattatgc gtggagaagc atatcataaa tga          4193
```

<210> SEQ ID NO 232
<211> LENGTH: 2996
<212> TYPE: DNA

<213> ORGANISM: Staphylococcus aureus

<400> SEQUENCE: 232

```
atgaaacgag ccattggtta tttgcgccaa agtacaacga acaacaatc actcccagct      60
caaaagcaag caatagaatt attagctcca aagcacaata ttcaaaatat ccaatacatt    120
agtgataagc aatcaggcag aacagataat cgaacaggct atcaacaagt caccgaacgc    180
atccaacaaa gacaatgtga cgtattatgt tgttatcgct tgaatcgact tcatcgcaac    240
ttgaaaaatg cattaaaact catgaaactc tgtcaaaaat atcatgttca tattctaagt    300
gttcatgatg ctattttga tatggataaa gcgtttgatc gcctaaaact caatatattc    360
atgagtctgg ctgaacttga atccgataat attggagaac aagtcaaaaa tggacttaga    420
gaaaaggcaa acaaggtaa actcataacg acccatgcgc ctttcggtta tcactatcaa     480
aatggtactt tcatcattaa taatgatgaa tcacctaccg tcaaagctgt attcaattat    540
tatcttcaag gatatggcta caagaagatt gcacaatatt tagaagacga taataaactt    600
attcccgca agcctatca ggtacgaaat ataattatga acccaaatta ttgtggtcgt      660
gtcatcaatc aatatggtca atataacaat atggtaccac ctattgtttc ggcaacgaaa    720
tatgaacatg ctcaagcaat ccgtaataag aagcaacttc actgtatacc ttcagagaat    780
cagctgaaac aaaagatcaa atgtccttgt tgtgactcaa cactgacaaa tatgacaata    840
agaaaaaaac atacattgcg atattatatt tgtcctaaaa atatgaatga atctcgcttt    900
gtctgttcat tcaaaggaat aaatgcacaa aaattagaag ttcaagtctt agctacatgt    960
cagaacttct ttcaaaacca acagctctat tcaaaaatta ataatgcaat tcatcaacgc   1020
ctcaaaaaac aaagagtgat agaagctaaa agtacgctaa ctcaagaaca actgatagat   1080
aaacttgcca aggtatgat tgatgctgaa tcattcagaa aacagactca tttgatgaat    1140
caaaagcaca aaccatatc ctccataagt gataatcagt tacaaacatc actacaaaag    1200
gttatacaga aaagtttcac gttaaacatg ctgcatccct atattgatga aattcgcatt   1260
acaaaaaata agccccttgt tgggatctat ttcaaaaatg aaccattgaa cattgtgaac   1320
caaacctcgc aatcatcgat tgcttaatca gaaaggatga aaaaatcatg caacaactca   1380
aacaaaaacg tgtcggtatc tatgttcgtg tatcaacgga aatccaaagt actgaaggct   1440
atagtatcga tggacaaatc aatcaaattc gagaatattg tgatttcaat aactttgttg   1500
ttgtagatgt atacgcggat agaggtatct ctggaaaatc tatgaaccga ccagaactac   1560
aacgtttgtt aaaagatgcg aacgaaggtc agattgattc tgttatggtc tacaaaacaa   1620
accgactagc acgtaacact tctgacttac tcaaaattgt tgaagacctt catcgtcaaa   1680
atgtcgaatt cttcagctta tctgagcgta tggaagtcaa tacaagcagt ggtaaattga   1740
tgctacaaat tctagcgagt ttttcagaat ttgaaagaaa taatattgtc gaaaatgtat   1800
tcatgggtca aacccgacgc gctcaagaag gctattatca aggcaatttg ccgctgggct   1860
atgacaaaat accggatagc aagcatgaac tcatgataaa ccaacatgaa gcgaatattg   1920
tcaaatatat atttgagtca tatgctaaag gccacggata tcgtaaaatt gcgaatgcac   1980
tcaatcacaa aggatacgtg actaaaaaag gaaagccttt cagtattggt tcagtgacct   2040
atatcttatc taatccattc tatgttggta aaattcaatt cgcaaagtac aaagattgga   2100
atgaaaagcg tcgtaaaggg ctgaatgata aaccaataa agctgaaggt aagcattccc    2160
ctattattat tcaagactta tgggataaag tccaattacg taaaaacaa gtcagtcaaa    2220
aacctcaagt ccacggtaaa ggaactaatc tattaacagg tatcgttcat tgtccacaat   2280
```

```
gtggtgcacc aatggcagct agtaacacaa cgaacacatt gaaagatggt accaagaagc    2340
gaatacgtta ttattcttgc agtaacttcc gaaacaaagg ctcaaaagta tgttctgcga    2400
atagcgttag agctgatgtg attgagaaat acgtcatgga tcaaatactc gaaattgtca    2460
aaagtgataa agtcattaac caagtcttag aacgtgtcaa tcaagaaaat aaagtcgata    2520
ttggtgcatt gaaccacgat atcgcttata acaacaaca atacgatgaa gtcagcggga    2580
aactccataa tttagttaaa accattgaag ataatccgga cctaacatct gcattgaaag    2640
caactattca tcaatatgaa acacaactca atgacattac aaatcaaatg aatcaactca    2700
aacagcaaca aaatcaagag aaactatctt atgatacgaa acaaatcgct gccctattac    2760
aacgaatatt tcaaaatata gaatcaatgg ataaagcaca actcaaagca ttatatctta    2820
cagtcattga ccgtattgat attcgtaaag acggtaatca taaaaaacag ttctacgtta    2880
cactaaaact caataatgaa attattaaac aacttttcaa taatacccct ctcgacgaag    2940
tgctcctcag cacttcgtct ttatttttgc ctcaaacgct ctttcttcaa atctaa        2996

<210> SEQ ID NO 233
<211> LENGTH: 1410
<212> TYPE: DNA
<213> ORGANISM: Staphylococcus aureus

<400> SEQUENCE: 233
gctgtaggga aactaaaaga gaaatattgg aagcaagcca tagcagaata tgaaaaacgt      60
ttaggcccat acaccaagat agacatcata gaagttccag acgaaaaagc accagaaaat    120
atgagcgaca agaaattga gcaagtaaaa gaaaagaag gccaacgaat actagccaaa      180
attaaaccac aatccacagt cattacatta gaaatacaag gaaagatgct atcttccgaa    240
ggattggccc aagaattgaa ccaacgcatg acccaagggc aaagcgactt tgtattcgtc    300
attggcggat caaacggcct gcacaaggac gtcttacaac gcagtaacta cgcactatca    360
ttcagcaaaa tgacattccc acatcaaatg atgcgggttg tgttaattga gcaagtgtat    420
agagcattta agattatgcg tggagaagca tatcataaat gatgcggttt tttcagccgc    480
ttcataaagg gattttgaat gtatcagaac atatgaggtt tatgtgaatt gctgttatgt    540
ttttaagaag catatcataa gtgatgcggt ttttattaat tagttgctaa aaaatgaagt    600
atgcaatatt aattattatt aaattttgat atatttaaag aaagattaag tttagggtga    660
atgaatggct tatcaaagtg aatatgcatt agaaaatgaa gtacttcaac aacttgagga    720
attgaactat gaaagagtaa atatacataa tattaaatta gaaattaatg aatatctcaa    780
agaactagga gtgttgaaaa atgaataagc agacaaatac tccagaacta agatttccag    840
agtttgatga ggaatggaaa aaaggaaatt aggtgaagt agtaaattat aaaaatggtg    900
gttcatttga agtttagtg aaaaaccatg gtgtatataa actcataact cttaaatctg    960
ttaatacaga aggaaagttg tgtaattctg gaaatatat cgatgataaa tgtgttgaaa    1020
cattgtgtaa tgatacttta gtaatgatac tgagcgagca agcaccagga ctagttggaa    1080
tgactgcaat tatacctaat aataatgagt atgtactaaa tcaacgagta gcagcactag    1140
tgcctaaaca atttatagat agtcaatttc tatctaagtt aattaataga aaccagaaat    1200
atttcagtgt gagatctgct ggaacaaaag tgaaaaatat ttctaaagga catgtagaaa    1260
actttaattt tttatctcct aattcacactg aacaacaaaa aataggtaat ttcttcagca    1320
aactcgaccg ccagattgag ttagaagaag agaaacttga actcttatag caacaaaagc    1380
```
gtggatatat ttcagaagat ttttctcaag        1410

<210> SEQ ID NO 234
<211> LENGTH: 60
<212> TYPE: DNA
<213> ORGANISM: Staphylococcus aureus

<400> SEQUENCE: 234
tatgtcaaaa atcatgaacc tcattactta tgataccttg tgcaggccgt ttgatccgcc        60

<210> SEQ ID NO 235
<211> LENGTH: 60
<212> TYPE: DNA
<213> ORGANISM: Staphylococcus aureus

<400> SEQUENCE: 235
tatgtcaaaa atcatgaacc tcattactta tgataccttg tgcaggccgt ttgatccgcc        60

<210> SEQ ID NO 236
<211> LENGTH: 60
<212> TYPE: DNA
<213> ORGANISM: Staphylococcus aureus

<400> SEQUENCE: 236
tatgtcaaaa atcatgaacc tcattactta tgataccttg tgcaggccgt ttgatccgcc        60

<210> SEQ ID NO 237
<211> LENGTH: 60
<212> TYPE: DNA
<213> ORGANISM: Staphylococcus aureus

<400> SEQUENCE: 237
tatgtcaaaa atcatgaacc tcattactta tgataccttg tgcaggccgt ttgatccgcc        60

<210> SEQ ID NO 238
<211> LENGTH: 60
<212> TYPE: DNA
<213> ORGANISM: Staphylococcus aureus

<400> SEQUENCE: 238
tatgtcaaaa atcatgaacc tcattactta tgataccttg tgcaggccgt ttgatccgcc        60

<210> SEQ ID NO 239
<211> LENGTH: 60
<212> TYPE: DNA
<213> ORGANISM: Staphylococcus aureus

<400> SEQUENCE: 239
tatgtcaaaa atcatgaacc tcattactta tgataccttg tgcaggccgt ttgatccgcc        60

<210> SEQ ID NO 240
<211> LENGTH: 60
<212> TYPE: DNA
<213> ORGANISM: Staphylococcus aureus

<400> SEQUENCE: 240
tatgtcaaaa atcatgaacc tcattactta tgataccttg tgcaggccgt ttgatccgcc        60

<210> SEQ ID NO 241
<211> LENGTH: 60
<212> TYPE: DNA
<213> ORGANISM: Staphylococcus aureus

<400> SEQUENCE: 241

-continued

```
tatgtcaaaa atcatgaacc tcattactta tgataccttg tgcaggccgt ttgatccgcc    60

<210> SEQ ID NO 242
<211> LENGTH: 60
<212> TYPE: DNA
<213> ORGANISM: Staphylococcus aureus

<400> SEQUENCE: 242
tatgtcaaaa atcatgaacc tcattactta tgataccttg tgcaggccgt ttgatccgcc    60

<210> SEQ ID NO 243
<211> LENGTH: 60
<212> TYPE: DNA
<213> ORGANISM: Staphylococcus aureus

<400> SEQUENCE: 243
tatgtcaaaa atcatgaacc tcattactta tgataccttg tgcaggccgt ttgatccgcc    60

<210> SEQ ID NO 244
<211> LENGTH: 60
<212> TYPE: DNA
<213> ORGANISM: Staphylococcus aureus

<400> SEQUENCE: 244
tatgtcaaaa atcatgaacc tcattactta tgataccttg tgcaggccgt ttgatccgcc    60

<210> SEQ ID NO 245
<211> LENGTH: 60
<212> TYPE: DNA
<213> ORGANISM: Staphylococcus aureus

<400> SEQUENCE: 245
tatgtcaaaa atcatgaacc tcattactta tgataccttg tgcaggccgt ttgatccgcc    60

<210> SEQ ID NO 246
<211> LENGTH: 25
<212> TYPE: DNA
<213> ORGANISM: Staphylococcus aureus

<400> SEQUENCE: 246
cttggtgtaa accattggag ccacc                                           25

<210> SEQ ID NO 247
<211> LENGTH: 21
<212> TYPE: DNA
<213> ORGANISM: Staphylococcus aureus

<400> SEQUENCE: 247
cctcatgcaa tccatttgat c                                               21

<210> SEQ ID NO 248
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 248
gtcaaaaatc atgaacctca ttacttatg                                       29

<210> SEQ ID NO 249
<211> LENGTH: 19
<212> TYPE: DNA
```

```
<213> ORGANISM: Artificial Sequence
<220> FEATURE:
<223> OTHER INFORMATION: Synthetic nucleic acid sequence

<400> SEQUENCE: 249
tgtgcaggcc gtttgatcc                                                   19

<210> SEQ ID NO 250
<211> LENGTH: 35
<212> TYPE: DNA
<213> ORGANISM: Staphylococcus aureus

<400> SEQUENCE: 250
acaaggacgt cttacaacgc agtaactatg cacta                                 35

<210> SEQ ID NO 251
<211> LENGTH: 35
<212> TYPE: DNA
<213> ORGANISM: Staphylococcus aureus

<400> SEQUENCE: 251
acaaggacgt cttacaacgc agtaactatg cacta                                 35

<210> SEQ ID NO 252
<211> LENGTH: 35
<212> TYPE: DNA
<213> ORGANISM: Staphylococcus aureus

<400> SEQUENCE: 252
acaaggacgt cttacaacgc agtaactatg cacta                                 35

<210> SEQ ID NO 253
<211> LENGTH: 35
<212> TYPE: DNA
<213> ORGANISM: Staphylococcus aureus

<400> SEQUENCE: 253
acaaggacgt cttacaacgc agtaactatg cacta                                 35

<210> SEQ ID NO 254
<211> LENGTH: 35
<212> TYPE: DNA
<213> ORGANISM: Staphylococcus aureus

<400> SEQUENCE: 254
acaaggacgt cttacaacgc agtaactatg cacta                                 35

<210> SEQ ID NO 255
<211> LENGTH: 35
<212> TYPE: DNA
<213> ORGANISM: Staphylococcus aureus

<400> SEQUENCE: 255
acaaggacgt cttacaacgc agtaactatg cacta                                 35

<210> SEQ ID NO 256
<211> LENGTH: 35
<212> TYPE: DNA
<213> ORGANISM: Staphylococcus aureus

<400> SEQUENCE: 256
acaaggacgt cttacaacgc agtaactatg cacta                                 35
```

```
<210> SEQ ID NO 257
<211> LENGTH: 35
<212> TYPE: DNA
<213> ORGANISM: Staphylococcus aureus

<400> SEQUENCE: 257
acaaggacgt cttacaacgt agtaactacg cacta                              35

<210> SEQ ID NO 258
<211> LENGTH: 35
<212> TYPE: DNA
<213> ORGANISM: Staphylococcus aureus

<400> SEQUENCE: 258
acaaggacgt cttacaacgt agtaactacg cacta                              35

<210> SEQ ID NO 259
<211> LENGTH: 35
<212> TYPE: DNA
<213> ORGANISM: Staphylococcus aureus

<400> SEQUENCE: 259
acaaggacgt cttacaacgt agtaactacg cacta                              35

<210> SEQ ID NO 260
<211> LENGTH: 35
<212> TYPE: DNA
<213> ORGANISM: Staphylococcus aureus

<400> SEQUENCE: 260
acaaggacgt cttacaacgt agtaactacg cacta                              35

<210> SEQ ID NO 261
<211> LENGTH: 35
<212> TYPE: DNA
<213> ORGANISM: Staphylococcus aureus

<400> SEQUENCE: 261
acaaggacgt cttacaacgt agtaactacg cacta                              35

<210> SEQ ID NO 262
<211> LENGTH: 35
<212> TYPE: DNA
<213> ORGANISM: Staphylococcus aureus

<400> SEQUENCE: 262
acaaggacgt cttacaacgt agtaactacg cacta                              35

<210> SEQ ID NO 263
<211> LENGTH: 35
<212> TYPE: DNA
<213> ORGANISM: Staphylococcus aureus

<400> SEQUENCE: 263
acaaggacgt cttacaacgc agtaactacg cacta                              35

<210> SEQ ID NO 264
<211> LENGTH: 35
<212> TYPE: DNA
<213> ORGANISM: Staphylococcus aureus

<400> SEQUENCE: 264
acaaggacgt cttacaacgc agtaactacg cacta                              35
```

```
<210> SEQ ID NO 265
<211> LENGTH: 35
<212> TYPE: DNA
<213> ORGANISM: Staphylococcus aureus

<400> SEQUENCE: 265
accaagacgt cttacaacgc agcaactatg cttta                              35

<210> SEQ ID NO 266
<211> LENGTH: 35
<212> TYPE: DNA
<213> ORGANISM: Staphylococcus aureus

<400> SEQUENCE: 266
atgaggacgt cttacaacgc agcaactacg cactt                              35

<210> SEQ ID NO 267
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 267
gacgtcttac aacgcagtaa ctatg                                         25

<210> SEQ ID NO 268
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 268
gacgtcttac aacgtagtaa ctacg                                         25

<210> SEQ ID NO 269
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 269
gacgtcttac aacgcagtaa ctacg                                         25
```

METHOD FOR THE DETECTION AND IDENTIFICATION OF METHICILLIN-RESISTANT *STAPHYLOCOCCUS AUREUS*

CROSS-REFERENCE TO RELATED APPLICATIONS

This application is a continuation of U.S. patent application Ser. No. 15/707,421, filed Sep. 18, 2017, which is a continuation of U.S. patent application Ser. No. 11/416,500, now U.S. Pat. No. 9,777,335, which is a continuation of U.S. patent application Ser. No. 10/479,674, now U.S. Pat. No. 7,449,289, to Huletsky, et al., "SEQUENCES FOR DETECTION AND IDENTIFICATION OF METHICILLIN-RESISTANT *STAPHYLOCOCCUS AUREUS*," filed Sep. 7, 2004 which is a National Phase Application of International Patent Application PCT/CA02/00824, filed Jun. 4, 2002, now closed, which claims priority to Canadian Patent Application No. 2,348,042, filed Jun. 4, 2001, now abandoned.

REFERENCE TO SEQUENCE LISTING, TABLE, OR COMPUTER PROGRAM LISTING

The present application is being filed along with a sequence listing in electronic format. The sequence listing is provided as a file entitled GENOM_051C3.TXT, created Sep. 11, 2019 which is 187 KB in size. The information in the electronic format of the sequence listing is incorporated herein by reference in its entirety.

BACKGROUND OF THE INVENTION

Clinical Significance of *Staphylococcus aureus*

The coagulase-positive species *Staphylococcus aureus* is well documented as a human opportunistic pathogen. Nosocomial infections caused by *S. aureus* are a major cause of morbidity and mortality. Some of the most common infections caused by *S. aureus* involve the skin, and they include furuncles or boils, cellulitis, impetigo, and postoperative wound infections at various sites. Some of the more serious infections produced by *S. aureus* are bacteremia, pneumonia, osteomyelitis, acute endocarditis, myocarditis, pericarditis, cerebritis, meningitis, scalded skin syndrome, and various abcesses. Food poisoning mediated by staphylococcal enterotoxins is another important syndrome associated with *S. aureus*. Toxic shock syndrome, a community-acquired disease, has also been attributed to infection or colonization with toxigenic *S. aureus* (Murray et al. Eds, 1999, Manual of Clinical Microbiology, 7$^{th}$ Ed., ASM Press, Washington, D.C.).

Methicillin-resistant *S. aureus* (MRSA) emerged in the 1980s as a major clinical and epidemiologic problem in hospitals. MRSA are resistant to all β-lactams including penicillins, cephalosporins, carbapenems, and monobactams, which are the most commonly used antibiotics to cure *S. aureus* infections. MRSA infections can only be treated with more toxic and more costly antibiotics, which are normally used as the last line of defence. Since MRSA can spread easily from patient to patient via personnel, hospitals over the world are confronted with the problem to control MRSA. Consequently, there is a need to develop rapid and simple screening or diagnostic tests for detection and/or identification of MRSA to reduce its dissemination and improve the diagnosis and treatment of infected patients.

Methicillin resistance in *S. aureus* is unique in that it is due to acquisition of DNA from other coagulase-negative staphylococci (CNS), coding for a surnumerary β-lactam-resistant penicillin-binding protein (PBP), which takes over the biosynthetic functions of the normal PBPs when the cell is exposed to β-lactam antibiotics. *S. aureus* normally contains four PBPs, of which PBPs 1, 2 and 3 are essential. The low-affinity PBP in MRSA, termed PBP 2a (or PBP2'), is encoded by the choromosomal mecA gene and functions as a β-lactam-resistant transpeptidase. The mecA gene is absent from methicillin-sensitive *S. aureus* but is widely distributed among other species of staphylococci and is highly conserved (Ubukata et al., 1990, Antimicrob. Agents Chemother. 34:170-172).

By nucleotide sequence determination of the DNA region surrounding the mecA gene from *S. aureus* strain N315 (isolated in Japan in 1982), Hiramatsu et al. have found that the mecA gene is carried by a novel genetic element, designated staphylococcal cassette chromosome mec (SCCmec), inserted into the chromosome. SCCmec is a mobile genetic element characterized by the presence of terminal inverted and direct repeats, a set of site-specific recombinase genes (ccrA and ccrB), and the mecA gene complex (Ito et al., 1999, Antimicrob. Agents Chemother. 43:1449-1458; Katayama et al., 2000, Antimicrob. Agents Chemother. 44:1549-1555). The element is precisely excised from the chromosome of *S. aureus* strain N315 and integrates into a specific *S. aureus* chromosomal site in the same orientation through the function of a unique set of recombinase genes comprising ccrA and ccrB. Two novel genetic elements that shared similar structural features of SCCmec were found by cloning and sequencing the DNA region surrounding the mecA gene from MRSA strains NCTC 10442 (the first MRSA strain isolated in England in 1961) and 85/2082 (a strain from New Zealand isolated in 1985). The three SCCmec have been designated type I (NCTC 10442), type II (N315) and type III (85/2082) based on the year of isolation of the strains (Ito et al., 2001, Antimicrob. Agents Chemother. 45:1323-1336) (FIG. 1). Hiramatsu et al. have found that the SCCmec DNAs are integrated at a specific site in the methicillin-sensitive *S. aureus* (MSSA) chromosome. They characterized the nucleotide sequences of the regions around the left and right boundaries of SCCmec DNA (i.e. attL and attR, respectively) as well as those of the regions around the SCCmec DNA integration site (i.e. attBscc which is the bacterial chromosome attachment site for SCCmec DNA). The attBscc site was located at the 3' end of a novel open reading frame (ORF), orfX. The orfX potentially encodes a 159-amino acid polypeptide sharing identity with some previously identified polypeptides, but of unknown function (Ito et al., 1999, Antimicrob. Agents Chemother. 43:1449-1458). Recently, a new type of SCCmec (type IV) has been described by both Hiramatsu et al. (Ma et al, 2002, Antimicrob. Agents Chemother. 46:1147-1152) and Oliveira et al. (Oliveira et al, 2001, Microb. Drug Resist. 7:349-360). The sequences of the right extremity of the new type IV SCCmec from *S. aureus* strains CA05 and 8/6-3P published by Hiramatsu et al. (Ma et al., 2002, Antimicrob. Agents Chemother. 46:1147-1152) were nearly identical over 2000 nucleotides to that of type II SCCmec of *S. aureus* strain N315 (Ito et al., 2001, Antimicrob. Agents Chemother. 45:1323-1336). No sequence at the right extremity of the SCCmec type IV is available from the *S. aureus* strains HDE288 and PL72 described by Oliveira et al. (Oliveira et al., 2001, Microb. Drug Resist. 7:349-360).

Previous methods used to detect and identify MRSA (Saito et al., 1995, J. Clin. Microbiol. 33:2498-2500; Ubukata et al., 1992, J. Clin. Microbiol. 30:1728-1733; Murakami et al., 1991, J. Clin. Microbiol. 29:2240-2244; Hiramatsu et al., 1992, Microbiol. Immunol. 36:445-453), which are based on the detection of the mecA gene and *S. aureus*-specific chromosomal sequences, encountered difficulty in discriminating MRSA from methicillin-resistant coagulase-negative staphylococci (CNS) because the mecA gene is widely distributed in both *S. aureus* and CNS species (Suzuki et al., 1992, Antimicrob. Agents. Chemother. 36:429-434). Hiramatsu et al. (U.S. Pat. No. 6,156,507) have described a PCR assay specific for MRSA by using primers that can specifically hybridize to the right extremities of the 3 types of SCCmec DNAs in combination with a primer specific to the *S. aureus* chromosome, which corresponds to the nucleotide sequence on the right side of the SCCmec integration site. Since nucleotide sequences surrounding the SCCmec integration site in other staphylococcal species (such as *S. epidermidis* and *S. haemolyticus*) are different from those found in *S. aureus*, this PCR assay was specific for the detection of MRSA. This PCR assay also supplied information for MREP typing (standing for «mec right extremity polymorphism») of SCCmec DNA (Ito et al., 2001, Antimicrob. Agents Chemother. 45:1323-1336; Hiramatsu et al., 1996, J. Infect. Chemother. 2:117-129). This typing method takes advantage of the polymorphism at the right extremity of SCCmec DNAs adjacent to the integration site among the three types of SCCmec. Type III has a unique nucleotide sequence while type II has an insertion of 102 nucleotides to the right terminus of SCCmec type I. The MREP typing method described by Hiramatsu et al. (Ito et al., 2001, Antimicrob. Agents Chemother. 45:1323-1336; Hiramatsu et al., 1996, J. Infect. Chemother. 2:117-129) defines the SCCmec type I as MREP type i, SCCmec type II as MREP type ii and SCCmec type III as MREP type iii. It should be noted that the MREP typing method cannot differentiate the new SCCmec type IV described by Hiramatsu et al. (Ma et al., 2002, Antimicrob. Agents Chemother. 46:1147-1152) from SCCmec type II because these two SCCmec types exhibit the same nucleotide sequence to the right extremity.

The set of primers described by Hiramatsu et al. as being the optimal primer combination (SEQ ID NOs.: 22, 24, 28 in U.S. Pat. No. 6,156,507 corresponding to SEQ ID NOs.: 56, 58 and 60, respectively, in the present invention) have been used in the present invention to test by PCR a variety of MRSA and MSSA strains (FIG. 1 and Table 1). Twenty of the 39 MRSA strains tested were not amplified by the Hiramatsu et al. multiplex PCR assay (Tables 2 and 3). Hiramitsu's method indeed was successful in detecting less than 50% of the tested 39 MRSA strains.

This finding demonstrates that some MRSA strains have sequences at the right extremity of SCCmec-chromosome right extremity junction different from those identified by Hiramatsu et al. Consequently, the system developed by Hiramatsu et al. does not allow the detection of all MRSA. The present invention relates to the generation of SCCmec-chromosome right extremity junction sequence data required to detect more MRSA strains in order to improve the Hiramatsu et al. assay. There is a need for developing more ubiquitous primers and probes for the detection of most MRSA strains around the world.

SUMMARY OF THE INVENTION

It is an object of the present invention to provide a specific, ubiquitous and sensitive method using probes and/or amplification primers for determining the presence and/or amount of nucleic acids from all MRSA strains.

Ubiquity of at least 50% amongst the strains representing MRSA strains types IV to X is an objective of this invention.

Therefore, in accordance with the present invention is provided a method to detect the presence of a methicillin-resistant *Staphylococcus aureus* (MRSA) strain in a sample, the MRSA strain being resistant because of the presence of an SCCmec insert containing a mecA gene, said SCCmec being inserted in bacterial nucleic acids thereby generating a polymorphic right extremity junction (MREJ), the method comprising the step of annealing the nucleic acids of the sample with a plurality of probes and/or primers, characterized by:

the primers and/or probes are specific for MRSA strains and capable of annealing with polymorphic MREJ nucleic acids, the polymorphic MREJ comprising MREJ types i to x; and the primers and/or probes altogether can anneal with at least four MREJ types selected from MREJ types i to x.

In a specific embodiment, the primers and/or probes are all chosen to anneal under common annealing conditions, and even more specifically, they are placed altogether in the same physical enclosure.

A specific method has been developed using primers and/or probes having at least 10 nucleotides in length and capable of annealing with MREJ types i to iii, defined in any one of SEQ ID NOs: 1, 20, 21, 22, 23, 24, 25, 41, 199 ; 2, 17, 18, 19, 26, 40, 173, 174, 175, 176, 177, 178, 179, 180, 181, 182, 183, 185, 186, 197 ; 4, 5, 6, 7, 8, 9, 10, 11, 12, 13, 14, 15, 16, 104, 184, 198 and with one or more of MREJ types iv to ix, having SEQ ID NOs: 42, 43, 44, 45, 46, 51; 47, 48, 49, 50; 171; 165, 166; 167; 168. To be perfectly ubiquitous with the all the sequenced MREJs, the primers and/or probes altogether can anneal with said SEQ ID NOs of MREJ types i to ix.

The following specific primers and/or probes having the following sequences have been designed:

66, 100, 101, 105, 52, 53, 54, 55, 56, 57, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type i 66, 97, 99, 100, 101, 106, 117, 118, 124, 125, 52, 53, 54, 55, 56, 57 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89 for the detection of MREJ type ii 67, 98, 102, 107, 108, 64, 71, 72, 73, 74, 75, 76, 70, 103, 130, 132, 158, 159, 58, 59, 62, 126, 127, 128, 129, 131, 200, 201, 60, 61, 63, 32, 83, 84, 160, 161, 162, 163, 164, 85, 86, 87, 88, 89, for the detection of MREJ type iii 79, 77, 145, 147, 64, 71, 72, 73, 74, 75, 76, 70, 103, 130, 132, 158, 159, 59, 62, 126, 127, 128, 129, 131, 200, 201, 60, 61, 63, 68, 32, 83, 84, 160, 161, 162, 163, 164, 85, 86, 87, 88, 89, for the detection of MREJ type iv 65, 80, 146, 154, 155, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type v 202, 203, 204, 4, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vi 112, 113, 114, 119, 120, 121, 122, 123, 150, 151, 153, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type vii;

115, 116, 187, 188, 207, 208, 64, 71, 72, 73, 74, 75, 76, 70, 103, 130, 132, 158, 159

59, 62, 126, 127, 128, 129, 131, 200, 201, 60, 61, 63, 32, 83, 84, 160, 161, 162, 163, 164, 85, 86, 87, 88, 89, for the detection of MREJ type viii 109, 148, 149, 205, 206, 64, 71, 72, 73, 74, 75, 76, 70, 103, 130, 132, 158, 159, 59, 62, 126, 127, 128, 129, 131, 200, 201, 60, 61, 63, 32, 83, 84, 160, 161, 162, 163, 164, 85, 86, 87, 88, 89, for the detection of MREJ type ix.

Amongst these, the following primer pairs having the following sequences are used:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ As well, amongst these, the following probes having the following sequences are used:

SEQ ID NOs: 32, 83, 84, 160, 161, 162, 163, 164 for the detection of MREJ types i to ix.

In the most preferred embodied method, the following primers and/or probes having the following nucleotide sequences are used together. The preferred combinations make use of:

SEQ ID NOs: 64, 66, 84, 163, 164 for the detection of MREJ type i

SEQ ID NOs: 64, 66, 84, 163, 164 for the detection of MREJ type ii

SEQ ID NOs: 64, 67, 84, 163, 164 for the detection of MREJ type iii

SEQ ID NOs: 64, 79, 84, 163, 164 for the detection of MREJ type iv

SEQ ID NOs: 64, 80, 84, 163, 164 for the detection of MREJ type v

SEQ ID NOs: 64, 112, 84, 163, 164 for the detection of MREJ type vii.

All these probes and primers can even be used together in the same physical enclosure.

It is another object of this invention to provide a method for typing a MREJ of a MRSA strain, which comprises the steps of: reproducing the above method with primers and/or probes specific for a determined MREJ type, and detecting an annealed probe or primer as an indication of the presence of a determined MREJ type.

It is further another object of this invention to provide a nucleic acid selected from SEQ ID NOs:

SEQ ID NOs: 42, 43, 44, 45, 46, 51 for sequence of MREJ type iv;

SEQ ID NOs: 47, 48, 49, 50 for sequence of MREJ type v;

SEQ ID NOs: 171 for sequence of MREJ type vi;

SEQ ID NOs: 165, 166 for sequence of MREJ type vii;

SEQ ID NOs: 167 for sequence of MREJ type viii;

SEQ ID NOs: 168 for sequence of MREJ type ix.

Oligonucleotides of at least 10 nucleotides in length which hybridize with any of these nucleic acids and which hybridize with one or more MREJ of types selected from iv to ix are also objects of this invention. Amongst these, primer pairs (or probes) having the following SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57 for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53,62/54, 62/55, 62/56, 62/57, 63/52, 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, are also within the scope of this invention.

Further, internal probes having nucleotide sequences defined in any one of SEQ ID NOs: 32, 83, 84, 160, 161, 162, 163, 164, are also within the scope of this invention. Compositions of matter comprising the primers and/or probes annealing or hybridizing with one or more MREJ of types selected from iv to ix as well as with the above nucleic acids, comprising or not primers and/or probes, which hybridize with one or more MREJ of types selected from i to iii, are further objects of this invention. The preferred compositions would comprise the primers having the nucleotide sequences defined in SEQ ID NOs:

64/66, 64/100, 64/101; 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52, 63/53, 63/54, 63/55, 63/56, 63/57, for the detection of type i MREJ 64/66, 64/97, 64/99, 64/100, 64/101, 59/52, 59/53, 59/54, 59/55, 59/56, 59/57, 60/52, 60/53, 60/54, 60/55, 60/56, 60/57, 61/52, 61/53, 61/54, 61/55, 61/56, 61/57, 62/52, 62/53, 62/54, 62/55, 62/56, 62/57, 63/52 63/53, 63/54, 63/55, 63/56, 63/57 for the detection of type ii MREJ 64/67, 64/98, 64/102; 59/58, 60/58, 61/58, 62/58, 63/58 for the detection of type iii MREJ 64/79 for the detection of type iv MREJ 64/80 for the detection of type v MREJ 64/204 for the detection of type vi MREJ 64/112, 64/113 for the detection of type vii MREJ 64/115, 64/116 for the detection of type viii MREJ 64/109 for the detection of type ix MREJ, or probes, which SEQ ID NOs are: 32, 83, 84, 160, 161, 162, 163, 164, or both.

BRIEF DESCRIPTION OF THE DRAWINGS

FIGS. 2A-2C is a diagram illustrating the position of the primers selected in the present invention in the SCCmec-orfX right extremity junction for detection and identification of MRSA.

FIGS. 4A-4D illustrate a sequence alignment of nine MREP types (represented by portions of SEQ ID NOs.: 1, 2, 104, 51, 50, 171, 165, 167 and 168 for types i, ii, iii, iv, v, vi, vii, viii and ix, respectively).

DETAILED DESCRIPTION OF THE INVENTION

Figure 1:
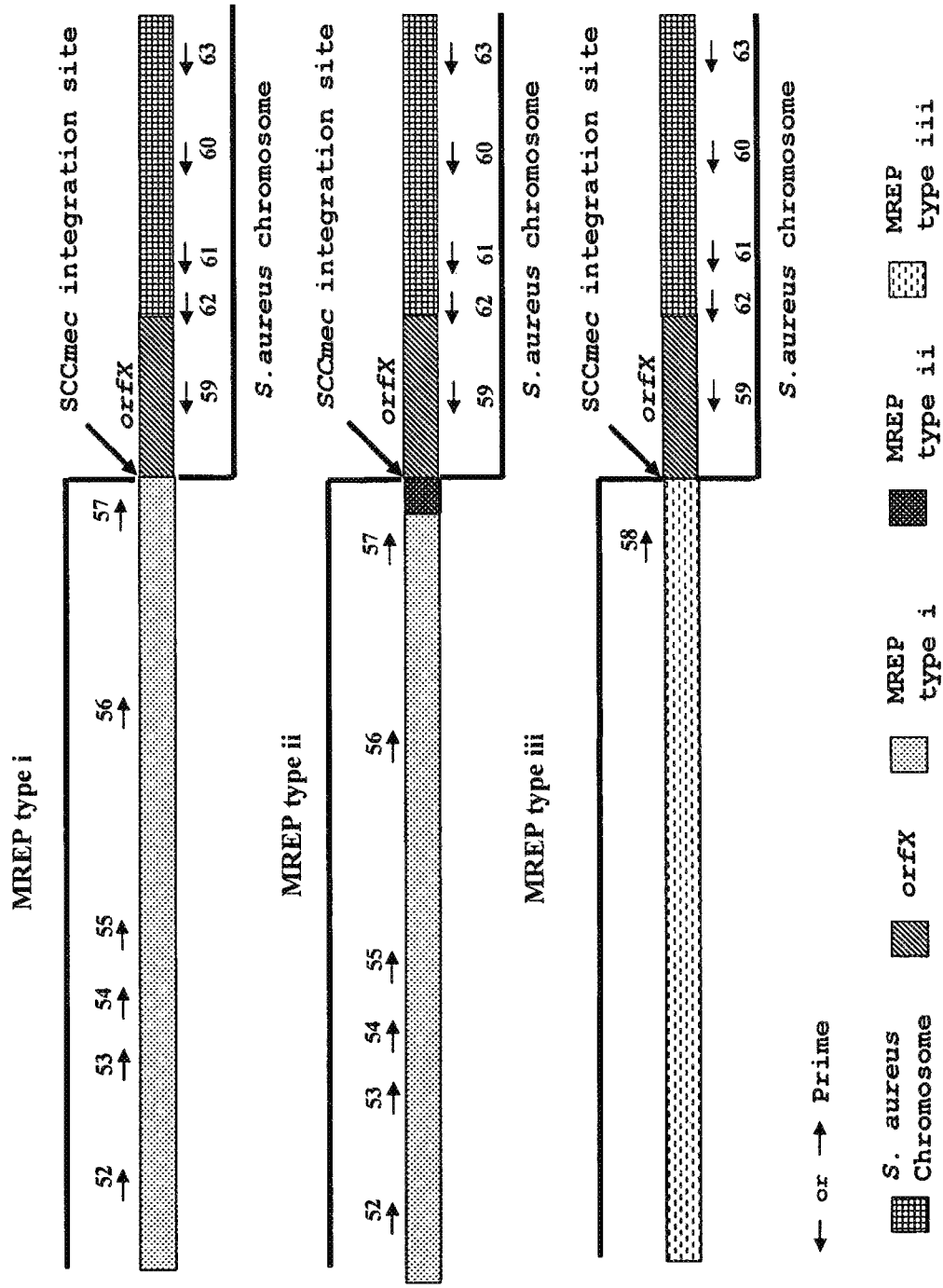
FIG. 1 is a diagram illustrating the position of the primers developed by Hiramatsu et al. (U.S. Pat. No. 6,156,507) in the SCCmec-chromosome right extremity junction for detection and identification of MRSA.

Here is particularly provided a method wherein each of MRSA nucleic acids or a variant or part thereof comprises a selected target region hybridizable with said primers or probes developed to be ubiquitous;

wherein each of said nucleic acids or a variant or part thereof comprises a selected target region hybridizable with said primers or probes;

said method comprising the steps of contacting said sample with said probes or primers and detecting the presence and/or amount of hybridized probes or amplified products as an indication of the presence and/or amount of MRSA.

In the method, sequences from DNA fragments of SCCmec-chromosome right extremity junction, thereafter named MREJ standing for « mec right extremity junction» including sequences from SCCmec right extremity and chromosomal DNA to the right of the SCCmec integration site are used as parental sequences from which are derived the primers and/or the probes. MREJ sequences include our proprietary sequences as well as sequences obtained from public databases and from U.S. Pat. No. 6,156,507 and were selected for their capacity to sensitively, specifically, ubiquitously and rapidly detect the targeted MRSA nucleic acids.

Our proprietary DNA fragments and oligonucleotides (primers and probes) are also another object of this invention.

Compositions of matter such as diagnostic kits comprising amplification primers or probes for the detection of MRSA are also objects of the present invention.

In the above methods and kits, probes and primers are not limited to nucleic acids and may include, but are not restricted to, analogs of nucleotides. The diagnostic reagents constituted by the probes and the primers may be present in any suitable form (bound to a solid support, liquid, lyophilized, etc.).

In the above methods and kits, amplification reactions may include but are not restricted to: a) polymerase chain reaction (PCR), b) ligase chain reaction (LCR), c) nucleic acid sequence-based amplification (NASBA), d) self-sustained sequence replication (3SR), e) strand displacement amplification (SDA), f) branched DNA signal amplification (bDNA), g) transcription-mediated amplification (TMA), h) cycling probe technology (CPT), i) nested PCR, j) multiplex PCR, k) solid phase amplification (SPA), l) nuclease dependent signal amplification (NDSA), m) rolling circle amplification technology (RCA), n) Anchored strand displacement amplification, o) Solid-phase (immobilized) rolling circle amplification.

In the above methods and kits, detection of the nucleic acids of target genes may include real-time or post-amplification technologies. These detection technologies can include, but are not limited to fluorescence resonance energy transfer (FRET)-based methods such as adjacent hybridization of probes (including probe-probe and probe-primer methods), TaqMan probe, molecular beacon probe, Scorpion probe, nanoparticle probe and Amplifluor probe. Other detection methods include target gene nucleic acids detection via immunological methods, solid phase hybridization methods on filters, chips or any other solid support. In these systems, the hybridization can be monitored by fluorescence, chemiluminescence, potentiometry, mass spectrometry, plasmon resonance, polarimetry, colorimetry, flow cytometry or scanometry. Nucleotide sequencing, including sequencing by dideoxy termination or sequencing by hybridization (e.g. sequencing using a DNA chip) represents another method to detect and characterize the nucleic acids of target genes.

In a preferred embodiment, a PCR protocol is used for nucleic acid amplification.

A method for detection of a plurality of potential MRSA strains having different MREJ types may be conducted in separate reactions and physical enclosures, one type at the time. Alternatively, it could be conducted simultaneously for different types in separate physical enclosures, or in the same physical enclosures. In the latter scenario a multiplex PCR reaction could be conducted which would require that the oligonucleotides are all capable of annealing with a target region under common conditions. Since many probes or primers are specific for a determined MREJ type, typing a MRSA strain is a possible embodiment. When a mixture of oligonucleotides annealing together with more than one type is used in a single physical enclosure or container, different labels would be used to distinguish one type from another.

We aim at developing a DNA-based test or kit to detect and identify MRSA. Although the sequences from orfX genes and some SCCmec DNA fragments are available from public databases and have been used to develop DNA-based tests for detection of MRSA, new sequence data allowing to improve MRSA detection and identification which are object of the present invention have either never been characterized previously or were known but not shown to be located at the right extremity of SCCmec adjacent to the integration site (Table 4). These novel sequences could not have been predicted nor detected by the MRSA-specific PCR assay developed by Hiramatsu et al. (U.S. Pat. No. 6,156,507). These sequences will allow to improve current DNA-based tests for the diagnosis of MRSA because they allow the design of ubiquitous primers and probes for the detection and identification of more MRSA strains including all the major epidemic clones from around the world.

The diagnostic kits, primers and probes mentioned above can be used to detect and/or identify MRSA, whether said diagnostic kits, primers and probes are used for in vitro or in situ applications. The said samples may include but are not limited to: any clinical sample, any environmental sample, any microbial culture, any microbial colony, any tissue, and any cell line.

It is also an object of the present invention that said diagnostic kits, primers and probes can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

In the methods and kits described herein below, the oligonucleotide probes and amplification primers have been derived from larger sequences (i.e. DNA fragments of at least 100 base pairs). All DNA sequences have been obtained either from our proprietary sequences or from public databases (Tables 5, 6, 7, 8 and 9).

It is clear to the individual skilled in the art that oligonucleotide sequences other than those described in the present invention and which are appropriate for detection and/or identification of MRSA may also be derived from the proprietary fragment sequences or selected public database sequences. For example, the oligonucleotide primers or probes may be shorter but of a length of at least 10 nucleotides or longer than the ones chosen; they may also be selected anywhere else in the proprietary DNA fragments or in the sequences selected from public databases; they may also be variants of the same oligonucleotide. If the target DNA or a variant thereof hybridizes to a given oligonucleotide, or if the target DNA or a variant thereof can be amplified by a given oligonucleotide PCR primer pair, the converse is also true; a given target DNA may hybridize to a variant oligonucleotide probe or be amplified by a variant oligonucleotide PCR primer. Alternatively, the oligonucleotides may be designed from said DNA fragment sequences for use in amplification methods other than PCR. Consequently, the core of this invention is the detection and/or identification of MRSA by targeting genomic DNA sequences which are used as a source of specific and ubiquitous oligonucleotide probes and/or amplification primers. Although the selection and evaluation of oligonucleotides suitable for diagnostic purposes require much effort, it is quite possible for the individual skilled in the art to derive, from the selected DNA fragments, oligonucleotides other than the ones listed in Tables 5, 6, 7, 8 and 9 which are suitable for diagnostic purposes. When a proprietary fragment or a public database sequence is selected for its specificity and ubiquity, it increases the probability that subsets thereof will also be specific and ubiquitous.

The proprietary DNA fragments have been obtained as a repertory of sequences created by amplifying MRSA nucleic acids with new primers. These primers and the repertory of nucleic acids as well as the repertory of nucleotide sequences are further objects of this invention (Tables 4, 5, 6, 7, 8 and 9).

Claims therefore are in accordance with the present invention.

Sequences for Detection and Identification of MRSA

In the description of this invention, the terms «nucleic acids» and «sequences» might be used interchangeably. However, «nucleic acids» are chemical entities while «sequences» are the pieces of information encoded by these «nucleic acids». Both nucleic acids and sequences are equivalently valuable sources of information for the matter pertaining to this invention.

Oligonucleotide Primers and Probes Design and Synthesis

As part of the design rules, all oligonucleotides (probes for hybridization and primers for DNA amplification by PCR) were evaluated for their suitability for hybridization or PCR amplification by computer analysis using standard programs (i.e. the GCG Wisconsin package programs, the primer analysis software Oligo™ 6 and MFOLD 3.0). The potential suitability of the PCR primer pairs was also evaluated prior to their synthesis by verifying the absence of unwanted features such as long stretches of one nucleotide and a high proportion of G or C residues at the 3' end (Persing et al., 1993, Diagnostic Molecular Microbiology: Principles and Applications, American Society for Microbiology, Washington, D.C.). Oligonucleotide amplification primers were synthesized using an automated DNA synthesizer (Applied Biosystems). Molecular beacon designs were evaluated using criteria established by Kramer et al. (http://www.molecular-beacons.org).

The oligonucleotide sequence of primers or probes may be derived from either strand of the duplex DNA. The primers or probes may consist of the bases A, G, C, or T or analogs and they may be degenerated at one or more chosen nucleotide position(s) (Nichols et al., 1994, Nature 369:492-493). Primers and probes may also consist of nucleotide analogs such as Locked Nucleic Acids (LNA) (Koskin et al., 1998, Tetrahedron 54:3607-3630), and Peptide Nucleic Acids (PNA) (Egholm et al., 1993, Nature 365:566-568). The primers or probes may be of any suitable length and may be selected anywhere within the DNA sequences from proprietary fragments, or from selected database sequences which are suitable for the detection of MRSA.

Variants for a given target microbial gene are naturally occurring and are attributable to sequence variation within that gene during evolution (Watson et al., 1987, Molecular Biology of the Gene, $4^{th}$ ed., The Benjamin/Cummings Publishing Company, Menlo Park, Calif.; Lewin, 1989, Genes IV, John Wiley & Sons, New York, N.Y.). For example, different strains of the same microbial species may have a single or more nucleotide variation(s) at the oligonucleotide hybridization site. The person skilled in the art is well aware of the existence of variant nucleic acids and/or sequences for a specific gene and that the frequency of sequence variations depends on the selective pressure during evolution on a given gene product. The detection of a variant sequence for a region between two PCR primers may be demonstrated by sequencing the amplification product. In order to show the presence of sequence variations at the primer hybridization site, one has to amplify a larger DNA target with PCR primers outside that hybridization site. Sequencing of this larger fragment will allow the detection of sequence variation at this primer hybridization site. A similar strategy may be applied to show variations at the hybridization site of a probe. Insofar as the divergence of the target nucleic acids and/or sequences or a part thereof does not affect significantly the sensitivity and/or specificity and/or ubiquity of the amplification primers or probes, variant microbial DNA is under the scope of this invention. Variants of the selected primers or probes may also be used to amplify or hybridize to a variant target DNA.

DNA Amplification

For DNA amplification by the widely used PCR method, primer pairs were derived from our proprietary DNA fragments or from public database sequences.

During DNA amplification by PCR, two oligonucleotide primers binding respectively to each strand of the heat-denatured target DNA from the microbial genome are used to amplify exponentially in vitro the target DNA by successive thermal cycles allowing denaturation of the DNA, annealing of the primers and synthesis of new targets at each cycle (Persing et al, 1993, Diagnostic Molecular Microbiology: Principles and Applications, American Society for Microbiology, Washington, D.C.).

Briefly, the PCR protocols on a standard thermocycler (PTC-200 from MJ Research Inc., Watertown, Mass.) were as follows: Treated standardized bacterial suspensions or genomic DNA prepared from bacterial cultures or clinical specimens were amplified in a 20 μl PCR reaction mixture.

Each PCR reaction contained 50 mM KCl, 10 mM Tris-HCl (pH 9.0), 2.5 mM $MgCl_2$, 0.4 μM of each primer, 200 μM of each of the four dNTPs (Pharmacia Biotech), 3.3 μg/μl bovine serum albumin (BSA) (Sigma-Aldrich Canada Ltd, Oakville, Ontario, Canada) and 0.5 unit of Taq DNA polymerase (Promega Corp., Madison, Wis.) combined with the TaqStart™ antibody (BD Biosciences, Palo Alto, Calif.). The TaqStart™ antibody, which is a neutralizing monoclonal antibody to Taq DNA polymerase, was added to all PCR reactions to enhance the specificity and the sensitivity of the amplifications (Kellogg et al., 1994, Biotechniques 16:1134-1137). The treatment of bacterial cultures or of clinical specimens consists in a rapid protocol to lyse the microbial cells and eliminate or neutralize PCR inhibitors (described in co-pending application U.S. 60/306,163). For amplification from purified genomic DNA, the samples were added directly to the PCR amplification mixture. An internal control, derived from sequences not found in the target MREJ sequences or in the human genome, was used to verify the efficiency of the PCR reaction and the absence of significant PCR inhibition.

The number of cycles performed for the PCR assays varies according to the sensitivity level required. For example, the sensitivity level required for microbial detection directly from a clinical specimen is higher than for detection from a microbial culture. Consequently, more sensitive PCR assays having more thermal cycles are probably required for direct detection from clinical specimens.

The person skilled in the art of nucleic acid amplification knows the existence of other rapid amplification procedures such as ligase chain reaction (LCR), reverse transcriptase PCR (RT-PCR), transcription-mediated amplification (TMA), self-sustained sequence replication (3SR), nucleic acid sequence-based amplification (NASBA), strand displacement amplification (SDA), branched DNA (bDNA), cycling probe technology (CPT), solid phase amplification (SPA), rolling circle amplification technology (RCA), solid phase RCA, anchored SDA and nuclease dependent signal amplification (NDSA) (Lee et al., 1997, Nucleic Acid Amplification Technologies: Application to Disease Diagnosis, Eaton Publishing, Boston, Mass.; Persing et al., 1993, Diagnostic Molecular Microbiology: Principles and Applications, American Society for Microbiology, Washington, D.C.; Westin et al., 2000, Nat. Biotechnol. 18:199-204). The scope of this invention is not limited to the use of amplification by PCR, but rather includes the use of any nucleic acid amplification method or any other procedure which may be used to increase the sensitivity and/or the rapidity of nucleic acid-based diagnostic tests. The scope of the present invention also covers the use of any nucleic acids amplification and detection technology including real-time or post-amplification detection technologies, any amplification technology combined with detection, any hybridization nucleic acid chips or array technologies, any amplification chips or combination of amplification and hybridization chip technologies. Detection and identification by any nucleotide sequencing method is also under the scope of the present invention.

Any oligonucleotide derived from the S. aureus MREJ DNA sequences and used with any nucleic acid amplification and/or hybridization technologies are also under the scope of this invention.

Evaluation of the MRSA Detection Method Developed by Hiramatsu et al.

According to Hiramatsu et al. (Ito et al., 1999, Antimicrob. Agents Chemother. 43:1449-1458; Katayama et al., 2000, Antimicrob. Agents Chemother. 44:1549-1555; Ito et al., 2001, Antimicrob. Agents Chemother. 45:1323-1336, Ma et al., 2002, Antimicrob. Agents Chemother. 46:1147-1152), four types of SCCmec DNA are found among MRSA strains. They have found that SCCmec DNAs are integrated at a specific site of the MSSA chromosome (named orfX). They developed a MRSA-specific multiplex PCR assay including primers that can hybridize to the right extremity of SCCmec types I, II and III (SEQ ID NOs.: 18, 19, 20, 21, 22, 23, 24 in U.S. Pat. No. 6,156,507 corresponding to SEQ ID NOs.: 52, 53, 54, 55, 56, 57, 58, respectively, in the present invention) as well as primers specific to the S. aureus chromosome to the right of the SCCmec integration site (SEQ ID NO.: 25, 28, 27, 26, 29 in U.S. Pat. No. 6,156,507 corresponding to SEQ ID NOs.: 59, 60, 61, 62, 63, respectively, in the present invention) (Table 1 and FIG. 1). The set of primers described by Hiramatsu et al. as being the optimal primer combination (SEQ ID NOs.: 22, 24 and 28 in U.S. Pat. No. 6,156,507 corresponding to SEQ ID NOs.: 56, 58 and 60 in the present invention) was used in the present invention to test by PCR a variety of MRSA, MSSA, methicillin-resistant CNS (MRCNS) and methicillin-sensitive CNS (MSCNS) strains (Table 2). A PCR assay performed using a standard thermocycler (PTC-200 from MJ Research Inc.) was used to test the ubiquity, the specificity and the sensitivity of these primers using the following protocol: one μl of a treated standardized bacterial suspension or of a genomic DNA preparation purified from bacteria were amplified in a 20 μl PCR reaction mixture. Each PCR reaction contained 50 mM KCl, 10 mM Tris-HCl (pH 9.0), 0.1% Triton X-100, 2.5 mM $MgCl_2$, 0.4 μM of each of the SCCmec- and S. aureus chromosome-specific primers (SEQ ID NOs.: 22, 24 and 28 in U.S. Pat. No. 6,156,507 corresponding to SEQ ID NOs.: 56, 58 and 60 in the present invention), 200 μM of each of the four dNTPs (Pharmacia Biotech), 3.3 μg/μl BSA (Sigma), and 0.5 U Taq polymerase (Promega) coupled with TaqStart™ Antibody (BD Biosciences).

PCR reactions were then subjected to thermal cycling 3 min at 94° C. followed by 40 cycles of 60 seconds at 95° C. for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 μg/ml of ethidium bromide. Twenty of the 39 MRSA strains tested were not amplified with the PCR assay developed by Hiramatsu et al. (Example 1, Tables 2 and 3).

Figure 2B:
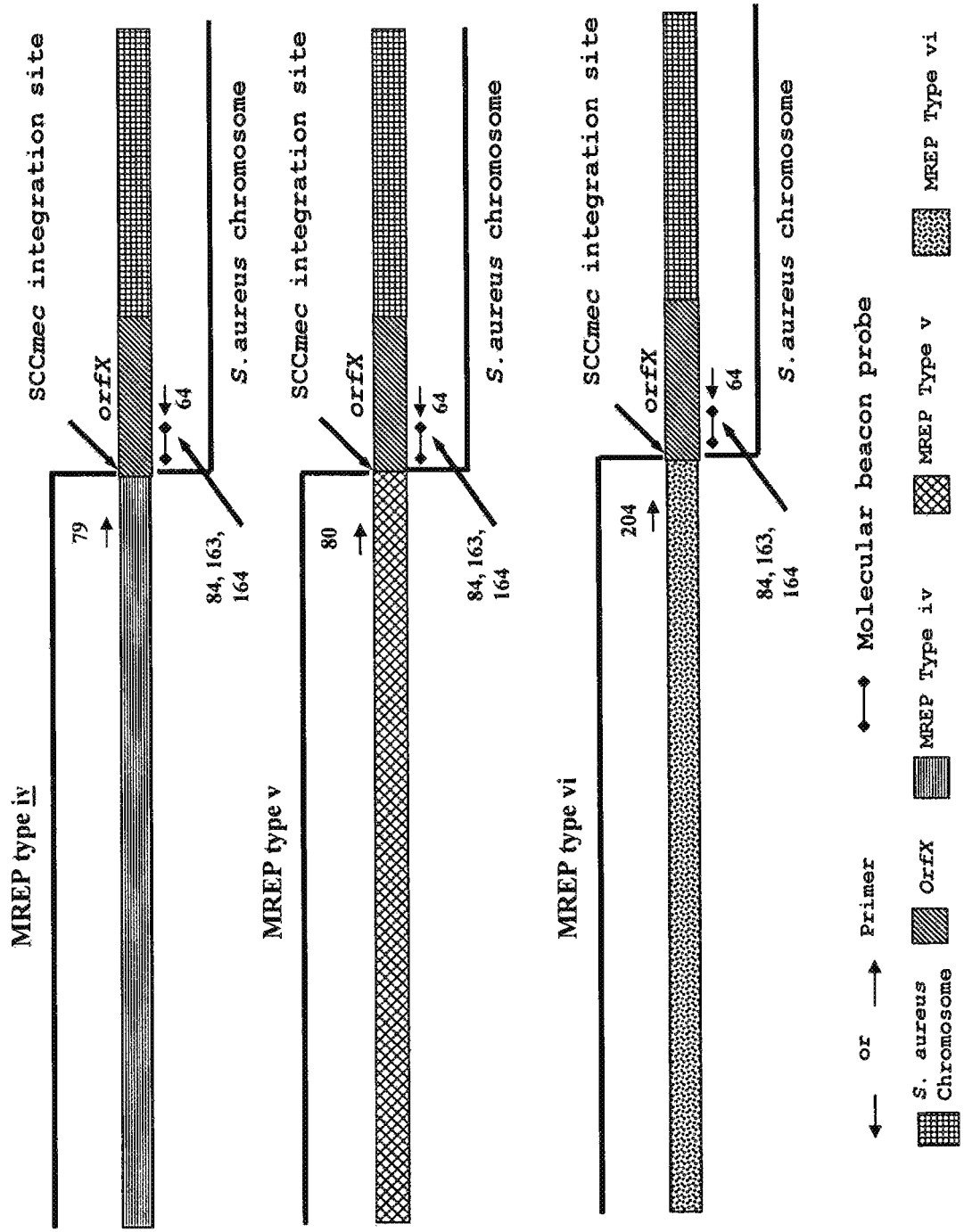
Figure 2C:
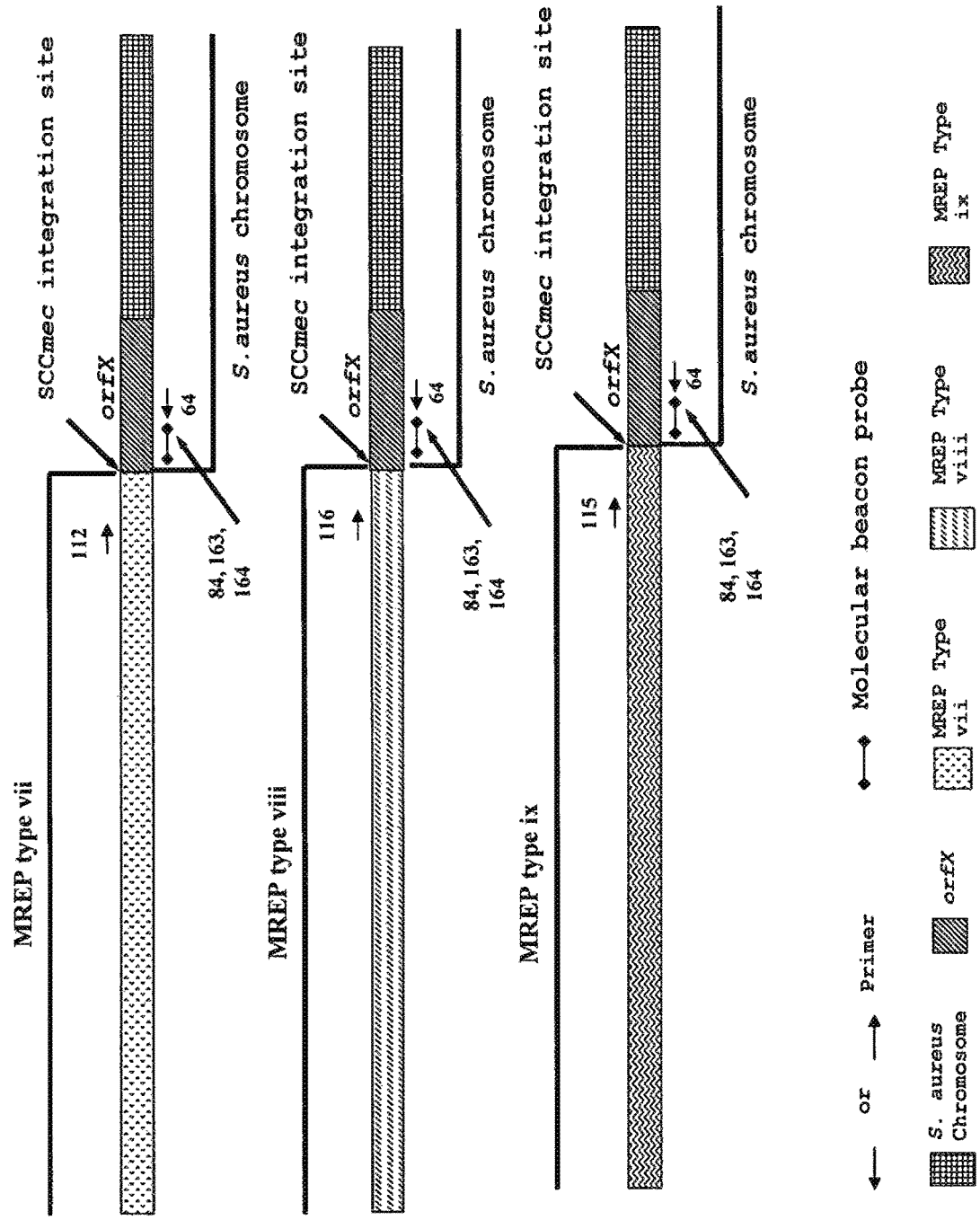

With a view of establishing a rapid diagnostic test for MRSAs, the present inventors developed new sets of primers specific to the right extremity of SCCmec types I and II (SEQ ID NOs.: 66, 100 and 101) (Annex 1), SCCmec type II (SEQ ID NOs.: 97 and 99), SCCmec type III (SEQ ID NOs.: 67, 98 and 102) and in the S. aureus chromosome to the right of the SCCmec integration site (SEQ ID NOs.: 64, 70, 71, 72, 73, 74, 75 and 76) (Table 5). These primers, amplifying short amplicons (171 to 278 bp), are compatible for use in rapid PCR assays (Table 7). The design of these primers was based on analysis of multiple sequence alignments of orfX and SCCmec sequences described by Hiramatsu et al. (U.S. Pat. No. 6,156,507) or available from GenBank (Table 10, Annex I). These different sets of primers were used to test by PCR a variety of MRSA, MSSA, MRCNS and MSCNS strains. Several amplification primers were developed to detect all three SCCmec types (SEQ ID NOs.: 97 and 99 for SCCmec type II, SEQ ID NOs.: 66, 100 and 101 for SCCmec types I and II and SEQ ID NOs.: 67, 98 and 102 for SCCmec type III). Primers were chosen according to their specificity for MRSA strains, their analytical sensitivity in PCR and the length of the PCR product. A set of two primers was chosen for the SCCmec right extremity region (SEQ ID NO.: 66 specific to SCCmec types I and II; SEQ ID NO.: 67 specific to SCCmec type III). Of the 8 different primers designed to anneal on the *S. aureus* chromosome to the right of the SCCmec integration site (targeting orfX gene) (SEQ ID NOs.: 64, 70, 71, 72, 73, 74, 75 and 76), only one (SEQ ID.: 64) was found to be specific for MRSA based on testing with a variety of MRSA, MSSA, MRCNS and MSCNS strains (Table 12). Consequently, a PCR assay using the optimal set of primers (SEQ ID NOs.: 64, 66 and 67) which could amplify specifically MRSA strains containing SCCmec types I, II and III was developed (FIG. 2, Annex I). While the PCR assay developed with this novel set of primers was highly sensitive (i.e allowed the detection of 2 to 5 copies of genome for all three SCCmec types) (Table 11), it had the same shortcomings (i.e. lack of ubiquity) of the test developed by Hiramatsu et al. The 20 MRSA strains which were not amplified by the Hiramatsu et al. primers were also not detected by the set of primers comprising SEQ ID NOs.: 64, 66 and 67 (Tables 3 and 12). Clearly, diagnostic tools for achieving at least 50% ubiquity amongst the tested strains are needed.

With a view to establish a more ubiquitous (i.e. ability to detect all or most MRSA strains) detection and identification method for MRSA, we determined the sequence of the MREJ present in these 20 MRSA strains which were not amplified. This research has led to the discovery and identification of seven novel distinct MREJ target sequences which can be used for diagnostic purposes. These seven new MREJ sequences could not have been predicted nor detected with the system described in U.S. Pat. No. 6,156,507 by Hiramatsu et al. Namely, the present invention represents an improved method for the detection and identification of MRSA because it provides a more ubiquitous diagnostic method which allows for the detection of all major epidemic MRSA clones from around the world.

Sequencing of MREJ Nucleotide Sequences from MRSA Strains not Amplifiable with Primers Specific to SCCmec Types I, II and III Since DNA from twenty MRSA strains were not amplified with the set of primers developed by Hiramatsu et al. (SEQ ID NOs.: 22, 24 and 28 in U.S. Pat. No. 6,156,507 corresponding to SEQ ID NOs.: 56, 58 and 60 in the present invention) (Tables 2 and 3) nor with the set of primers developed in the present invention based on the same three SCCmec types (I, II and III) sequences (SEQ ID NOs.: 64, 66 and 67) (Table 12), the nucleotide sequence of the MREJ was determined for sixteen of these twenty MRSA strains.

Figure 3A:
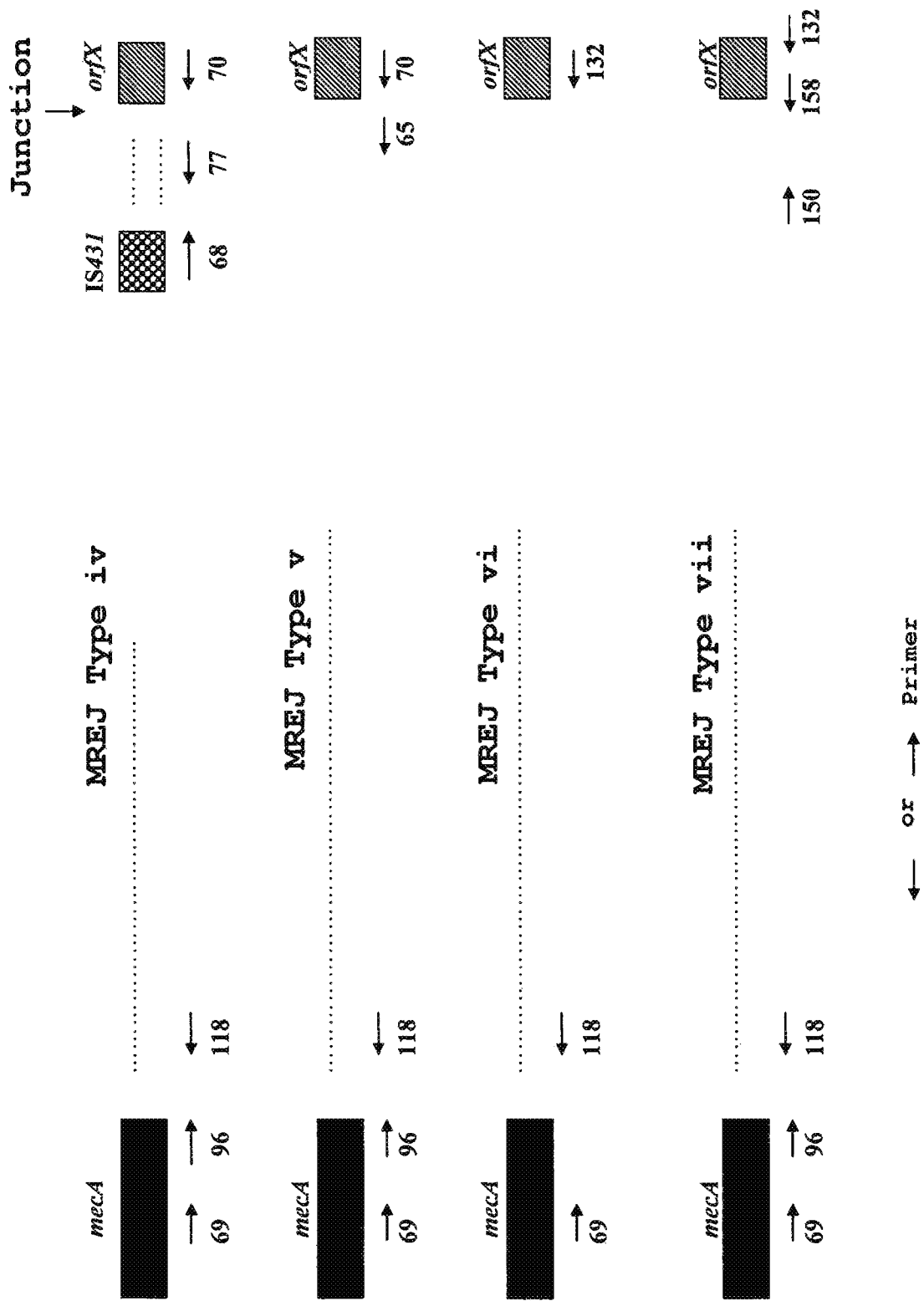
FIGS. 3A and 3B is a diagram illustrating the position of the primers selected in the present invention to sequence new MREP types.
Figure 3B:
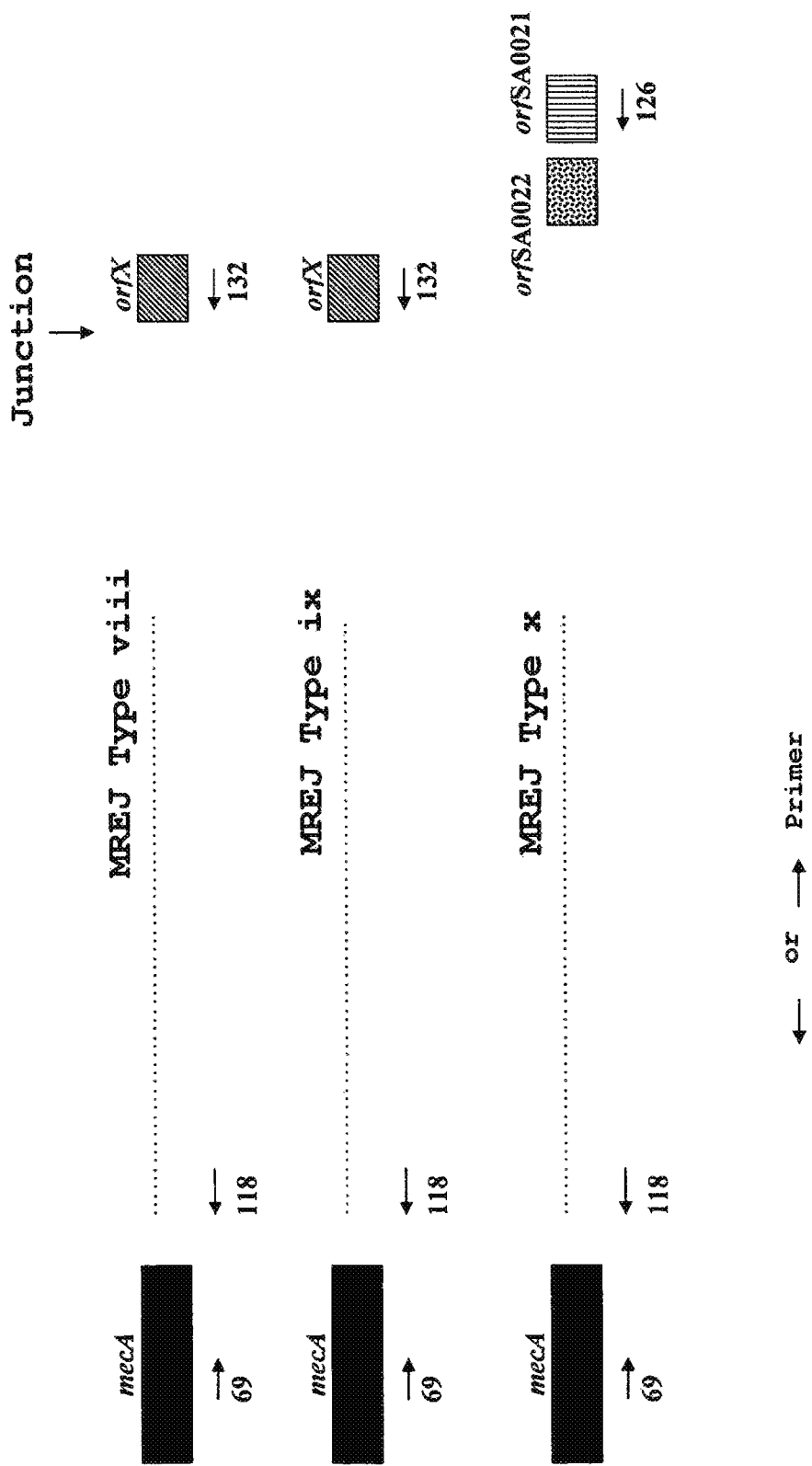

Transposase of IS431 is often associated with the insertion of resistance genes within the mec locus. The gene encoding this transposase has been described frequently in one or more copies within the right segment of SCCmec (Oliveira et al., 2000, Antimicrob. Agents Chemother. 44:1906-1910; Ito et al., 2001, Antimicrob. Agents Chemother. 45:1323-36). Therefore, in a first attempt to sequence the novel MREJ for 16 of the 20 MRSA strains described in Table 3, a primer was designed in the sequence of the gene coding for the transposase of IS431 (SEQ ID NO.: 68) and combined with an orfX-specific primer to the right of the SCCmec integration site (SEQ ID NO.: 70) (Tables 5 and 8). The strategy used to select these primers is illustrated in FIG. 3.

The MREJ fragments to be sequenced were amplified using the following amplification protocol: one µL of treated cell suspension (or of a purified genomic DNA preparation) was transferred directly into 4 tubes containing 39 µL of a PCR reaction mixture. Each PCR reaction contained 50 mM KCl, 10 mM Tris-HCl (pH 9.0), 0.1% Triton X-100, 2.5 mM $MgCl_2$, 1 µM of each of the 2 primers (SEQ ID NOs.: 68 and 70), 200 µM of each of the four dNTPs, 3.3 µg/µl of BSA (Sigma-Aldrich Canada Ltd) and 0.5 unit of Taq DNA polymerase (Promega) coupled with the TaqStart™ Antibody (BD Bisociences). PCR reactions were submitted to cycling using a standard thermocycler (PTC-200 from MJ Research Inc.) as follows: 3 min at 94° C. followed by 40 cycles of 5 sec at 95° C. for the denaturation step, 30 sec at 55° C. for the annealing step and 2 min at 72° C. for the extension step.

Subsequently, the four PCR-amplified mixtures were pooled and 10 µL of the mixture were resolved by electrophoresis in a 1.2% agarose gel containing 0.25 µg/mL of ethidium bromide. The amplicons were then visualized with an Alpha-Imager (Alpha Innotech Corporation, San Leandro, Calif.) by exposing to UV light at 254 nm. Amplicon size was estimated by comparison with a 1 kb molecular weight ladder (Life Technologies, Burlington, Ontario, Canada). The remaining PCR-amplified mixture (150 µL, total) was also resolved by electrophoresis in a 1.2% agarose gel. The amplicons were then visualized by staining with methylene blue (Flores et al., 1992, Biotechniques, 13:203-205). Amplicon size was once again estimated by comparison with a 1 kb molecular weight ladder. Of the sixteen strains selected from the twenty described in Table 3, six were amplified using SEQ ID NOs.: 68 and 70 as primers (CCRI-178, CCRI-8895, CCRI-8903, CCRI-1324, CCRI-1331 and CCRI-9504). For these six MRSA strains, an amplification product of 1.2 kb was obtained. The band corresponding to this specific amplification product was excised from the agarose gel and purified using the QIAquick™ gel extraction kit (QIAGEN Inc., Chatsworth, Calif.). The gel-purified DNA fragment was then used directly in the sequencing protocol. Both strands of the MREJ amplification products were sequenced by the dideoxynucleotide chain termination sequencing method by using an Applied Biosystems automated DNA sequencer (model 377) with their Big Dye™ Terminator Cycle Sequencing Ready Reaction Kit (Applied Biosystems, Foster City, Calif.). The sequencing reactions were performed by using the same primers (SEQ ID NOs.: 68 and 70) and 10 ng/100 bp per reaction of the gel-purified amplicons. Sequencing of MREJ from the six MRSA strains (CCRI-178, CCRI-8895, CCRI-8903, CCRI-1324, CCRI-1331 and CCRI-9504) described in Table 3 yielded SEQ ID NOs.: 42, 43, 44, 45, 46 and 51, respectively (Table 4).

In order to ensure that the determined sequence did not contain errors attributable to the sequencing of PCR artefacts, we have sequenced two preparations of the gel-purified MREJ amplification products originating from two independent PCR amplifications. For most target fragments, the sequences determined for both amplicon preparations were identical. Furthermore, the sequences of both strands were 100% complementary thereby confirming the high accuracy of the determined sequence. The MREJ sequences determined using the above strategy are described in the Sequence Listing and in Table 4.

In order to sequence MREJ in strains for which no amplicon had been obtained using the strategy including primers specific to the transposase gene of IS431 and orfX, another strategy using primers targeting mecA and orfX sequences was used to amplify longer genomic fragments. A new PCR primer targeting mecA (SEQ ID NO.: 69) (Table 8) to be used in combination with the same primer in the orfX sequence (SEQ ID NO.: 70). The strategy used to select these primers is illustrated in FIG. 3.

The following amplification protocol was used: Purified genomic DNA (300 ng) was transferred to a final volume of 50 µl of a PCR reaction mixture. Each PCR reaction contained 1X Herculase buffer (Stratagene, La Jolla, Calif.), 0.8 µM of each of the 2 primers (SEQ ID NOs.: 69 and 70), 0.56 mM of each of the four dNTPs and 5 units of Herculase (Stratagene). PCR reactions were subjected to cycling using a standard thermal cycler (PTC-200 from MJ Research Inc.) as follows: 2 min at 92° C. followed by 35 or 40 cycles of 10 sec at 92° C. for the denaturation step, 30 sec at 55° C. for the annealing step and 30 min at 68° C. for the extension step.

Subsequently, 10 µL of the PCR-amplified mixture were resolved by electrophoresis in a 0.7% agarose gel containing 0.25 µg/mL of ethidium bromide. The amplicons were then visualized as described above. Amplicon size was estimated by comparison with a 1 kb molecular weight ladder (Life Technologies). A reamplification reaction was then performed in 2 to 5 tubes using the same protocol with 3 µl of the first PCR reaction used as test sample for the second amplification. The PCR-reamplified mixtures were pooled and also resolved by electrophoresis in a 0.7% agarose gel. The amplicons were then visualized by staining with methylene blue as described above. An amplification product of approximately 12 kb was obtained using this amplification strategy for all strains tested. The band corresponding to the specific amplification product was excised from the agarose gel and purified as described above. The gel-purified DNA fragment was then used directly in the sequencing protocol as described above. The sequencing reactions were performed by using the same amplification primers (SEQ ID NOs.: 69 and 70) and 425-495 ng of the gel-purified amplicons per reaction. Subsequently, internal sequencing primers (SEQ ID NOs.: 65, 77 and 96) (Table 8) were used to obtain sequence data on both strands for a larger portion of the amplicon. Five of the 20 MRSA strains (CCRI-1331, CCRI-1263, CCRI-1377, CCRI-1311 and CCRI-2025) described in Table 3 were sequenced using this strategy, yielding SEQ ID NOs.: 46, 47, 48, 49 and 50, respectively (Table 4). Sequence within mecA gene was also obtained from the generated amplicons yielding SEQ ID NOs: 27, 28, 29, 30 and 31 from strains CCRI-2025, CCRI-1263, CCRI-1311, CCRI-1331 and CCRI-1377, respectively (Table 4). Longer sequences within the mecA gene and from downstream regions were also obtained for strains CCRI-2025, CCRI-1331, and CCRI-1377 as described below.

In order to obtain longer sequences of the orfX gene, two other strategies using primers targeting mecA and orfX sequences (at the start codon) was used to amplify longer chromosome fragments. A new PCR primer was designed in orfX (SEQ ID NO.: 132) to be used in combination with the same primer in the mecA gene (SEQ ID NO.: 69). The strategy used to select these primers is illustrated in FIG. 3. Eight S. aureus strains were amplified using primers SEQ ID NOs.: 69 and 132 (CCRI-9860, CCRI-9208, CCRI-9504, CCRI-1331, CCRI-9583, CCRI-9681, CCRI-2025 and CCRI-1377). The strategy used to select these primers is illustrated in FIG. 3.

The following amplification protocol was used: Purified genomic DNA (350 to 500 ng) was transferred to a 50 µl PCR reaction mixture. Each PCR reaction contained 1X Herculase buffer (Stratagene), 0.8 µM of each of the set of 2 primers (SEQ ID NOs.: 69 and 132), 0.56 mM of each of the four dNTPs and 7.5 units of Herculase (Stratagene) with 1 mM MgCl$_2$. PCR reactions were subjected to thermocycling as described above.

Subsequently, 5 µL of the PCR-amplified mixture were resolved by electrophoresis in a 0.8% agarose gel containing 0.25 µg/mL of ethidium bromide. The amplicons were then visualized as described above. For one S. aureus strain (CCRI-9583), a reamplification was then performed by using primers SEQ ID NOs.: 96 and 158 (FIG. 3) in 4 tubes, using the same PCR protocol, with 2 µl of the first PCR reaction as test sample for the second amplification. The PCR-reamplified mixtures were pooled and also resolved by electrophoresis in a 0.8% agarose gel. The amplicons were then visualized by staining with methylene blue as described above. A band of approximately 12 to 20 kb was obtained using this amplification strategy depending on the strains tested. The band corresponding to the specific amplification product was excised from the agarose gel and purified using the QIAquick™ gel extraction kit or QIAEX II gel extraction kit (QIAGEN Inc.). Two strains, CCRI-9583 and CCRI-9589, were also amplified with primers SEQ ID NOs.: 132 and 150, generating an amplification product of 1.5 kb. Long amplicons (12-20 kb) were sequenced using 0.6 to 1 µg per reaction, while short amplicons (1.5 kb) were sequenced using 150 ng per reaction. Sequencing reactions were performed using different sets of primers for each S. aureus strain: 1) SEQ ID NOs.: 68, 70, 132, 145, 146, 147, 156, 157 and 158 for strain CCRI-9504; 2) SEQ ID NOs.: 70, 132, 154 and 155 for strain CCRI-2025; 3) SEQ ID NOs.: 70, 132, 148, 149, 158 and 159 for strain CCRI-9681; 4) SEQ ID NOs.: 70, 132, 187, and 188 for strain CCRI-9860; 5) SEQ ID NOs: 70, 132, 150 and 159 for strain CCRI-9589, 6) SEQ ID NOs.: 114, 123, 132, 150 and 158 for strain CCRI-9583; 7) SEQ ID NOs: 70, 132, 154 and 155 for strain CCRI-1377, 8) SEQ ID NOs.: 70, 132, 158 and 159 for strain CCRI-9208; 9) SEQ ID NOs: 68, 70, 132, 145, 146, 147 and 158 for strain CCRI-1331; and 10) SEQ ID NOs.: 126 and 127 for strain CCRI-9770.

In one strain (CCRI-9770), the orfX and orfSA0022 genes were shown to be totally or partially deleted based on amplification using primers specific to these genes (SEQ ID NOs: 132 and 159 and SEQ ID NOs.: 128 and 129, respectively) (Table 8). Subsequently, a new PCR primer was designed in orfSA0021 (SEQ ID NO.: 126) to be used in combination with the same primer in the mecA gene (SEQ ID NO.: 69). An amplification product of 4.5 kb was obtained with this primer set. Amplification, purification of amplicons and sequencing of amplicons were performed as described above.

To obtain the sequence of the SSCmec region containing mecA for ten of the 20 MRSA strains described in Table 3 (CCRI-9504, CCRI-2025, CCRI-9208, CCRI-1331, CCRI-9681, CCRI-9860, CCRI-9770, CCRI-9589, CCRI-9583 and CCRI-1377), the primer described above designed in mecA (SEQ ID NO.: 69) was used in combination with a primer designed in the downstream region of mecA (SEQ ID NO.: 118) (Table 8). An amplification product of 2 kb was obtained for all the strains tested. For one strain, CCRI-9583, a re-amplification with primers SEQ ID NOs.: 96 and 118 was performed with the amplicon generated with primers SEQ ID NOs.: 69 and 132 described above. The amplication, re-amplification, purification of amplicons and sequencing reactions were performed as described above. Sequencing reactions were performed with amplicons generated with SEQ ID NOs.: 69 and 132 described above or SEQ ID NOs.: 69 and 118. Different sets of sequencing primers were used for each S. aureus strain: 1) SEQ ID NOs.: 69, 96, 117, 118, 120, 151, 152 for strains CCRI-9504, CCRI-2025, CCRI-1331, CCRI-9770 and CCRI-1377; 2) SEQ ID NOs.: 69, 96, 118 and 120 for strains CCRI-9208, CCRI-9681 and CCRI-9589; 3) SEQ ID NOs.: 69, 96, 117, 118, 120 and 152 for strain CCRI-9860; and 4) SEQ ID NOs.: 96, 117, 118, 119, 120, 151 and 152 for strain CCRI-9583.

The sequences obtained for 16 of the 20 strains non-amplifiable by the Hiramatsu assay (Table 4) were then compared to the sequences available from public databases. In all cases, portions of the sequence had an identity close to 100% to publicly available sequences for orfX (SEQ ID NOs.: 42-51, 165-168 and 171) or mecA and downstream region (SEQ ID NOs.: 27-31, 189-193, 195, 197-199 and 225). However, while the orfX portion of the fragments (SEQ ID NOs.: 42-51, 165-168 and 171) shared nearly 100% identity with the orfX gene of MSSA strain NCTC 8325 described by Hiramatsu et al. (SEQ ID NO.: 3), the DNA sequence within the right extremity of SCCmec itself was shown to be very different from those of types I, II, III and IV described by Hiramatsu et al. (Table 13, FIG. 4). Six different novel sequence types were obtained.

It should be noted that Hiramatsu et al. demonstrated that SCCmec type I could be associated with MREP type i, SCCmec types II and IV are associated with MREP type ii, and SCCmec type III is associated with MREP type iii. Our MREJ sequencing data from various MRSA strains led to the discovery of 6 novel MREP types designated types iv, v vi, vii, viii, and ix. The MREJ comprising distinct MREP types were named according to the MREP numbering scheme. Hence, MREP type i is comprised within MREJ type i, MREP type ii is comprised within MREJ type ii and so on up to MREP type ix.

The sequences within the right extremity of SCCmec obtained from strains CCRI-178, CCRI-8895, CCRI-8903, CCRI-1324, CCRI-1331 and CCRI-9504 (SEQ ID NOs.: 42, 43, 44, 45, 46 and 51) were nearly identical to each other and exhibited nearly 100% identity with IS431 (GenBank accession numbers AF422691, AB037671, AF411934). However, our sequence data revealed for the first time the location of this IS431 sequence at the right extremity of SCCmec adjacent to the integration site. Therefore, as the sequences at the right extremity of SCCmec from these 6 MRSA strains were different from those of SCCmec type I from strain NCTC 10442, SCCmec type II from strain N315, SCCmec type III from strain 85/2082 and SCCmec type IV from strains CA05 and 8/6-3P described by Hiramatsu et al. (Ito et al., 2001, Antimicrob. Agents Chemother. 45:1323-1336; Ma et al., 2002, Antimicrob. Agents Chemother. 46:1147-1152), these new sequences were designated as MREP type iv (SEQ ID NOs.: 42-46 and 51). A BLAST search with the SCCmec portion of MREP type iv sequences produced significant alignments with sequences coding for portions of a variety of known transposases. For example, when compared to Genbank accession no. AB037671, MREP type iv from SEQ ID NO. 51 shared 98% identity with the putative transposase of IS431 and its downstream region; two gaps of 7 nucleotides each were also present in the alignment.

Sequences obtained from strains CCRI-1263, CCRI-1377, CCRI-1311 and CCRI-2025 (SEQ ID NOs.: 47-50) were nearly identical to each other and different from all three SCCmec types and MREP type iv and, consequently, were designated as MREP type v. When compared with Genbank sequences using BLAST, MREP type v sequences did not share any significant homology with any published sequence, except for the first 28 nucleotides. That short stretch corresponded to the last 11 coding nucleotides of orfX, followed by the 17 nucleotides downstream, including the right inverted repeat (IR-R) of SCCmec.

Sequence obtained from strain CCRI-9208 was also different from all three SCCmec types and MREP types iv and v and, consequently, was designated as MREP type vi (SEQ ID NO.: 171). Upon a BLAST search, MREP type vi was shown to be unique, exhibiting no significant homology to any published sequence.

Sequences obtained from strains CCRI-9583 and CCRI-9589 were also different from all three SCCmec types and MREP types iv to vi and were therefore designated as MREP type vii (SEQ ID NOs.: 165 and 166). Upon a BLAST search, MREP type vii was also shown to be unique, exhibiting no significant homology to any published sequence.

Sequence obtained from strain CCRI-9860 was also different from all three SCCmec types and MREP types iv to vii and was therefore designated as MREP type viii (SEQ ID NO.: 167). Sequence obtained from strain CCRI-9681 was also different from all three SCCmec types and MREP types iv to viii and was therefore designated as MREP type ix (SEQ ID NO.: 168). BLAST searches with the SCCmec portion of MREP types viii and ix sequences yielded significant alignments, but only for the first ~150 nucleotides of each MREP type. For example, the beginning of the MREP type viii sequence had 88% identity with a portion of Genbank accession no. AB063173, but no significant homology with any published sequence was found for the rest of the sequence. In the same manner, the first ~150 nucleotides of MREP type ix had 97% identity with the same portion of AB063173, with the rest of the sequence being unique. The short homologous portion of MREP types viii and ix corresponds in AB063173 to the last 14 coding nucleotides of orfX, the IR-R of SCCmec, and a portion of orfCM009. Although sharing resemblances, MREP types viii and ix are very different from one another; as shown in Table 13, there is only 55.2% identity between both types for the first 500 nucleotides of the SCCmec portion.

Finally, we did not obtain any sequence within SSCmec from strain CCRI-9770. However, as described in the section "Sequencing of MREJ nucleotide sequences from MRSA strains not amplifiable with primers specific to SCCmec types I, II and III", this strain has apparently a partial or total deletion of the orfX and orfSA0022 genes in the chromosomal DNA to the right of the SCCmec integration site and this would represent a new right extremity junction. We therefore designated this novel sequence as MREP type x (SEQ ID NO.: 172). Future sequencing should reveal whether this so called MREJ type x contains a novel MREP type x or if the lack of amplification is indeed caused by variation in the chromosomal part of the MREJ.

The sequences of the first 500-nucleotide portion of the right extremity of all SCCmec obtained in the present invention were compared to those of SCCmec types I, II and III using GCG programs Pileup and Gap. Table 13 depicts the identities at the nucleotide level between SCCmec right extremities of the six novel sequences with those of SCCmec types I, II and III using the GCG program Gap. While SCCmec types I and II showed nearly 79.2% identity (differing only by a 102 bp insertion present in SCCmec type II) (FIGS. 1, 2 and 4), all other MREP types showed identities varying from 40.9 to 57.1%. This explains why the right extremities of the novel MREP types iv to ix disclosed in the present invention could not have been predicted nor detected with the system described by Hiramatsu et al.

Four strains (CCRI-1312, CCRI-1325, CCRI-9773 and CCRI-9774) described in Table 3 were not sequenced but rather characterized using PCR primers. Strains CCRI-1312 and CCRI-1325 were shown to contain MREP type v using specific amplification primers described in Examples 4, 5 and 6 while strains CCRI-9773 and CCRI-9774 were shown to contain MREP type vii using specific amplification primers described in Example 7.

To obtain the complete sequence of the SCCmec present in the MRSA strains described in the present invention, primers targeting the *S. aureus* chromosome to the left (upstream of the mecA gene) of the SCCmec integration site were developed. Based on available public database sequences, 5 different primers were designed (SEQ ID NOs.: 85-89) (Table 9). These primers can be used in combination with *S. aureus* chromosome-specific primers in order to sequence the entire SCCmec or, alternatively, used in combination with a mecA-specific primer (SEQ ID NO.: 81) in order to sequence the left extremity junction of SCCmec. We have also developed several primers specific to known SCCmec sequences spread along the locus in order to obtain the complete sequence of SCCmec (Table 9). These primers will allow to assign a SCCmec type to the MRSA strains described in the present invention.

Selection of Amplification Primers from SCCmec/orfX Sequences

The MREJ sequences determined by the inventors or selected from public databases were used to select PCR primers for detection and identification of MRSA. The strategy used to select these PCR primers was based on the analysis of multiple sequence alignments of various MREJ sequences.

Upon analysis of the six new MREP types iv to ix sequence data described above, primers specific to each new MREP type sequence (SEQ ID NOs.: 79, 80, 109, 112, 113, 115, 116 and 204) were designed (FIG. 2, Table 5, Examples 3, 4, 5, 6, 7 and 8). Primers specific to MREP types iv, v and vii (SEQ ID NOs.: 78, 80 and 112) were used in multiplex with the three primers to detect SCCmec types I, II and III (SEQ ID NOs: 64, 66 and 67) and the primer specific to the *S. aureus* orfX (SEQ ID NO. 64) (Examples 3, 4, 5, 6 and 7). Primers specific to MREP types vi, viii and ix (SEQ ID NOs.: 204, 115, 116 and 109) were also designed and tested against their specific target (Example 8).

Detection of Amplification Products

Classically, the detection of PCR amplification products is performed by standard ethidium bromide-stained agarose gel electrophoresis as described above. It is however clear that other methods for the detection of specific amplification products, which may be faster and more practical for routine diagnosis, may be used. Examples of such methods are described in co-pending patent application WO01/23604 A2.

Amplicon detection may also be performed by solid support or liquid hybridization using species-specific internal DNA probes hybridizing to an amplification product. Such probes may be generated from any sequence from our repertory and designed to specifically hybridize to DNA amplification products which are objects of the present invention. Alternatively, amplicons can be characterized by sequencing. See co-pending patent application WO01/23604 A2 for examples of detection and sequencing methods.

In order to improve nucleic acid amplification efficiency, the composition of the reaction mixture may be modified (Chakrabarti and Schutt, 2002, Biotechniques, 32:866-874; Al-Soud and Radstrom, 2002, J. Clin. Microbiol., 38:4463-4470; Al-Soud and Radstrom, 1998, Appl. Environ. Microbiol., 64:3748-3753; Wilson, 1997, Appl. Environ. Microbiol., 63:3741-3751). Such modifications of the amplification reaction mixture include the use of various polymerases or the addition of nucleic acid amplification facilitators such as betaine, BSA, sulfoxides, protein gp32, detergents, cations, tetramethylamonium chloride and others.

In a preferred embodiment, real-time detection of PCR amplification was monitored using molecular beacon probes in a SMART CYCLER® apparatus (Cepheid, Sunnyvale, Calif.). A multiplex PCR assay containing primers specific to MREP types i to v and orfX of *S. aureus* (SEQ ID NOs.: 64, 66, 67, 79 and 80), a molecular beacon probe specific to the orfX sequence (SEQ ID NO. 84, see Annex II and FIG. 2) and an internal control to monitor PCR inhibition was developed. The internal control contains sequences complementary to MREP type iv- and orfX-specific primers (SEQ ID NOs. 79 and and 64). The assay also contains a molecular beacon probe labeled with tetrachloro-6-carboxyfluorescein (TET) specific to sequence within DNA fragment generated during amplification of the internal control. Each PCR reaction contained 50 mM KCl, 10 mM Tris-HCl (pH 9.0), 0.1% Triton X-100, 3.45 mM MgCl$_2$, 0.8 µM of each of the MREP-specific primers (SEQ ID NOs.: 66 and 67) and orfX-specific primer (SEQ ID NO.: 64), 0.4 µM of each of the MREP-specific primers (SEQ ID NOs.: 79 and 80), 80 copies of the internal control, 0.2 µM of the TET-labeled molecular beacon probe specific to the internal control, 0.2 µM of the molecular beacon probe (SEQ ID NO.: 84) labeled with 6-carboxyfluorescein (FAM), 330 µM of each of the four dNTPs (Pharmacia Biotech), 3.45 µg/µl of BSA (Sigma), and 0.875 U Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies (Example 5). None of the 26 MRCNS or 10 MSCNS tested were positive with this multiplex assay. The eight MRSA strains (CCRI-9208, CCRI-9770, CCRI-9681, CCRI-9860, CCRI-9583, CCRI-9773, CCRI-9774, CCRI-9589) which harbor the new MREP types vi, viii, ix and x sequences described in the present invention remained undetectable (Example 5).

In a preferred embodiment, detection of MRSA using the real-time multiplex PCR assay on the SMART CYCLER® apparatus (Cepheid, Sunnyvale, Calif.) directly from clinical specimens was evaluated. A total of 142 nasal swabs were collected during a MRSA hospital surveillance program at the Montreal General Hospital (Montreal, Quebec, Canada). The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in co-pending patent application No. U.S. 60/306,163. Classical identification of MRSA was performed by standard culture methods.

The PCR assay detected 33 of the 34 samples positive for MRSA based on the culture method. As compared to culture, the PCR assay detected 8 additional MRSA positive specimens for a sensitivity of 97.1% and a specificity of 92.6% (Example 6). This multiplex PCR assay represents a rapid and powerful method for the specific detection of MRSA carriers directly from nasal specimens and can be used with any types of clinical specimens such as wounds, blood or blood culture, CSF, etc.

In a preferred embodiment, a multiplex PCR assay containing primers specific to MREP types i, ii, iii, iv, v and vi and orfX of S. aureus (SEQ ID NOs.: 66, 67, 79, 80 and 112), and three molecular beacons probes specific to orfX sequence which allowed detection of the two sequence polymorphisms identified in this region of the orfX sequence was developed. Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable (Example 7). Primers specific to MREP types vi, viii and ix (SEQ ID NOs.: 204, 115, 116 and 109) were also designed and were shown to detect their specific target strains (Example 8). While the primers and probes derived from the teaching of Hiramatsu et al., permitted the detection of only 48.7% (19 strains out of 39) of the MRSA strains of Table 2, the primers and probes derived from the present invention enable the detection of 97.4% of the strains (38 strains out of 39) (see examples 7 and 8). Therefore it can be said that our assay has a ubiquity superior to 50% for the MRSA strains listed in Table 2.

Specificity, Ubiquity and Sensitivity Tests for Oligonucleotide Primers and Probes The specificity of oligonucleotide primers and probes was tested by amplification of DNA or by hybridization with staphylococcal species. All of the staphylococcal species tested were likely to be pathogens associated with infections or potential contaminants which can be isolated from clinical specimens. Each target DNA could be released from microbial cells using standard chemical and/or physical treatments to lyse the cells (Sambrook et al., 1989, Molecular Cloning: A Laboratory Manual, $2^{nd}$ ed., Cold Spring Harbor Laboratory Press, Cold Spring Harbor, N.Y.) or alternatively, genomic DNA purified with the GNOME™ DNA kit (Qbiogene, Carlsbad, Calif.) was used. Subsequently, the DNA was subjected to amplification with the set of primers. Specific primers or probes hybridized only to the target DNA.

Oligonucleotides primers found to amplify specifically DNA from the target MRSA were subsequently tested for their ubiquity by amplification (i.e. ubiquitous primers amplified efficiently most or all isolates of MRSA). Finally, the analytical sensitivity of the PCR assays was determined by using 10-fold or 2-fold dilutions of purified genomic DNA from the targeted microorganisms. For most assays, sensitivity levels in the range of 2-10 genome copies were obtained. The specificity, ubiquity and analytical sensitivity of the PCR assays were tested either directly with bacterial cultures or with purified bacterial genomic DNA.

Molecular beacon probes were tested using the SMART CYCLER® platform as described above. A molecular beacon probe was considered specific only when it hybridized solely to DNA amplified from the MREJ of S. aureus. Molecular beacon probes found to be specific were subsequently tested for their ubiquity (i.e. ubiquitous probes detected efficiently most or all isolates of the MRSA) by hybridization to bacterial DNAs from various MRSA strains.

Bacterial Strains

The reference strains used to build proprietary SCCmec-chromosome right extremity junction sequence data subrepertories, as well as to test the amplification and hybridization assays, were obtained from (i) the American Type Culture Collection (ATCC), (ii) the Laboratoire de santé publique du Québec (LSPQ) (Ste-Anne de Bellevue, Québec, Canada), (iii) the Centers for Disease Control and Prevention (CDC) (Atlanta, Ga.), (iv) the Institut Pasteur (Paris, France), and V) the Harmony Collection (London, United Kingdom) (Table 14). Clinical isolates of MRSA, MSSA, MRCNS and MSCNS from various geographical areas were also used in this invention (Table 15). The identity of our MRSA strains was confirmed by phenotypic testing and reconfirmed by PCR analysis using S. aureus-specific primers and mecA-specific primers (SEQ ID NOs.: 69 and 81) (Martineau et al., 2000, Antimicrob. Agents Chemother. 44:231-238).

For sake of clarity, below is a list of the Examples, Tables, Figures and Annexes of this invention.

DESCRIPTION OF THE EXAMPLES

Example 1: Primers developed by Hiramatsu et al. can only detect MRSA strains belonging to MREP types i, ii, and iii while missing prevalent novel MREP types.

Example 2: Detection and identification of MRSA using primers specific to MREP types i, ii and iii sequences developed in the present invention.

Example 3: Development of a multiplex PCR assay on a standard thermocycler for detection and identification of MRSA based on MREP types i, ii, iii, iv and v sequences.

Example 4: Development of a real-time multiplex PCR assay on the SMART CYCLER® for detection and identification of MRSA based on MREP types i, ii, iii, iv and v sequences.

Example 5: Development of a real-time multiplex PCR assay on the SMART CYCLER® for detection and identification of MRSA based on MREP types i, ii, iii, iv and v sequences and including an internal control.

Example 6: Detection of MRSA using the real-time multiplex assay on the SMART CYCLER® based on MREP types i, ii, iii, iv and v sequences for the detection of MRSA directly from clinical specimens.

Example 7: Development of a real-time multiplex PCR assay on the SMART CYCLER® for detection and identification of MRSA based on MREP types i, ii, iii, iv, v, vi and vii sequences.

Example 8: Development of real-time PCR assays on the SMART CYCLER® for detection and identification of MRSA based on MREP types vi, viii and ix.

DESCRIPTION OF THE TABLES

Table 1 provides information about all PCR primers developed by Hiramatsu et al. in U.S. Pat. No. 6,156,507.

Table 2 is a compilation of results (ubiquity and specificity) for the detection of SCCmec-orfX right extremity junction using primers described by Hiramatsu et al. in U.S. Pat. No. 6,156,507 on a standard thermocycler.

Table 3 is a list of MRSA strains not amplifiable using primers targeting types I, II and III of SCCmec-orfX right extremity junction sequences.

Table 4 is a list of novel sequences revealed in the present invention.

Table 5 provides information about all primers developed in the present invention.

Table 6 is a list of molecular beacon probes developed in the present invention.

Table 7 shows amplicon sizes of the different primer pairs described by Hiramatsu et al. in U.S. Pat. No. 6,156,507 or developed in the present invention.

Table 8 provides information about primers developed in the present invention to sequence the SCCmec-chromosome right extremity junction.

Table 9 provides information about primers developed in the present invention to obtain sequence of the complete SCCmec.

Table 10 is a list of the sequences available from public databases (GenBank, genome projects or U.S. Pat. No. 6,156,507) used in the present invention to design primers and probes.

Table 11 gives analytical sensitivity of the PCR assay developed in the present invention using primers targeting types I, II and III of SCCmec-orfX right extremity junction sequences and performed using a standard thermocycler.

Table 12 is a compilation of results (ubiquity and specificity) for the detection of MRSA using primers developed in the present invention which target types I, II and III of SCCmec-orfX right extremity junction sequences and performed using a standard thermocycler.

Table 13 shows a comparison of sequence identities between the first 500 nucleotides of SCCmec right extremities between 9 types of MREP.

Table 14 provides information about the reference strains of MRSA, MSSA, MRCNS and MSCNS used to validate the PCR assays developed in the present invention.

Table 15 provides information about the origin of clinical strains of MRSA, MSSA, MRCNS and MSCNS used to validate the PCR assays described in the present invention.

Table 16 depicts the analytical sensitivity of the PCR assay developed in the present invention using primers targeting 5 types of MREP sequences and performed on a standard thermocycler.

Table 17 is a compilation of results (ubiquity and specificity) for the PCR assay developed in the present invention using primers targeting 5 types of MREP sequences and performed on a standard thermocycler.

Table 18 depicts the analytical sensitivity of the PCR assay developed in the present invention using the SMART CYCLER® platform for the detection of 5 types of MREP.

Table 19 is a compilation of results (ubiquity and specificity) for the PCR assay developed in the present invention using primers and a molecular beacon probe targeting 5 types of MREP sequences and performed on the SMART CYCLER® platform.

Table 20 depicts the analytical sensitivity of the PCR assay developed in the present invention using the SMART CYCLER® platform for the detection of 6 MREP types.

Table 21 is a compilation of results (ubiquity and specificity) for the PCR assay developed in the present invention using primers and a molecular beacon probe targeting 6 types of MREP sequences and performed on the SMART CYCLER® platform.

FIGURE LEGENDS

FIG. 1. Schematic organization of types I, II and III SCCmec-orfX right extremity junctions and localization of the primers (SEQ ID NOs: 52-63) described by Hiramatsu et al. for the detection and identification of MRSA. Amplicon sizes are depicted in Table 7.

FIG. 2. Schematic organization of MREP types i, ii, iii, iv, v, vi, vii, viii and ix and localization of the primers and molecular beacon targeting all MREP types (SEQ ID NOs. 20, 64, 66, 67, 79, 80, 84, 112, 115, 116, 84, 163 and 164) which were developed in the present invention. Amplicon sizes are depicted in Table 7.

FIG. 3. Schematic organization of the SCCmec-chromosome right extremity junctions and localization of the primers (SEQ ID NOs. 65, 68, 69, 70, 77, 96, 118, 126, 132, 150 and 158) developed in the present invention for the sequencing of MREP types iv, v, vi, vii, viii, ix and x.

Figures 4, 4A, 4C:
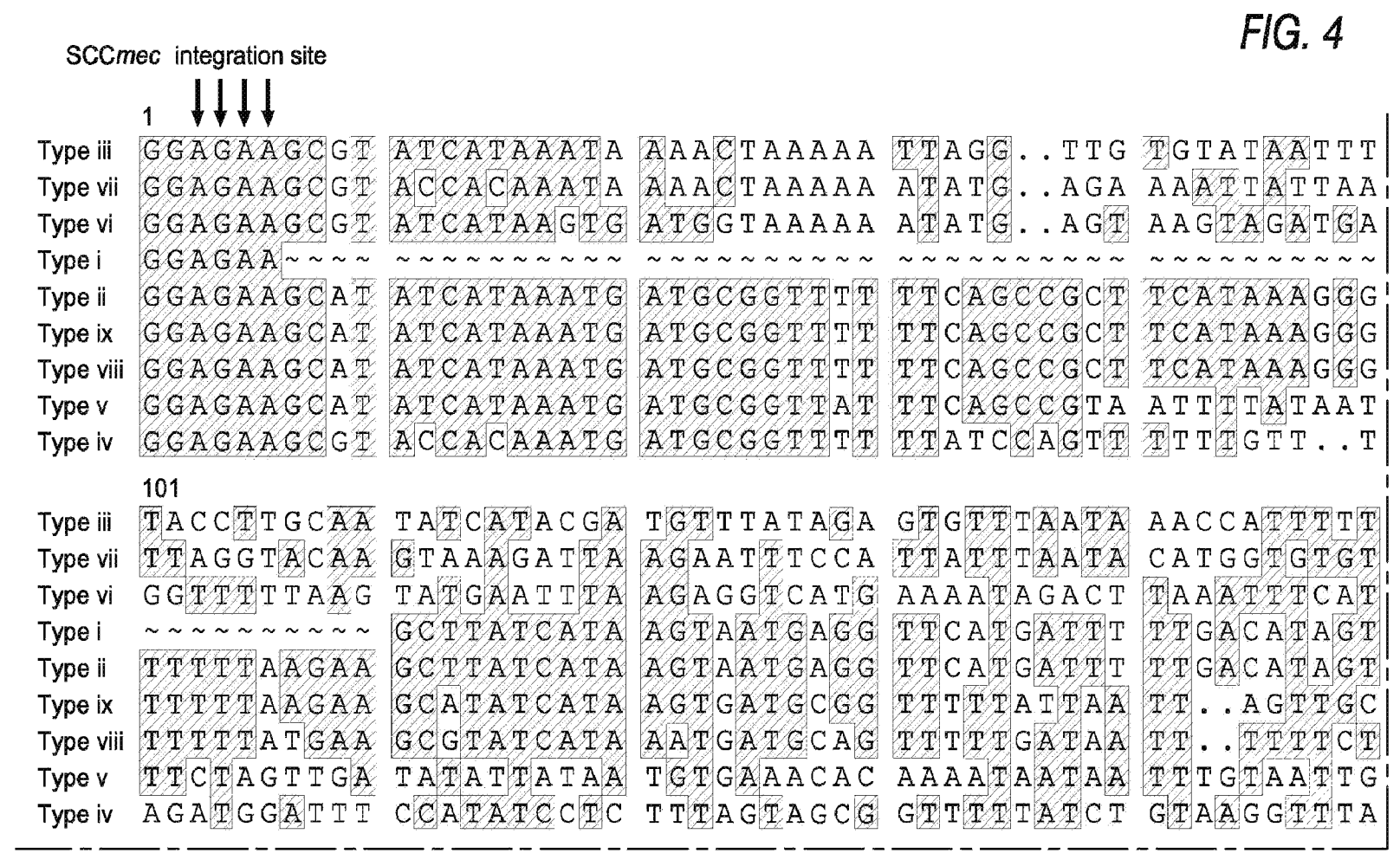
Figure 4B:
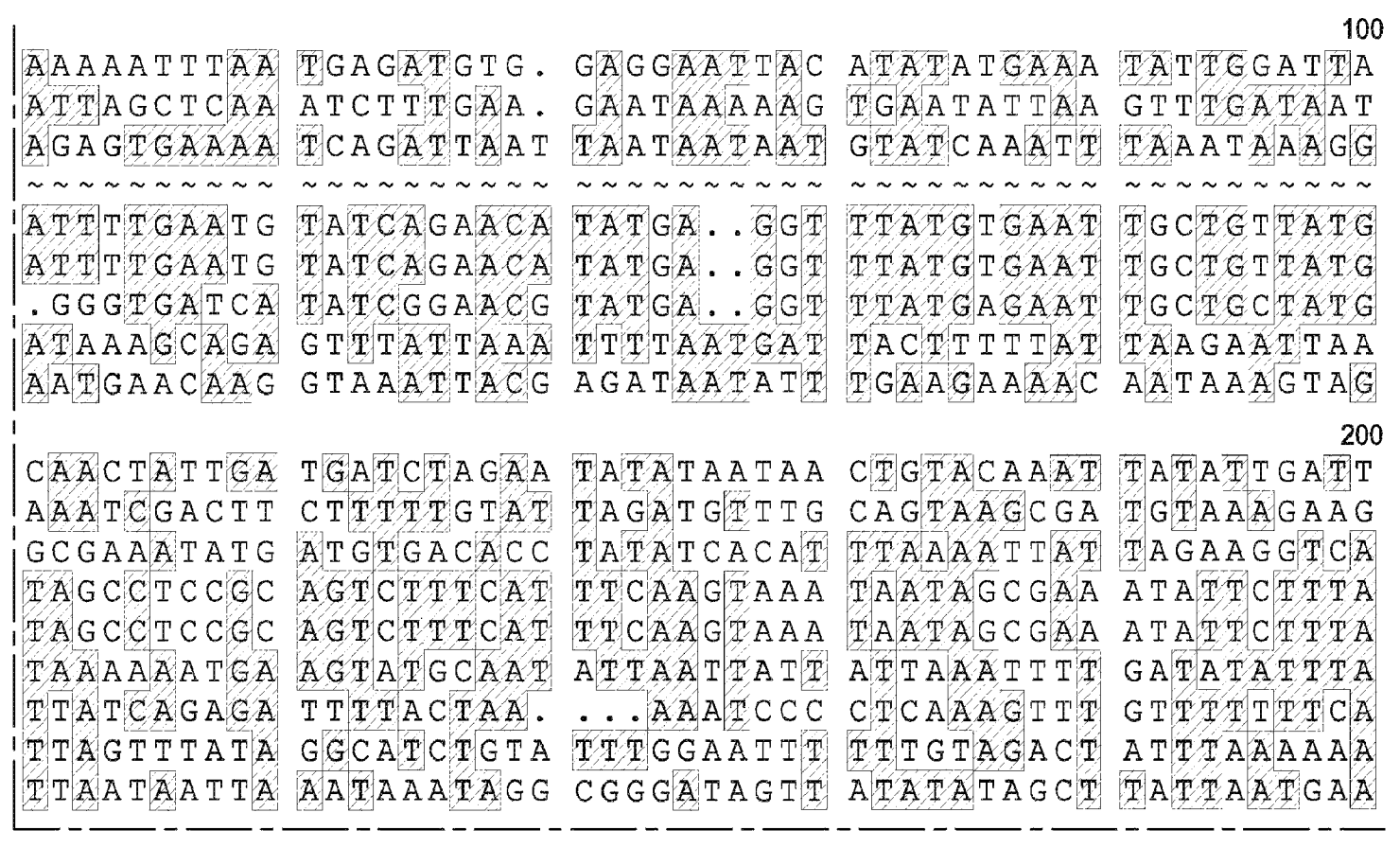
Figure 4C:
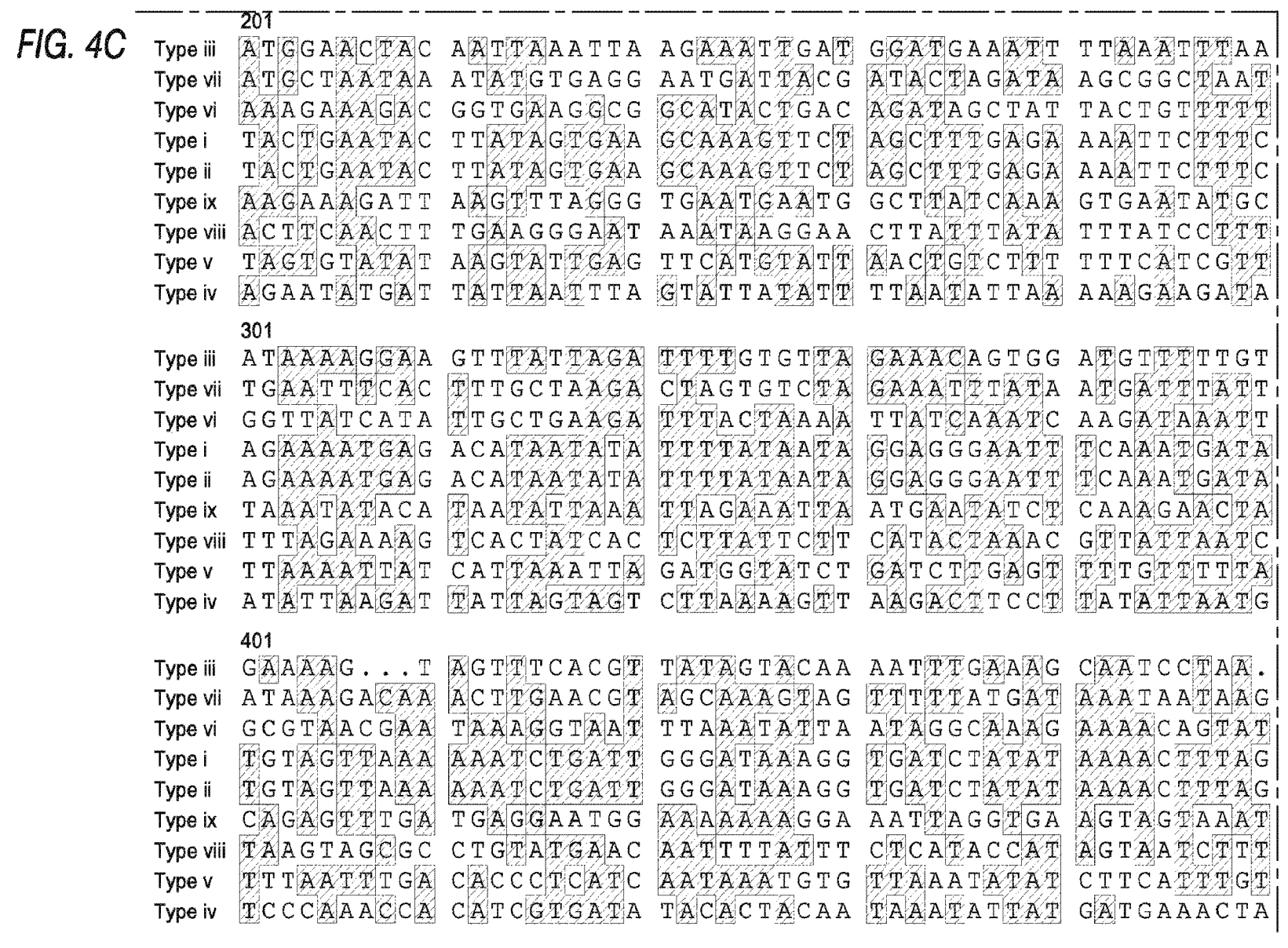

FIG. 4. Multiple sequence alignment of representatives of nine MREP types (represented by portions of SEQ ID NOs.: 1, 2, 104, 51, 50, 171, 165, 167 and 168 for types i, iii, iv, v, vi, vii, viii and ix, respectively).

DESCRIPTION OF THE ANNEXES

The Annexes show the strategies used for the selection of primers and internal probes:

Annex I illustrates the strategy for the selection of primers from SCCmec and orfX sequences specific for SCCmec types I and II.

Annex II illustrates the strategy for the selection of specific molecular beacon probes for the real-time detection of SCCmec-orfX right extremity junctions.

As shown in these Annexes, the selected amplification primers may contain inosines and/or base ambiguities. Inosine is a nucleotide analog able to specifically bind to any of the four nucleotides A, C, G or T. Alternatively, degenerated oligonucleotides which consist of an oligonucleotide mix having two or more of the four nucleotides A, C, G or T at the site of mismatches were used. The inclusion of inosine and/or of degeneracies in the amplification primers allows mismatch tolerance thereby permitting the amplification of a wider array of target nucleotide sequences (Dieffenbach and Dveksler, 1995, PCR Primer: A Laboratory Manual, Cold Spring Harbor Laboratory Press, Plainview, N.Y.).

EXAMPLES

Example 1

Primers Developed by Hiramatsu et al. can only Detect MRSA Strains Belonging to MREP Types i, ii, and iii while Missing Prevalent Novel MREP Types.

As shown in FIG. 1, Hiramatsu et al. have developed various primers that can specifically hybridize to the right extremities of types I, II and III SCCmec DNAs. They combined these primers with primers specific to the *S. aureus* chromosome region located to the right of the SCCmec integration site for the detection of MRSA. The primer set (SEQ ID NOs.: 22, 24 and 28 in U.S. Pat. No. 6,156,507 corresponding to SEQ ID NOs.: 56, 58 and 60 in the present invention) was shown by Hiramatsu et al. to be the most specific and ubiquitous for detection of MRSA. This set of primers gives amplification products of 1.5 kb for SCCmec type I, 1.6 kb for SCCmec type II and 1.0 kb for SCCmec type III (Table 7). The ubiquity and specificity of this multiplex PCR assay was tested on 39 MRSA strains, 41 MSSA strains, 9 MRCNS strains and 11 MSCNS strains (Table 2). One µL of a treated standardized bacterial suspension or of a bacterial genomic DNA preparation purified from bacteria were amplified in a 20 µl PCR reaction mixture. Each PCR reaction contained 50 mM KCl, 10 mM Tris-HCl (pH 9.0), 0.1% Triton X-100, 2.5 mM $MgCl_2$, 0.4 µM of each of the SCCmec- and orfX-specific primers (SEQ ID NOs.: 56, 58 and 60), 200 µM of each of the four dNTPs (Pharmacia Biotech), 3.3 µg/µl of BSA (Sigma), and 0.5 U Taq polymerase (Promega) coupled with TaqStart™ Antibody (BD Biosciences).

PCR reactions were then subjected to thermal cycling: 3 min at 94° C. followed by 40 cycles of 60 seconds at 95° C.

for the denaturation step, 60 seconds at 55° C. for the annealing step, and 60 seconds at 72° C. for the extension step, then followed by a terminal extension of 7 minutes at 72° C. using a standard thermocycler (PTC-200 from MJ Research Inc.). Detection of the PCR products was made by electrophoresis in agarose gels (2%) containing 0.25 µg/ml of ethidium bromide.

None of the MRCNS or MSCNS strains tested were detected with the set of primers detecting SCCmec types I, II and III. Twenty of the 39 MRSA strains tested were not detected with this multiplex PCR assay (Tables 2 and 3). One of these undetected MRSA strains corresponds to the highly epidemic MRSA Portuguese clone (strain CCRI-9504; De Lencastre et al., 1994. Eur. J. Clin. Microbiol. Infect. Dis. 13:64-73) and another corresponds to the highly epidemic MRSA Canadian clone CMRSA1 (strain CCRI-9589; Simor et al. CCDR 1999, 25-12, June 15). These data demonstrate that the primer set developed by Hiramatsu et al. (SEQ ID NOs.: 22, 24 and 28 in U.S. Pat. No. 6,156,507 corresponding to SEQ ID NOs.: 56, 58 and 60 in the present invention) is not ubiquitous for the detection of MRSA and suggest that some MRSA strains have sequences at the SCCmec right extremity junction which are different from those identified by Hiramatsu et al. other types of SCCmec sequences or other sequences at the right extremity of SCCmec (MREP type) are found in MRSA. A limitation of this assay is the non-specific detection of 13 MSSA strains (Table 2).

Example 2

Detection and Identification of MRSA Using Primers Specific to MREP Types i, ii and iii Sequences Developed in the Present Invention.

Based on analysis of multiple sequence alignments of orfX and SCCmec sequences described by Hiramatsu et al. or available from GenBank, a set of primers (SEQ ID NOs: 64, 66, 67) capable of amplifying short segments of types I, II and III of SCCmec-orfX right extremity junctions from MRSA strains and discriminating from MRCNS (Annex I and FIG. 2) were designed. The chosen set of primers gives amplification products of 176 bp for SCCmec type I, 278 pb for SCCmec type II and 223 bp for SCCmec type III and allows rapid PCR amplification. These primers were used in multiplex PCR to test their ubiquity and specificity using 208 MRSA strains, 252 MSSA strains, 41 MRCNS strains and 21 MRCNS strains (Table 12). The PCR amplification and detection was performed as described in Example 1. PCR reactions were then subjected to thermal cycling (3 minutes at 94° C. followed by 30 or 40 cycles of 1 second at 95° C. for the denaturation step and 30 seconds at 60° C. for the annealing-extension step, and then followed by a terminal extension of 2 minutes at 72° C.) using a standard thermocycler (PTC-200 from MJ Research Inc.). Detection of the PCR products was made as described in Example1.

None of the MRCNS or MSCNS strains tested were detected with this set of primers (Table 12). However, the twenty MRSA strains which were not detected with the primer set developed by Hiramatsu et al. (SEQ ID NOs: 56, 58 and 60) were also not detected with the primers developed in the present invention (Tables 3 and 12). These data also demonstrate that some MRSA strains have sequences at the SCCmec-chromosome right extremity junction which are different from those identified by Hiramatsu et al. Again, as observed with the Hiramatsu primers, 13 MSSA strains were also detected non-specifically (Table 12). The clinical significance of this finding remains to be established since these apparent MSSA strains could be the result of a recent deletion in the mec locus (Deplano et al., 2000, J. Antimicrob. Chemotherapy, 46:617-619; Inglis et al., 1990, J. Gen. Microbiol., 136:2231-2239; Inglis et al., 1993, J. Infect. Dis., 167:323-328; Lawrence et al. 1996, J. Hosp. Infect., 33:49-53; Wada et al., 1991, Biochem. Biophys. Res. Comm., 176:1319-1326).

Example 3

Development of a Multiplex PCR Assay on a Standard Thermocycler for Detection and Identification of MRSA Based on MREP types i, ii, iii, iv and v Sequences.

Upon analysis of two of the new MREP types iv and v sequence data described in the present invention, two new primers (SEQ ID NOs.: 79 and 80) were designed and used in multiplex with the three primers SEQ ID NOs.: 64, 66 and 67 described in Example 2. PCR amplification and detection of the PCR products was performed as described in Example 2. Sensitivity tests performed by using ten-fold or two-fold dilutions of purified genomic DNA from various MRSA strains of each MREP type showed a detection limit of 5 to 10 genome copies (Table 16). Specificity tests were performed using 0,1 ng of purified genomic DNA or 1 µl of a standardized bacterial suspension. All MRCNS or MSCNS strains tested were negative with this multiplex assay (Table 17). Twelve of the 20 MRSA strains which were not detected with the multiplex PCR described in Examples 1 and 2 were now detected with this multiplex assay. Again, as observed with the Hiramatsu primers, 13 MSSA strains were also detected non-specifically (Table 12). The eight MRSA strains (CCRI-9208, CCRI-9583, CCRI-9773, CCRI-9774, CCRI-9589, CCRI-9860, CCRI-9681, CCRI-9770) and which harbor the new MREP types vi, vii, viii, ix and x sequences described in the present invention remained undetectable.

Example 4

Development of a Real-Time Multiplex PCR Assay on the SMART CYCLER® for Detection and Identification of MRSA Based on MREP Types i, ii, iii, iv and v Sequences.

The multiplex PCR assay described in Example 3 containing primers (SEQ ID NOs.: 64, 66, 67, 79 and 80) was adapted to the SMART CYCLER® platform (Cepheid). A molecular beacon probe specific to the orfX sequence was developed (SEQ ID NO. 84, see Annex II). Each PCR reaction contained 50 mM KCl, 10 mM Tris-HCl (pH 9.0), 0.1% Triton X-100, 3.5 mM MgCl$_2$, 0.4 µM of each of the SCCmec- and orfX-specific primers (SEQ ID NOs.: 64, 66, 67, 79 and 80), 0.2 µM of the FAM-labeled molecular beacon probe (SEQ ID NO.: 84), 200 µM of each of the four dNTPs, 3.3 µg/µl of BSA, and 0.5 U Taq polymerase coupled with TaqStart™ Antibody. The PCR amplification on the SMART CYCLER® was performed as follows: 3 min. at 94° C. for initial denaturation, then forty-five cycles of three steps consisting of 5 seconds at 95° C. for the denaturation step, 15 seconds at 59° C. for the annealing step and 10 seconds at 72° C. for the extension step. Fluorescence detection was performed at the end of each annealing step. Sensitivity tests performed by using purified genomic DNA from several MRSA strains of each MREP type showed a detection limit of 2 to 10 genome copies (Table 18). None of the MRCNS or MSCNS were positive with this multiplex assay (Table 19). Again, as observed with the Hiramatsu primers, 13 MSSA strains were also detected non-specifically. Twelve of the twenty MRSA strains which were not detected with the multiplex PCR described in Examples 1 and 2 were detected by this multiplex assay. As described in Example 3, the eight MRSA strains which harbor the new MREP types vi, vii, viii, ix and x sequences described in the present invention remained undetectable.

Example 5

Development of a Real-Time Multiplex PCR Assay on the SMART CYLCER® for Detection and Identification of MRSA Based on MREP Types i, ii, iii, iv and v Sequences Including an Internal Control.

The multiplex PCR assay described in Example 4 containing primers specific to MREP types i to v and orfX of *S. aureus* (SEQ ID NOs.: 64, 66, 67, 79 and 80) and a molecular beacon probe specific to the orfX sequence (SEQ ID NO. 84, see Annex II) was optimized to include an internal control to monitor PCR inhibition. This internal control contains sequences complementary to MREP type iv- and orfX-specific primers (SEQ ID NOs. 79 and and 64). The assay also contains a TET-labeled molecular beacon probe specific to sequence within the amplicon generated by amplification of the internal control. Each PCR reaction contained 50 mM KCl, 10 mM Tris-HCl (pH 9.0), 0.1% Triton X-100, 3.45 mM MgCl$_2$, 0.8 µM of each of the MREP-specific primers (SEQ ID NOs.: 66 and 67) and orfX-specific primer (SEQ ID NO.: 64), 0.4 µM of each of the MREP-specific primers (SEQ ID NOs.: 79 and 80), 80 copies of the internal control, 0.2 µM of the TET-labeled molecular beacon probe specific to the internal control, 0.2 µM of the FAM-labeled molecular beacon probe (SEQ ID NO.: 84), 330 µM of each of the four dNTPs (Pharmacia Biotech), 3.45 µg/µl of BSA (Sigma), and 0.875 U Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. Sensitivity tests performed by using purified genomic DNA from one MRSA strain of each MREP type (i to v) showed a detection limit of 2 to 10 genome copies. None of the 26 MRCNS or 10 MSCNS were positive with this multiplex assay. Again, as observed with the Hiramatsu primers, 13 MSSA strains were also detected non-specifically. As described in Examples 3 and 4, the eight MRSA strains which harbor the new MREP types vi to x sequences described in the present invention remained undetectable.

Example 6

Detection of MRSA Using the Real-Time Multiplex Assay on the SMART CYLCER® Based on MREP Types i, ii, iii, iv and v Sequences Directly from Clinical Specimens.

The assay described in Example 5 was adapted for detection directly from clinical specimens. A total of 142 nasal swabs collected during a MRSA hospital surveillance program at the Montreal General Hospital (Montreal, Quebec, Canada) were tested. The swab samples were tested at the Centre de Recherche en Infectiologie de l'Université Laval within 24 hours of collection. Upon receipt, the swabs were plated onto mannitol agar and then the nasal material from the same swab was prepared with a simple and rapid specimen preparation protocol described in co-pending patent application No. U.S. 60/306,163. Classical identification of MRSA was performed by standard culture methods.

The PCR assay described in Example 5 detected 33 of the 34 samples positive for MRSA based on the culture method. As compared to culture, the PCR assay detected 8 additional MRSA positive specimens for a sensitivity of 97.1% and a specificity of 92.6%. This multiplex PCR assay represents a rapid and powerful method for the specific detection of MRSA carriers directly from nasal specimens and can be used with any type of clinical specimens such as wounds, blood or blood culture, CSF, etc.

Example 7

Development of a Real-Time Multiplex PCR Assay on the SMART CYCLER® for Detection and Identification of MRSA Based on MREP Types i, ii, iii, iv, v and vii Sequences.

Upon analysis of the new MREP type vii sequence data described in the present invention (SEQ ID NOs.:165 and 166), two new primers (SEQ ID NOs.: 112 and 113) were designed and tested in multiplex with the three primers SEQ ID NOs.: 64, 66 and 67 described in Example 2. Primer SEQ ID NO.: 112 was selected for use in the multiplex based on its sensitivity. Three molecular beacon probes specific to the orfX sequence which allowed detection of two sequence polymorphisms identified in this region of the orfX sequence, based on analysis of SEQ ID NOs.: 173-186, were also used in the multiplex (SEQ ID NOs.: 84, 163 and 164). Each PCR reaction contained 50 mM KCl, 10 mM Tris-HCl (pH 9.0), 0.1% Triton X-100, 3.45 mM MgCl$_2$, 0.8 µM of each of the SCCmec-specific primers (SEQ ID NOs.: 66 and 67) and orfX-specific primer (SEQ ID NO.: 64), 0.4 µM of each of the SCCmec-specific primers (SEQ ID NOs.: 79 and 80), 0.2 µM of the FAM-labeled molecular beacon probe (SEQ ID NO.: 84), 330 µM of each of the four dNTPs (Pharmacia Biotech), 3.45 µg/µl of BSA (Sigma), and 0.875 U of Taq polymerase (Promega) coupled with TaqStart™ Antibody (BD Biosciences). The PCR amplification on the SMART CYCLER® was performed as follows: 3 min. at 95° C. for initial denaturation, then forty-eight cycles of three steps consisting of 5 seconds at 95° C. for the denaturation step, 15 seconds at 60° C. for the annealing step and 15 seconds at 72° C. for the extension step. The detection of fluorescence was done at the end of each annealing step. Sensitivity tests performed by using purified genomic DNA from several MRSA strains of each MREP type showed a detection limit of 2 genome copies (Table 20). None of the 26 MRCNS or 8 MSCNS were positive with this multiplex assay. Again, as observed with the Hiramatsu primers, 13 MSSA strains were also detected non-specifically (Table 21). Four of the strains which were not detected with the multiplex assay for the detection of MREP types i to v were now detected with this multiplex assay while the four MRSA strains (CCRI-9208, CCRI-9770, CCRI-9681, CCRI-9860) which harbor the MREP types vi, viii, ix and x described in the present invention remained undetectable.

Example 8

Development of Real-Time PCR Assays on the SMART CYCLER® for Detection and Identification of MRSA Based on MREP Types vi, viii, ix.

Upon analysis of the new MREP types vi, viii and ix sequence data described in the present invention, one new primers specific to MREP type vi (SEQ ID NO.: 201), one primer specific to MREP type viii (SEQ ID NO.: 115), a primer specific to MREP type ix (SEQ ID NO.: 109) and a primer specific to both MREP types viii and ix (SEQ ID NO.: 116) were designed. Each PCR primer was used in combination with the orfX-specific primer (SEQ ID NO.: 64) and tested against its specific target strain. Each PCR reaction contained 50 mM KCl, 10 mM Tris-HCl (pH 9.0), 0.1% Triton X-100, 3.45 mM MgCl$_2$, 0.4 µM of each of the SCCmec- and orfX-specific primers, 200 µM of each of the four dNTPs, 3.4 µg/µl of BSA, and 0.875 U Taq polymerase coupled with TaqStart™ Antibody. The PCR amplification was performed as described en Example 7. Sensitivity tests performed by using genomic DNA purified from their respective MRSA target strains showed that the best primer pair combination was SEQ ID NOs.: 64 and 115 for the detection of MREP types viii and ix simultaneously. These new SCCmec-specific primers may be used in multiplex with primers specific to MREP types i, ii, ii, iv, v and vii (SEQ ID NOs.: 64, 66, 67, 79 and 80) described in previous examples to provide a more ubiquitous MRSA assay.

In conclusion, we have improved the ubiquity of detection of MRSA strains. New MREJ types iv to x have been identified. Amongst strains representative of these new types, Hiramitsu's primers and/or probes succeeded in detecting less than 50% thereof. We have therefore amply passed the bar of at least 50% ubiquity, since our primers and probes were designed to detect 100% of the strains tested as representatives of MREJ types iv to ix. Therefore, although ubiquity depends on the pool of strains and representatives that are under analysis, we know now that close to 100% ubiquity is an attainable goal, when using the sequences of the right junctions (MREJ) to derive probes and primers dealing with polymorphism in this region. Depending on how many unknown types of MREJ exist, we have a margin of maneuver going from 50% (higher than Hiramatsu's primers for the tested strains) to 100% if we sequence all the existing MREJs to derive properly the present diagnostic tools and methods, following the above teachings.

This invention has been described herein above, and it is readily apparent that modifications can be made thereto without departing from the spirit of this invention. These modifications are under the scope of this invention, as defined in the appended claims.

TABLE 1

PCR amplification primers reported by Hiramatsu et al. in U.S. Pat. No. 6,156,507 found in the sequence listing

| SEQ ID NO.: (present invention) | Target | Position[a,b] | SEQ ID NO.: (U.S. Pat. No. 6,156,507) |
|---|---|---|---|
| 52 | MREP types i and ii | 480 | 18 |
| 53 | MREP types i and ii | 758 | 19 |
| 54 | MREP types i and ii | 927 | 20 |
| 55 | MREP types i and ii | 1154 | 21 |
| 56 | MREP types i and ii | 1755 | 22 |
| 57 | MREP types i and ii | 2302 | 23 |
| 58 | MREP type iii | 295[c] | 24 |
| 59 | orfX | 1664 | 25 |
| 60 | orfSA0022[d] | 3267 | 28 |
| 61 | orfSA0022[d] | 3585 | 27 |
| 62 | orfX | 1389 | 26 |
| 63 | orfSA0022[d] | 2957 | 29 |

[a]Position refers to nucleotide position of the 5' end of primer.
[b]Numbering for SEQ ID NOs.: 52-57 refers to SEQ ID NO.: 2; numbering for SEQ ID NO.: 58 refers to SEQ ID NO.: 4; numbering for SEQ ID NOs.: 59-63 refers to SEQ ID NO.: 3.
[c]Primer is reverse-complement of target sequence.
[d]orfSA0022 refers to the open reading frame designation from GenBank accession number AP003129 (SEQ ID NO.: 231).

TABLE 2

Specificity and ubiquity tests performed on a standard thermocycler using the optimal set of primers described by Hiramatsu et al. (SEQ ID NOs.: 22, 24 and 28 in U.S. Pat. No. 6,156,507 corresponding to SEQ ID NOs.: 56, 58 and 60, respectively, in the present invention) for the detection of MRSA

| | PCR results for SCCmec orfX right extremity junction | |
|---|---|---|
| Strains | Positive (%) | Negative (%) |
| MRSA - 39 strains | 19 (48.7) | 20 (51.2) |
| MSSA - 41 strains | 13 (31.7) | 28 (68.3) |
| MRCNS - 9 strains* | 0 (0%) | 9 (100%) |
| MSCNS - 11 strains* | 0 (0%) | 11 (100%) |

*Details regarding CNS strains:
MRCNS:
S. caprae (1)
S. cohni cohnii (1)
S. epidermidis (1)
S. haemolyticus (2)
S. hominis (1)
S. sciuri (1)
S. simulans (1)
S. warneri (1)
MSCNS:
S. cohni cohnii (1)
S. epidermidis (1)
S. equorum (1)
S. gallinarum (1)
S. haemolyticus (1)
S. lentus (1)
S. lugdunensis (1)
S. saccharolyticus (1)
S. saprophyticus (2)
S. xylosus (1)

TABLE 3

Origin of MRSA strains not amplifiable using primers developed by Hiramatsu et al. (SEQ ID NOs.: 22, 24 and 28 in U.S. Pat. No. 6,156,507 corresponding to SEQ ID NOs.: 56, 58 and 60, respectively, in the present invention) as well as primers developed in the present invention targeting MREP types i, ii and iii (SEQ ID NOs.: 64, 66 and 67)

| Staphylococcus aureus strain designation: | | |
|---|---|---|
| Original | CCRI[a] | Origin |
| ATCC BAA-40[b] | CCRI-9504 | Portugal |
| ATCC 33592 | CCRI-178 | USA |
| R991282 | CCRI-2025 | Québec, Canada |
| 4508 | CCRI-9208 | Québec, Canada |
| 19121 | CCRI-8895 | Denmark |
| Z109 | CCRI-8903 | Denmark |
| 45302 | CCRI-1263 | Ontario, Canada |
| R655 | CCRI-1324 | Québec, Canada |
| MA 50428 | CCRI-1311 | Québec, Canada |
| MA 50609 | CCRI-1312 | Québec, Canada |
| MA 51363 | CCRI-1331 | Québec, Canada |
| MA 51561 | CCRI-1325 | Québec, Canada |
| 14A0116 | CCRI-9681 | Poland |
| 23 (CCUG 41787) | CCRI-9860 | Sweden |
| SE26-1 | CCRI-9770 | Ontario, Canada |
| SE1-1 | CCRI-9583 | Ontario, Canada |
| ID-61880[c] | CCRI-9589 | Ontario, Canada |
| SE47-1 | CCRI-9773 | Ontario, Canada |
| SE49-1 | CCRI-9774 | Ontario, Canada |
| 39795-2 | CCRI-1377 | Québec, Canada |

[a]CCRI stands for "Collection of the Centre de Recherche en Infectiologie".
[b]Portuguese clone.
[c]Canadian clone EMRSA1.

TABLE 4

Staphylococcus aureus MREJ nucleotide sequences revealed in the present invention

| SEQ ID NO. | Staphylococcus aureus strain designation: Original | CCRI[a] | Genetic Target |
|---|---|---|---|
| 27 | R991282 | CCRI-2025 | mecA |
| 28 | 45302 | CCRI-1263 | mecA |
| 29 | MA 50428 | CCRI-1311 | mecA |
| 30 | MA 51363 | CCRI-1331 | mecA |
| 31 | 39795-2 | CCRI-1377 | mecA and 1.5 kb of downstream region |
| 42 | ATCC 33592 | CCRI-178 | MREP type iv |
| 43 | 19121 | CCRI-8895 | MREP type iv |
| 44 | Z109 | CCRI-8903 | MREP type iv |
| 45 | R655 | CCRI-1324 | MREP type iv |
| 46 | MA 51363 | CCRI-1331 | MREP type iv |
| 47 | 45302 | CCRI-1263 | MREP type v |
| 48 | 39795-2 | CCRI-1377 | MREP type v |
| 49 | MA 50428 | CCRI-1311 | MREP type v |
| 50 | R991282 | CCRI-2025 | MREP type v |
| 51 | ATCC BAA-40 | CCRI-9504 | MREP type iv |
| 165 | SE1-1 | CCRI-9583 | MREP type vii |
| 166 | ID-61880 | CCRI-9589 | MREP type vii |
| 167 | 23 (CCUG 41787) | CCRI-9860 | MREP type viii |
| 168 | 14A016 | CCRI-9681 | MREP type ix |
| 171 | 4508 | CCRI-9208 | MREP type vi |
| 172 | SE26-1 | CCRI-9770 | orfSA0021[b] and 75 bp of orfSA0022[b] |
| 173 | 26 (98/10618) | CCRI-9864 | MREP type ii |
| 174 | 27 (98/26821) | CCRI-9865 | MREP type ii |
| 175 | 28 (24344) | CCRI-9866 | MREP type ii |
| 176 | 12 (62305) | CCRI-9867 | MREP type ii |
| 177 | 22 (90/14719) | CCRI-9868 | MREP type ii |
| 178 | 23 (98/14719) | CCRI-9869 | MREP type ii |
| 179 | 32 (97S99) | CCRI-9871 | MREP type ii |
| 180 | 33 (97S100) | CCRI-9872 | MREP type ii |
| 181 | 38 (825/96) | CCRI-9873 | MREP type ii |
| 182 | 39 (842/96) | CCRI-9874 | MREP type ii |
| 183 | 43 (N8-892/99) | CCRI-9875 | MREP type ii |
| 184 | 46 (9805-0137) | CCRI-9876 | MREP type iii |
| 185 | 1 | CCRI-9882 | MREP type ii |
| 186 | 29 | CCRI-9885 | MREP type ii |
| 189 | SE1-1 | CCRI-9583 | mecA and 2.2 kb of downstream region, including IS431mec |
| 190 | ATCC BAA-40 | CCRI-9504 | mecA and 1.5 kb of downstream region |
| 191 | 4508 | CCRI-9208 | mecA and 0.9 kb of downstream region |
| 192 | ID-61880 | CCRI-9589 | mecA and 0.9 kb of downstream region |
| 193 | 14A016 | CCRI-9681 | mecA and 0.9 kb of downstream region |
| 195 | SE26-1 | CCRI-9770 | mecA and 1.5 kb of downstream region, including IS431mec |
| 197 | ATCC 43300 | CCRI-175 | MREP type ii |
| 198 | R522 | CCRI-1262 | MREP type iii |
| 199 | 13370 | CCRI-8894 | MREP type i |
| 219 | ATCC BAA-40 | CCRI-9504 | tetK |
| 220 | MA 51363 | CCRI-1331 | mecA and 1.5 kb of downstream region |
| 221 | 39795-2 | CCRI-1377 | IS431mec and 0.6 kb of upstream region |
| 222 | R991282 | CCRI-2025 | mecA and 1.5 kb of downstream region |
| 223 | R991282 | CCRI-2025 | IS431mec and 0.6 kb of upstream region |
| 224 | 23 (CCUG 41787) | CCRI-9860 | mecA and 1.5 kb of downstream region |
| 225 | 23 (CCUG 41787) | CCRI-9860 | IS431mec and 0.6 kb of upstream region |
| 233 | 14A016 | CCRI-9681 | MREP type ix |

[a]CCRI stands for "Collection du Centre de Recherche en Infectiologie".
[b]orfSA0021 and orfSA0022 refer to the open reading frame designation from GenBank accession number AP003129 (SEQ ID NO.: 231).

TABLE 5

PCR primers developed in the present invention

| SEQ ID NO. | Target | Position[a] | Originating DNA SEQ ID NO. |
|---|---|---|---|
| 64 | orfX | 1720 | 3 |
| 70 | orfX | 1796 | 3 |
| 71 | orfX | 1712 | 3 |
| 72 | orfX | 1749 | 3 |
| 73 | orfX | 1758 | 3 |
| 74 | orfX | 1794 | 3 |
| 75 | orfX | 1797 | 3 |
| 76 | orfX | 1798 | 3 |
| 66 | MREP types i and ii | 2327 | 2 |
| 100 | MREP types i and ii | 2323 | 2 |
| 101 | MREP types i and ii | 2314 | 2 |
| 97 | MREP type ii | 2434 | 2 |
| 99 | MREP type ii | 2434 | 2 |
| 67 | MREP type iii | 207[b] | 4 |
| 98 | MREP type iii | 147[b] | 4 |
| 102 | MREP type iii | 251[b] | 4 |
| 79 | MREP type iv | 74[b] | 43 |
| 80 | MREP type v | 50[b] | 47 |
| 109 | MREP type ix | 652[b] | 168 |
| 204 | MREP type vi | 642[b] | 171 |
| 112 | MREP type vii | 503[b] | 165 |
| 113 | MREP type vii | 551[b] | 165 |
| 115 | MREP type viii | 514[b] | 167 |
| 116 | MREP type viii | 601[b] | 167 |

[a]Position refers to nucleotide position of 5' end of primer.
[b]Primer is reverse-complement of target sequence.

TABLE 6

Molecular beacon probes developed in the present invention

| SEQ ID NO. | Target | Position |
|---|---|---|
| 32 | orfX | 86[a] |
| 83 | orfX | 86[a] |
| 84 | orfX | 34[a,b] |
| 160 | orfX | 55[a,b] |
| 161 | orfX | 34[a,b] |
| 162 | orfX | 114[a] |
| 163 | orfX | 34[a,b] |
| 164 | orfX | 34[a,b] |

[a]Position refers to nucleotide position of the 5' end of the molecular beacon's loop on SEQ ID NO.: 3.
[b]Sequence of molecular beacon's loop is reverse-complement of SEQ ID NO.: 3.

TABLE 7

Length of amplicons obtained with the different primer pairs which are objects of the present invention

| SEQ ID NO. | Target[a] | Amplicon length[a] |
|---|---|---|
| 59/52[b] | orfX/MREP type i and ii | 2079 (type i); 2181 (type ii) |
| 59/53[b] | orfX/MREP type i and ii | 1801 (type i); 1903 (type ii) |
| 59/54[b] | orfX/MREP type i and ii | 1632 (type i); 1734 (type ii) |
| 59/55[b] | orfX/MREP type i and ii | 1405 (type i); 1507 (type ii) |
| 59/56[b] | orfX/MREP type i and ii | 804 (type i); 906 (type ii) |
| 59/57[b] | orfX/MREP type i and ii | 257 (type i); 359 (type ii) |
| 60/52[b] | orfSA0022/MREP type i and ii | 2794 (type i); 2896 (type ii) |
| 60/53[b] | orfSA0022/MREP type i and ii | 2516 (type i); 2618 (type ii) |
| 60/54[b] | orfSA0022/MREP type i and ii | 2347 (type i); 2449 (type ii) |
| 60/55[b] | orfSA0022/MREP type i and ii | 2120 (type i); 2222 (type ii) |
| 60/56[b] | orfSA0022/MREP type i and ii | 1519 (type i); 1621 (type ii) |
| 60/57[b] | orfSA0022/MREP type i and ii | 972 (type i); 1074 (type ii) |
| 61/52[b] | orfSA0022/MREP type i and ii | 2476 (type i); 2578 (type ii) |
| 61/53[b] | orfSA0022/MREP type i and ii | 2198 (type i); 2300 (type ii) |
| 61/54[b] | orfSA0022/MREP type i and ii | 2029 (type i); 2131 (type ii) |
| 61/55[b] | orfSA0022/MREP type i and ii | 1802 (type i); 1904 (type ii) |
| 61/56[b] | orfSA0022/MREP type i and ii | 1201 (type i); 1303 (type ii) |

TABLE 7-continued

Length of amplicons obtained with the different primer pairs which are objects of the present invention

| SEQ ID NO. | Target[d] | Amplicon length[a] |
|---|---|---|
| 61/57[b] | orfSA0022/MREP type i and ii | 654 (type i); 756 (type ii) |
| 62/52[b] | orfX/MREP type i and ii | 2354 (type i); 2456 (type ii) |
| 62/53[b] | orfX/MREP type i and ii | 2076 (type i); 2178 (type ii) |
| 62/54[b] | orfX/MREP type i and ii | 1907 (type i); 2009 (type ii) |
| 62/55[b] | orfX/MREP type i and ii | 1680 (type i); 1782 (type ii) |
| 62/56[b] | orfX/MREP type i and ii | 1079 (type i); 1181 (type ii) |
| 62/57[b] | orfX/MREP type i and ii | 532 (type i); 634 (type ii) |
| 63/52[b] | orfSA0022/MREP type i and ii | 3104 (type i); 3206 (type ii) |
| 63/53[b] | orfSA0022/MREP type i and ii | 2826 (type i); 2928 (type ii) |
| 63/54[b] | orfSA0022/MREP type i and ii | 2657 (type i); 2759 (type ii) |
| 63/55[b] | orfSA0022/MREP type i and ii | 2430 (type i); 2532 (type ii) |
| 63/56[b] | orfSA0022/MREP type i and ii | 1829 (type i); 1931 (type ii) |
| 63/57[b] | orfSA0022/MREP type i and ii | 1282 (type i); 1384 (type ii) |
| 59/58[b] | orfX/MREP type iii | 361 |
| 60/58[b] | orfSA0022/MREP type iii | 1076 |
| 61/58[b] | orfSA0022/MREP type iii | 758 |
| 62/58[b] | orfX/MREP type iii | 656 |
| 63/58[b] | orfSA0022/MREP type iii | 1386 |
| 70/66 | orfX/MREP type i and ii | 100 (type i); 202 (type ii) |
| 70/67 | orfX/MREP type iii | 147 (type iii) |
| 64/66[c] | orfX/MREP type i and ii | 176 (type i); 278 (type ii) |
| 64/67[c] | orfX/MREP type iii | 223 |
| 64/79[c] | orfX/MREP type iv | 215 |
| 64/80[c] | orfX/MREP type v | 196 |
| 64/97[c] | orfX/MREP type ii | 171 |
| 64/98[c] | orfX/MREP type iii | 163 |
| 64/99[c] | orfX/MREP type ii | 171 |
| 64/100[c] | orfX/MREP types i and ii | 180 (type i); 282 (type ii) |
| 64/101[c] | orfX/MREP types i and ii | 189 (type i); 291 (type ii) |
| 64/102[c] | orfX/MREP type iii | 263 |
| 64/109[c] | orfX/MREP type ix | 369 |
| 64/204[c] | orfX/MREP type vi | 348 |
| 64/112[c] | orfX/MREP type vii | 214 |
| 64/113[c] | orfX/MREP type vii | 263 |
| 64/115[c] | orfX/MREP type viii | 227 |
| 64/116[c] | orfX/MREP type viii | 318 |

[a]Amplicon length is given in base pairs for MREP types amplified by the set of primers.
[b]Set of primers described by Hiramatsu et al. in U.S. Pat. No. 6,156,507.
[c]Set of primers developed in the present invention.
[d]orfSA0022 refers to the open reading frame designation from GenBank accession number AP003129 (SEQ ID NO.: 231).

TABLE 8

Other primers developed in the present invention

| | | Originating DNA | |
|---|---|---|---|
| SEQ ID NO. | Target | Position[a] | SEQ ID NO. |
| 77 | MREP type iv | 993 | 43 |
| 65 | MREP type v | 636 | 47 |
| 70 | orfX | 1796 | 3 |
| 68 | IS431 | 626 | 92 |
| 69 | mecA | 1059 | 78 |
| 96 | mecA | 1949 | 78 |
| 81 | mecA | 1206 | 78 |
| 114 | MREP type vii | 629[b] | 165 |
| 117 | MREP type ii | 856 | 194 |
| 118 | MREP type ii | 974[b] | 194 |
| 119 | MREP type vii | 404 | 189 |
| 120 | MREP type vii | 477[b] | 189 |
| 123 | MREP type vii | 551 | 165 |
| 124 | MREP type ii | 584 | 170 |
| 125 | MREP type ii | 689[b] | 170 |
| 126 | orfSA0021 | 336 | 231 |
| 127 | orfSA0021 | 563 | 231 |
| 128 | orfSA0022[d] | 2993 | 231 |
| 129 | orfSA0022[d] | 3467[b] | 231 |
| 132 | orfX | 3700 | 231 |
| 145 | MREP type iv | 988 | 51 |
| 146 | MREP type v | 1386 | 51 |

TABLE 8-continued

Other primers developed in the present invention

| | | Originating DNA | |
|---|---|---|---|
| SEQ ID NO. | Target | Position[a] | SEQ ID NO. |
| 147 | MREP type iv | 891[b] | 51 |
| 148 | MREP type ix | 664 | 168 |
| 149 | MREP type ix | 849[b] | 168 |
| 150 | MREP type vii | 1117[b] | 165 |
| 151 | MREP type vii | 1473 | 189 |
| 152 | IS431mec | 1592[b] | 189 |
| 154 | MREP type v | 996[b] | 50 |
| 155 | MREP type v | 935 | 50 |
| 156 | tetK from plasmid pT181 | 1169[b] | 228 |
| 157 | tetK from plasmid pT181 | 136 | 228 |
| 158 | orfX | 2714[b] | 2 |
| 159 | orfX | 2539 | 2 |
| 187 | MREP type viii | 967[b] | 167 |
| 188 | MREP type viii | 851 | 167 |

[a]Position refers to nucleotide position of the 5' end of primer.
[b]Primer is reverse-complement of target sequence.

TABLE 9

Amplification and/or sequencing primers developed in the present invention

| | | Originating DNA | |
|---|---|---|---|
| SEQ ID NO. | Target | Position[a] | SEQ ID NO. |
| 85 | S. aureus chromosome | 197[b] | 35 |
| 86 | S. aureus chromosome | 198[b] | 37 |
| 87 | S. aureus chromosome | 197[b] | 38 |
| 88 | S. aureus chromosome | 1265[b] | 39 |
| 89 | S. aureus chromosome | 1892 | 3 |
| 103 | orfX | 1386 | 3 |
| 105 | MREP type i | 2335 | 2 |
| 106 | MREP type ii | 2437 | 2 |
| 107 | MREP type iii | 153[b] | 4 |
| 108 | MREP type iii | 153[b] | 4 |
| 121 | MREP type vii | 1150 | 165 |
| 122 | MREP type vii | 1241[b] | 165 |
| 130 | orfX | 4029[b] | 231 |
| 131 | region between orfSA0022 and orfSA0023[d] | 3588 | 231 |
| 133 | merB from plasmid pI258 | 262 | 226 |
| 134 | merB from plasmid pI258 | 539[b] | 226 |
| 135 | merR from plasmid pI258 | 564 | 226 |
| 136 | merR from plasmid pI258 | 444 | 227 |
| 137 | merR from plasmid pI258 | 529 | 227 |
| 138 | merR from plasmid pI258 | 530[b] | 227 |
| 139 | rep from plasmid pUB110 | 796 | 230 |
| 140 | rep from plasmid pUB110 | 761[b] | 230 |
| 141 | rep from plasmid pUB110 | 600 | 230 |
| 142 | aadD from plasmid pUB110 | 1320[b] | 229 |
| 143 | aadD from plasmid pUB110 | 759 | 229 |
| 144 | aadD from plasmid pUB110 | 646 | 229 |
| 153 | MREP type vii | 1030 | 165 |
| 200 | orfSA0022[d] | 871[c] | 231 |
| 201 | orfSA0022[d] | 1006 | 231 |
| 202 | MREP type vi | 648 | 171 |
| 203 | MREP type vi | 883[b] | 171 |
| 205 | MREP type ix | 1180 | 168 |
| 206 | MREP type ix | 1311[b] | 233 |
| 207 | MREP type viii | 1337 | 167 |
| 208 | MREP type viii | 1441[b] | 167 |
| 209 | ccrA | 184 | 232 |
| 210 | ccrA | 385 | 232 |
| 211 | ccrA | 643[b] | 232 |

TABLE 9-continued

Amplification and/or sequencing primers developed in the present invention

| SEQ ID NO. | Target | Originating DNA Position[a] | SEQ ID NO. |
|---|---|---|---|
| 212 | ccrA | 1282[b] | 232 |
| 213 | ccrB | 1388 | 232 |
| 214 | ccrB | 1601 | 232 |
| 215 | ccrB | 2139[b] | 232 |
| 216 | ccrB | 2199[b] | 232 |
| 217 | ccrB | 2847[b] | 232 |
| 218 | ccrB | 2946[b] | 232 |

[a]Position refers to nucleotide position of the 5' end of primer.
[b]Primer is reverse-complement of target sequence.
[c]Primer contains two mismatches.
[d]orfSA0022 and orfSA0023 refer to the open reading frame designation from GenBank accession number AP003129 (SEQ ID NO.: 231).

TABLE 10

Origin of the nucleic acids and/or sequences available from public databases found in the sequence listing

| SEQ ID NO. | Staphylococcal strain | Source | Accession number | Genetic Target[a,b] |
|---|---|---|---|---|
| 1 | NCTC 10442 | Database | AB033763 | SCCmec type I MREJ |
| 2 | N315 | Database | D86934 | SCCmec type II MREJ |
| 3 | NCTC 8325 | Database | AB014440 | MSSA chromosome |
| 4 | 86/560 | Database | AB013471 | SCCmec type III MREJ |
| 5 | 86/961 | Database | AB013472 | SCCmec type III MREJ |
| 6 | 85/3907 | Database | AB013473 | SCCmec type III MREJ |
| 7 | 86/2652 | Database | AB013474 | SCCmec type III MREJ |
| 8 | 86/1340 | Database | AB013475 | SCCmec type III MREJ |
| 9 | 86/1762 | Database | AB013476 | SCCmec type III MREJ |
| 10 | 86/2082 | Database | AB013477 | SCCmec type III MREJ |
| 11 | 85/2111 | Database | AB013478 | SCCmec type III MREJ |
| 12 | 85/5495 | Database | AB013479 | SCCmec type III MREJ |
| 13 | 85/1836 | Database | AB013480 | SCCmec type III MREJ |
| 14 | 85/2147 | Database | AB013481 | SCCmec type III MREJ |
| 15 | 85/3619 | Database | AB013482 | SCCmec type III MREJ |
| 16 | 85/3566 | Database | AB013483 | SCCmec type III MREJ |
| 17 | 85/2232 | Database | AB014402 | SCCmec type II MREJ |
| 18 | 85/2235 | Database | AB014403 | SCCmec type II MREJ |
| 19 | MR108 | Database | AB014404 | SCCmec type II MREJ |
| 20 | 85/9302 | Database | AB014430 | SCCmec type I MREJ |
| 21 | 85/9580 | Database | AB014431 | SCCmec type I MREJ |
| 22 | 85/1940 | Database | AB014432 | SCCmec type I MREJ |
| 23 | 85/6219 | Database | AB014433 | SCCmec type I MREJ |
| 24 | 64/4176 | Database | AB014434 | SCCmec type I MREJ |
| 25 | 64/3846 | Database | AB014435 | SCCmec type I MREJ |
| 26 | HUC19 | Database | AF181950 | SCCmec type II MREJ |
| 33 | G3 | U.S. Pat. No. 6,156,507 | SEQ ID NO.: 15 | S. epidermidis SCCmec type II MREJ |
| 34 | SH 518 | U.S. Pat. No. 6,156,507 | SEQ ID NO.: 16 | S. haemolyticus SCCmec type II MREJ |
| 35 | ATCC 25923 | U.S. Pat. No. 6,156,507 | SEQ ID NO.: 9 | S. aureus chromosome |
| 36 | STP23 | U.S. Pat. No. 6,156,507 | SEQ ID NO.: 10 | S. aureus chromosome |
| 37 | STP43 | U.S. Pat. No. 6,156,507 | SEQ ID NO.: 12 | S. aureus chromosome |
| 38 | STP53 | U.S. Pat. No. 6,156,507 | SEQ ID NO.: 13 | S. aureus chromosome |
| 39 | 476 | Genome project[c] | | S. aureus chromosome |
| 40 | 252 | Genome project[c] | | SCCmec type II MREJ |
| 41 | COL | Genome project[d] | | SCCmec type I MREJ |
| 78 | NCTC 8325 | Database | X52593 | mecA |
| 82 | NCTC 10442 | Database | AB033763 | mecA |
| 90 | N315 | Database | D86934 | mecA |
| 91 | 85/2082 | Database | AB037671 | mecA |
| 92 | NCTC 10442 | Database | AB033763 | IS431 |
| 93 | N315 | Database | D86934 | IS431 |
| 94 | HUC19 | Database | AF181950 | IS431 |
| 95 | NCTC 8325 | Database | X53818 | IS431 |
| 104 | 85/2082 | Database | AB037671 | SCCmec type III MREJ |
| 226 | unknown | Database | L29436 | merB on plasmid pI258 |
| 227 | unknown | Database | L29436 | merR on plasmid pI258 |
| 228 | unknown | Database | S67449 | tetK on plasmid pT181 |
| 229 | HUC19 | Database | AF181950 | aadD on plasmid pUB110 |
| 230 | HUC19 | Database | AF181950 | rep on plasmid pUB110 |
| 231 | N315 | Database | AP003129 | orfSA0021, orfSA0022, orfSA0023 |
| 232 | 85/2082 | Database | AB037671 | ccrA/ccrB |

TABLE 10-continued

Origin of the nucleic acids and/or sequences available from public databases found in the sequence listing

| SEQ ID NO. | Staphylococcal strain | Source | Accession number | Genetic Target[a,b] |
|---|---|---|---|---|

[a] MREJ refers to mec right extremity junction and includes sequences from SCCmec-right extremity and chromosomal DNA to the right of SCCmec integration site.
[b] Unless otherwise specified, all sequences were obtained from *S. aureus* strains.
[c] Sanger Institute genome project (http://www.sanger.ac.uk).
[d] TIGR genome project (http://www.tigr.org).

TABLE 11

Analytical sensitivity of the MRSA-specific PCR assay targeting MREP types i, ii and iii on a standard thermocycler using the set of primers developed in the present invention (SEQ ID NOs.: 64, 66 and 67)

| Strain designation: | | Detection limit |
|---|---|---|
| Original | CCRI[a] (MREP type) | (number of genome copies) |
| 13370 | CCRI-8894 (I) | 5 |
| ATCC 43300 | CCRI-175 (II) | 2 |
| 35290 | CCRI-1262 (III) | 2 |

[a] CCRI stands for "Collection of the Centre de Recherche en Infectiologie".

TABLE 12

Specificity and ubiquity tests performed on a standard thermocycler using the set of primers targeting MREP types i, ii and iii developed in the present invention (SEQ ID NOs.: 64, 66 and 67) for the detection of MRSA

| | PCR results for MREJ | |
|---|---|---|
| Strains | Positive (%) | Negative (%) |
| MRSA - 208 strains | 188 (90.4) | 20 (9.6) |
| MSSA - 252 strains | 13 (5.2) | 239 (94.8) |
| MRCNS - 41 strains* | 0 | 42 (100) |
| MSCNS - 21 strains* | 0 | 21 (100) |

*Details regarding CNS strains:
MRCNS:
S. caprae (2)
S. cohni cohnii (3)
S. cohni urealyticum (4)
S. epidermidis (8)
S. haemolyticus (9)
S. hominis (4)
S. sciuri (4)
S. sciuri sciuri (1)
S. simulans (3)
S. warneri (3)
MSCNS:
S. cohni cohnii (1)
S. epidermidis (3)
S. equorum (2)
S. felis (1)
S. gallinarum (1)
S. haemolyticus (1)
S. hominis (1)
S. lentus (1)
S. lugdunensis (1)
S. saccharolyticus (1)
S. saprophyticus (5)
S. simulans (1)
S. warneri (1)
S. xylosus (1)

TABLE 13

Percentage of sequence identity for the first 500 nucleotides of SCCmec right extremities between all 9 types of MREP[a,b]

| MREP type | i | ii | iii | iv | v | vi | vii | viii | ix |
|---|---|---|---|---|---|---|---|---|---|
| i | — | 79.2 | 42.8 | 42.8 | 41.2 | 44.4 | 44.6 | 42.3 | 42.1 |
| ii | | | 43.9 | 47.5 | 44.7 | 41.7 | 45.0 | 52.0 | 57.1 |
| iii | | | | 46.8 | 44.5 | 45.0 | 42.9 | 45.0 | 42.8 45.2 |
| iv | | | | | 45.8 | 41.4 | 44.3 | 48.0 | 41.3 |
| v | | | | | | 45.4 | 43.7 | 47.5 | 44.3 |
| vi | | | | | | | 45.1 | 41.1 | 47.2 |
| vii | | | | | | | | 42.8 | 40.9 |
| viii | | | | | | | | | 55.2 |
| ix | | | | | | | | | — |

[a] "First 500 nucleotides" refers to the 500 nucleotides within the SCCmec right extremity, starting from the integration site of SCCmec in the *Staphylococcus aureus* chromosome as shown on FIG. 4.
[b] Sequences were extracted from SEQ ID NOs.: 1, 2, 104, 51, 50, 171, 165, 167, and 168 for types i to ix, respectively.

TABLE 14

Reference strains used to test sensitivity and/or specificity and/or ubiquity of the MRSA-specific PCR assays targeting MREJ sequences

| Staphylococcal species | Strains | Source[a] |
|---|---|---|
| MRSA (n = 45) | 33591 | ATCC |
| | 33592 | ATCC |
| | 33593 | ATCC |
| | BAA-38 | ATCC |
| | BAA-39 | ATCC |
| | BAA-40 | ATCC |
| | BAA-41 | ATCC |
| | BAA-42 | ATCC |
| | BAA-43 | ATCC |
| | BAA-44 | ATCC |
| | F182 | CDC |
| | 23 (CCUG 41787) | HARMONY Collection |
| | ID-61880 (EMRSA1) | LSPQ |
| | MA 8628 | LSPQ |
| | MA 50558 | LSPQ |
| | MA 50428 | LSPQ |
| | MA 50609 | LSPQ |
| | MA 50884 | LSPQ |
| | MA 50892 | LSPQ |
| | MA 50934 | LSPQ |
| | MA 51015 | LSPQ |
| | MA 51056 | LSPQ |
| | MA 51085 | LSPQ |
| | MA 51172 | LSPQ |
| | MA 51222 | LSPQ |
| | MA 51363 | LSPQ |
| | MA 51561 | LSPQ |
| | MA 52034 | LSPQ |
| | MA 52306 | LSPQ |
| | MA 51520 | LSPQ |
| | MA 51363 | LSPQ |
| | 98/10618 | HARMONY Collection |

TABLE 14-continued

Reference strains used to test sensitivity and/or specificity and/or ubiquity of the MRSA-specific PCR assays targeting MREJ sequences

| Staphylococcal species | Strains | |
|---|---|---|
| | 98/26821 | HARMONY Collection |
| | 24344 | HARMONY Collection |
| | 62305 | HARMONY Collection |
| | 90/10685 | HARMONY Collection |
| | 98/14719 | HARMONY Collection |
| | 97S99 | HARMONY Collection |
| | 97S100 | HARMONY Collection |
| | 825/96 | HARMONY Collection |
| | 842/96 | HARMONY Collection |
| | N8-890/99 | HARMONY Collection |
| | 9805-01937 | HARMONY Collection |
| | 1 | Kreiswirth-1 |
| | 29 | Kreiswirth-1 |
| MRCNS (n = 4) | 29060 | ATCC |
| | 35983 | ATCC |
| | 35984 | ATCC |
| | 2514 | LSPQ |
| | | Source |
| MSSA (n = 28) | MA 52263 | LSPQ |
| | 6538 | ATCC |
| | 13301 | ATCC |
| | 25923 | ATCC |
| | 27660 | ATCC |
| | 29213 | ATCC |
| | 29247 | ATCC |
| | 29737 | ATCC |
| | RN 11 | CDC |
| | RN 3944 | CDC |
| | RN 2442 | CDC |
| | 7605060113 | CDC |
| | BM 4611 | Institut Pasteur |
| | BM 3093 | Institut Pasteur |
| | 3511 | LSPQ |
| | MA 5091 | LSPQ |
| | MA 8849 | LSPQ |
| | MA 8871 | LSPQ |
| | MA 50607 | LSPQ |
| | MA 50612 | LSPQ |
| | MA 50848 | LSPQ |
| | MA 51237 | LSPQ |
| | MA 51351 | LSPQ |
| | MA 52303 | LSPQ |
| | MA 51828 | LSPQ |
| | MA 51891 | LSPQ |
| | MA 51504 | LSPQ |
| | MA 52535 | LSPQ |
| | MA 52783 | LSPQ |
| MSCNS (n = 17) | 12228 | ATCC |
| | 14953 | ATCC |
| | 14990 | ATCC |
| | 15305 | ATCC |
| | 27836 | ATCC |
| | 27848 | ATCC |
| | 29070 | ATCC |
| | 29970 | ATCC |
| | 29974 | ATCC |
| | 35539 | ATCC |
| | 35552 | ATCC |
| | 35844 | ATCC |
| | 35982 | ATCC |
| | 43809 | ATCC |
| | 43867 | ATCC |
| | 43958 | ATCC |
| | 49168 | ATCC |

[a]ATCC stands for "American Type Culture Collection". LSPQ stands for "Laboratoire de Santé Publique du Québec". CDC stands for "Center for Disease Control and Prevention".

TABLE 15

Clinical isolates used to test the sensitivity and/or specificity and/or ubiquity of the MRSA-specific PCR assays targeting MREJ sequences

| Staphylococcal species | Number of strains | Source |
|---|---|---|
| MRSA (n = 177) | 150 | Canada |
| | 10 | China |
| | 10 | Denmark |
| | 9 | Argentina |
| | 1 | Egypt |
| | 1 | Sweden |
| | 1 | Poland |
| | 3 | Japan |
| | 1 | France |
| MSSA (n = 224) | 208 | Canada |
| | 10 | China |
| | 4 | Japan |
| | 1 | USA |
| | 1 | Argentina |
| MRCNS (n = 38) | 32 | Canada |
| | 3 | China |
| | 1 | France |
| | 1 | Argentina |
| | 1 | USA |
| MSCNS (n = 17) | 14 | UK |
| | 3 | Canada |

TABLE 16

Analytical sensitivity of tests performed on a standard thermocycler using the set of primers targeting MREP types i, ii, iii, iv and v (SEQ ID NOs.: 64, 66, 67, 79 and 80) developed in the present invention for the detection and identification of MRSA

| Staphylococcus aureus strain designation: | | Detection limit |
|---|---|---|
| Original | CCRI[a] (MREP type) | (number of genome copies) |
| 13370 | CCRI-8894 (i) | 10 |
| ATCC 43300 | CCRI-175 (ii) | 5 |
| 9191 | CCRI-2086 (ii) | 10 |
| 35290 | CCRI-1262 (iii) | 5 |
| 352 | CCRI-1266 (iii) | 10 |
| 19121 | CCRI-8895 (iv) | 5 |
| ATCC 33592 | CCRI-178 (iv) | 5 |
| MA 50428 | CCRI-1311 (v) | 5 |
| R991282 | CCRI-2025 (v) | 5 |

[a]CCRI stands for "Collection of the Centre de Recherche en Infectiologie".

TABLE 17

Specificity and ubiquity tests performed on a standard thermocycler using the set of primers targeting MREP types i, ii, iii, iv and v (SEQ ID NO.: 64, 66, 67, 79 and 80) developed in the present invention for the detection and identification of MRSA

| | PCR results for SCCmec - orfX right extremity junction | |
|---|---|---|
| Strains | Positive (%) | Negative (%) |
| MRSA - 35 strains[a] | 27 (77.1) | 8 (22.9) |
| MSSA - 44 strains | 13 (29.5) | 31 (70.5) |
| MRCNS - 9 strains* | 0 | 9 (100) |
| MSCNS - 10 strains* | 0 | 10 (100) |

[a]MRSA strains include the 20 strains listed in Table 3.
*Details regarding CNS strains:
MRCNS:
*S. caprae* (1)
*S. cohnii cohnii* (1)

TABLE 17-continued

Specificity and ubiquity tests performed on a standard thermocycler using the set of primers targeting MREP types i, ii, iii, iv and v (SEQ ID NO.: 64, 66, 67, 79 and 80) developed in the present invention for the detection and identification of MRSA

| Strains | PCR results for SCCmec - orfX right extremity junction | |
|---|---|---|
| | Positive (%) | Negative (%) |
| S. epidermidis (1) | | |
| S. haemolyticus (2) | | |
| S. hominis (1) | | |
| S. sciuri (1) | | |
| S. simulans (1) | | |
| S. warneri (1) | | |
| MSCNS: | | |
| S. cohni (1) | | |
| S. epidermidis (1) | | |
| S. equorum (1) | | |
| S. haemolyticus (1) | | |
| S. lentus (1) | | |
| S. lugdunensis (1) | | |
| S. saccharolyticus (1) | | |
| S. saprophyticus (2) | | |
| S. xylosus (1) | | |

TABLE 18

Analytical sensitivity of tests performed on the SMART CYCLER ® thermocycler using the set of primers targeting MREP types i, ii, iii, iv and v (SEQ ID NOs.: 64, 66, 67, 79 and 80) and molecular beacon probe (SEQ ID NO.: 84) developed in the present invention for the detection and identification of MRSA

| Staphylococcus aureus strain designation: | | Detection limit |
|---|---|---|
| Original | CCRI[a](MREP type) | (number of genome copies) |
| 13370 | CCRI-8894 (i) | 2 |
| ATCC 43300 | CCRI-175 (ii) | 2 |
| 9191 | CCRI-2086 (ii) | 10 |
| 35290 | CCRI-1262 (iii) | 2 |
| 352 | CCRI-1266 (iii) | 10 |
| ATCC 33592 | CCRI-178 (iv) | 2 |
| MA 51363 | CCRI-1331 (iv) | 5 |
| 19121 | CCRI-8895 (iv) | 10 |
| Z109 | CCRI-8903 (iv) | 5 |
| 45302 | CCRI-1263 (v) | 10 |
| MA 50428 | CCRI-1311 (v) | 5 |
| MA 50609 | CCRI-1312 (v) | 5 |
| MA 51651 | CCRI-1325 (v) | 10 |
| 39795-2 | CCRI-1377 (v) | 10 |
| R991282 | CCRI-2025 (v) | 2 |

[a]CCRI stands for "Collection of the Centre de Recherche en Infectiologie".

TABLE 19

Specificity and ubiquity tests performed on the SMART CYCLER ® thermocycler using the set of primers targeting MREP types i, ii, iii, iv and v (SEQ ID NO.: 64, 66, 67, 79 and 80) and molecular beacon probe (SEQ ID NO.: 84) developed in the present invention for the detection of MRSA

| Strains | PCR results for MREJ | |
|---|---|---|
| | Positive (%) | Negative (%) |
| MRSA - 29 strains[a] | 21 (72.4) | 8 (27.6) |
| MSSA - 35 strains | 13 (37.1) | 22 (62.9) |

TABLE 19-continued

Specificity and ubiquity tests performed on the SMART CYCLER ® thermocycler using the set of primers targeting MREP types i, ii, iii, iv and v (SEQ ID NO.: 64, 66, 67, 79 and 80) and molecular beacon probe (SEQ ID NO.: 84) developed in the present invention for the detection of MRSA

| Strains | PCR results for MREJ | |
|---|---|---|
| | Positive (%) | Negative (%) |
| MRCNS - 14 strains | 0 | 14 (100) |
| MSCNS - 10 strains | 0 | 10 (100) |

[a]MRSA strains include the 20 strains listed in Table 3.
Details regarding CNS strains:
MRCNS:
S. epidermidis (1)
S. haemolyticus (5)
S. simulans (5)
S. warneri (3)
MSCNS:
S. cohni cohnii (1)
S. epidermidis (1)
S. gallinarum (1)
S. haemolyticus (1)
S. lentus (1)
S. lugdunensis (1)
S. saccharolyticus (1)
S. saprophyticus (2)
S. xylosus (1)

TABLE 20

Analytical sensitivity of tests performed on the SMART CYCLER ® thermocycler using the set of primers targeting MREP types i, ii, iii, iv, v and vii (SEQ ID NOs.: 64, 66, 67, 79 and 80) and molecular beacon probe (SEQ ID NO.: 84) developed in the present invention for the detection and identification of MRSA

| Staphylococcus aureus strain designation: | | Detection limit |
|---|---|---|
| Original | CCRI[a](MREP type) | (number of genome copies) |
| 13370 | CCRI-8894 (i) | 2 |
| ATCC 43300 | CCRI-175 (ii) | 2 |
| 35290 | CCRI-1262 (iii) | 2 |
| ATCC 33592 | CCRI-178 (iv) | 2 |
| R991282 | CCRI-2025 (v) | 2 |
| SE-41-1 | CCRI-9771 (vii) | 2 |

[a]CCRI stands for "Collection of the Centre de Recherche en Infectiologie".

TABLE 21

Specificity and ubiquity tests performed on the SMART CYCLER ® thermocycler using the set of primers targeting MREP types i, ii, iii, iv, vi and vii (SEQ ID NOs.: 64, 66, 67, 79 and 80) and molecular beacon probe (SEQ ID NO.: 84) developed in the present invention for the detection and identification of MRSA

| Strains | PCR results for MREJ | |
|---|---|---|
| | Positive (%) | Negative (%) |
| MRSA - 23 strains[a] | 19 (82.6) | 4 (17.4) |
| MSSA - 25 strains | 13 (52) | 12 (48) |

TABLE 21-continued

Specificity and ubiquity tests performed on the SMART CYCLER ® thermocycler using the set of primers targeting MREP types i, ii, iii, iv, vi and vii (SEQ ID NOs.: 64, 66, 67, 79 and 80) and molecular beacon probe (SEQ ID NO.: 84) developed in the present invention for the detection and identification of MRSA

| Strains | PCR results for MREJ | |
|---|---|---|
| | Positive (%) | Negative (%) |
| MRCNS - 26 strains | 0 | 26 (100) |
| MSCNS - 8 strains | 0 | 8 (100) |

[a]MRSA strains include the 20 strains listed in Table 3.
Details regarding CNS strains:
MRCNS:
S. capitis (2)
S. caprae (1)
S. cohnii (1)
S. epidermidis (9)
S. haemolyticus (5)
S. hominis (2)
S. saprophyticus (1)
S. sciuri (2)
S. simulans (1)
S. warneri (2)
MSCNS:
S. cohni cohnii (1)
S. epidermidis (1)
S. haemolyticus (1)
S. lugdunensis (1)
S. saccharolyticus (1)
S. saprophyticus (2)
S. xylosus (1)

Annex I: Strategy for the selection of specific amplification primers for types i and ii MREP

| | SEQ ID NO.: | Types i and ii MREP | | orfX | |
|---|---|---|---|---|---|
| | | 2324 | 2358 | 2583 | 2607 |
| A. | 2 | TAT GTCAAAAATC ATGAACCTCA TTACTTATGA TA...CCT TGTGCAGGCC GTTTGATCCG CC | | | |
| | 1 | TAT GTCAAAAATC ATGAACCTCA TTACTTATGA TA...CCT TGTGCAGGCC GTTTGATCCG CC | | | |
| | 17[a] | TAT GTCAAAAATC ATGAACCTCA TTACTTATGA TA...CCT TGTGCAGGCC GTTTGATCCG CC | | | |
| | 18[a] | TAT GTCAAAAATC ATGAACCTCA TTACTTATGA TA...CCT TGTGCAGGCC GTTTGATCCG CC | | | |
| | 19[a] | TAT GTCAAAAATC ATGAACCTCA TTACTTATGA TA...CCT TGTGCAGGCC GTTTGATCCG CC | | | |
| | 20[a] | TAT GTCAAAAATC ATGAACCTCA TTACTTATGA TA...CCT TGTGCAGGCC GTTTGATCCG CC | | | |
| | 21[a] | TAT GTCAAAAATC ATGAACCTCA TTACTTATGA TA...CCT TGTGCAGGCC GTTTGATCCG CC | | | |
| | 22[a] | TAT GTCAAAAATC ATGAACCTCA TTACTTATGA TA...CCT TGTGCAGGCC GTTTGATCCG CC | | | |
| | 23[a] | TAT GTCAAAAATC ATGAACCTCA TTACTTATGA TA...CCT TGTGCAGGCC GTTTGATCCG CC | | | |
| | 24[a] | TAT GTCAAAAATC ATGAACCTCA TTACTTATGA TA...CCT TGTGCAGGCC GTTTGATCCG CC | | | |
| | 25[a] | TAT GTCAAAAATC ATGAACCTCA TTACTTATGA TA...CCT TGTGCAGGCC GTTTGATCCG CC | | | |
| | 26 | TAT GTCAAAAATC ATGAACCTCA TTACTTATGA TA...CCT TGTGCAGGCC GTTTGATCCG CC | | | |
| | 33[c] | | | CtT gGTGtAaaCC aTTgGAgCCa CC | |
| | 34[c] | | | CCT caTGCAatCC aTTTGATC | |
| Selected sequence for type i MREP and ii primer (SEQ ID NO:. 66) | | GTCAAAAATC ATGAACCTCA TTACTTATG | | | |
| Selected sequence for orfX primer[b] (SEQ ID NO.: 64) | | | | TGTGCAGGCC GTTTGATCC | |

The sequence positions refer to SEQ ID NO.: 2.
Nucleotides in capitals are identical to the selected sequences or match those sequences.
Mismatches are indicated by lower-case letters. Dots indicate gaps in the displayed sequences.
[a]These sequences are the reverse-complements of SEQ ID NOs.: 17-25.
[b]This sequence is the reverse-complement of the selected primer.
[c]SEQ ID NOs.: 33 and 34 were obtained from CNS species.

Annex II: Strategy for the selection of a specific
molecular beacon probe for the real-time detection of MREJ

| | orfX | |
|---|---|---|
| SEQ ID NO.: | 327 | 371 |
| 165 | ACAAG GACGT CTTACAACGC AGTAACTAtG CACTA | |
| 180 | ACAAG GACGT CTTACAACGC AGTAACTAtG CACTA | |
| 181 | ACAAG GACGT CTTACAACGC AGTAACTAtG CACTA | |
| 182 | ACAAG GACGT CTTACAACGC AGTAACTAtG CACTA | |
| 183 | ACAAG GACGT CTTACAACGC AGTAACTAtG CACTA | |
| 184 | ACAAG GACGT CTTACAACGC AGTAACTAtG CACTA | |
| 186 | ACAAG GACGT CTTACAACGC AGTAACTAtG CACTA | |
| 174 | ACAAG GACGT CTTACAACGt AGTAACTACG CACTA | |
| 175 | ACAAG GACGT CTTACAACGt AGTAACTACG CACTA | |
| 178 | ACAAG GACGT CTTACAACGt AGTAACTACG CACTA | |
| 176 | ACAAG GACGT CTTACAACGt AGTAACTACG CACTA | |
| 173 | ACAAG GACGT CTTACAACGt AGTAACTACG CACTA | |
| 177 | ACAAG GACGT CTTACAACGt AGTAACTACG CACTA | |
| 169 | ACAAG GACGT CTTACAACGC AGTAACTACG CACTA | |
| 199 | ACAAG GACGT CTTACAACGC AGTAACTACG CACTA | |
| 33[a,b] | ACcAa GACGT CTTACAACGC AGcAACTAtG CttTA | |
| 34[a,b] | AtgAG GACGT CTTACAACGC AGcAACTACG CACTt | |
| Selected sequence for orfX molecular beacon probes (SEQ ID NO.: 163)[c] | GACGT CTTACAACGC AGTAACTAtG | |
| (SEQ ID NO.: 164)[c] | GACGT CTTACAACGt AGTAACTACG | |
| (SEQ ID NO.: 84)[c] | GACGT CTTACAACGC AGTAACTACG | |

Nucleotide discrepancies between the orfX sequences and SEQ ID NO.: 84 are
shown in lower-case. Other entries in the sequence listing also present similar
variations. The stem of the molecular beacon probes are not shown for the sake
of clarity. The sequence positions refer to SEQ ID NO.: 165.
[a]These sequences are the reverse-complements of SEQ ID NOs.: 33 and 34.
[b]SEQ ID NOs.: 33 and 34 were obtained from CNS species.
[c]The sequences presented are the reverse-complement of the selected molecular
beacon probes.

---

What is claimed is:

1. A method to detect the presence of an MREJ type vii methicillin-resistant *Staphylococcus aureus* (MRSA) strain nucleic acid in a sample, comprising:
   a) performing an amplification reaction comprising contacting a sample to be analyzed for the presence of said MREJ type vii MRSA strain nucleic acid with a first amplification primer and a second amplification primer to generate a first amplicon if said MREJ type vii MRSA strain nucleic acid is present in said sample, said MREJ type vii MRSA strain nucleic acid including a staphylococcal cassette chromosome mec (SCCmec) element containing a mecA gene inserted into chromosomal DNA, said chromosomal DNA being orfX, thereby generating a polymorphic right extremity junction (MREJ) type vii nucleic acid sequence that comprises nucleic acid sequences from both the SCCmec element right extremity and orfX adjoining said right extremity;

wherein said first primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with an SCCmec element right extremity of an MREJ type vii nucleic acid sequence selected from the group consisting of: SEQ ID NOs: 165, 166, and the complements thereof, wherein said second primer is at least 10 nucleotides in length and specifically hybridizes at least under conditions of 50 mM KCl, 10 mM Tris-HCl (pH 9.0), 0.1% Triton X-100, 2.5 mM $MgCl_2$ at 55° C. with orfX, wherein said first amplicon generated if said MREJ type vii MRSA strain nucleic acid is present in said sample comprises polymorphic right extremity junction (MREJ) type vii sequence and orfX sequence, including the junction of the two, and is indicative of the presence of MREJ type vii MRSA strain nucleic acid in said sample; and b) generating and detecting said first amplicon.

2. The method of claim 1, wherein said first amplification primer that specifically hybridizes with said SCCmec element right extremity of an MREJ type vii nucleic acid sequence comprises at least 10 consecutive residues of SEQ ID NO: 112, or the complement thereof, or SEQ ID NO: 113, or the complement thereof.

3. The method of claim 2, wherein said second amplification primer comprises at least ten consecutive residues of SEQ ID NO: 64 or the complement thereof.

4. The method of claim 1, wherein said amplification reaction comprises PCR.

5. The method of claim 1, wherein said method comprises the use of at least one first or second amplification primer and/or a probe comprising a nucleic acid sequence or complement thereof selected from the group consisting of SEQ ID NOs: 112, 113, 114, 119, 120, 121, 122, 123, 150, 151, 153, 64, 71, 72, 73, 74, 75, 76, 70, 103, 130, 132, 158, 159, 59, 62, 32, 83, 84, 160, 161, 162, 163, and 164 for the detection of MREJ type vii nucleic acid.

6. The method of claim 1, wherein said second and first amplification primers are a primer pair consisting of SEQ ID NOs: 64 and 112 or SEQ ID NOs: 64 and 113, or the complements thereof.

7. The method of claim 6, further comprising the use of at least one probe having a nucleic acid sequence selected from the group consisting of SEQ ID NOs: 32, 83, 84, 160, 161, 162, 163, 164, and the complements thereof.

8. The method of claim 1, wherein said method comprises the use of at least one first or second amplification primer and/or a probe comprising a nucleic acid sequence or complement thereof selected from the group consisting of: SEQ ID NOs: 64, 112, 113, 84, 163, and 164, for the detection of MREJ type vii nucleic acid.

9. The method of claim 1, further comprising detecting the presence of at least one further methicillin-resistant *Staphylococcus aureus* (MRSA) strain nucleic acid in said sample, said at least one further MRSA strain nucleic acid including an SCCmec element containing a mecA gene inserted into chromosomal DNA, thereby generating a polymorphic right extremity junction (MREJ) type i, ii, iii, iv, v, vi, viii or ix nucleic acid sequence that comprises nucleic acid sequences from both the SCCmec element right extremity and chromosomal DNA adjoining said right extremity, wherein said method further comprises contacting said sample with at least one additional primer to generate a second amplicon if said at least one further MREJ type i, ii, iii, iv, v, vi, viii or ix MRSA strain nucleic acid is present in said sample, wherein said at least one additional primer is at least 10 nucleotides in length and specifically hybridizes at least under conditions of 50 mM KCl, 10 mM Tris-HCl (pH 9.0), 0.1% Triton X-100, 2.5 mM MgCl2 at 55° C. with said polymorphic nucleic acid sequences from the SCCmec element right extremity of said at least one of MREJ type i, ii, iii, iv, v, vi, viii and ix nucleic acid sequences, or complements thereof, selected from the group consisting of:

a) SEQ ID NOs: 1, 20-25, and 41 for MREJ type i;
b) SEQ ID NOs: 2, 17-19, 26, 40, 173-183, 185, 186 and 197 for MREJ type ii;
c) SEQ ID NOs: 4-16, 104, 184 and 198 for MREJ type iii;
d) SEQ ID NOs: 42-46 and 51 for MREJ type iv;
e) SEQ ID NOs: 47-50 for MREJ type v;
f) SEQ ID NO: 171 for MREJ type vi;
g) SEQ ID NO: 167 for MREJ type viii; and
h) SEQ ID NO: 168 for MREJ type ix,
wherein said second amplicon generated if said at least one further MREJ type i, ii, iii, iv, v, vi, viii or ix MRSA strain nucleic acid is present in said sample comprises polymorphic right extremity junction (MREJ) type i, ii, iii, iv, v, vi, viii or ix sequence and orfX sequence, including the junction of the two, and is indicative of the presence of said at least one further MREJ type i, ii, iii, iv, v, vi, viii or ix MRSA strain nucleic acid in said sample; and
detecting said second amplicon if present.

10. The method of claim 9, wherein multiple primers and/or probes are used together in the same physical enclosure.

11. The method of claim 9, further comprising distinctively detecting said first amplicon as an indication of the presence of said MREJ type vii nucleic acid and said second amplicon if present as an indication of said at least one further MREJ type nucleic acid selected from MREJ types i, ii, iii, iv, v, vi, viii and ix, wherein the presence or absence of said second amplicon produced by a primer is indicative of the presence or absence, respectively, of the corresponding MREJ type i, ii, iii, iv, v, vi, viii or ix MRSA nucleic acid.

12. The method of claim 9, wherein a plurality of primers and/or probes all chosen to hybridize under the same hybridization conditions are used.

13. The method of claim 1, comprising detecting the presence or absence of at least three further MRSA strain nucleic acids in said sample, said at least three further MRSA strain nucleic acids including an SCCmec element containing a mecA gene inserted into chromosomal DNA, thereby generating a polymorphic right extremity junction (MREJ) type i, ii, iii, iv, v, vi, viii or ix nucleic acid sequence that comprises nucleic acid sequences from both the SCCmec element right extremity and chromosomal DNA adjoining said right extremity, wherein said method further comprises contacting said sample with at least three additional primers to generate a second, third or fourth amplicon if said at least three further MREJ type i, ii, iii, iv, v, vi, viii or ix MRSA strain nucleic acids are present in said sample, wherein said at least three additional primers are at least 10 nucleotides in length and each specifically hybridizes under conditions of 50 mM KCl, 10 mM Tris-HCl (pH 9.0), 0.1% Triton X-100, 2.5 mM MgCl2 at 55° C. with said polymorphic nucleic acid sequences from the SCCmec element right extremity of one of said at least three further MRSA strains of MREJ type i-vi, and viii-ix nucleic acid sequences, or complements thereof, selected from the group consisting of:

a) SEQ ID NOs: 1, 20-25, and 41 for MREJ type i;
b) SEQ ID NOs: 2, 17-19, 26, 40, 173-183, 185, 186 and 197 for MREJ type ii;
c) SEQ ID NOs: 4-16, 104, 184 and 198 for MREJ type iii;
d) SEQ ID NOs: 42-46 and 51 for MREJ type iv;
e) SEQ ID NOs: 47-50 for MREJ type v;
f) SEQ ID NO: 171 for MREJ type vi;
g) SEQ ID NO: 167 for MREJ type viii; and
h) SEQ ID NO: 168 for MREJ type ix
wherein said second, third and fourth amplicon generated if said at least three further MREJ type i, ii, iii, iv, v, vi, viii or ix MRSA strain nucleic acids are present in said sample comprises polymorphic right extremity junction (MREJ) type i, ii, iii, iv, v, vi, viii or ix nucleic acid sequence and orfX sequence, including the junction of the two, and said second, third and fourth amplicons are indicative of the presence of said at least three further MREJ type i, ii, iii, iv, v, vi, viii or ix MRSA strain nucleic acids in said sample; and detecting the presence or absence of each second, third and/or fourth amplicon distinctively, wherein the presence or absence of each second, third and/or fourth amplicon produced by a primer is indicative of the presence or absence, respectively, of the corresponding one of said three further MREJ type MRSA nucleic acids, thereby determining the presence or absence in a sample of at least three further MREJ types of MRSA nucleic acids.

14. The method of claim 1, wherein said method comprises the use of at least one second amplification primer and/or a probe specific for the *S. aureus* chromosome comprising a nucleic acid sequence, or the complement thereof, selected from the group consisting of SEQ ID NOs: 32, 59, 62, 70-76, 83, 84, 103, 130, 132, and 160-164.

15. The method of claim 9, wherein multiplex PCR is used.

16. The method of claim 1, comprising the use of at least one probe having a nucleic acid sequence, or the complement thereof, selected from the group consisting of SEQ ID NOs: 84, 163 and 164.

17. The method of claim 1, wherein said method comprises the use of at least one first amplification primer comprising a nucleic acid sequence or complement thereof selected from the group consisting of SEQ ID NOs: 112, 113, 114, 119, 120, 121, 122, 123, 150, 151, and 153, for the detection of MREJ type vii nucleic acid.

18. The method of claim 17, wherein said method further comprises the use of at least one second amplification primer and/or probe comprising a nucleic acid sequence or complement thereof selected from the group consisting of SEQ ID NOs: 64, 71, 72, 73, 74, 75, 76, 70, 103, 130, 132, 158, 159, 59, 62, 32, 83, 84, 160, 161, 162, 163, and 164.

* * * * *